(12) United States Patent
Peled et al.

(10) Patent No.: US 10,959,979 B2
(45) Date of Patent: *Mar. 30, 2021

(54) SMALL MOLECULES AGAINST CANCER

(71) Applicant: Biokine Therapeutics Ltd., Nes Ziona (IL)

(72) Inventors: Amnon Peled, Tel-Aviv (IL); Michal Abraham Karni, Mevasseret Zion (IL); Orly Eizenberg, Rechovot (IL)

(73) Assignee: Biokine Therapeutics Ltd., Nes Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/868,558

(22) Filed: May 7, 2020

(65) Prior Publication Data

US 2020/0268709 A1   Aug. 27, 2020

Related U.S. Application Data

(63) Continuation of application No. 16/063,278, filed as application No. PCT/IL2016/051346 on Dec. 15, 2016, now Pat. No. 10,646,465.

(60) Provisional application No. 62/268,568, filed on Dec. 17, 2015, provisional application No. 62/268,575, filed on Dec. 17, 2015, provisional application No. 62/268,579, filed on Dec. 17, 2015.

(51) Int. Cl.
| | |
|---|---|
| *A61K 31/352* | (2006.01) |
| *C07D 311/76* | (2006.01) |
| *C07D 215/26* | (2006.01) |
| *C07D 401/12* | (2006.01) |
| *C07D 471/04* | (2006.01) |
| *C07D 405/12* | (2006.01) |
| *A61K 31/192* | (2006.01) |
| *A61K 45/06* | (2006.01) |
| *A61K 31/341* | (2006.01) |
| *A61K 31/167* | (2006.01) |
| *A61K 31/366* | (2006.01) |
| *A61K 31/661* | (2006.01) |
| *A61K 31/37* | (2006.01) |
| *A61P 35/00* | (2006.01) |

(52) U.S. Cl.
CPC .......... *A61K 31/352* (2013.01); *A61K 31/167* (2013.01); *A61K 31/192* (2013.01); *A61K 31/341* (2013.01); *A61K 31/366* (2013.01); *A61K 31/37* (2013.01); *A61K 31/661* (2013.01); *A61K 45/06* (2013.01); *A61P 35/00* (2018.01); *C07D 215/26* (2013.01); *C07D 311/76* (2013.01); *C07D 401/12* (2013.01); *C07D 405/12* (2013.01); *C07D 471/04* (2013.01)

(58) Field of Classification Search
CPC .............. A61K 31/352; A61K 31/353

USPC .................................... 514/456, 457
See application file for complete search history.

(56) References Cited

U.S. PATENT DOCUMENTS

| | | | |
|---|---|---|---|
| 5,116,964 A | 5/1992 | Capon et al. | |
| 6,002,008 A | 12/1999 | Wissner et al. | |
| 9,493,557 B2 | 11/2016 | Abraham et al. | |
| 10,646,465 B2* | 5/2020 | Peled .................. | A61K 31/341 |
| 2008/0299130 A1 | 12/2008 | Ambati | |
| 2011/0027643 A1 | 2/2011 | Li et al. | |
| 2012/0087921 A1 | 4/2012 | Abraham et al. | |
| 2014/0154249 A1 | 6/2014 | Abraham et al. | |
| 2017/0015708 A1 | 1/2017 | Abraham et al. | |
| 2017/0226157 A1 | 8/2017 | Peled | |
| 2019/0240188 A1 | 8/2019 | Peled et al. | |
| 2019/0336492 A1 | 11/2019 | Peled et al. | |

FOREIGN PATENT DOCUMENTS

| | | |
|---|---|---|
| EA | 003933 | 10/2003 |
| JP | 2003-512011 | 2/2003 |
| JP | 2003-530318 | 10/2003 |
| WO | WO 92/20642 | 11/1992 |
| WO | WO 95/15758 | 6/1995 |
| WO | WO 95/21613 | 8/1995 |
| WO | WO 97/30035 | 8/1997 |
| WO | WO 99/61428 | 12/1999 |
| WO | WO 00/10981 | 3/2000 |
| WO | WO 00/24782 | 5/2000 |
| WO | WO 00/56720 | 9/2000 |
| WO | WO 01/21598 | 3/2001 |
| WO | WO 02/42248 | 5/2002 |
| WO | WO 03/072599 | 9/2003 |
| WO | WO 2007/052173 | 5/2007 |
| WO | WO 2007/094005 | 8/2007 |

(Continued)

OTHER PUBLICATIONS

Nomura, H. et al.: The antibacterial activity of compounds isolated from oakmoss against legionella pneumophila and other *Legionella* spp. Biolog. & Pharmaceut. Bulletin, vol. 35 (9), pp. 1560-1567, 2012.*

(Continued)

*Primary Examiner* — Charanjit Aulakh

(57) ABSTRACT

Compounds capable of, or usable in, killing cancer cells, and/or modulating a biological activity of a chemokine, and/or inhibiting a kinase, and/or treating diseases and disorders associated with a biological activity of a chemokine and/or cell migration, and/or treating disease and disorders such as cancer and inflammatory diseases and disorders, are provided herein. The compounds are listed in Tables 2, 4 and 5, and/or are represented by Formulae I, IV, V and VI, as defined in the specification. Methods utilizing these compounds are also provided.

3 Claims, 48 Drawing Sheets

(56) References Cited

FOREIGN PATENT DOCUMENTS

| WO | WO 2008/115870 | 9/2008 |
|----|----------------|--------|
| WO | WO 2010/143168 | 12/2010 |
| WO | WO 2010/146584 | 12/2010 |
| WO | WO 2016/092544 | 6/2016 |
| WO | WO 2017/103931 | 6/2017 |
| WO | WO 2017/103932 | 6/2017 |

OTHER PUBLICATIONS

Advisory Action Before the Filing of an Appeal Brief dated Sep. 23, 2013 From the US Patent and Trademark Office Re. U.S. Appl. No. 13/378,063.
Communication Pursuant to Article 94(3) EPC dated Jun. 3, 2019 From the European Patent Office Re. Application No. 16875067.7. (3 Pages).
Communication Pursuant to Article 94(3) EPC dated May 7, 2014 From the European Patent Office Re. Application No. 10735337.7.
Communication Pursuant to Article 94(3) EPC dated Dec. 14, 2012 From the European Patent Office Re. Application No. 10735337.7.
Communication Relating to the Results of the Partial International Search dated Feb. 26, 2017 From the International Searching Authority Re. Application No. PCT/IL2016/051346. (20 Pages).
Examination Report dated Feb. 18, 2014 From the Instituto Mexicano de la Propiedad Industrial Re. Application No. MX/a/2011/013457 and Its Translation Into English.
Examination Report dated Aug. 19, 2019 From the Australian Government, IP Australia Re. Application No. 2016371466. (2 Pages).
Examination Report Under Sections 12 & 13 of the Patents Act, 1970 and the Patents Rules, 2003 dated Apr. 26, 2020 From the Government of India, Intellectual Property India, Patents, Designs, Trade Marks, Geographical Indications, The Patent Office Re. Application No. 201837025290. (5 Pages).
International Preliminary Report on Patentability dated Jun. 22, 2017 From the International Bureau of WIPO Re. Application No. PCT/IL2015/051190. (8 Pages).
International Preliminary Report on Patentability dated Jun. 28, 2018 From the International Bureau of WIPO Re. Application No. PCT/IL2016/051346. (11 Pages).
International Preliminary Report on Patentability dated Jun. 28, 2018 From the International Bureau of WIPO Re. Application No. PCT/IL2016/051347. (7 Pages).
International Preliminary Report on Patentability dated Dec. 29, 2011 From the International Bureau of WIPO Re. Application No. PCT/IL2010/000473.
International Search Report and the Written Opinion dated Mar. 19, 2017 From the International Searching Authority Re. Application No. PCT/IL2016/051347. (10 Pages).
International Search Report and the Written Opinion dated Oct. 22, 2010 From the International Searching Authority Re. Application No. PCT/IL2010/000473.
International Search Report and the Written Opinion dated Mar. 28, 2016 From the International Searching Authority Re. Application No. PCT/IL2015/051190.
International Search Report and the Written Opinion dated Mar. 29, 2017 From the International Searching Authority Re. Application No. PCT/IL2016/051346. (33 Pages).
Notice of Allowance dated Jul. 1, 2016 From the US Patent and Trademark Office Re. U.S. Appl. No. 14/178,301.
Notice of Preliminary Rejection dated Feb. 8, 2017 From the Korean Intellectual Property Office Re. Application No. 2012-7000920. (6 Pages).
Notice of Reason for Rejection dated Oct. 17, 2014 From the Japanese Patent Office Re. Application No. 2012-515627 and Its Translation Into English.
Notification of Office Action dated Oct. 31, 2013 From the State Intellectual Property Office of the People's Republic of China Re. Application No. 201080036127.9 and Its Translation Into English.

Office Action dated Jul. 8, 2013 From the Israel Patent Office Re. Application No. 216978 and Its Translation Into English.
Office Action dated Nov. 17, 2019 From the Israel Patent Office Re. Application No. 260082 and Its Translation Into English. (7 Pages).
Office Action dated Mar. 26, 2015 From the Israel Patent Office Re. Application No. 216978 and Its Translation Into English.
Official Action dated Jul. 1, 2013 From the US Patent and Trademark Office Re. U.S. Appl. No. 13/378,063.
Official Action dated Jul. 7, 2015 From the US Patent and Trademark Office Re. U.S. Appl. No. 14/178,301.
Official Action dated Jan. 8, 2013 From the US Patent and Trademark Office Re. U.S. Appl. No. 13/378,063.
Official Action dated Feb. 9, 2016 From the US Patent and Trademark Office Re. U.S. Appl. No. 14/178,301.
Official Action dated Sep. 2019 From the US Patent and Trademark Office Re. U.S. Appl. No. 16/063,278. (25 pages).
Official Action dated Aug. 21, 2017 From the US Patent and Trademark Office Re. U.S. Appl. No. 15/326,512. (42 pages).
Official Action dated Aug. 28, 2017 From the US Patent and Trademark Office Re. U.S. Appl. No. 15/285,492. (31 pages).
Request for Examination and Search Report dated Apr. 3, 2020 From the Federal Government Institution, Federal Institute of Industrial Property of the Federal Service of Intellectual Property, Patents and Trademarks of the Russian Federation, FIPS Re. Application No. 2018125293 and Its Translation Into English. (11 Pages).
Requisition by the Examiner Dated May 25, 2016 From the Canadian Intellectual Property Office Re. Application No. 2,765,188.
Requisition by the Examiner Dated Jun. 27, 2017 From the Canadian Intellectual Property Office Re. Application No. 2,765,188. (8 Pages).
Restriction Official Action dated Jul. 2, 2019 From the US Patent and Trademark Office Re. U.S. Appl. No. 16/063,278. (7 pages).
Restriction Official Action dated Mar. 10, 2015 From the US Patent and Trademark Office Re. U.S. Appl. No. 14/178,301.
Restriction Official Action dated Aug. 23, 2012 From the US Patent and Trademark Office Re. U.S. Appl. No. 13/378,063.
Supplementary European Search Report and the European Search Opinion dated Nov. 7, 2019 From the European Patent Office Re. Application No. 16875066.9. (13 Pages).
Supplementary European Search Report and the European Search Opinion dated Sep. 19, 2018 From the European Patent Office Re. Application No. 16875067.7. (5 Pages).
Supplementary Partial European Search Report and the European Provisional Opinion dated Aug. 5, 2019 From the European Patent Office Re. Application No. 16875066.9. (18 Pages).
Translation of Notice of Preliminary Rejection dated Feb. 8, 2017 From the Korean Intellectual Property Office Re. Application No. 2012-7000920. (4 Pages).
Translation of Office Action dated May 2, 2013 From the State Intellectual Property Office of the People's Republic of China Re. Application No. 201080036127.9.
Translation of Search Report dated May 2, 2013 From the State Intellectual Property Office of the People's Republic of China Re. Application No. 201080036127.9.
Baggiolini et al. "CC Chemokines in Allergic Inflammation", Immunology Today, 15(3): 127-133, 1994.
Bork "Powers and Pitfalls in Sequence Analysis: The 70% Hurdle", Genome Research, 10: 398-400, 2000.
Carreras Puigvert et al. "Targeting DNA Repair, DNA Metabolism and Replication Stress as Anti-Cancer Strategies", The FEBS Journal, XP055607460, 283(2): 232-245, Published Online Oct. 28, 2015.
Cocchi et al. "Identification of RANTES, MIP-1[Alpha], and MIP-1[Beta] as the Major HIV-Suppressive Factors Produced by CD8+ T Cells", Science, 270(5243): 1811-1815, Dec. 15, 1995.
Debnath et al. "Small Molecule Inhibitors of CSCR4", Theranostics, XP055391478, 3(1): 47-75, Jan. 15, 2013. Abstract, Figs.
Doercks et al. "Protein Annotation: Detective Work for Function Prediction", Trends in Genetics, TiG, 14(6): 248-250, Jun. 1998.
Duan et al. "Inhaled P38[Alpha] Mitogen-Activated Protein Kinase Antisense Oligonucleotide Attenuates Asthma in Mice", American Journal of Respiratory and Critical Care Medicine, 171: 571-578, Originally Published Nov. 19, 2004.

(56) References Cited

OTHER PUBLICATIONS

Elix et al. "Annelated Furans. XVIII. The Photocyclization of 2-Methoxyphenyl Phenyl Ethers", Australian Journal of Chemistry, 28(7): 1559-1582, Dec. 31, 1975. p. 1562, Compounds 11, 12, 14.
Epifano et al. "Auraptene and Its Effects on the Re-Emergence of Colon Cancer Stem Cells", Phytotherapy Research, 27(5): 784-786, Epub Jul. 4, 2012.
Escott et al. "Effect of the P38 Kinase Inhibitor, SB 203580, on Allergic Airway Inflammation in the Rat", British Journal of Pharmacology, 131(2): 173-176, Sep. 2000.
Haddad et al. "Role of P38 MAP Kinase in LPS-Induced Airway Inflammation in the Rat", British Journal of Pharmacology, 132(8): 1715-1724, Apr. 2001.
Hu et al. "Design, Synthesis, and Biological Evaluation of Novel Quinazoline Derivatives as Anti-Inflammatory Agents Against Lipopolysaccharide-Induced Acute Lung Injury in Rats", Chemical Biology & Drug Design, 85(6): 672-684, Published Online Nov. 6, 2014. Schemes 1, p. 7, Compounds 6a, 6b, 6c, 6d, 6g, 6i, Schemes 1, p. 7, 6o, 6p, 6q, Scheme 2, p. 7.
Huang et al. "Anticancer Activities of Polyynes From the Root Bark of Oplopanax Horridus and Their Acetylated Derivatives", Molecules, 19: 6142-6162, May 14, 2014.
Joulain et al. "Lichen Extracts as Raw Materials in Perfumery. Part 2: Treemoss", Flavour and Fragrance Journal, 24(3): 105-116, Mar. 11, 2009. p. 5, Fig.4, Compounds 32-33.
Kasuga et al. "Sensitization of Human Glioblastomas to Tumor Necrosis Factor-Related Apoptosis-Inducing Ligand (TRAIL) by NF-KB Inhibitors", Cancer Science, 95(10): 840-844, Oct. 2004.
Kim et al. "Isolation and Characterization of Antitumor Agents From Dictamnus Albus", Saengyak Hakhoe Chi, 28(4): 209-214, Dec. 28, 1997.
Kioi et al. "Inhibition of Vasculogenesis, But Not Angiogenesis, Prevents the Recurrence of Glioblastoma After Irradiation In Mice", the Journal of Clincal Investigation, 120(3): 694-705, Mar. 2010.
Kryczek et al. "Stroma-Derived Factor (SDF-1/CXCL12) and Human Tumor Pathogenesis", American Journal of Physioloy, Cell Physiology, 292(3): C987-C995, First Published Aug. 30, 2006.
Lee et al. "Ocular Neovascularization: An Epidemiologic Review", Survey of Ophthalmology, 43(3): 245-269, Nov.-Dec. 1998.
Lo et al. "High Level Expression and Secretion of Fc-X Fusion Proteins in Mammalian Cells", Protein Engineering, 11(6): 495-500, Jun. 1998.
Luhmann et al. The Relevance of Chemokine Signalling in Modulating Inherited and Age-Related Retinal Degenerations:, Retinal Degenerative Diseases, Chap.54: 427-433, Mar. 25, 2014.
Ma et al. "Impaired B-Lymphopoiesis, Myelopoiesis, and Derailed Cerebellar Neuron Migration in CXCR4- and SDF-1-Deficient Mice", Proc. Natl. Acad. Sci. USA, 95(16): 9448-9453, Aug. 1998.
Mathebula "A Review of Ocular Genetics and Inherited Eye Diseases", African Vision and Eye Health, 71(4): 179-189. 2012.
Niu et al. "New Polyphenols From a Deep sea *Spiromastix* Sp. Fungus, and Their Antibacterial Activities", Marine Drugs, 13(4): 2526-2540, Apr. 22, 2015. Fig.1, Compound 9, p. 2527.
Nomura et al. "Effects of Oakmoss and Its Components on Biofilm Formation of Legionella Pneumophila", Biological and Pharmaceutical Bulletin, 36(5): 833-837, May 2013. Compounds 14, 17, 20, p. 834.
Nomura et al. "The Antibacterial Activity of Compounds Isolated From Oakmoss Against Legionella Pneumophila and Other *Legionella* Spp.", Biological & Pharmaceutical Bulletin, XP055391465, 35(9): 1560-1567, Jun. 20, 2012. p. 1562-1563, Fig. 1, Table 1, Compounds 14, 17, 20.
Reeck et al. "'Homology' in Proteins and Nucleic Acids: A Terminology Muddle and a Way Out of It", Cell, 50(5): 667, Aug. 28, 1987.
Rutar et al. "Small Interfering RNA-Mediated Suppression of Ccl2 in Mueller Cells Attenuates Microglial Recruitment and Photoreceptor Death Following Retinal Degeneration", Journal of Neuroinflammation, 9(221): 1-15, Published Online Sep. 19, 2012.
Skolnick et al. "From Genes to Protein Structure and Function: Novel Applications of Computational Approaches in the Genomic Era", Trends in Biotechnology, TiBTech, 18(1): 34-39, Jan. 2000.
Smith et al. "CXCR4 Regulates Growth of Both Primary and Metastatic Breast Cancer", Cancer Research, 64: 8604-8612, Dec. 1, 2004.
Stedman "Allograft Rejection", Stedman's Online, Lippincott Williams and Wilkins, Jun. 23, 2015.
Stedman "Malignant", Stedman's Online, Lippincott Williams and Wilkins, Jun. 23, 2015.
Stedman "Myasthenia Gravis", Stedman's Online, Lippincott Williams and Wilkins, Jun. 23, 2015.
Stedman "Systemic Lupus Erythematosus" Stedman's Online, Lippincott Williams and Wilkins, Jun. 23, 2015.
Strieter et al. "The Functional Role of the ELR Motif in CXC Chemokine-Mediated Angiogenesis", The Journal of Biological Chemistry, 270(45): 27348-27357, Nov. 10, 1995.
Sulaiman et al. "In Vitro and in Silico Studies of Lunacridine From Lunasia Amara Blanco as Anticancer", Journal of Life Sciences, 5(8): 639-645, Published Online Aug. 30, 2011. Abstract.
Tannock et al. "The Basic Science of Oncology", Third Edition, New York: McGraw-Hill; p. 357-358, 1998.
Tokuriki et al. "Stability Effects of Mutations and Protein Evolvability", Current Opinion in Structural Biology, 19: 596-604, 2009.
Toyooka et al. "CD28 Co-Stimulatory Signals Induce IL-2 Receptor Expression on antigen-Stimulated Virgin T Cells by an IL-2-Independent Mechanism", International Immunology, 8(2): 159-169, Feb. 1996.
Underwood et al. "SB 239063, A P38 MAPK Inhibitor, Reduces Neutrophilia, Inflammatory Cytokines, MMP-9, and Fibrosis in Lung", American Journal of Physiology, Lung Cellular and Molecular Physiology, 279(5): L895-L902, Nov. 2000.
Underwood et al. "SB 239063, A Potent P38 MAP Kinase Inhibitor, Reduces Inflammatory Cytokine Production, Airways Eosinophil Infiltration, and Persistence", The Journal of Pharmacology and Experimental Therapeutics, 293(1): 281-288, Apr. 2000.
Vaddi et al. "Regulation of Monocyte Integrin Expression by Beta-Family Chemokines", The Journal of Immunology, 153(10): 4721-4732, Nov. 15, 1994.
Wallace et al. "The Role of Chemokines and Their Receptors in Ocular Disease", Progress in Retinal and Eye Research, 23(4): 435-448, Jul. 2004. p. 446, Pont No. 10.
Wang et al. "Identification of Potential Anticancer Compounds From Oplopanax Horridus", Phytomedicine, 20(11): 999-1006, Aug. 15, 2013.
Wells "Additivity of Mutational Effects in Proteins", Biochemistry, 29(37): 8509-8517, Sep. 18, 1990.
Williams et al. "Depsides Isolated From the Sri Lankan Lichen *Parmotrema* Sp. Exhibit Selective Plk1 Inhibitory Activity", Pharmaceutical Biology, XP055607658, 49(3): 296-301, Feb. 1, 2011.
Wilson et al. "CXCR4 Signaling Mediates Morphine-Induced Tactile Hyperalgesia", Brain, Behavior, and Immunity, 25(3): 565-573, Epub Dec. 28, 2010.
Zheng et al. "Migration of Endothelial Progenitor Cells Mediated by Stromal Cell-Derived Factor-1[Alpha]/CXCR4 Via P13K/Akt/ eNOS Signal Transduction Pathway", Journal of Cardiovascular Pharmacology, 50(3): 274-280, Sep. 2007.
Communication Pursuant to Article 94(3) dated Sep. 4, 2020 From the European Patent Office Re. Application No. 16875066.9. (6 Pages).
Examination Report dated Aug. 13, 2020 From the Instituto Mexicano de la Propiedad Industrial, IMPI, Secretario de Economia, Direccion Divisional de Patentes Re. Application No. MX/a/2018/ 007361. (3 Pages).
International Search Report and the Written Opinion dated Jul. 30, 2020 From the International Searching Authority Re. Application No. PCT/IL2020/050535. (11 Pages).
European Search Report and the European Search Opinion dated Aug. 21, 2020 From the European Patent Office Re. Application No. 20185763.8. (7 Pages).
Official Action dated Sep. 20, 2019 From the US Patent and Trademark Office Re. U.S. Appl. No. 16/063,278. (25 pages).

(56) References Cited

OTHER PUBLICATIONS

Translation of Search Report May 2, 2013 From the State Intellectual Property Office of the People's Republic of China Re. Application No. 201080036127.9.
Debnath et al. "Small Molecule Inhibitors of CXCR4", Theranostics, XP055391478, 3(1): 47-75, Jan. 15, 2013. Abstract, Figs.
Rutar et al. "Small Interfering RNa-Mediated Suppression of Ccl2 in Mueller Cells Attenuates Microglial Recruitment and Photoreceptor Death Following Retinal Degeneration", Journal of Neuroinflammation, 9(221): 1-15, Published Online Sep. 19, 2012.
Office Action dated Jun. 11, 2020 From the Israel Patent Office Re. Application No. 260081 and Its Translation Into English. (5 Pages).
Notice of Reason for Rejection dated Dec. 8, 2020 From the Japan Patent Office Re. Application No. 2018-531613. and Its Translation Into English. (5 Pages).
Sechi et al. "Design and Synthesis of Novel Dihydroquinoline-3-Carboxylic Acids as HIV-1 Integrase Inhibitors", Bioorganic & Medicinal Chemistry, 17(7): 2925-2935, Available Online Nov. 6, 2008.

\* cited by examiner

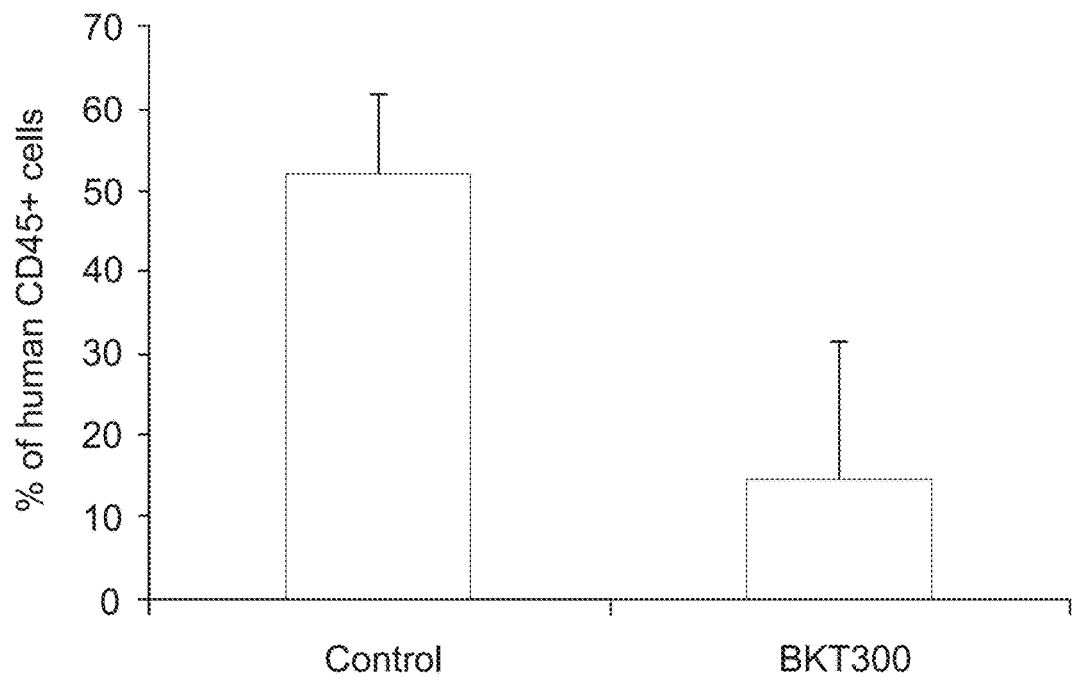
FIG. 47A
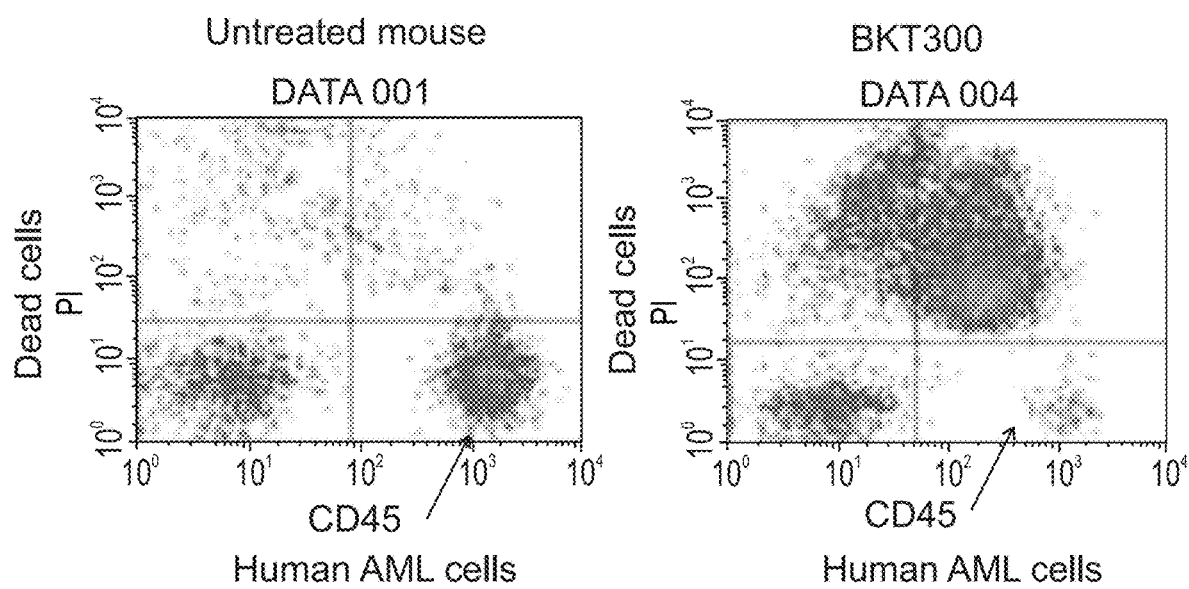
FIG. 47B
FIG. 47C

SMALL MOLECULES AGAINST CANCER

RELATED APPLICATIONS

This application is a continuation of U.S. patent application Ser. No. 16/063,278 filed on Jun. 17, 2018, which is a National Phase of PCT Patent Application No. PCT/IL2016/051346 having International Filing Date of Dec. 15, 2016, which claims the benefit of priority under 35 USC § 119(e) of U.S. Provisional Patent Application Nos. 62/268,568, 62/268,575 and 62/268,579, all filed on Dec. 17, 2015. The contents of the above applications are all incorporated by reference as if fully set forth herein in their entirety.

FIELD AND BACKGROUND OF THE INVENTION

The present invention, in some embodiments thereof, relates to therapy and more particularly, but not exclusively, to compounds, compositions and methods useful in inhibiting a kinase, in modulating a biological activity of a chemokine, in inhibiting cancel cells, in inhibiting chemokine-dependent cell migration and/or in treating diseases and disorders associated with kinase activity, biological activities of chemokines and/or cell migration, such as cancer and inflammatory diseases and disorders.

Chemokines are among the many biological factors that are involved in the inflammatory disease process. Chemokines belong to a group of small, about 8-14 kDa, mostly basic, heparin-binding proteins that are related both in their primary structure and the presence of 4 conserved cysteine residues.

The chemokines are chemotactic cytokines that have been shown to be selective chemoattractants for leukocyte subpopulations in vitro, and to elicit the accumulation of inflammatory cells in vivo. In addition to chemotaxis, chemokines mediate leukocyte de-granulation [Baggiolini and Dahinden, *Immunol Today* 1994, 15:127-133], up-regulation of adhesion receptors [Vaddi and Newton, *J Immunol* 1994, 153:4721-4732], and suppression of human immunodeficiency virus replication [Cocchi et al., *Science* 1995, 270:1811-1815].

Chemokines play an essential role in the recruitment and activation of cells from the immune system. They also have a wide range of effects in many different cell types beyond the immune system, including for example, in various cells of the central nervous system [Ma et al., *PNAS* 1998, 95:9448-9453], and in endothelial cells, where they result in either angiogenic or angiostatic effects [Strieter et al., *J Biol Chem* 1995, 270:27348-27357]. Particular chemokines may have multiple effects on tumors, including angiogenesis, promotion of growth and metastasis, and suppression of the immune response to cancer, while other chemokines inhibit tumor-mediated angiogenesis and promote anti-tumor immune responses.

Chemokine receptors have received increasing attention due to their critical role in the progression of inflammation and associated conditions such as asthma, atherosclerosis, graft rejection, AIDS and autoimmune conditions (e.g., multiple sclerosis, arthritis, myasthenia gravis, lupus).

SDF-1 (stromal cell-derived factor 1), also known as CXCL12 (C-X-C motif chemokine 12), is a chemokine which is strongly chemotactic for lymphocytes. SDF-1 plays an important role in angiogenesis, including angiogenesis associated with tumor progression, by recruiting endothelial progenitor cells from the bone marrow, an effect mediated by the CXCR4, the receptor for SDF-1 [Zheng et al., *Cardiovasc Pharmacol* 2007, 50:274-280; Kryczek et al., *Am J Physiol Cell Physiol* 2007, 292:C987-C995]. In addition, cancer cells that express CXCR4 are attracted to metastasis target tissues that release SDF-1.

Plerixafor, an antagonist of CXCR4, is used in combination with G-CSF (granulocyte colony-stimulating factor) to mobilize hematopoietic stem cells in cancer patients, particularly lymphoma and multiple myeloma patients. The stem cells are subsequently transplanted back to the patient after chemotherapy or radiotherapy.

In animal studies, plerixafor has also been reported to reduce metastasis Smith et al., *Cancer Res* 2004, 64:8604-8612], to reduce recurrence of glioblastoma associated with vasculogenesis [Kioi et al., *J Clin Investigation* 2010, 120: 694-705], and to counteract opioid-induced hyperalgesia [Wilson et al., *Brain Behav Immun* 2011, 25:565-573].

Kinases are a family of enzymes that mediate the transfer of a phosphate moiety from a high energy molecule (such as ATP) to a substrate. Kinases are involved in many cell-signaling pathways. Protein kinases act on proteins, phosphorylating serine, threonine, tyrosine, or histidine residues in the protein, and thereby affecting the protein's activity.

Mitogen activated protein kinases (MAPK) constitute a family of proline-directed serine/threonine kinases that activate their substrates by dual phosphorylation. The p38 MAPKs (p38α, p38β, p38γ and p38δ), for example, are responsible for phosphorylating and activating transcription factors (such as ATF-2, MAX, CHOP and C/ERPb) as well as other kinases (such as MAPKAP-K2/3 or MK2/3), and are themselves activated by physical and chemical stress (e.g. UV, osmotic stress), pro-inflammatory cytokines and bacterial lipopolysaccharide (LPS) [Stein et al., *Ann Rep Med Chem* 1996, 31:289-298; Herlaar & Brown, *Molecular Medicine Today* 1999, 5:439-447]. The products of p38 phosphorylation have been shown to mediate the production of pro-inflammatory cytokines.

The implication of kinases pathways on various diseases and disorders, and an anti-inflammatory activity of kinase inhibitors have been described in the art. For example, anti-inflammatory activities have been reported for p38 kinase inhibitors [Badger et al., *J Pharm Exp Thera* 1996, 279:1453-1461; Griswold et al., *Pharmacol Comm* 1996, 7:323-229]. In particular, p38 kinase inhibitors have been described as potential agents for treating rheumatoid arthritis, and to exhibit beneficial effects in models of airway diseases such as COPD and asthma [Haddad et al, *Br J Pharmacol* 2001, 132:1715-1724; Underwood et al., *Am J Physiol Lung Cell Mol* 2000, 279:895-902; Duan et al., *Am J Respir Crit Care Med* 2005, 171:571-578; Escott et al., *Br J Pharmacol* 2000, 131:173-176; Underwood et al., *J Pharmacol Exp Ther* 2000, 293:281-288]. The implication of the p38MAPK pathway in various diseases has been reviewed by Chopra et al. [*Expert Opinion on Investigational Drugs* 2008, 17:1411-1425].

The compound 8-(2,4-dihydroxy-6-(2-oxoheptyl)-phenoxy)-6-hydroxy-3-pentyl-1H-isochromen-1-one was isolated from oakmoss, and reported to exhibit potent antibacterial activity against *Legionella*, but not against other bacteria [Nomura et al., *Biol Pharm Bull* 2012, 35:1560-1567].

Arjunolic acid [Ramesh et al., *Nat Prod Res* 2012, 26:1549-1552], auraptene [Epifano et al., *Phytother Res* 2013, 27:784-786; Genovese & Epifano, *Curr Drug Targets* 2011, 1:381-386] and falcarindiol [Huang et al., *Molecules* 2014, 19:6142-6162; Wang et al., *Phytomedicine* 2013, 20:999-1006] have been reported to inhibit cancer cells. Auraptene has also been reported to suppress MCP-1 expression in adipocytes [Kuroyanagi et al., *Biochem Biophys Res Commun* 2008, 366:219-215].

SUMMARY OF THE INVENTION

According to an aspect of some embodiments of the invention, there is provided a compound for use in treating cancer, inflammation or a non-cancerous hyperproliferative disorder in a subject in need thereof, the compound being BKT-300, having the formula:

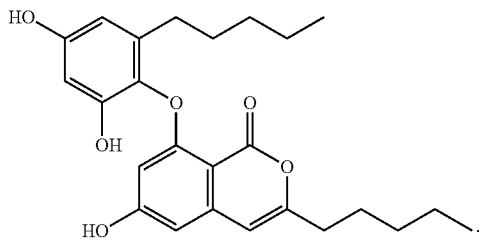

BKT-300

According to an aspect of some embodiments of the invention, there is provided a compound BKT-300 for use in treating cancer.

According to an aspect of some embodiments of the invention, there is provided a compound BKT-300 for use in inhibiting SDF-1 and/or CXCR4.

According to an aspect of some embodiments of the invention, there is provided a compound BKT-300 for use in inducing cell death.

According to an aspect of some embodiments of the invention, there is provided a compound for use in treating cancer, inflammation or a non-cancerous hyperproliferative disorder in a subject in need thereof, the compound being selected from the group of compounds presented in Table 2 and/or the compound having a general formula selected from the group consisting of:

Formula I

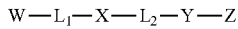

W—$L_1$—X—$L_2$—Y—Z

Formula IV

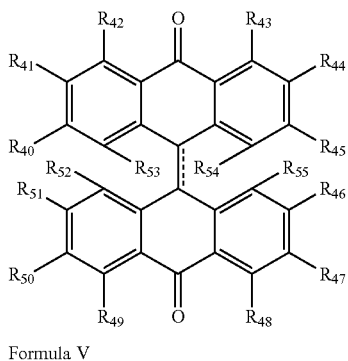

Formula V

-continued

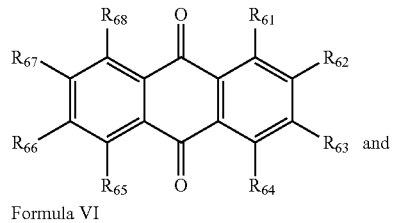

Formula VI and

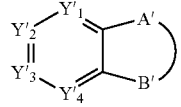

Formula VI wherein treating a cancer does not comprise illuminating the compound in situ at a wavelength absorbed by the compound of formula IV and/or formula V, wherein:

W is a hydrocarbon moiety having from 4 to 20 carbon atoms, optionally comprising one or more hydroxy substituents and/or oxygen atoms between two carbon atoms, wherein a ratio of oxygen atoms to carbon atoms in W is no more than 1:4;

$L_1$ is absent or is selected from the group consisting of —O—, —C(=O)—, —C(=O)O—, and —CR$_1$(OH)—, wherein when $L_1$ is absent, W is attached directly to X;

X is selected from the group consisting of —C≡C—C≡C—; —CR$_3$=CR$_4$—CR$_5$=CR$_6$—, a substituted or unsubstituted bicyclic hydrocarbon moiety, and substituted or unsubstituted phenylene;

$L_2$ is absent or is selected from the group consisting of —O—, —C(=O)—, —C(=O)O—, and —C(R$_2$)(OH)—;

Y is absent or is selected from the group consisting of an aliphatic hydrocarbon moiety from 1 to 8 atoms in length, being substituted or unsubstituted, or alternatively, Y attaches to X and/or to Z to form one or two five- or six-membered rings;

Z is absent or is selected from the group consisting of —C(=O)OH and aryl substituted by at least one hydroxy group; and $R_1$-$R_6$ are each independently selected from the group consisting of hydrogen, alkyl, alkenyl, alkynyl and cycloalkyl, wherein when $L_2$ is absent, Y is absent and Z is —C(=O)OH attached directly to X, and when Y is absent, $L_2$ is attached directly to Z, or $L_2$ is absent and Z is —C(=O)OH attached directly to X;

wherein:

$R_{40}$-$R_{51}$ and $R_{61}$-$R_{68}$ are each selected from the group consisting of hydrogen, hydroxy, alkyl, C-carboxy and a saccharide moiety;

$R_{52}$-$R_{55}$ are hydrogen, or alternatively, $R_{52}$ and $R_{53}$, and/or $R_{54}$ and $R_{55}$, are together a covalent bond which forms a six-membered carbon ring; and the dashed line denotes a saturated or unsaturated bond; and wherein:

wherein:

A' is selected from the group consisting of —C(=O)—O—; —NR$_{71}$—C(=O)—; =C(R$_{72}$)—N=; —C(R$_{72}$)=N— and —C(R$_{73}$)=C(R$_{74}$)—;

B' is selected from the group consisting of —NR$_{75}$—C(=O)—; —C(R$_{76}$)—N=; —C(R$_{76}$)=N—; —C(R$_{77}$)—C(=O)—; and —C(R$_{77}$)=C(R$_{78}$)—;

Y'$_1$ and Y'$_2$ are each independently selected from C-Q', C—R$_{79}$ and N, provided that at least one of Y'$_1$ and Y'$_2$ is C-Q';

Y'$_3$ is selected from N and C—R$_{80}$;

Y'$_4$ is selected from N and C—R$_{81}$;

R$_{71}$ and R$_{75}$ are each independently hydrogen or alkyl;

R$_{72}$-R$_{74}$ are each independently selected from hydrogen, alkyl, alkyne, hydroxy, amine, alkoxy, aryloxy, thioalkoxy, thioaryloxy, carbonyl and carboxylate;

R$_{76}$-R$_{78}$ are each independently selected from hydrogen, alkyl, hydroxy, amine, alkoxy, aryloxy, thioalkoxy, thioaryloxy, carbonyl, carboxylate, cinnamic acid, acyl, S(OH)$_3$ and S—O—O—OH;

R$_{79}$ is hydrogen or cyano;

R$_{80}$ and R$_{81}$ are each independently selected from hydrogen, hydroxy, halo, alkoxy, thioalkoxy, thiol, aryloxy, thioalkoxy, thioaryloxy, carbonyl, amine, and SO$_3$H; and Q' is

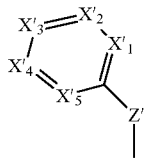

wherein:

Z' is selected from O, NH, C(=O), S, CH$_2$ and S(=O);

X'$_1$ is C(R$_{82}$) or N;

X'$_3$ is C(R$_{84}$) or N;

X'$_4$ is C(R$_{85}$) or N; and

X'$_5$ is C(R$_{86}$) or N, provided that at least two of X$_{71}$-X$_{75}$ are not N, R$_{82}$ is selected from hydrogen, alkyl and halo; and R$_{83}$-R$_{86}$ are each independently selected from hydrogen, halo, alkyl, amine, alkoxy, aryloxy and hydroxy;

or, alternatively, two of R$_{82}$-R$_{86}$ are joined together to form an aryl or heteroaryl.

According to an aspect of some embodiments of the invention, there is provided a compound for use in modulating a biological activity of a chemokine in a subject in need thereof, the compound being selected from the group of compounds presented in Table 2 and/or the compound having a general formula selected from the group consisting of Formulae I, IV, V and VI, as defined herein in any of the respective embodiments.

According to an aspect of some embodiments of the invention, there is provided a compound for use in inducing cell death in a subject in need thereof, the compound being selected from the group of compounds presented in Table 2 and/or the compound having a general formula selected from the group consisting of Formulae I, IV, V and VI, as defined herein in any of the respective embodiments.

According to an aspect of some embodiments of the invention, there is provided a compound for use in inhibiting a kinase and/or in treating a disease or disorder associated with an activity of a kinase, the compound being represented by formula VI, as defined herein in any of the respective embodiments.

According to an aspect of some embodiments of the invention, there is provided a compound being represented by Formula VIA:

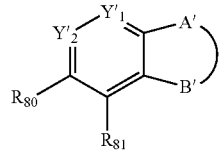

Formula VIA wherein:

A' is selected from the group consisting of —C(=O)—O— and —NR$_1$—C(=O)—;

B' is selected from the group consisting of —NR$_{75}$—C(=O)—; —C(R$_{77}$)—C(=O)—; and —C(R$_{77}$)=C(R$_{78}$)—;

Y'$_1$ and Y'$_2$ are each independently selected from C-Q', CH and N, provided that at least one of Y'$_1$ and Y'$_2$ is C-Q';

R$_{71}$ and R$_{75}$ are each independently hydrogen or alkyl; and

R$_{77}$ and R$_{78}$ are each independently hydrogen and alkyl, at least one of R$_{71}$, R$_{77}$ and R$_{78}$ is an alkyl being at least 4 atoms in length;

R$_{80}$ and R$_{81}$ are each independently selected from hydrogen, alkoxy, aryloxy and hydroxyl, at least one of R$_{80}$ and R$_{81}$ being hydroxyl or alkoxy; and Q' is

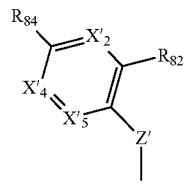

wherein:

Z' is O;

X$_1$ is C(R$_{82}$);

X'$_2$ is C(R$_{83}$) or N;

X'$_3$ is C(R$_{84}$);

X'$_4$ is C(R$_{85}$) or N; and

X'$_5$ is C(R$_{86}$) or N,

R$_{82}$ is selected from hydrogen and alkyl; and

R$_{83}$-R$_{86}$ are each independently selected from hydrogen, alkoxy, aryloxy and hydroxyl, at least one of R$_{83}$-R$_{86}$ being independently hydroxyl, alkoxy or aryloxy.

According to some embodiments of any one of the embodiments of the invention relating to cancer, the cancer is selected from the group consisting of a leukemia, a lymphoma and a lung cancer.

According to some embodiments of any one of the embodiments of the invention relating to cancer, the cancer is selected from the group consisting of acute myeloid leukemia, acute lymphoblastic leukemia, Burkitt lymphoma, multiple myeloma, large cell lung cancer and small cell lung cancer.

According to some embodiments of any one of the embodiments of the invention relating to cancer, the cancer is characterized by expression of CXCR4.

According to some embodiments of any one of the respective embodiments of the invention, treating a cancer further comprises administering an additional anti-cancer agent.

According to some embodiments of the invention, the additional anti-cancer agent is selected from the group consisting of combretastatin A-4 phosphate and ombrabulin.

According to some embodiments of any one of the respective embodiments of the invention, treating a cancer increases a level of hematopietic stem cells in peripheral blood of the subject, and further comprises obtaining hematopietic stem cells from peripheral blood of the subject, administering a cytotoxic therapy to the subject, and transplanting the stem cells back into the subject subsequent to the cytotoxic therapy.

According to some embodiments of any one of the embodiments of the invention relating to inhibiting SDF-1 and/or CXCR4, the compound is for use in treating a disease or disorder associated with an activity of SDF-1 and/or CXCR4.

According to some embodiments of the invention, the disease or disorder associated with an activity of SDF-1 and/or CXCR4 is selected from the group consisting of harmful angiogenesis, tumor metastasis, WHIM syndrome and opioid-induced hyperalgesia.

According to some embodiments of any one of the respective embodiments of the invention, inhibiting SDF-1 and/or CXCR4 is for effecting immunostimulation.

According to some embodiments of any one of the embodiments of the invention relating to modulating a chemokine activity, the activity is chemokine induced cell migration.

According to some embodiments of any one of the respective embodiments of the invention, the chemokine is selected from the group consisting of MIP3a, MCP-1 and SDF-1.

According to some embodiments of any one of the embodiments of the invention relating to modulating a chemokine activity, the compound is for use in inhibiting a biological activity of SDF-1 and/or CXCR4.

According to some embodiments of any one of the embodiments of the invention relating to compounds of Formula I, the compound is for use in treating a cancer, wherein:

X is selected from the group consisting of —$CR_3$=$CR_4$—$CR_5$=$CR_6$—, a substituted or unsubstituted bicyclic hydrocarbon moiety and substituted or unsubstituted phenylene; and $L_2$ is absent or is selected from the group consisting of —C(=O)— and —C($R_2$)(OH)—

According to some embodiments of any one of the embodiments of the invention relating to compounds of Formula I, $R_1$ and $R_2$ are each hydrogen.

According to some embodiments of any one of the embodiments of the invention relating to compounds of Formula I, the phenylene is substituted by at least one substituent selected from the group consisting hydroxy and a saccharide moiety.

According to some embodiments of any one of the embodiments of the invention relating to compounds of Formula I, $R_3$-$R_6$ are each hydrogen.

According to some embodiments of any one of the embodiments of the invention relating to compounds of Formula I, when Y attaches to X to form one or two five- or six-membered rings, Y is selected from the group consisting of —CH=$CR_7$-A- and —$CH_2$—$CHR_8$—B—,
wherein:
A and B are each independently absent or an oxygen atom attached to X or to $L_2$, wherein when A or B is attached to $L_2$, $L_2$ is —C(=O)—; and
$R_7$ and $R_8$ are each independently selected from the group consisting of hydrogen, alkyl and Z.

According to some embodiments of any one of the embodiments of the invention relating to compounds of Formula I, at least one ring atom of each of the five- or six-membered rings is an oxygen atom.

According to some embodiments of any one of the embodiments of the invention relating to compounds of Formula I, Z is selected from the group consisting of hydroxyphenyl, dihydroxyphenyl and —C(=O)OH.

According to some embodiments of any one of the embodiments of the invention relating to compounds of Formula I, W comprises a substituted or unsubstituted alkyl or alkenyl group, the substituted or unsubstituted alkyl or alkenyl comprising at least 4 carbon atoms.

According to some embodiments of any one of the embodiments of the invention relating to compounds of Formula I, the one or more oxygen atoms in W are each within a hydroxy or furanyl group.

According to some embodiments of any one of the embodiments of the invention relating to compounds of Formula I, $L_1$ is absent or is selected from the group consisting of —O—, —C(=O)—, and —$CR_1$(OH)—.

According to some embodiments of the invention, the compound is a compound having the general formula II:

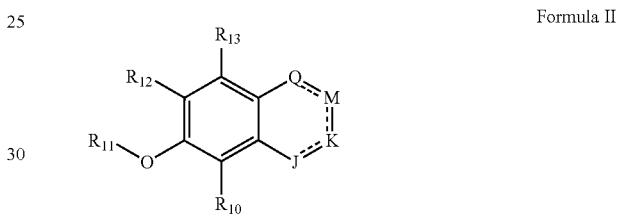

Formula II wherein:
each of the dashed lines independently denotes a saturated or unsaturated bond;

J is selected from the group consisting of —O— and —$CR_{14}$=;

K is selected from the group consisting of —C(=O)—, —$CR_{15}$= and —$CR_{16}R_{17}$—;

M is selected from the group consisting of —O—, —$CR_{18}$= and —$CR_{19}R_{20}$—;

Q is selected from the group consisting of —C(=O)— and —$CR_{21}$=;

$R_{10}$, $R_{12}$ and $R_{13}$ are each independently selected from the group consisting of hydrogen, hydroxy, alkyl, alkenyl, alkynyl, cycloalkyl, alkoxy and aryloxy;

$R_{11}$ is selected from the group consisting of hydrogen, alkyl, alkenyl, alkynyl, cycloalkyl and heteroalicyclic, or alternatively, $R_{11}$ and $R_{12}$ together form a five- or six-membered heteroaryl or heteroalicyclic ring;

$R_{14}$-$R_{21}$ are each independently selected from the group consisting of hydrogen, alkyl, alkenyl, alkynyl, cycloalkyl and aryl; and and at least one of K and Q is —C(=O)—, and at least one of J and M is —O—.

According to some embodiments of any one of the embodiments of the invention relating to compounds of Formula II, no more than one of K and Q is —C(=O)—.

According to some embodiments of any one of the embodiments of the invention relating to compounds of Formula II, no more than one of J and M is —O—.

According to some embodiments of the invention, the compound is a compound having the general formula III:

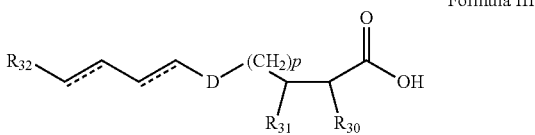

Formula III wherein:

D is selected from the group consisting of —CH$_2$— and —C(=O)—;

the dashed lines each denote a saturated or unsaturated bond;

p is an integer in a range of from 0 to 6;

$R_{30}$ and $R_{31}$ are each hydrogen or $R_{30}$ and $R_{31}$ to together form an aromatic ring substituted by at least one hydroxy group, wherein when $R_{30}$ and $R_{31}$ are each hydrogen, D is —C(=O)— and each of the dashed lines denotes an unsaturated bond; and $R_{32}$ is selected from the group consisting of an alkyl, alkenyl and acyl, each being from 2 to 12 carbon atoms in length.

According to some embodiments of any one of the embodiments of the invention relating to compounds of Formula IV and/or V, $R_{40}$-$R_{51}$ and $R_{61}$-$R_{68}$ are each selected from the group consisting of hydrogen, hydroxy, alkyl and alkylcarboxy.

According to some embodiments of any one of the embodiments of the invention relating to compounds of Formula IV:

the dashed line in Formula IV denotes an unsaturated bond, $R_{52}$ and $R_{53}$ are together a covalent bond which forms a six-membered aromatic carbon ring, and $R_{54}$ and $R_{55}$ are together a covalent bond which forms a six-membered aromatic carbon ring; or the dashed line in Formula IV denotes a saturated bond, and $R_{52}$-$R_{55}$ are each hydrogen.

According to some embodiments of any one of the embodiments of the invention relating to compounds of Formula VI:

A' is selected from the group consisting of —C(=O)—O—; and —NR$_{71}$—C(=O)—;

B' is selected from the group consisting of —NR$_{75}$—C(=O)—; —C(R$_{77}$)—C(=O)—; and C(R$_{77}$)=C(R$_{78}$);

Y'$_1$ and Y'$_2$ are each independently selected from C-Q', C—R$_{79}$ and N, provided that at least one of Y'$_1$ and Y'$_2$ is C-Q';

Y'$_3$ is C—R$_{80}$;

Y'$_4$ is C—R$_{81}$;

$R_{71}$ and $R_{75}$ are each independently hydrogen or alkyl;

$R_{77}$ and $R_{78}$ are each independently selected from hydrogen and alkyl, wherein at least one of $R_{71}$, $R_{77}$ and $R_{78}$ is an alkyl being at least 4 atoms in length;

$R_{79}$ is hydrogen;

$R_{80}$ and $R_{18}$ are each independently selected from hydrogen, alkoxy and hydroxyl, at least one of $R_{80}$ and $R_{18}$ being hydroxyl or alkoxy; and Q' is

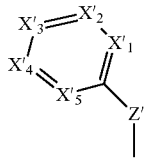

wherein:

Z' is O;

X'$_1$ is C(R$_{82}$);

X'$_2$ is C(R$_{83}$) or N;

X'$_3$ is C(R$_{84}$);

X'$_4$ is C(R$_{85}$) or N; and

X'$_5$ is C(R$_{86}$) or N, provided that at least two of $X_{71}$-$X_{75}$ are not N, $R_{82}$ is selected from hydrogen and alkyl; and $R_{83}$-$R_{86}$ are each independently selected from hydrogen, alkoxy and hydroxyl, at least one of $R_{83}$-$R_{86}$ being hydroxyl or alkoxy.

According to some embodiments of any one of the embodiments of the invention relating to compounds of Formula VI:

A' is C(=O)—O—; and

B' is C(R$_{77}$)=C(R$_{78}$), and wherein $R_{77}$ is the alkyl being at last 4 carbon atoms in length.

According to some embodiments of any one of the embodiments of the invention relating to compounds of Formula VI:

A' is —NR$_{71}$—C(=O)—; and

B' is —NR$_{75}$—C(=O)—, and wherein $R_{71}$ is the alkyl being 4 carbon atoms in length.

According to some embodiments of any one of the embodiments of the invention relating to compounds of Formula VI, each of $X_{71}$-$X_{75}$ is other than N.

According to some embodiments of any one of the embodiments of the invention relating to compounds of Formula VI, at least one of $X_{72}$, $X_{74}$ or $X_{75}$ is N.

According to some embodiments of the invention, the compound is selected from the compounds presented in Table 4 and/or in Table 5.

According to some embodiments of the invention, the compound is selected from the compounds presented in Table 2.

According to some embodiments of the invention, the compound selected from the group consisting of BKT206, BKT211, BKT215 and BKT300 in Table 2, the compound being for use in treating a cancer.

According to some embodiments of any one of the embodiments of the invention relating to inhibiting a kinase, the compound is BKT-300.

According to some embodiments of any one of the embodiments of the invention relating to inhibiting a kinase, the kinase is selected from the group consisting of DYRK3, EPHA8, GRK4, GRK5, MAP4K1, MAP4K2, MAP4K4, MELK, PAK7, SGK2, SRC N1, ACVRL1, BMPR1A, CDC7/DBF4, CDK1/cyclin A2, CDK11, CDK8/cyclin C, CLK4, DAPK2, DURK2, ICK, MAPK10, MLCK, MYLK, NUAK2, STK17A, STK17B, STK38, STK38L, TGFBR2, TTK, DAPK1, PIK3CA and PIK3CD.

According to some embodiments of any one of the embodiments of the invention relating to compounds of Formula VIA:

A' is C(=O)—O—; and

B' is C(R$_{77}$)=C(R$_{78}$), and wherein $R_{77}$ is the alkyl being at last 4 carbon atoms in length.

According to some embodiments of any one of the embodiments of the invention relating to compounds of Formula VIA:

A' is —NR$_{71}$—C(=O)—; and

B' is —NR$_{75}$—C(=O)—, and wherein $R_{71}$ is the alkyl being 4 carbon atoms in length.

According to some embodiments of any one of the embodiments of the invention relating to compounds of Formula VIA, at least one of X'$_2$, X'$_4$ or X'$_5$ is N.

According to some embodiments of any one of the embodiments of the invention relating to compounds of Formula VIA, the compound is selected from the compounds presented in Table 5.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 47A-47C present bar graphs showing the effect of intraperitoneal administration of BKT300 (at 98% purity) on the percentage of CD45-positive cells in the bone marrow of mice injected with $10 \times 10^6$ MV4-11 cancer cells 21 days before administration of BKT300 (FIG. 47A), and data of the FACS analysis showing human MV4-11 cancer cells in the bone marrow of untreated (FIG. 47B) and treated with BKT300 (FIG. 47C) mouse 21 days following transplantation of $10 \times 10^6$ MV4-11 cancer cells.

DESCRIPTION OF SPECIFIC EMBODIMENTS OF THE INVENTION

Figure 1:
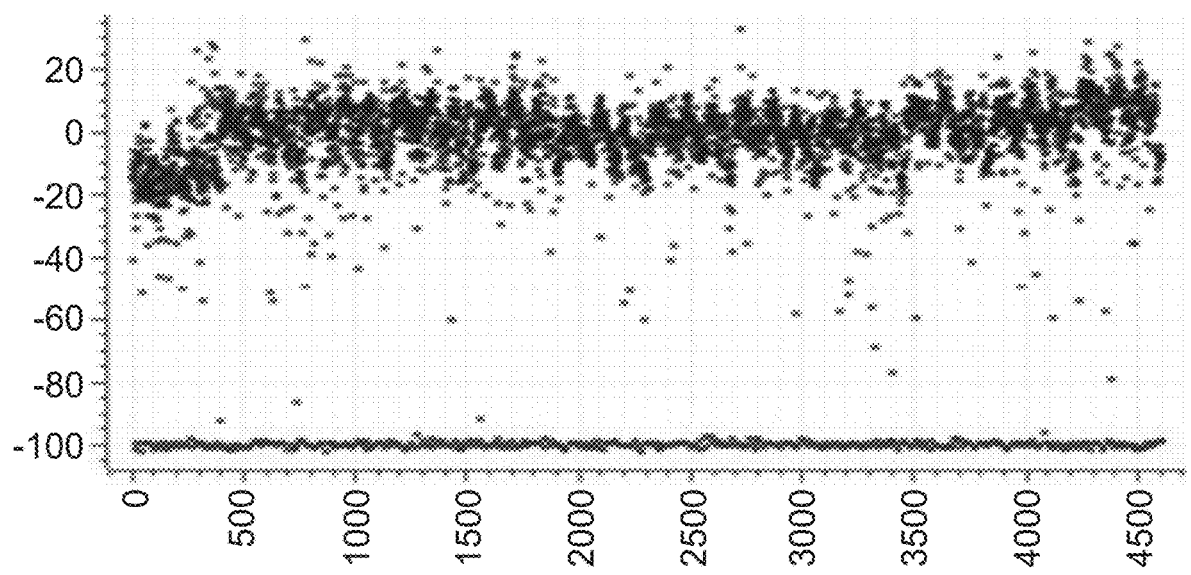
FIG. 1 is a graph showing effects of 3,500 compounds (black dots) on binding of BKT130 to MIP3a, as determined by high-throughput screening, as well as control samples (blue dots) in which MIP3a is absent; x-axis shows sample numbers, whereas y-axis values represent binding, wherein zero represents no effect on binding, and −100 represents absence of binding (full inhibition, or absence of MIP3a).

The present invention, in some embodiments thereof, relates to therapy and more particularly, but not exclusively, to compounds, compositions and methods useful in inhibiting a kinase, in modulating a biological activity of a chemokine, in inhibiting cancel cells, in inhibiting chemokine-dependent cell migration and/or in treating diseases and disorders associated with kinase activity, biological activities of chemokines and/or cell migration, such as cancer and inflammatory diseases and disorders.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In a search for compounds suitable for modulating chemokine activity, and treating conditions associated with the biological activity of chemokines, the present inventors have screened a library of about 3,500 natural compounds for chemokine-binding activity, and then further screened the chemokine-binding molecules for an ability to modulate the effect of individual chemokines on cells, as well as for an ability to affect cancer cells (e.g., by killing cancer cells, inhibiting growth of cancer cells and/or inhibiting chemokine-dependent migration of cancer cells) and/or kill pathogenic cells such as cancer cells.

Using this laborious screening process, the present inventors have uncovered that compounds characterized by certain structural features, as detailed herein, were shown to exhibit an ability to modulate chemokine activity and/or inhibit cancer cells.

Exemplary such compounds, which were identified through the laborious screening process as chemokine-binding small molecules, are presented by their chemical structures in Table 2 in the Examples section herein. Many of said compounds surprisingly exhibits relatively selective inhibition of SDF-1/CXCR4 activity and/or induction of cancer cell death. For example, the present inventors have identified the compound referred to herein as BKT300 (see the Examples section that follows) as a promising modulator of chemokine activity, a selective inhibitor of SDF-1/CXCR4 activity and/or as inducing cancer cell death.

Reference is made to FIGS. 2A-13, which show inhibition of the chemokine MIP3a by exemplary chemokine-binding compounds according to embodiments of the present invention. FIGS. 14A-27 show inhibition by exemplary chemokine-binding compounds of cell migration towards the chemokine SDF-1. FIGS. 28-35 show inhibition by exemplary chemokine-binding compounds of cell migration towards the chemokine MCP-1. FIGS. 3, 4, 6, 7, 9, 14A, 14B, 16, 19, 23, 27-29, 31 and 33 show that some exemplary inhibitors of SDF-1 are relatively selective inhibitors of SDF-1.

Further reference is made to FIGS. 36A-46B, which show that Compounds BKT206, BKT211, BKT215 and BKT300 induce cell death in cancer cells. In addition, FIGS. 47A-47C shows that BKT300 reduces cancer cell numbers in an in vivo mouse model.

The small molecule BKT300 was also screened for its activity on a selected list of human kinases and was shown to inhibit activity of certain kinases (see, Table 3, Example 5, in the Examples section that follows).

Encouraged by the pronounced activity of BKT300, the present inventors have studied the interactions of BKT300 with the binding site of kinases, using computational modeling (see, for example, FIGS. 49-51), and based on the data retrieved in these computational study, have designed small molecules that are structural analogs of BKT300, which maintain the structural features of BKT300 which were considered as attributing to its activity (see, for non-limiting examples, FIGS. 52A-56). The present inventors have further identified small molecules which feature a structural topology similar to BKT300, and which can be useful in inhibiting a kinase activity and/or in treating a disease or disorder in which inhibition of kinase is beneficial. The small molecules described herein are further useful in modulating a biological activity of chemokines and accordingly in treating a disease or disorder that is associated with a biological activity of a chemokine. The small molecules described herein are particularly useful as anti-cancer agents, by inducing cancer cells death (e.g., via apoptotic cell death) and/or effecting cancel cells migration (by inhibiting angiogenesis and/or metastasis), as described in further detail hereinbelow. The small molecules described herein are further useful in treating inflammation (e.g., in treating inflammatory diseases and disorders as described herein). The small molecules described herein are further useful in treating non-cancerous proliferative diseases, as described herein. Embodiments of the present invention therefore generally relate to newly designed small molecules and to uses thereof.

Embodiments of the present invention further relate to a method of identifying a compound (small molecule) usable in any of the uses described herein, which method is also referred to herein as a screening assay or method.

Compounds:

The compounds described in some embodiments of any of the aspects of the present embodiments, and any combination thereof are characterized by a relatively rigid core hydrocarbon moiety, which is preferably cyclic and/or unsaturated, attached directly to one or more small, relatively polar oxygen-containing groups (for example, —C(=O)—, —CH(OH)— or —C(=O)OH). The core hydrocarbon moiety is further attached to a second hydrocarbon moiety having at least 4 carbon atoms, which is preferably relatively non-polar and at least partially aliphatic. The core hydrocarbon moiety may be attached to the second hydrocarbon moiety directly or via one of the abovementioned small, oxygen-containing groups.

The compounds described in some embodiments of any of the aspects of the present embodiments, and any combination thereof are, are collectively represented by Formula I:

W-L$_1$-X-L$_2$-Y—Z             Formula I wherein X in Formula I is a rigid hydrocarbon moiety.

Herein, a "rigid" moiety is a moiety comprising a backbone in which no more than one bond within the backbone (i.e., a bond between two atoms which are each part of the backbone) is a free-to-rotate bond (as defined herein) in which rotation of the free-to-rotate bond affects the relative positions of at least one these moieties, and in which at least one bond within the backbone is not a free-to-rotate bond. For example, rotation of the single bond in a C≡C—C≡C moiety does not affect the relative position of any of the atoms in the moiety, even though it is a free-to-rotate bond (as defined herein).

A "backbone" of X in Formula I is a chain of carbon atoms in which the carbon atom at one end of the chain is attached to W-L$_1$- and the carbon atom at the other end of the chain is attached to -L$_2$-Y—Z.

The phrase "free-to-rotate bond", as used herein, describes a bond that connects two moieties in a compound, the bond capable of rotating around an axis, whereby such a rotation affects the relative positions of these moieties, without requiring simultaneous rotation around the axis of another bond. A free-to-rotate bond includes a single (sigma) bond which has an ability to rotate along its axis, and which is not a bond between two atoms which both form a part of the same ring.

In some embodiments, the rigid moiety comprises one or more unsaturated bonds (which are not free-to-rotate bonds). In some embodiments, the rigid moiety comprises two or more unsaturated bonds which are coplanar.

The rigid core X can be, for example, and unsaturated linear alkylene chain which comprise one or more moeities such as, but not limited to, —C≡C—C≡C—; —CR$_3$=CR$_4$—CR$_5$=CR$_6$—. Alternatively, the rigid core X can be a substituted or unsubstituted bicyclic hydrocarbon moiety, or a substituted or unsubstituted phenylene, as described in more detail hereinafter.

Herein, a moiety (e.g., an X moiety) may be considered "unsubstituted" when attached to a neighboring moiety in a formula described herein (e.g., a W, L$_1$, L$_2$ or Z moiety in Formula I), that is, the moieties described herein are not considered herein to be substituents.

The core moiety represented by X is attached to a relatively polar oxygen-containing group represented by the linking group L$_2$. Alternatively, X is attached to an oxygen-containing group which is a terminal group (e.g., —C(=O)OH) rather than a linking group, in which case, the oxygen-containing group is represented by variable Z in Formula I, and L$_2$ and Y are absent. X is optionally attached to one or more additional relatively polar oxygen-containing groups, represented by the optional linking moiety L$_1$ and/or in one or more substituents of X.

In embodiments wherein L$_2$ is not absent, L$_2$ can be, for example (without limitation), —O—, —C(=O)—, —C(=O)O— (wherein either the carbon atom or oxygen atom may be attached to X), and/or —C(R$_2$)(OH)—. In some embodiments, L$_2$ is absent or is —C(=O)— or —C(R$_2$)(OH)—. In some embodiments, L$_2$ is absent or is —C(=O)—.

In some embodiments, L$_2$ is absent, Y is absent and Z is a terminal polar oxygen-containing group (e.g., as described herein for L$_2$) which is attached directly to X. In some of these embodiments, Z is —C(=O)OH.

L$_1$ in Formula I can be absent or an optional oxygen-containing linking group, as described herein for L$_2$. In embodiments where L$_1$ is not absent, it can be, for example, —O—, —C(=O)—, —C(=O)O— (wherein either the carbon atom or oxygen atom may be attached to X), and/or —CR$_1$(OH)—. In some embodiments, L$_1$ is absent or is —O—, —C(=O)—, and/or —CR$_1$(OH)—. In embodiments wherein L$_1$ is absent, W is attached directly to X.

The abovementioned substituents R$_1$-R$_6$ can be, for example, hydrogen, alkyl, alkenyl, alkynyl and/or cycloalkyl.

In some embodiments of any of the embodiments described herein relating to Formula I, R$_1$ is hydrogen.

In some embodiments of any of the embodiments described herein relating to Formula I, R$_2$ is hydrogen. In some such embodiments, R$_1$ and R$_2$ are each hydrogen.

W in Formula I is a hydrocarbon moiety having from 4 to 20 carbon atoms, which is attached to X directly or via the L$_1$ linking group. The hydrocarbon moiety optionally comprises one or more hydroxy substituents and/or oxygen atoms between two carbon atoms (e.g., interrupting a hydrocarbon chain), wherein a ratio of oxygen atoms to carbon atoms in W is no more than 1:4 (oxygen atoms:carbon atoms). In some embodiments, W comprises from 5 to 20 carbon atoms. In some embodiments, W comprises from 5 to 15 carbon atoms.

As used herein throughout, the term "hydrocarbon" describes an organic moiety that includes, as its basic skeleton, a chain of carbon atoms, substituted mainly or entirely by hydrogen atoms. The hydrocarbon can be saturated or non-saturated, be comprised of aliphatic, alicyclic or aromatic moieties, and can optionally (unless indicated otherwise) be substituted by one or more substituents (other than hydrogen). The hydrocarbon moiety is optionally interrupted by one or more oxygen atoms (unless indicated otherwise). When substituted, the substituent group can be, for example, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, thiocarbonyl, urea, thiourea, O-carbamyl, N-carbamyl, O-thiocarbamyl, N-thiocarbamyl, C-amido, N-amido, C-carboxy, O-carboxy, sulfonamido, and amine, as these terms are defined herein.

The W moiety is attached to X or L$_1$ via a covalent bond, or alternatively, W comprises a cyclic (e.g., substituted or nonsusbstituted cycloalkyl or aryl moiety) which is fused to a ring of the X moiety (i.e., to a phenylene ring or one or both rings of a bicyclic hydrocarbon moiety, according to any of the respective embodiments described herein), and L$_1$ is absent. In some such embodiments, W comprises a substituted or unsubstituted cycloalkyl group fused to X. In some such embodiments, X is a saturated or unsaturated aliphatic bicyclic hydrocarbon moiety (according to any of the respective embodiments described herein). Compound BKT216 is an example of a compound comprising a cycloalkyl group of the W moiety fused to a ring of an X moiety (which is a saturated aliphatic bicyclic moiety).

In some embodiments of any of the embodiments described herein relating to Formula I, W is attached to L$_1$ or X via a covalent bond, that is, W is not fused to X. In some such embodiments, $L_1$ is absent and W is attached to X directly via a covalent bond.

Without being bound by any particular theory, it is believed that the moiety denoted as W in Formula I interacts with a substrate (e.g., a chemokine) via hydrophobic interactions. Accordingly, in some embodiments, W is a hydrophobic moiety, and in some such embodiments, the number of oxygen moieties moiety is such that do not affect its capability of participating in hydrophobic interactions.

In some embodiments of any of the embodiments described herein relating to Formula I, a ratio of oxygen atoms to carbon atoms in the moiety denoted as W is no more than 1:5 (oxygen atoms:carbon atoms). Thus, for example, when W contains 4 carbon atoms, no oxygen atoms are present in W. In some such embodiments, the ratio is no more than 1:6. In some such embodiments, the ratio is no more than 1:7. In some such embodiments, the ratio is no more than 1:8. In some such embodiments, the ratio is no more than 1:9. In some such embodiments, the ratio is no more than 1:10. In some such embodiments, the ratio is no more than 1:12. In some such embodiments, W is devoid of oxygen atoms.

In some embodiments of any of the embodiments described herein relating to Formula I, an oxygen atom between two carbon atoms in W is within a furan heteroaryl ring. In some such embodiments, each oxygen atom in W is within a hydroxy or furanyl (optionally unsubstituted furanyl) group. In some such embodiments, each oxygen atom in W is within a furan ring (e.g., unsubstituted furanyl). It is to be appreciated that furan groups are relatively hydrophobic in comparison to other oxygen containing groups.

In some embodiments of any of the embodiments described herein relating to Formula I, W comprises at least one substituted or unsubstituted alkyl or alkenyl group. In some such embodiments, the substituted or unsubstituted alkyl or alkenyl comprises at least 4 carbon atoms (including any carbon atoms in a substituent thereof). In some embodiments, the substituted or unsubstituted alkyl or alkenyl comprises at least 5 carbon atoms (including any carbon atoms in a substituent thereof).

Examples of hydrocarbon moieties comprising at least one alkyl or alkenyl group include, without limitation, alkyl or alkenyl, optionally substituted by hydroxy, cycloalkyl, aryl (e.g., phenyl) and/or heteroaryl (e.g., furanyl); cycloalkyl, aryl (e.g., phenyl) or heteroaryl (e.g., furanyl) substituted by one or more alkyl or alkenyl groups (e.g., alkyl or alkenyl groups which comprise at least 4 carbon atoms, and optionally at least 5 carbon atoms), and being optionally further substituted (e.g., by one or more hydroxy groups), as these terms are defined herein.

Without being bound by any particular theory, it is believed that an alkyl or alkenyl group in the W hydrocarbon moiety provides the moiety with flexibility (e.g., multiple possible configurations, as a result of a presence of one or more free-to-rotate bonds, as defined herein) which enhances interactions thereof (e.g., hydrophobic interactions), especially when the alkyl or alkenyl is of a substantial size (e.g., at least 4 or 5 carbon atoms, as described herein).

In some embodiments of any of the embodiments described herein wherein W is alkyl or alkenyl, the alkyl or alkenyl is an unsubstituted alkyl or alkenyl at least 9 carbon atoms in length. In some embodiments, the alkyl or alkenyl is at least 10 carbon atoms in length. In some embodiments, the alkyl or alkenyl is at least 12 carbon atoms in length.

X optionally comprises one or more substituents (in addition to the W-$L_1$- and —$L_2$-Y—Z moieties described herein) which comprise a hydrocarbon moiety. Such a substituent is optionally identical to the W-$L_1$-moiety, according to any of the embodiments described herein. In some embodiments, X comprises 0 or 1 substituent which is identical to the W-$L_1$-moiety.

Y in Formula I is absent or is an aliphatic hydrocarbon moiety being from 1 to 8 atoms in length, which can be substituted or unsubstituted, or alternatively, Y attaches to X and/or to Z to form one or two five- or six-membered cycloalkyl or heteroalicyclic rings.

In embodiments wherein Y forms a heteroalicyclic ring, at least one ring atom in the heteroalicyclic rings is an oxygen atom. In some such embodiments, one ring atom (and no more) in the heteroalicyclic ring is an oxygen atom, such that the ring is a pyran ring or derivative thereof.

In embodiments wherein Y is absent, $L_2$ is attached directly to Z, or $L_2$ is absent and Z is —C(=O)OH (a terminal group) attached directly to X.

In some embodiments of any of the embodiments described herein wherein Y is an aliphatic hydrocarbon, the aliphatic hydrocarbon is non-substituted. In some embodiments, the aliphatic hydrocarbon is a substituted or unsubstituted linear hydrocarbon. In some embodiments, the aliphatic hydrocarbon is am unsubstituted linear hydrocarbon. In some embodiments, the aliphatic hydrocarbon is saturated. In some embodiments, the aliphatic hydrocarbon is saturated and non-substituted. In some embodiments, the aliphatic hydrocarbon is a saturated linear hydrocarbon. In some embodiments, the aliphatic hydrocarbon is an unsubstituted and linear saturated hydrocarbon.

In some embodiments of any of the embodiments described herein wherein Y is an aliphatic hydrocarbon, the aliphatic hydrocarbon is from 2 to 7 carbon atoms in length. In some embodiments, the aliphatic hydrocarbon is from 3 to 7 carbon atoms in length.

In some embodiments of any of the embodiments described herein wherein Y is an aliphatic hydrocarbon, the aliphatic hydrocarbon is from 1 to 3 carbon atoms in length.

Herein, the length of an aliphatic hydrocarbon refers to the number of carbon atoms in a hydrocarbon chain separating $L_2$ and Z, or if Z is absent, the number of carbon atoms in the longest hydrocarbon chain in Y beginning with (and including) a carbon atom attached to $L_2$.

Herein, a "linear" hydrocarbon is a hydrocarbon in which all of the carbon atoms therein are within a hydrocarbon chain, wherein in the context of Y, the hydrocarbon chain begins a carbon atom attached to $L_2$, and ends in a carbon atom attached to Z, or if Z is absent, ends in a terminal carbon atom (i.e., a carbon atom attached to only one other carbon atom). The length, in carbon atoms, of a linear hydrocarbon equals the number of carbon atoms in the linear hydrocarbon.

In some embodiments of any of the embodiments described herein wherein Y attaches to X and/or to Z to form one or two five- or six-membered cycloalkyl or heteroalicyclic rings, Y can be, for example, —CH=$CR_7$-A- or —$CH_2$—$CHR_8$—B—, wherein A and B are each independently absent or an oxygen atom attached to X or to an $L_2$ group which is —C(=O)— or —C(=O)O— (wherein A or B is attached to the carbon atom of —C(=O)O—), optionally —C(=O)—; and $R_7$ and $R_8$ are each independently hydrogen, alkyl and/or a Z moiety according to any of the respective embodiments described herein. In some such embodiments, the Z moiety is a phenyl substituted by one or more hydroxy groups, according to any of the respective embodiments described herein. In some such embodiments, the alkyl represented by $R_7$ and/or $R_8$ comprises from 1 to 10 carbon atoms, and in some such embodiments, from 3 to 7 carbon atoms.

Z in Formula I is an optional moiety comprising a polar group, such as, but not limited to, —C(=O)OH and aryl substituted by at least one hydroxy group, or alternatively, Z is absent.

In some embodiments of any of the embodiments described herein wherein Z is aryl, the aryl is hydroxyphenyl or dihydroxyphenyl. In some embodiments, the hydroxyphenyl is 4-hydroxyphenyl and/or the dihydroxyphenyl is 3,4-dihydroxyphenyl.

In some embodiments of any of the embodiments described herein wherein Z is —C(=O)OH, Y is absent or is an aliphatic hydrocarbon moiety from 1 to 8 atoms in length, according to any of the respective embodiments described herein.

In some embodiments of any of the embodiments described herein wherein Z is —C(=O)OH, Y is absent and $L_2$ is absent or is —C($R_2$)(OH)—. In some such embodiments, X is cyclic, being, for example, a substituted or unsubstituted bicyclic hydrocarbon moiety, and/or substituted or unsubstituted phenylene, according to any of the respective embodiments described herein. In some such embodiments, $L_2$ is absent.

In some embodiments of any of the embodiments described herein wherein Z is —C(=O)OH and Y is an aliphatic hydrocarbon moiety, the aliphatic hydrocarbon moiety is from 2 to 7 carbon atoms in length. In some such embodiments, the aliphatic hydrocarbon moiety is from 3 to 7 carbon atoms in length. In some such embodiments, the aliphatic hydrocabon moiety is a saturated hydrocarbon moiety. In some embodiments, the aliphatic hydrocabon moiety is a linear, unsubstituted hydrocarbon moiety. In some embodiments, the aliphatic hydrocabon moiety is a linear and unsubstituted saturated hydrocarbon moiety.

In some embodiments of any of the embodiment described herein wherein Y is an aliphatic hydrocarbon moiety, $L_2$ is —C(=O)—.

In some embodiments of any of the embodiments described herein wherein Z is —C(=O)OH, and Y is absent or is an aliphatic hydrocarbon moiety, the compound is a compound having the general formula III:

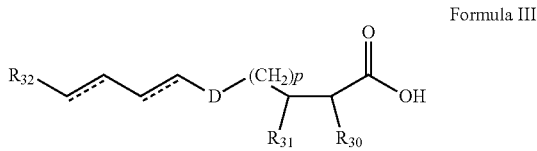

Formula III wherein:

D is $CH_2$ or —C(=O)—;

the dashed lines each denote a saturated or unsaturated bond;

p is an integer in a range of from 0 to 6;

$R_{30}$ and $R_{31}$ are each hydrogen or $R_{30}$ and $R_{31}$ to together form an aromatic ring substituted by at least one hydroxy group, wherein when $R_{30}$ and $R_{31}$ are each hydrogen, D is —C(=O)— and each of the dashed lines denotes an unsaturated bond; and $R_{32}$ is an alkyl, alkenyl and/or acyl, each being from 2 to 12 carbon atoms in length.

In some embodiments of any of the embodiments relating to Formula III, the compound is from 16 to 20 carbon atoms in length, e.g., such that the sum of the value of p+8, and the length in carbon atoms of $R_{32}$ is in a range of from 16 to 20. In some embodiments, the compound is from 17 to 19 carbon atoms in length. In some embodiments, the compound is 18 carbon atoms in length.

In some embodiments of any of the embodiments relating to Formula III, $R_{32}$ is an unsubstituted alkyl, alkenyl or acyl. In some embodiments $R_{32}$ is an unsubstituted alkyl or acyl.

In some embodiments of any of the embodiments relating to Formula III, $R_{32}$ is a linear alkyl, alkenyl or acyl. In some such embodiments $R_{32}$ is linear and unsubstituted alkyl, alkenyl or acyl. Compounds BKT205 and BKT209 are examples of compounds in which $R_{32}$ is linear and unsubstituted alkyl or acyl.

In some embodiments of any of the embodiments, an aromatic ring formed by $R_{30}$ and $R_{31}$ is a phenylene substituted by at least one hydroxy group. In some such embodiments, the phenylene is substituted only by one hydroxy group. In some such embodiments, the hydroxy group is at an ortho position with respect to the —C(=O)OH group.

In some embodiments of any of the embodiments wherein $R_{30}$ and $R_{31}$ together form an aromatic ring, D is $CH_2$. In some such embodiments, the aromatic ring is phenylene, according to any of the respective embodiments described herein.

Compound BKT206 is an example of a compound in which D is $CH_2$, and $R_{30}$ and $R_{31}$ together form a phenylene substituted only by a hydroxy group at an ortho position with respect to the —C(=O)OH group.

In some embodiments of any of the embodiment described herein wherein Y is an aliphatic hydrocarbon moiety, X is —C≡C—C≡C— or —$CR_3$=$CR_4$—$CR_5$=$CR_6$—, according to any of the respective embodiments described herein. In some embodiments, X is —$CR_3$=$CR_4$—$CR_5$=$CR_6$—. In some embodiments, $L_2$ is —C(=O)—. In some embodiments, $L_2$ is —C(=O)— and X is —$CR_3$=$CR_4$—$CR_5$=$CR_6$—.

Returning to the X moiety of Formula I, in some embodiments of any one of the embodiments described herein relating to Formula I, X is —$CR_3$=$CR_4$—$CR_5$=$CR_6$—, a substituted or unsubstituted bicyclic hydrocarbon moiety, and/or a substituted or unsubstituted phenylene, according to any of the respective embodiments described herein.

In some embodiments of any one of the embodiments described herein relating to Formula I, X in Formula I is a substituted or unsubstituted bicyclic hydrocarbon moiety, and/or a substituted or unsubstituted phenylene, according to any of the respective embodiments described herein.

In some embodiments of any one of the embodiments described herein relating to Formula I, X in Formula I is —$CR_3$=$CR_4$—$CR_5$=$CR_6$—, and/or a substituted or unsubstituted phenylene, according to any of the respective embodiments described herein.

In some embodiments of any one of the embodiments described herein relating to Formula I, X in Formula I is —C≡C—C≡C— and/or —$CR_3$=$CR_4$—$CR_5$=$CR_6$—, according to any of the respective embodiments described herein.

In some embodiments of any of the embodiments described herein wherein X is —C≡C—C≡C—, $L_2$ is —C($R_2$)(OH)—. In some such embodiments, $L_2$ is —CH(OH)—.

In some embodiments of any of the embodiments wherein X is —C≡C—C≡C—, $L_1$ is —$CR_1$(OH)— (e.g., —CH(OH)—). In some such embodiments, $L_1$ is —$CR_1$(OH)— and $L_2$ is —C($R_2$)(OH)—. In some such embodiments, $L_1$ and $L_2$ are each —CH(OH)—.

In some embodiments of any of the embodiments wherein X is —C≡C—C≡C—, Z is absent.

In some embodiments of any of the embodiments wherein X is —C≡C—C≡C—, Y is an aliphatic hydrocarbon moiety. In some such embodiments Y is an unsaturated aliphatic hydrocarbon moiety (e.g., alkenyl). In some such embodiments, Y is CH=CH$_2$.

In some embodiments of any of the embodiments described herein wherein X is —CR$_3$=CR$_4$—CR$_5$=CR$_6$—, L$_2$ is —C(=O)—.

In some embodiments of any of the embodiments wherein X is —CR$_3$=CR$_4$—CR$_5$=CR$_6$—, L$_1$ is —C(=O)— or absent. In some such embodiments, L$_1$ is —C(=O)— or absent and L$_2$ is —C(=O)—.

In some embodiments of any of the embodiments wherein X is —CR$_3$=CR$_4$—CR$_5$=CR$_6$—, Z is —C(=O)OH.

In some embodiments of any of the embodiments wherein X is —CR$_3$=CR$_4$—CR$_5$=CR$_6$—, Y is an aliphatic hydrocarbon moiety. In some such embodiments Y is a saturated hydrocarbon moiety. In some such embodiments, Y is an unsubstituted saturated hydrocarbon.

In some embodiments of any of the embodiments wherein X is —CR$_3$=CR$_4$—CR$_5$=CR$_6$—, R$_3$-R$_6$ are each hydrogen.

In some embodiments, X is a bicyclic hydrocarbon moiety.

Herein, the phrase "bicyclic hydrocarbon moiety" refers to a hydrocarbon moiety comprising a pair of carbon atoms covalently bound to each other, wherein the pair of carbon atoms is shared by two fused hydrocarbon rings, each of which may independently be cycloalkyl or aryl.

In some embodiments of any of the embodiments wherein X is a bicyclic moiety, the bicyclic moiety is an aromatic bicyclic moiety, comprising two aryl rings, for example, a substituted or unsubstituted naphthalenylene moiety.

In some embodiments of any of the embodiments wherein X is a bicyclic moiety, the bicyclic moiety is aliphatic (i.e., alicyclic), that is, both hydrocarbon rings are cycloalkyl.

In some embodiments of any of the embodiments wherein X is a bicyclic moiety, at least one of the two fused hydrocarbon rings is a six-membered ring.

In some embodiments, the two fused hydrocarbon rings are both six-membered ring. That is, X is a substituted or unsubstituted decalin moiety, or an unsaturated derivative thereof (a dehydrogenated decalin moiety).

In some embodiments of any of the embodiments wherein X is a bicyclic moiety, the bicyclic moiety is unsaturated, that is, at least two ring carbons are attached via an unsaturated bond. In some such embodiments, the bicyclic moiety is a substituted or unsubstituted dehydrogenated decalin. In some such embodiments, the dehydrogenated decalin is a substituted or unsubstituted 1,2,3,4,5,6,7,8-octahydronaphthalene moiety, wherein the unsaturated carbon-carbon bond is the bond shared by the two fused rings.

In some embodiments of any of the embodiments wherein X is a substituted bicyclic moiety, the substituent(s) of the bicyclic moiety is alkyl. In some embodiments, the alkyl is C$_{1-4}$ alkyl. In some embodiments, the substituent(s) of the bicyclic moiety is methyl.

In some embodiments of any of the embodiments wherein X is a substituted bicyclic moiety, L$_2$ or Z is attached to a carbon atom in X which is shared by two fused rings or to a carbon atom in X which is directly attached to a carbon atom shared by two fused rings.

In some embodiments of any of the embodiments wherein X is a substituted bicyclic moiety, W or L$_1$ is attached to a carbon atom in X which is shared by two fused rings or to a carbon atom in X which is directly attached to a carbon atom shared by two fused rings.

Without being bound by any particular theory, it is believed that a bicyclic structure can provide rigidity to the X moiety, particularly to the portion of the bicyclic structure represented by the carbon atoms shared by two fused rings and carbon atoms attached thereto.

In some embodiments, X is a phenylene moiety.

Herein, the term "phenylene" refers to a substituted or unsubstituted six-membered aromatic carbon ring having at least two valence bonds (e.g., one bond to L$_1$ or W, and one bond to L$_2$ or Z, in the context of the X moiety of Formula I), and optionally more than two valence bonds (e.g., one bond to L$_1$ or W, and one bond to L$_2$, and one bond to Y, in the context of the X moiety of Formula I).

In some embodiments of any of the embodiments wherein X is a substituted phenylene, the phenylene is substituted by at least one substituent, optionally comprising one or more hydroxy and/or a saccharide moieties. In some such embodiments, X is substituted by one or two such substituents. In some embodiments, the saccharide moiety is a monosaccharide moiety. In some embodiments, the saccharide moiety is a hexose moiety. In some embodiments, the saccharide moiety is a glucose moiety.

The saccharide moiety may optionally be bound to the phenylene ring, for example, via a carbon atom in the saccharide moiety (e.g., via a C-glycosidic bond), via an oxygen atom in the saccharide moiety (e.g., via an O-glycosidic bond), via a sulfur atom in the saccharide moiety (e.g., via an S-glycosidic bond) or via a nitrogen atom in the saccharide moiety (e.g., via an N-glycosidic bond). In some embodiments of any of the respective embodiments described herein, the phenylene ring is attached to an oxygen atom of the saccharide moiety. In some embodiments, the saccharide moiety and phenylene are attached via an O-glycosidic bond.

Herein, the term "glycosidic bond" refers to a bond with an anomeric carbon of a saccharide moiety, optionally via a heteroatom (e.g., oxygen atom) attached to the anomeric carbon.

In some embodiments of any of the embodiments wherein X is a substituted phenylene, the substitution is in a form of a cycloalkyl, heteroalicyclic, aryl or heteroaryl ring fused to the phenylene, each being substituted or unsubstituted. It is to be understood that such a ring is not a ring formed by a Y moiety described herein (as the Y moiety is not considered herein to be a substituent). In some such embodiments, the ring is a heteroalicyclic or heteroaryl ring (optionally unsubstituted) comprising an oxygen atom attached to a carbon atom of the phenylene ring. In some such embodiments, the ring is a furan ring (optionally unsubstituted) fused to the phenylene to form a benzofuran moiety. Compound BKT208 is an example of a compound in which X is such a benzofuran moiety.

In some embodiments of any of the embodiments wherein X is phenylene, Y attaches to X to form a six-membered ring wherein at least one ring atom is an oxygen atom, according to any of the respective embodiments described herein. In some such embodiments, no more than one ring atom is an oxygen atom. In some such embodiments, the ring is substituted or unsubstituted pyrone ring (e.g., a 2-pyrone ring or 4-pyrone ring wherein L$_2$ is —C(=O)— and Y is —CH=CHR$_7$—O—, or a 2-pyrone wherein L$_2$ is —C(=O)O— and Y is —CH=CHR$_7$—) or a dihydropyrone ring (e.g., wherein L$_2$ is —C(=O)— and Y is —CH$_2$=CHR$_8$—O—, or L$_2$ is —C(=O)O— and Y is —CH$_2$=CHR$_8$—).

According to an aspect of embodiments of the invention, there is provided a compound having the general formula II:

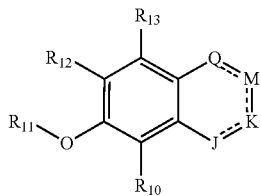

Formula II for use in modulating a biological activity of a chemokine, for use in inhibiting SDF-1 and/or CXCR4 and/or in treating a cancer, an inflammation and/or a non-cancerous hyperproliferative disorder, according to any of the respective embodiments described herein, wherein:

each of the dashed lines independently denotes a saturated or unsaturated bond;

J is —O— (when the dashed line between J and K denotes a saturated bond, and J is thus divalent) or —$CR_{14}$= (when the dashed line between J and K denotes an unsaturated bond, and J is trivalent);

K is —$CR_{15}$= (when K is trivalent), or is —$CR_{16}R_{17}$— or —C(=O)— (when K is divalent);

M is —$CR_{18}$= (when M is trivalent), or is —$CR_{19}R_{20}$— or —C(=O)— (when K is divalent);

Q is —C(=O)— (when the dashed line between Q and M denotes a saturated bond, and Q is thus divalent) or —$CR_{21}$= (when the dashed line between Q and M denotes an unsaturated bond, and Q is thus trivalent);

$R_{10}$, $R_{12}$ and $R_{13}$ are each independently hydrogen, hydroxy, alkyl, alkenyl, alkynyl, cycloalkyl, alkoxy and/or aryloxy;

$R_{11}$ is hydrogen, alkyl, alkenyl, alkynyl, cycloalkyl or heteroalicyclic, or alternatively, $R_{11}$ and $R_{12}$ together form a five- or six-membered heteroaryl or heteroalicyclic ring;

$R_{14}$-$R_{21}$ are each independently hydrogen, alkyl, alkenyl, alkynyl, cycloalkyl and/or aryl;

and at least one of K and Q is —C(=O)—, and at least one of J and M is —O—.

Whether the dashed line denotes a saturated or unsaturated bond will be clear to the skilled person based on the valences of J, K, M and Q. For example, the dashed line linking J and K denotes an unsaturated bond only if J is $CR_{14}$ and K is $CR_{15}$; the dashed line linking K and M denotes an unsaturated bond only if K is $CR_{15}$ and M is $CR_{18}$; and the dashed line linking M and Q denotes an unsaturated bond only if M is $CR_{18}$ and Q is $CR_{21}$.

In some embodiments of any of the embodiments described herein with respect to Formula II, the compound of Formula II is a compound of Formula I, as described herein, wherein X is the phenylene ring attached to $R_{10}$, $R_{12}$ and $R_{13}$; at least one of $R_{10}$-$R_{13}$ is a W moiety (as defined according to any of the respective embodiments described herein); Q is —C(=O)—, corresponding to $L_2$, and M, K and J together correspond to Y (optionally further including Z), or alternatively, J and K together are —C(=O)O—, corresponding to $L_2$, and M and Q together correspond to Y (optionally further including Z).

In some embodiments of any of the embodiments described herein with respect to Formula II, no more than one of K and Q is —C(=O)—.

In some embodiments of any of the embodiments described herein with respect to Formula II, no more than one of J and M is —O—. In some such embodiments, one of K and Q is —C(=O)— and one of J and M is —O—, e.g., such that the ring formed by J, K, M and Q is a pyrone or dihydropyrone ring.

In some embodiments of any of the embodiments described herein with respect to Formula II, $R_{17}$-$R_{21}$ are each hydrogen.

In some embodiments of any of the embodiments described herein with respect to Formula II, $R_{10}$ and $R_{12}$ are each independently hydrogen, alkyl and/or alkenyl. In some embodiments, the alkyl and alkenyl are unsubstituted. In some embodiments, the alkyl and alkenyl have up to 6 carbon atoms (i.e., the alkyl has from 1 to 6 carbon atoms and the alkenyl has from 2 to 6 carbon atoms). In some embodiments, the alkyl and alkenyl have from 4 to 6 carbon atoms. Isoprenyl (3-methyl 2-butenyl) is an exemplary alkenyl group. Compound BKT201 is an example of a compound wherein $R_{10}$ and $R_{12}$ are hydrogen and/or isoprenyl.

In some embodiments of any of the embodiments described herein with respect to Formula II, $R_{10}$ and $R_{12}$ are alkyl and/or alkenyl, having up to 3 carbon atoms (i.e., the alkyl has from 1 to 3 carbon atoms and the alkenyl has 2 or 3 carbon atoms). In some such embodiments, the alkyl is methyl. Compound BKT204 is an example of a compound, in which $R_{10}$ and $R_{12}$ are each methyl.

In some embodiments of any of the embodiments described herein with respect to Formula II, J is —O— or —CH=. In some such embodiments, J is —O—.

In some embodiments of any of the embodiments described herein with respect to Formula II, J is —O— and K is —$CR_{16}R_{17}$—.

In some embodiments of any of the embodiments described herein with respect to Formula II, $R_{16}$ is alkyl or phenyl, each being substituted or unsubstituted. In some embodiments, the alkyl is unsubstituted (e.g., pentyl). In some embodiments, the phenyl is substituted by one or more hydroxy groups. In some such embodiments, the phenyl is hydroxyphenyl (e.g., 3, hydroxyphenyl) or dihydroxyphenyl (e.g., 3,4-dihydroxyphenyl).

In some embodiments of any of the embodiments described herein with respect to Formula II, Q is —C(=O)—. In some such embodiments, J is —O— or —CH=, optionally —O—. In some such embodiments, K is —$CR_{16}R_{17}$— wherein $R_{16}$ is alkyl or phenyl, each being substituted or unsubstituted. Compounds BKT201, BKT204 and BKT300 are examples of compounds in which Q is —C(=O)—.

In some embodiments of any of the embodiments described in which Q is —C(=O)—, $R_{11}$ is hydrogen or glucosyl. Compounds BKT204 and BKT300 are examples of compounds in which Q is —C(=O)— and $R_{11}$ is hydrogen. Compound BKT201 is an example of a compound in which $R_{11}$ is glucosyl.

In some embodiments of any of the embodiments described herein with respect to Formula II, M is —$CH_2$—. In some such embodiments, Q is —C(=O)—. In some such embodiments, J is —O—. In some such embodiments, Q is —C(=O)— and J is —O—.

In some embodiments of any of the embodiments described herein with respect to Formula II, $R_{13}$ is —OH, alkoxy or aryloxy (optionally —OH). In some such embodiments, Q is —C(=O)— and J is —O—. In some such embodiments, M is —$CH_2$—. In some such embodiments, Q is —C(=O)—, J is —O— and M is —$CH_2$—. Compounds BKT201 and BKT204 are examples of compounds in which M is $CH_2$, Q is —C(=O)— and $R_{13}$ is —OH.

In some embodiments of any of the embodiments described herein with respect to Formula II, M is —O—. In some such embodiments, Q is —C(=O)—. In some such embodiments, J is —CH=. In some such embodiments, Q is —C(=O)— and J is —CH=. Compound BKT300 is an example of a compound in which M is —O—, Q is —C(=O)— and J is —CH=.

In some embodiments of any of the embodiments described herein with respect to Formula II, K is —C(=O)—.

In some embodiments of any of the embodiments described herein with respect to Formula II, M and Q are linked via an unsaturated bond. In some such embodiments, M and Q are each —CH=. In some such embodiments, K is —C(=O)—. In some such embodiments, K is —C(=O)— and M and Q are each —CH=.

In some embodiments of any of the embodiments described herein with respect to Formula II, $R_{13}$ is hydrogen. In some such embodiments, K is —C(=O)— and J is —O. In some such embodiments, M and Q are each is —CH=. In some such embodiments, K is —C(=O)—, J is —O— and M and Q are each is —CH=. Compounds BKT202, BKT208 and BKT215 are examples of compounds in which $R_{13}$ is hydrogen, K is —C(=O)—, J is —O— and M and Q are each —CH=.

In some embodiments of any of the embodiments described herein wherein K is —C(=O)— and J is —O—, $R_{10}$ and/or $R_{12}$ is hydrogen. In some such embodiments, both $R_{10}$ and $R_{12}$ are hydrogen.

In some embodiments of any of the embodiments described herein wherein K is —C(=O)— and J is —O—, $R_{11}$ is substituted or unsubstituted alkyl, alkenyl or cycloalkyl, each having from 4 to 20 carbon atoms, optionally from 5 to 20 carbon atoms. In some such embodiments, $R_{10}$ and/or $R_{12}$ is hydrogen. In some such embodiments, both $R_{10}$ and $R_{12}$ are hydrogen. In some such embodiments, $R_{11}$ is substituted or unsubstituted alkyl or alkenyl (e.g., as in Compounds BKT202 and BKT215).

In some embodiments of any of the embodiments described herein wherein K is —C(=O)— and J is —O—, $R_1$ and $R_{12}$ together form a furan ring. Compound BKT208 is an example of such a compound.

According to an aspect of some embodiments of the present invention, there is provided a compound which is an anthracene dione derivative having a general formula which is Formula IV (which comprises two anthracene moieties):

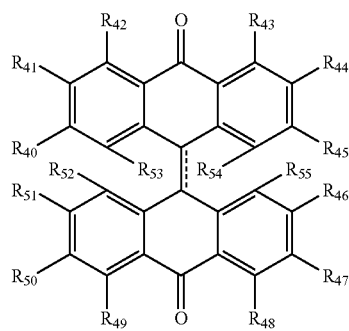

Formula IV or Formula V (which comprises one anthracene moiety):

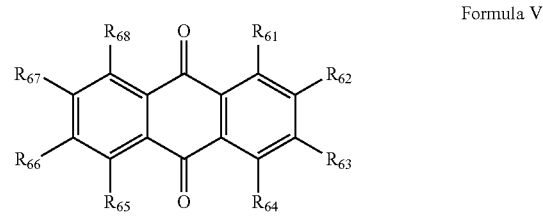

Formula V wherein:

$R_{40}$-$R_{51}$ and $R_{61}$-$R_{68}$ are each hydrogen, hydroxy, alkyl, C-carboxy and/or a saccharide moiety;

$R_{52}$-$R_{55}$ are hydrogen, or alternatively, $R_{52}$ and $R_{53}$, and/or $R_{54}$ and $R_{55}$, are together a covalent bond which forms a six-membered carbon ring; and the dashed line denotes a saturated or unsaturated bond.

It is to be appreciated that $R_{61}$-$R_{63}$ and $R_{66}$-$R_{68}$ in Formula V correspond respectively to $R_{43}$-$R_{45}$ and $R_{40}$-$R_{42}$ and/or to $R_{49}$-$R_{51}$ and $R_{46}$-$R_{48}$ in Formula IV.

In some embodiments of any of the embodiments relating to Formulas IV and V, $R_{40}$-$R_{51}$ and $R_{61}$-$R_{68}$ are each hydrogen, hydroxy, alkyl and/or alkylcarboxy.

In some embodiments of any of the embodiments relating to Formulas IV and V, the alkyl is methyl and/or the C-carboxy is methylcarboxy (i.e., $CH_3$—O—C(=O)—).

In some embodiments of any of the embodiments relating to Formulas IV and V, $R_{41}$, $R_{44}$, $R_{47}$, $R_{50}$, $R_{61}$-$R_{63}$ and $R_{68}$ are each hydrogen.

In some embodiments of any of the embodiments relating to Formula IV, the dashed line denotes an unsaturated bond, $R_{52}$ and $R_{53}$ are together a covalent bond which forms a six-membered aromatic carbon ring, and $R_{54}$ and $R_{55}$ are together a covalent bond which forms a six-membered aromatic carbon ring. Compound BKT203 is an example of such a compound.

In some embodiments of any of the embodiments relating to Formula IV, the dashed line denotes a saturated bond, and $R_{52}$-$R_{55}$ are each hydrogen. Compound BKT210 is an example of such a compound.

According to an aspect of some embodiments of the present invention, there are provided compounds, which are collectively represented by Formula VI:

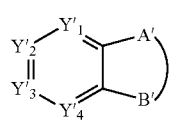

Formula VI wherein:

A' is selected from the group consisting of —C(=O)—O—; —NR$_{71}$—C(=O)—; —C(R$_{72}$)=N—; —C(R$_{72}$)=N—; and —C(R$_{73}$)=C(R$_{74}$)—;

B is selected from the group consisting of NR$_{75}$—C(=O)—; C(R$_{76}$)=N—; —C(R$_{76}$)=N—; —C(R$_{77}$)—C(=O)—; and —C(R$_{77}$)=C(R$_{78}$)—;

Y'$_1$ and Y'$_2$ are each independently selected from C-Q', C—R$_{79}$ and N, provided that at least one of Y'$_1$ and Y'$_2$ is C-Q';

Y'$_3$ is selected from N and C—R$_{80}$;

Y'$_4$ is selected from N and C—R$_{81}$;

$R_{71}$ and $R_{75}$ are each independently hydrogen or alkyl;

$R_{72}$-$R_{74}$ are each independently selected from hydrogen, alkyl, alkyne, hydroxy, amine, alkoxy, aryloxy, thioalkoxy, thioaryloxy, carbonyl and carboxylate;

$R_{76}$-$R_{78}$ are each independently selected from hydrogen, alkyl, hydroxy, amine, alkoxy, aryloxy, thioaryloxy, carboxylate, cinnamic acid, acyl, S(OH)$_3$ and S—O—O—OH;

$R_{79}$ is hydrogen or cyano;

$R_{80}$ and $R_{81}$ are each independently selected from hydrogen, hydroxy, halo, alkoxy, thioalkoxy, aryloxy, thioaryloxy, thiol, amine, and SO$_3$H; and Q' is

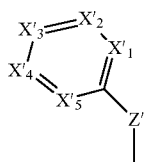

wherein:

Z' is selected from O, NH, C(=O), S, CH$_2$ and S(=O);

X'$_1$ is C($R_{82}$) or N;

X'$_2$ is C($R_{83}$) or N;

X'$_3$ is C($R_{84}$) or N;

X'$_4$ is C($R_{85}$) or N; and

X'$_5$ is C($R_{86}$) or N, provided that at least two of X'$_1$-X'$_5$ are not N, $R_{82}$ is selected from hydrogen, alkyl and halo; and $R_{83}$-$R_{86}$ are each independently selected from hydrogen, halo, alkyl, amine, alkoxy, aryloxy, carboxy and hydroxy;

or, alternatively, two of $R_{82}$-$R_{86}$ are joined together to form an aryl or heteroaryl.

In some of any of the embodiments described herein for Formula VI, $R_{83}$-$R_{86}$ are each independently selected from hydrogen, halo, alkyl, amine, alkoxy, aryloxy and hydroxy.

In some of any of the embodiments described herein for Formula VI, A' is selected from the group consisting of —C($R_{72}$)—N=; —C($R_{72}$)=N—; and —C($R_{73}$)=C($R_{74}$)—; and B' is selected from the group consisting of —C($R_{76}$)—N=; —C($R_{76}$)=N—; and C($R_{77}$)=C($R_{78}$).

In some of any of the embodiments described herein for Formula VI, Y'$_1$ is C-Q'.

In some of any of the embodiments described herein for Formula VI, A' is selected from the group consisting of —C($R_{72}$)—N=; —C($R_{72}$)=N—; and —C($R_{73}$)=C($R_{74}$)—; B' is selected from the group consisting of —C($R_{76}$)—N=; —C($R_{76}$)=N—; and —C($R_{77}$)=C($R_{78}$)—; and Y'$_1$ is C-Q'.

In some of these embodiments, Y'$_2$ is C—$R_{79}$; Y'$_3$ is C—$R_{80}$; and Y'$_4$ is selected from N and C—$R_{81}$.

Exemplary such compounds are presented in Table 4 herein below.

In some of any of the embodiments described herein for Formula VI, Y'$_1$ is C-Q', and Z' is O, NH, C(=O), S, CH$_2$ or S(=O).

In some of any of the embodiments described herein for Formula VI, A' is —C($R_{73}$)=C($R_{74}$)— and B' is —C($R_{77}$)=C($R_{78}$)—, such that the bicyclic skeleton presented in Formula VI is of a naphthalene.

In some of these embodiments, Y'$_1$ is C-Q', Y'$_2$ is C—$R_{79}$; Y'$_3$ is C—$R_{80}$; and Y'$_4$ is C—$R_{81}$.

In some of these embodiments, Y'$_1$ is C-Q', Y'$_2$ is C—$R_{79}$; Y'$_3$ is C—$R_{80}$; and Y'$_4$ is N.

In some of any of the embodiments described herein for Formula VI, A' is =C($R_{72}$)—N=; and B' is —C($R_{76}$)—N=, such that the bicyclic skeleton presented in Formula VI is of a quinazoline. Such a skeleton can alternatively be presented as A' being —C($R_{72}$)=N—; and B' being —C($R_{76}$)=N—.

In some of these embodiments, Y'$_1$ is C-Q', Y'$_2$ is C—$R_{79}$; Y'$_3$ is C—$R_{80}$; and Y'$_4$ is C—$R_{81}$.

In some of any of the embodiments described herein for Formula VI, A' is —C($R_{73}$)=C($R_{74}$)—; B is —C($R_{77}$)=C($R_{78}$)—, Y'$_1$ is C-Q', Y'$_2$ is C—$R_{79}$; Y'$_3$ is C—$R_{80}$; Y'$_4$ is C—$R_{81}$, and Z' is NH.

In some of these embodiments, one or more of $R_{77}$, $R_{80}$ and $R_{81}$ is sulfonate (-S(=O)$_2$—OH).

In some of these embodiments, $R_{80}$ and $R_{81}$ is sulfonate (—S(=O)$_2$—OH), and $R_{77}$ is —S(OH)$_3$.

In some of any of the embodiments of Formula VI, in which A' is —C($R_{73}$)=C($R_{74}$)—; B' is —C($R_{77}$)=C($R_{78}$)—, Y'$_1$ is C-Q', Y'$_2$ is C—$R_{79}$; Y'$_3$ is C—$R_{80}$; Y'$_4$ is C—$R_{81}$, and Z' is NH, $R_{73}$ is OH.

In some of any of the embodiments of Formula VI, in which A' is —C($R_{73}$)=C($R_{74}$)—; B' is —C($R_{77}$)=C($R_{78}$)—, Y'$_1$ is C-Q', Y'$_2$ is C—$R_{79}$; Y'$_3$ is C—$R_{80}$; Y'$_4$ is C—$R_{81}$, and Z' is NH, Q' is such that X'$_1$, X'$_3$ and X'$_5$ are each N, and X'$_2$ and X'$_4$ are each C—$R_{73}$ and C—$R_{75}$, respectively.

In some of these embodiments, $R_{83}$ and $R_{85}$ are each independently selected from halo, alkyl, and amine. In some of these embodiments, the amine is a secondary amine, such that it is substituted by e.g., a substituted or unsubstituted alkyl or aryl.

In some of any of the embodiments described herein for Formula VI, A' is —C($R_{73}$)=C($R_{74}$)—; B' is —C($R_{77}$)=C($R_{78}$)—, Y'$_1$ is C-Q', Y'$_2$ is C—$R_{79}$; Y'$_3$ is C—$R_{80}$; Y'$_4$ is C—$R_{81}$, and Z' is —C(=O) or —S(=O).

In some of these embodiments, Z' is C=O, and $R_{73}$ is OH.

In some of these embodiments, Z' is C=O, $R_{73}$ is OH, and $R_{78}$ is carbonyl, —C(=O)—R, with R being, for example, phenyl.

In some of these embodiments, Q' is phenyl, for example, unsubstituted phenyl, (such that $X_{71}$—$X_{75}$ are each C—H), or a substituted phenyl, in which one or more of $R_{82}$-$R_{86}$ is other than H.

In some of the embodiments in which A' is —C($R_{73}$)=C($R_{74}$)—; B' is —C($R_{77}$)=C($R_{78}$)—, Y'$_1$ is C-Q', Y'$_2$ is C—$R_{79}$; Y'$_3$ is C—$R_{80}$; Y'$_4$ is C—$R_{81}$, and Z' is —C(=O), $R_{73}$ is OH, Q' is phenyl, and one or more of $R_{77}$, $R_{78}$, $R_{80}$ and $R_{81}$ is sulfonate.

In some of any of the embodiments described herein for Formula VI, A' is —C($R_{73}$)=C($R_{74}$)—; B' is —C($R_{77}$)=C($R_{78}$)—, Y'$_1$ is C-Q', Y'$_2$ is C—$R_{79}$; Y'$_3$ is C—$R_{80}$; Y'$_4$ is C—$R_{81}$, and Z' is —S(=O).

In some of these embodiments, $R_{73}$ is carboxy.

In some of any of these embodiments, Q' is phenyl (substituted or unsubstituted). In some of these embodiments, the phenyl is substituted by one or more halo substituents.

In some of any of these embodiments, one or more of $R_{74}$, $R_{77}$ and $R_{78}$ is selected from hydroxy and alkoxy.

In some of any of the embodiments described herein for Formula VI, A' is —C($R_{73}$)=C($R_{74}$)—; B' is —C($R_{77}$)=C($R_{78}$)—, Y'$_1$ is C-Q', Y'$_2$ is C—$R_{79}$; Y'$_3$ is C—$R_{80}$; Y'$_4$ is C—$R_{81}$, and Z' is CH$_2$.

In some of any of these embodiments, one or more of $R_{74}$, $R_{77}$, $R_{78}$, $R_{80}$ and $R_{81}$ is selected from hydroxy and alkoxy.

In some of any of these embodiments, $R_{73}$ is alkyne, which can be substituted or unsubstituted.

In some of any of these embodiments, Q' is such that 2 of $X_1$-$X'_5$ are nitrogen atoms.

In some of any of these embodiments, Q' is phenyl.

In some of any of the embodiments described herein for Formula VI, A' is —C($R_{73}$)=C($R_{74}$)—, B' is —C($R_{77}$)=C($R_{78}$)—, $Y'_1$ is C-Q', $Y'_2$ is C—$R_{79}$; $Y'_3$ is C—$R_{80}$; $Y'_4$ is C—$R_{81}$, and Z' is O or S.

In some of any of the embodiments described herein for Formula VI, A' is =C($R_{72}$)—N=; B' is —C($R_{76}$)—N=; $Y'_1$ is C-Q', $Y'_2$ is C—$R_{79}$; $Y'_3$ is C—$R_{80}$; and $Y'_4$ is C—$R_{81}$.

In some of these embodiments, $R_{72}$ and $R_{76}$ are each an amine.

In some of these embodiments, $R_{79}$ is cyano (nitrile).

In some of these embodiments, $R_{81}$ is halo (e.g., fluoro or chloro).

In some of these embodiments, $R_{80}$ is a group that comprises an aryl (e.g., phenyl). In some embodiments, $R_{80}$ is anilino (—NH-phenyl), or aryloxy (e.g., —O— phenyl) or thioaryloxy.

In some of any of the embodiments described herein for Formula VI, in which A' is =C($R_{72}$)—N=; B' is —C($R_{76}$)—N= (or, alternatively, A' is —C($R_{72}$)=N—; and B' is —C($R_{76}$)=N—); $Y'_1$ is C-Q', $Y'_2$ is C—$R_{79}$; $Y'_3$ is C—$R_{80}$; and $Y'_4$ is C—$R_{81}$, Z' is S, O or NH.

In some of any of the embodiments described herein for Formula VI, in which A' is =C($R_{72}$)—N=; B' is —C($R_{76}$)—N=; $Y'_1$ is C-Q', $Y'_2$ is C—$R_{79}$; $Y'_3$ is C—$R_{80}$; and $Y'_4$ is C—$R_{81}$, Q' is phenyl, and in some embodiments, it is an unsubstituted phenyl (such that $X'_1$-$X'_5$ are each C—H).

In some of any of the embodiments described herein, the compound features an additional aromatic moiety (aryl or heteroaryl, preferably aryl, as defined herein). In some of these embodiments, the aromatic moiety is or forms a part of one or more of $R_{72}$-$R_{74}$, $R_{76}$-$R_{81}$, and $R_{82}$-$R_{86}$, when feasible.

In some of these embodiments, the aromatic moiety is in a form of an amine substituted by an aryl, an aryloxy, a thioaryloxy, and alkaryl, or as carboxyaryl.

In some of any of the embodiments described herein, the compounds are collectively represented by Formula VIA:

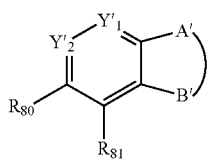

Formula VIA wherein:
A' is selected from the group consisting of —C(=O)—O— and —NR$_{71}$—C(=O)—;
B' is selected from the group consisting of —NR$_{75}$—C(=O)—; —C($R_{77}$)—C(=O)— and —C($R_{77}$)=C($R_{78}$)—;
$Y'_1$ and $Y'_2$ are each independently selected from C-Q', CH and N, provided that at least one of $Y'_1$ and $Y'_2$ is C-Q';
$R_{71}$ and $R_{75}$ are each independently hydrogen or alkyl; and
$R_{77}$ and $R_{78}$ are each independently hydrogen and alkyl, at least one of $R_{71}$, $R_{77}$ and $R_{78}$ is an alkyl being at least 4 atoms in length;
$R_{80}$ and $R_{81}$ are each independently selected from hydrogen and hydroxyl, at least one of $R_{80}$ and $R_{81}$ being hydroxyl; and Q' is

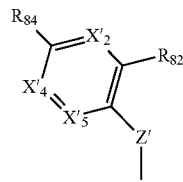

wherein:
Z' is O;
$X'_1$ is C($R_{82}$);
$X'_2$ is C($R_{83}$) or N;
$X'_3$ is C($R_{84}$);
$X'_4$ is C($R_{85}$) or N; and
$X'_5$ is C($R_{86}$) or N,
$R_{82}$ is selected from hydrogen and alkyl; and
$R_{83}$-$R_{86}$ are each independently selected from hydrogen, alkoxy, aryloxy and hydroxyl, at least one of $R_{83}$-$R_{86}$ being hydroxyl.

In some of any of the embodiments of Formula VIA, $R_{82}$ is an alkyl being at least 4 carbon atoms in length.

In some of any of these embodiments, A' is —C(=O)—O—; and B' is —C($R_{77}$)=C($R_{78}$)—. In some of these embodiments, $R_{77}$ is an alkyl being at last 4 carbon atoms in length.

In some embodiments of Formula VIA, $R_{82}$ is an alkyl being at least 4 carbon atoms in length, and $R_{77}$ is an alkyl being at last 4 carbon atoms in length.

In some of any of the embodiments of Formula VIA, $Y'_1$ is C-Q' and $Y'_2$ is C—$R_{79}$.

In some of these embodiments, $R_{80}$ is OH or alkoxy.

In some of any of the embodiments of Formula VIA, A' is —NR$_{71}$—C(=O)—; and B' is —NR$_{75}$—C(=O)—.

In some of these embodiments, $R_{71}$ is an alkyl being 4 carbon atoms in length.

In some of any of the embodiments of Formula VIA, A' is —NR$_{71}$—C(=O)—; and B' is —C($R_{77}$)—C(=O)—.

In some of these embodiments, $R_{77}$ is an alkyl being 4 carbon atoms in length.

In some of these embodiments, $Y'_1$ is C-Q' and $Y'_2$ is C—$R_{79}$.

In some of these embodiments, $R_{80}$ is OH or alkoxy.

In some of these embodiments each of $X'_1$-$X'_5$ is other than N, such that Q' is an aryl, more specifically phenyl.

In some of any of the embodiments of Formula VIA, A' is —NR$_{71}$—C(=O)—; and B' is —NR$_{75}$—C(=O)—; $Y'_1$ is N and $Y'_2$ is C-Q'.

In some of these embodiments, $R_{71}$ is an alkyl being 4 carbon atoms in length.

In some of these embodiments, $R_{81}$ is OH or alkoxy.

In some of any of the embodiments described herein for Formula VIA, each of $X'_1$-$X'_5$ is other than N, such that Q' is an aryl, more specifically phenyl.

In some of any of the embodiments described herein for Formula VIA, at least one of $X'_2$, $X'_4$ or $X'_5$ is N, such that Q' is a heteroaryl, more specifically, a nitrogen-containing heteroaryl.

In some of any of the embodiments described herein for Formula VIA, at least two of $X'_2$, $X'_4$ or $X'_5$ are N.

The nitrogen-containing heteroaryl can be, for example, pyridine, in a case of one nitrogen atom; pyridazine, pyrimidine or pyrazine, in a case of 2 nitrogen atoms; 1,2,4-triazine, or 1,2,3-triazine, in a case of 3 nitrogen atoms; or 1,2,3,4-tetrazine, 1,2,3,5-tetrazine, or 1,2,4,5-tetrazine, in a case of 4 nitrogen atoms, each can be substituted or unsubstituted, preferably substituted, as defined for $R_{82}$-$R_{86}$ in Formula VIA.

In some of any of the embodiments described herein for Formula VIA, $R_{84}$ is hydroxyl.

Exemplary compounds represented by Formula VIA as described herein are presented in Table 5 hereinafter.

Method of Identifying Small Molecules:

According to an aspect of some embodiments of the present invention, there is provided a method of identifying compounds which are usable in any of the methods and uses described herein. The method is generally effected by determining a pharmacophoric binding site of at least one kinase in which a small molecule is capable of interacting with at least two amino acid residues which are required for the activity of the kinase; determining a topology of BKT300 which exhibits interaction with the at least two amino acid residues in the pharmacophoric binding site; and screening a computer-readable database so as to identify a compound featuring a topology similar to the topology of BKT300, wherein a compound featuring the topology is identified as usable in inhibiting at least one kinase and/or in treating a disease or disorder associated with an activity of at least one kinase, and/or in modulating a biological activity of a chemokine and/or on treating cancer.

Herein throughout, the term "topology" means a spatial arrangement (2D or 3D arrangement) of the chemical groups composing the compound. For example, BKT300 is comprised of a bicylic heteroaromatic moiety which is linked to an aromatic moiety via an oxygen heteroatom, and which further comprises 2 flanking alkyl groups. In the computational docking assays performed, it was determined that BKT300 is arranged in the binding site of kinases in a certain conformation, namely, the heteroaromatic, aromatic and flanking alkyl groups are spatially arranged in that certain conformation. This conformation is referred to herein as a "topology" similar to the topology of BKT300.

According to some embodiments of this aspect of the present invention, the method further comprises computationally docking the compound within the pharmacophoric binding site, wherein a compound that features in the docking a spatial arrangement that allows it to interact with the at least two amino acid residues in the binding site is determined as usable in inhibiting the at least one kinase and/or in treating the disease or disorder associated with an activity of the at least one kinase.

According to some embodiments of this aspect of the present invention, the pharmacophoric binding site is constructed upon aligning structures of at least two kinases.

According to some embodiments of this aspect of the present invention, the kinase is selected from MELK and MAPK4K.

According to some embodiments of this aspect of the present invention, the at least two amino acid residues within the pharmacophoric binding site comprise Lys40 and Asp 150.

According to some embodiments of this aspect of the present invention, the compound is usable in modulating a biological activity of a chemokine, and the method further comprises determining a biological activity of the chemokine in the presence of the compound featuring the topology, for example, as described herein in the Examples section that follows.

According to some embodiments of this aspect of the present invention, the compound is usable in treating cancer, and the method further comprises determining an anti-cancer activity of the compound featuring the topology, for example, as described herein in the Examples section that follows. According to some of these embodiments, determining the anti-cancer activity is performed using compounds featuring the topology, which are further determined as modulators of a biological activity of a chemokine.

According to some embodiments of this aspect of the present invention, the compound is usable in treating inflammation, and the method further comprises determining an anti-inflammatory activity of the compound featuring the topology, using methods well known in the art. According to some of these embodiments, determining the anti-inflammatory activity is performed using compounds featuring the topology, which are further determined as modulators of a biological activity of a chemokine.

According to some embodiments of this aspect of the present invention, the compound is usable in inducing cell death, and the method further comprises determining an cell-killing activity of the compound featuring the topology, for example, as described herein in the Examples section that follows. According to some of these embodiments, determining the cell-killing activity is performed using compounds featuring the topology, which are further determined as modulators of a biological activity of a chemokine.

As exemplified herein, the method of identifying compounds as described herein was used to identify compounds having Formula VI.

Therapeutic Applications:

According some embodiments, a small molecule compound of Formula I, II, III, IV, V, VI, VIA and/or VIB, and/or a compound represented in Table 2, as described herein in any of the respective embodiments, and any combination thereof, is capable of, or is useful in, inhibiting a biological activity of a kinase, and/or inhibiting cancer cells, and/or killing cancer cells, and/or inducing apoptosis, and/or inducing growth arrest, and/or inhibiting chemokine-dependent cell migration, and/or modulating a biological activity of a chemokine (e.g., cell migration), and/or treating diseases and disorders associated with kinase activity and/or cell migration, such as cancer and inflammatory diseases and disorders; and/or treating proliferative diseases or disorders (where inducing apoptosis and/or growth arrest is desirable), as described herein.

For example, the compounds of Formula VI, according to some embodiment described herein, and any combination thereof, can be regarded as structural analogs of BKT300, an exemplary compound which is shown herein to act as a chemokine-binding compound, by modulating a biological activity of chemokines, as an inhibitor of chemokine-dependent cell migration, as an inhibitor of cancer cells (e.g., as inhibitor of cancer cells growth and/or as inducing apoptosis and/or as inhibitor of cancer cells migration), and/or as a kinase inhibitor.

As inflammation and cancer are typically governed by cell migration (e.g., infiltration, metastasis) and kinase activity, which is often associated with cell proliferation, such conditions are contemplated for treatment using the compounds of some embodiments of the invention.

Proliferative diseases and disorders as described herein, including medical conditions other than cancer (also referred to herein as "non-cancerous hyperproliferative diseases"), are also contemplated for treatment using the compounds of some embodiments of the invention, due to the apoptosis-inducing effect of the compounds.

Without being bound by any particular theory, it is believed that the compounds described herein are particularly useful as anti-cancer agents by inducing cancer cell death, by affecting chemokine-dependent cancer cell migration (e.g., by inhibiting metastasis) and/or angiogenesis, and/or by inhibiting kinase activity (e.g., pro-proliferation kinase activity) and/or by inducing apoptosis of cancer cells and/or by inducing growth arrest of cancer cells; and/or as anti-inflammatory agents by affecting chemokine-dependent immune cell migration (e.g., immune cell infiltration) and/or by inhibiting kinase activity (e.g., pro-inflammatory kinase activity), as described in further detail herein below.

In some of any of the embodiments described herein, a small molecule compound as described herein in any of the respective embodiments, is capable of, or usable in, inducing death of pathogenic cells (e.g., cancer cells or immune cells or hyper proliferative cells).

In some of any of the embodiments described herein, a small molecule compound as described herein in any of the respective embodiments, is capable of, or usable in, inducing cell death of pathogenic cells.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

Methods of monitoring cellular changes induced by the compounds are known in the art and include for example, the MTT test which is based on the selective ability of living cells to reduce the yellow salt MTT (3-(4, 5-dimethylthiazolyl-2)-2, 5-diphenyltetrazolium bromide) (Sigma, Aldrich St Louis, Mo., USA) to a purple-blue insoluble formazan precipitate; the BrDu assay [Cell Proliferation ELISA BrdU colorimetric kit (Roche, Mannheim, Germany]; the TUNEL assay [Roche, Mannheim, Germany]; the Annexin V assay [ApoAlert® Annexin V Apoptosis Kit (Clontech Laboratories, Inc., CA, USA)]; the Senescence associated-β-galactosidase assay (Dimri G P, Lee X, et al. 1995. A biomarker that identifies senescent human cells in culture and in aging skin in vivo. Proc Natl Acad Sci USA 92:9363-9367); 7-ADD viability staining (available from MDsystems), caspase-3 assay (available from MDsystems) as well as various RNA and protein detection methods (which detect level of expression and/or activity) which are further described hereinabove.

In some of any of the embodiments described herein, a small molecule compound as described herein in any of the respective embodiments, the cellular change is apoptosis such as via cleavage of caspase-3.

In some of any of the embodiments described herein, a small molecule compound as described herein in any of the respective embodiments, is capable of, or usable in, inducing apoptosis via cleavage of caspase-3.

In some of any of the embodiments described herein, a small molecule compound as described herein in any of the respective embodiments, is capable of, or usable in, inducing growth arrest of cells, and in some embodiments, the arrest is at the G2M phase of the cell cycle.

Chemokine Modulation:

According an aspect of some embodiments of the present invention, a small molecule compound of Formula I, II, III, IV, V, VI, VIA and/or VIB, and/or a compound presented in Table 2, as described herein in any of the respective embodiments, and any combination thereof, is capable of, or is usable, in modulating a biological activity of a chemokine, as described herein.

According to an aspect of some embodiments of the present invention, there is provided a method of modulating a biological activity of a chemokine, the method comprising contacting the chemokine with a compound according to any of the embodiments described herein.

According to an aspect of some embodiments of the present invention, there is provided a use of a compound according to any of the embodiments described herein in the manufacture of a medicament for modulating a biological activity of a chemokine.

According to an aspect of some embodiments of the present invention, there is provided a use of a compound according to any of the embodiments described herein in modulating a biological activity of a chemokine.

In some embodiments, the use and/or method for modulating a chemokine activity is effected in vivo, for example by administering a therapeutically effective amount of the compound to a subject in need thereof.

In some embodiments, the use and/or method for modulating a chemokine activity is effected ex vivo (e.g., in vitro), for example, in research.

In some embodiments of any one of the embodiments described herein relating to a method or use for modulating a biological activity of a chemokine, the chemokine is MIP3a, MCP-1 and/or SDF-1.

In some embodiments of any one of the embodiments described herein relating to a method, use or medicament for modulating a biological activity of a chemokine, the method, use or medicament is for treating a disease or disorder associated with a biological activity of a chemokine in a subject in need thereof, for example, by administering to the subject a therapeutically effective amount of a compound according to any of the embodiments described herein.

In some of any of the embodiments described herein, modulating a biological activity of a chemokine includes inhibiting a biological activity of a chemokine. This can be evidenced by the ability of a small molecule as described herein to inhibit chemokine-induced cell migration as exemplified herein on a plurality of cell types of different types.

In some embodiments of any one of the embodiments described herein relating to a method, use or medicament for modulating a biological activity of a chemokine, the method, use or medicament is for treating a disease or disorder in which modulating (e.g., inhibiting) a biological activity of a chemokine is beneficial, in a subject in need thereof, for example, by administering to the subject a therapeutically effective amount of a compound according to any of the embodiments described herein.

In some embodiments of any one of the embodiments described herein relating to a method, use or medicament for modulating a biological activity of a chemokine, the method, use or medicament is for treating a disease or disorder treatable by modulating (e.g., inhibiting) a biological activity of a chemokine, in a subject in need thereof, for example, by administering to the subject a therapeutically effective amount of a compound according to any of the embodiments described herein.

In some embodiments of any one of the embodiments described herein relating to a method, use or medicament for modulating a biological activity of a chemokine, the compound described herein (according to any of the respective embodiments) is effective in modulating chemokine-dependent cell migration. In some of these embodiments, the chemokine-dependent cell migration is associated with cancer and/or inflammation, as described herein.

In some of any of the embodiments described herein, the chemokine is MIP3a.

Examples of diseases and disorders associated with an activity of MIP3a (e.g., wherein inhibition of MIP3a activity is beneficial) include, without limitation, autoimmune diseases and disorders such as psoriasis, inflammatory bowel disease, chronic obstructive pulmonary diseases (COPD), rheumatoid arthritis, multiple sclerosis (MS), atopic dermatitis, dry eye disease and age-related macular degeneration (AMD).

Compounds BKT201, BKT202, BKT203, BKT205, BKT206, BKT207, BKT209, BKT210, BKT212, BKT213 and BKT300 are non-limiting examples of compounds suitable for inhibiting a MIP3a activity, according to any of the respective embodiments described herein. Compounds BKT202, BKT203, BKT206, BKT207 BKT210, BKT212 and BKT213 are non-limiting examples of relatively potent inhibitors of MIP3a activity. Compounds BKT203, BKT206, BKT207 and BKT212 are non-limiting examples of particularly potent inhibitors of MIP3a activity.

In some embodiments of any one of the embodiments described herein relating to use of a compound having general Formula I for inhibiting a biological activity of MIP3a, W is an unsubstituted alkyl or alkenyl at least 5 carbon atoms in length, optionally at least 6 carbon atoms in length, optionally at least 7 carbon atoms in length, and optionally at least 8 carbon atoms in length, according to any of the respective embodiments described herein.

Compounds BKT205, BKT206, BKT209 and BKT212 are examples of compounds comprising unsubstituted alkenyl at least 5 carbon atoms in length as the moiety denoted as W in Formula I. As exemplified herein, Compounds BKT205, BKT206, BKT209 and BKT212 each exhibited inhibition of MIP3a-induced cell migration.

In some embodiments of any one of the embodiments described herein relating to use of a compound having general Formula I for inhibiting a biological activity of MIP3a, W is an unsubstituted alkyl or alkenyl at least 9 carbon atoms in length, optionally at least 10 carbon atoms in length, and optionally at least 12 carbon atoms in length, according to any of the respective embodiments described herein.

Compounds BKT206 and BKT212 are examples of compounds comprising unsubstituted alkenyl at least 9 carbon atoms in length as the moiety denoted as W in Formula I. As exemplified herein, Compounds BKT206 and BKT212 both exhibited potent inhibition of MIP3a-induced cell migration.

In some embodiments of any one of the embodiments described herein relating inhibiting a biological activity of MIP3a and/or SDF-1, the compound has Formula IV or Formula V, according to any of the respective embodiments described herein. In some embodiments, $R_{40}$-$R_{51}$ and $R_{61}$-$R_{68}$ are each hydrogen, hydroxy, alkyl and/or alkylcarboxy.

As exemplified herein, Compound BKT203 (hypericin), which has general Formula IV, and Compound BKT207, which has general Formula V, are examples of compounds in which $R_{40}$-$R_{51}$ and $R_{61}$-$R_{68}$ are each hydrogen, hydroxy, alkyl and/or alkylcarboxy, and are highly effective at inhibiting SDF-1-induced and MIP3a-induced cell migration.

In some embodiments of any one of the embodiments described herein relating to a treatment of a disease or disorder, the disease or disorder is not a bacterial infection.

In some embodiments of any one of the embodiments described herein relating to a treatment of a disease or disorder, the disease or disorder is not a *Legionella* infection.

In some embodiments of any one of the embodiments described herein relating to a method or use for modulating a biological activity of a chemokine, the chemokine is MCP-1 and/or SDF-1. In some such embodiments, the chemokine is MCP-1. In some such embodiments, the chemokine is SDF-1.

In some embodiments of any one of the embodiments described herein relating to modulating a chemokine activity, the compound, method and/or medicament (according to any of the respective embodiments described herein) is for inhibiting a biological activity of a chemokine. In some such embodiments, the chemokine is MCP-1 and/or SDF-1. In some such embodiments, the chemokine is MCP-1. In some such embodiments, the chemokine is SDF-1.

MCP-1 Inhibition:

According to some embodiments, a small molecule compound of Formula I, II, III, IV, V, VI, VIA and/or VIB, and/or a compound represented in Table 2 herein, as described herein in any of the respective embodiments, and any combination thereof, is capable of, or is usable, in modulating a biological activity of MCP-1, as described herein.

According to an aspect of some embodiments of the present invention, there is provided a method of inhibiting a biological activity of MCP-1, the method comprising contacting the MCP-1 with a compound according to any of the embodiments described herein described herein.

According to an aspect of some embodiments of the present invention, there is provided a use of a compound according to any of the embodiments described herein described herein in the manufacture of a medicament for inhibiting a biological activity of MCP-1.

According to an aspect of some embodiments of the present invention, there is provided a use of a compound according to any of the embodiments described herein described herein in inhibiting a biological activity of MCP-1.

In some embodiments of any of the embodiments relating to a use and/or method for inhibiting a biological activity of MCP-1, the use and/or method is effected in vivo, for example, by administering a therapeutically effective amount of the compound to a subject in need thereof.

In some embodiments, the use and/or method for inhibiting a biological activity of MCP-1 is effected ex vivo (e.g., in vitro), for example, in research.

In some embodiments of any one of the embodiments described herein relating to a method, use or medicament for inhibiting a biological activity of MCP-1, the method, use or medicament is for treating a disease or disorder associated with a biological activity of MCP-1 in a subject in need thereof, for example, by administering to the subject a therapeutically effective amount of a compound according to any of the embodiments described herein described herein.

In some embodiments of any one of the embodiments described herein relating to a method, use or medicament for inhibiting a biological activity of MCP-1, the method, use or medicament is for treating a disease or disorder in which inhibiting a biological activity of a MCP-1 is beneficial, in a subject in need thereof, for example, by administering to the subject a therapeutically effective amount of a compound according to any of the embodiments described herein described herein.

In some embodiments of any one of the embodiments described herein relating to a method, use or medicament for inhibiting a biological activity of MCP-1, the method, use or medicament is for treating a disease or disorder treatable by inhibiting a biological activity of a MCP-1, in a subject in need thereof, for example, by administering to the subject a therapeutically effective amount of a compound according to any of the embodiments described herein described herein.

Examples of diseases and disorders associated with an activity of MCP-1 (e.g., wherein inhibition of MCP-1 activity is beneficial) include, without limitation, diseases and disorders which are characterized by monocytic infiltrates.

According to some embodiments, examples of diseases and disorders associated with an activity of MCP-1 (e.g., wherein inhibition of MCP-1 activity is beneficial) include, without limitation, tuberculosis; HIV-1; proliferative glomerulonephritis; neural tube defects; xanthogranulomatous pyelonephritis; scleritis; rapidly progressive glomerulonephritis; pneumoconiosis; encephalitis; peritonitis; atherosclerosis; psoriasis; dengue shock syndrome; temporal arteritis; relapsing polychondritis; diabetic angiopathy; mesangial proliferative glomerulonephritis; sympathetic ophthalmia; ureteral disease; lupus nephritis; pneumonia; periapical granuloma; erdheim-chester disease; glomerulonephritis; artery disease; viral encephalitis; primary cutaneous amyloidosis; arteriosclerosis; nonspecific interstitial pneumonia; acute poststreptococcal glomerulonephritis; coronary artery disease; venezuelan equine encephalitis; diabetic macular edema; extrapulmonary tuberculosis; nephritis; rheumatoid arthritis; kawasaki disease; arthritis; malaria; obesity; psychiatric disorders; cancer (e.g., as described herein); inflammation (e.g., inflammatory disease and disorders as described herein); neurodegenerative disorders; and age-related macular degeneration (AMD, e.g., dry or wet form), as described herein.

According to a specific embodiment, the disease includes, without limitation, psoriasis, rheumatoid arthritis, multiple sclerosis, atherosclerosis, glomerulonephritis, epilepsy, Alzheimer's disease, brain ischemia, traumatic brain injury, type II diabetes and AMD.

In some embodiments of any one of the embodiments described herein relating to use of a compound having general Formula I for inhibiting a biological activity of MCP-1, Z is —C(=O)OH, Y is absent and $L_2$ is absent or is —C($R_2$)(OH)—. In some such embodiments, X is cyclic, being, for example, a substituted or unsubstituted bicyclic hydrocarbon moiety, and/or a substituted or unsubstituted phenylene, according to any of the respective embodiments described herein. In some such embodiments, $L_2$ is absent.

Compound BKT206 is an example of a compound wherein Z is —C(=O)OH, $L_2$ and Y are each absent, and X is a phenylene. Compounds BKT211 and BKT216 are examples of a compound wherein Z is —C(=O)OH, $L_2$ and Y are each absent, and X is a bicyclic hydrocarbon. As exemplified herein, Compounds BKT206, BKT211 and BKT216 each inhibited MCP-1-induced migration.

Compounds BKT201, BKT204, BKT205, BKT206, BKT209, BKT211, BKT216 and BKT300 are non-limiting examples of compounds suitable for inhibiting an MCP-1 activity, according to any of the respective embodiments described herein. Compounds BKT204, BKT206, BKT211 and BKT216 are non-limiting examples of relatively potent inhibitors of MCP-1 activity, suitable for inhibiting an MCP-1 activity, according to any of the respective embodiments described herein. Compound BKT211 is a non-limiting example of a particularly potent inhibitor of MCP-1 activity.

Compounds BKT201, BKT204, BKT205, BKT206, BKT211 and BKT300 are non-limiting examples of compounds suitable for inhibiting MCP-1 in addition to inhibiting SDF-1, according to any of the respective embodiments described herein. Compounds BKT206 and BKT211 are non-limiting examples of compounds which are relatively potent inhibitors of MCP-1 and SDF-1.

SDF-1 and/or CXCR4 Inhibition:

According to some embodiments, a small molecule compound of Formula I, II, III, IV, V, V, VIA and VIB, and/or a compound presented in Table 2 herein, as described herein in any of the respective embodiments, and any combination thereof, is capable of, or is usable, in modulating a biological activity of SDF-1 and/or CXCR4, as described herein.

According to an aspect of some embodiments of the present invention, there is provided a method of inhibiting a biological activity of SDF-1 and/or CXCR4, the method comprising contacting the SDF-1 and/or CXCR4 with a compound according to any of the embodiments described herein described herein.

According to an aspect of some embodiments of the present invention, there is provided a use of a compound according to any of the embodiments described herein described herein in the manufacture of a medicament for inhibiting a biological activity of SDF-1 and/or CXCR4.

According to an aspect of some embodiments of the present invention, there is provided a use of a compound according to any of the embodiments described herein described herein in inhibiting a biological activity of SDF-1 and/or CXCR4.

In some embodiments of any of the embodiments relating to a use and/or method for inhibiting a biological activity of SDF-1 and/or CXCR4, the use and/or method is effected in vivo, for example, by administering a therapeutically effective amount of the compound to a subject in need thereof.

In some embodiments, the use and/or method for inhibiting a biological activity of SDF-1 and/or CXCR4 is effected ex vivo (e.g., in vitro), for example, in research.

In some embodiments of any one of the embodiments described herein relating to a method, use or medicament for inhibiting a biological activity of SDF-1 and/or CXCR4, the method, use or medicament is for treating a disease or disorder associated with a biological activity of SDF-1 and/or CXCR4 in a subject in need thereof, for example, by administering to the subject a therapeutically effective amount of a compound according to any of the embodiments described herein described herein.

In some embodiments of any one of the embodiments described herein relating to a method, use or medicament for inhibiting a biological activity of SDF-1 and/or CXCR4, the method, use or medicament is for treating a disease or disorder in which inhibiting a biological activity of a SDF-1 and/or CXCR4 is beneficial, in a subject in need thereof, for example, by administering to the subject a therapeutically effective amount of a compound according to any of the embodiments described herein described herein.

In some embodiments of any one of the embodiments described herein relating to a method, use or medicament for inhibiting a biological activity of SDF-1 and/or CXCR4, the method, use or medicament is for treating a disease or disorder treatable by inhibiting a biological activity of a SDF-1 and/or CXCR4 is beneficial, in a subject in need thereof, for example, by administering to the subject a therapeutically effective amount of a compound according to any of the embodiments described herein described herein.

The skilled person will appreciate that CXCR4 is a receptor which mediates activity of SDF-1, and that activities of SDF-1 and activities of CXCR4 typically overlap.

Examples of diseases and disorders associated with an activity of SDF-1 and/or CXCR4 (e.g., wherein inhibition of SDF-1 and/or CXCR4 activity is beneficial) include, without limitation, Whim Syndrome; Cervical Adenocarcinoma; Breast Cancer; Bursitis; Tuberculosis; Intraocular Lymphoma; Cytomegalovirus Retinitis; Chronic Inflammatory Demyelinating Polyradiculoneuropathy; Ocular Hypertension; Polyradiculoneuropathy; Dendritic Cell Tumor; Retinal Hemangioblastoma; Malaria; Endotheliitis; Leukemia; Rheumatoid Arthritis; Arthritis; Prostatitis; Prostate Cancer; Colorectal Cancer; Chronic Lymphocytic Leukemia; Pancreatitis; Neuronitis; Lung Cancer; Osteoarthritis; Hypoxia; Adenocarcinoma; Pancreatic Cancer; Multiple Myeloma; Neuroblastoma; Myeloid Leukemia; Astrocytoma; Periodontitis; Glioblastoma; Pre-Eclampsia; Melanoma; Hepatitis; Esophagitis; Myeloma; Eclampsia; Cervicitis; Periodontal Disease; Central Nervous System Lymphoma; Sporadic Breast Cancer; Hepatocellular Carcinoma; Systemic Lupus Erythematosus; Asthma; Renal Cell Carcinoma; Myocardial Infarction; Medulloblastoma; Endometrial Cancer; Lupus Erythematosus; Esophageal Cancer; Premature Ovarian Failure; Peritonitis; Vascular Disease; Alcoholic Hepatitis; Kidney Disease; Cutaneous Leishmaniasis; Encephalitis; Alopecia Areata; Lymphoblastic Leukemia; Adenoma; Mantle Cell Lymphoma; Oligodendroglioma; Malt Lymphoma; Pertussis; Ischemia; Uveal Melanoma; Gingivitis; Pituitary Adenoma; Bronchiolitis; Neuromyelitis Optica; Mesothelioma; Alopecia; Cervical Cancer, Somatic; Glioblastoma Multiforme; Bronchiolitis Obliterans; Brain Injury; Colorectal Adenoma; Tongue Squamous Cell Carcinoma; B-Cell Lymphomas; Traumatic Brain Injury; Intravascular Large B-Cell Lymphoma; Allergic Asthma; Tick-Borne Encephalitis; Blastic Plasmacytoid Dendritic Cell; Oligoastrocytoma; Childhood Type Dermatomyositis; Renal Oncocytoma; Endometrial Adenocarcinoma; Optic Neuritis; Seminoma; Sjogren's Syndrome; Pleurisy; Neuritis; Inflammatory Bowel Disease; Cytomegalovirus Infection; Malignant Pleural Mesothelioma; Oral Squamous Cell Carcinoma; Skeletal Muscle Regeneration; Emery-Dreifuss Muscular Dystrophy, Dominant Type.

In some embodiments, exemplary diseases and disorders associated with an activity of SDF-1 and/or CXCR4 (e.g., wherein inhibition of SDF-1 and/or CXCR4 activity is beneficial) include, without limitation, harmful angiogenesis, tumor metastasis, WHIM syndrome, Waldenstrom macroglobulinemia (WM) and opioid-induced hyperalgesia.

Herein, the term "harmful angiogenesis" refers to angiogenesis associated with a clinically and/or cosmetically undesirable result.

Angiogenesis associated with a tumor is a non-limiting example of a harmful angiogenesis.

As used herein the phrase "tumor metastasis" refers to a malignant tumor spreading out of its primary location to other parts of the body, e.g., breast cancer which metastasizes to the lungs. Tumor metastasis often involves migration of tumor cells.

In some embodiments of any one of the embodiments described herein relating to a method or use for modulating a biological activity of a chemokine, the modulating comprises inhibiting a biological activity of SDF-1 and/or CXCR4, according to any of the respective embodiments described herein.

In some embodiments of any one of the embodiments described herein relating to inhibiting a biological activity of SDF-1 and/or CXCR4, inhibiting a biological activity of SDF-1 and/or CXCR4 is for effecting immunostimulation.

In some embodiments, immunostimulation is effected as part of a cancer treatment, e.g., in order to stimulate immune activity against cancer cells.

In some embodiments, immunostimulation comprises increasing a level of hematopoietic stem cells in peripheral blood of a subject.

In some embodiments, increasing a level of hematopoietic stem cells in peripheral blood of a subject is effected as a preliminary part of hematopoietic stem cell transplantation (e.g., in order to generate hematopoietic stem cells available for collection and later transplantation back into the subject). Examples of conditions which may be treated by the hematopoietic stem cell transplantation include, without limitation, leukemia (e.g., acute lymphoblastic leukemia, acute myeloid leukemia, chronic lymphocytic leukemia, chronic myelogenous leukemia), lymphoma (e.g., Hodgkin's disease, non-Hodgkin's lymphoma), myeloma (e.g., multiple myeloma), neuroblastoma, desmoplastic small round cell tumor, Ewing's sarcoma, choriocarcinoma, myelodysplasia, anemias (e.g., paroxysmal nocturnal hemoglobinuria, aplastic anemia, Diamond-Blackfan anemia, Fanconi anemia, acquired pure red cell aplasia), hemoglobinopathies, sickle cell disease, beta-thalassemia major, myeloproliferative disorders (e.g., polycythemia vera, essential thrombocytosis, myelofibrosis), amyloid light chain amyloidosis, radiation poisoning, viral diseases (e.g., HTLV and/or HIC infection), neuronal ceroid lipofuscinosis, Niemann-Pick disease, Gaucher disease, leukodystrophies (adrenoleukodystrophy, metachromatic leukodystrophy, Krabbe disease), mucopolysaccharoidosis, glycoproteinoses (e.g., mucolipidosis II, fucosidosis, aspartylglucosaminuria, alpha-mannosidosis), Wolman disease, immunodeficiencies (e.g., ataxia telangiectasia, DiGeorge syndrome, severe combined immunodeficiency, Wiskott-Aldrich syndrome, Kostmann syndrome, Shwachman-Diamond syndrome, Griscelli syndrome, NF-kappa-B essential modulator deficiency), amegakaryocytic thrombocytopenia and hemophagocytic lymphohistiocytosis.

In some embodiments, the hematopoietic stem cell transplantation is for treating a proliferative disease, e.g., cancer (e.g., cancer as described herein according to any of the respective embodiments).

In some embodiments of any one of the embodiments described herein relating to hematopoietic stem cells, the treatment comprises increasing a level of hematopoietic stem cells in peripheral blood of the subject, obtaining hematopoietic stem cells from peripheral blood of the subject, administering a cytotoxic therapy to the subject (e.g., anti-proliferative chemotherapy, and/or radiotherapy), and transplanting at least a portion of the stem cells back into the patient, subsequent to the cytotoxic therapy.

Compounds presented in Table 2 are non-limiting examples of compounds which may be used for inhibiting a biological activity of SDF-1 and/or CXCR4 according to any of the respective embodiments described herein. In some such embodiments, the compound is Compound BKT204 in Table 2.

Compound BKT201, BKT203, BKT204, BKT205, BKT206, BKT207, BKT208, BKT209, BKT210, BKT211, BKT212, BKT213, BKT300 and BKT400 are non-limiting examples of compounds suitable for inhibiting an SDF-1 activity, according to any of the respective embodiments described herein. Compounds BKT201, BKT203, BKT205, BKT206, BKT207, BKT209, BKT211, BKT212, BKT213 and BKT300 are non-limiting examples of compounds which exhibit particularly potent inhibition of SDF-1 activity. Compounds BKT201, BKT205, BKT209, BKT213 and BKT300 are non-limiting examples of compounds which exhibit particularly potent and relatively selective inhibition of SDF-1 activity.

Compounds BKT201, BKT203, BKT205, BKT206, BKT207, BKT209, BKT210, BKT212, BKT213 and BKT300 are non-limiting examples of compounds suitable for inhibiting MIP3a in addition to inhibiting SDF-1, according to any of the respective embodiments described herein. Compounds BKT203, BKT206, BKT207 or BKT212 are non-limiting examples of potent inhibitors of both MIP3a and SDF-1.

In some embodiments of any one of the embodiments described herein relating to use of a compound having general Formula I for inhibiting a biological activity of SDF-1 and/or CXCR4, $L_2$ in Formula I is absent, or alternatively, is —C(=O)— or —C($R_2$)(OH)—, in accordance with any of the respective embodiments described herein.

In some embodiments of any one of the embodiments described herein relating to use of a compound having general Formula I for inhibiting a biological activity of SDF-1 and/or CXCR4, Z is —C(=O)OH.

In some embodiments, Z is —C(=O)OH, Y is absent and $L_2$ is absent or is —C($R_2$)(OH)—. In some such embodiments, X is cyclic, being, for example, a substituted or unsubstituted bicyclic hydrocarbon moiety, and/or a substituted or unsubstituted phenylene, according to any of the respective embodiments described herein. In some such embodiments, $L_2$ is absent.

Compound BKT206 is an example of a compound wherein Z is —C(=O)OH, $L_2$ and Y are each absent, and X is a phenylene. Compound BKT211 is an example of a compound wherein Z is —C(=O)OH, $L_2$ and Y are each absent, and X is a bicyclic hydrocarbon. As exemplified herein, Compounds BKT206 and BKT211 each exhibited SDF-1-induced cell migration.

Compound BKT213 is an example of a compound wherein Z is —C(=O)OH, Y is absent, $L_2$ is —C($R_2$)(OH)—, and X is a phenylene. As exemplified herein, Compound BKT213 inhibited SDF-1-induced cell migration.

In some embodiments, Z is —C(=O)OH, Y is an aliphatic hydrocarbon moiety, and X is —C≡C—C≡C— or —$CR_3$=$CR_4$—$CR_5$=$CR_6$—, according to any of the respective embodiments described herein. In some embodiments, X is —$CR_3$=$CR_4$—$CR_5$=$CR_6$—. In some embodiments, $L_2$ is —C(=O)—. In some embodiments, $L_2$ is —C(=O)— and X is —$CR_3$=$CR_4$—$CR_5$=$CR_6$—.

Compounds BKT205 and BKT209 are examples of compound wherein Z is —C(=O)OH, Y is an aliphatic hydrocarbon moiety (a linear and unsubstituted saturated hydrocarbon moiety) from 1 to 8 atoms in length, $L_2$ is —C(=O)— and X is —$CR_3$=$CR_4$—$CR_5$=$CR_6$—. As exemplified herein, Compounds BKT205 and BKT209 each inhibited SDF-1-induced cell migration.

In some embodiments of any one of the embodiments described herein relating to use of a compound having general Formula I for inhibiting a biological activity of SDF-1 and/or CXCR4, X is —C≡C—C≡C— or —$CR_3$=$CR_4$—$CR_5$=$CR_6$—, according to any of the respective embodiments described herein. In some embodiments, Y is an aliphatic hydrocarbon moiety.

In some embodiments, X is —C≡C—C≡C—, according to any of the respective embodiments described herein. In some embodiments, Z is absent and/or $L_1$ and $L_2$ are each —CH(OH)—.

Compound BKT212 (falcarindiol) is an example of a compound in which X is —C≡C—C≡C—, Z is absent and $L_1$ and $L_2$ are each —CH(OH)—. As exemplified herein, Compound BKT212 inhibited SDF-1-induced cell migration.

In some embodiments, X is —$CR_3$=$CR_4$—$CR_5$=$CR_6$—, according to any of the respective embodiments described herein. In some embodiments, $L_2$ is —C(=O)—. Compounds BKT205 and BKT209 are examples of compounds wherein X is —$CR_3$=$CR_4$—$CR_5$=$CR_6$—, and as exemplified herein, Compounds BKT205 and BKT209 each inhibited SDF-1-induced cell migration.

In some embodiments of any one of the embodiments described herein relating to use of a compound having general Formula II for inhibiting a biological activity of SDF-1 and/or CXCR4, Q is —C(=O)—. In some such embodiments, J is —O— or —CH=, optionally —O—. In some such embodiments, K is —$CR_{16}R_{17}$— wherein $R_{16}$ is alkyl or phenyl, each being substituted or unsubstituted.

Compounds BKT201, BKT204 and BKT300 are examples of compounds in which Q is —C(=O)—. As exemplified herein, each of compounds BKT201, BKT204 and BKT300 inhibited SDF-1-induced cell migration to a considerable extent.

In some embodiments of any one of the embodiments described herein relating inhibiting a biological activity of SDF-1 and/or CXCR4, the compound has Formula IV or Formula V, according to any of the respective embodiments described herein. In some embodiments, $R_{40}$-$R_{51}$ and $R_{61}$-$R_{68}$ are each hydrogen, hydroxy, alkyl and/or alkylcarboxy.

Kinase Inhibition:

According to some of any of the embodiments described herein, a compound represented by Formula I, II, III, IV, V, VI, VIA and/or VIB herein and/or a compound presented in Table 2, is capable of, or is usable in, inhibiting a biological activity of a kinase. In some such embodiments, the compound is represented Formula VIA and/or VIB herein.

According to some of any of the embodiments described herein, a compound represented Formula I, II, III, IV, V, VI, VIA and/or VIB herein and/or a compound presented in Table 2, is capable of, or is usable in, treating diseases or disorder in which inhibiting a biological activity of a kinase is beneficial, or a disease or disorder that is treatable by inhibiting a biological activity of a kinase. In some such embodiments, the compound is represented Formula VIA and/or VIB herein.

According to an aspect of some embodiments of the present invention, a compound according to any of the embodiments described herein, is for use in inhibiting a biological activity of a kinase. In some such embodiments, the compound is represented Formula VIA and/or VIB herein.

According to another aspect of some embodiments of the present invention, there is provided a method of inhibiting a biological activity of a kinase, the method comprising contacting the kinase with a compound according to any of the embodiments described herein. In some such embodiments, the compound is represented Formula VIA and/or VIB herein.

In some embodiments, the use and/or method for inhibiting a kinase is effected ex vivo (e.g., in vitro), for example, in research.

In some embodiments, the use and/or method for inhibiting a kinase is effected in vivo, for example by administering a therapeutically effective amount of the compound to a subject in need thereof.

According to another aspect of some embodiments of the present invention, there is provided a use of a compound according to any of the embodiments described herein in the manufacture of a medicament for use in inhibiting a biological activity of a kinase in a subject in need thereof. In some such embodiments, the compound is represented Formula VIA and/or VIB herein.

In some embodiments of any one of the embodiments described herein relating to a use, method and/or medicament for inhibiting a biological activity of a kinase, the use, method and/or medicament (according to any of the respective embodiments described herein) is for use in treating a disease or disorder associated with a biological activity of a kinase in a subject in need thereof.

In some embodiments of any one of the embodiments described herein relating to a use, method and/or medicament for inhibiting a biological activity of a kinase, the use, method and/or medicament is for use in treating a disease or disorder in which inhibition of a biological activity of a kinase is beneficial.

In some embodiments of any one of the embodiments described herein relating to a use, method and/or medicament for inhibiting a biological activity of a kinase, the use, method and/or medicament is for treating a disease or disorder which is treatable by inhibition of a biological activity of a kinase.

In some embodiments of any one of the embodiments described herein relating to a method or use for inhibiting a biological activity of a kinase, the inhibited kinase can be a kinase presented in Table 3 below, for example, DYRK3, EPHA8, GRK4, GRK5, MAP4K1, MAP4K2, MAP4K4, MELK, PAK7, SGK2, SRC N1, ACVRL1, BMPR1A, CDC7/DBF4, CDK1/cyclin A2, CDK11, CDK8/cyclin C, CLK4, DAPK2, DURK2, ICK, MAPK10, MLCK, MYLK, NUAK2, STK17A, STK17B, STK38, STK38L, TGFBR2, TTK, DAPK1, PIK3CA and/or PIK3CD.

According to a specific embodiment, the kinase is a PI3K.

In some embodiments of any one of the embodiments described herein relating to a method or use for inhibiting a biological activity of a kinase, the inhibited kinase is a serine/threonine kinase. In some embodiments, the serine/threonine kinase is a serine/threonine kinase presented in Table 3 below.

In some embodiments of any one of the embodiments described herein relating to a method or use for inhibiting a biological activity of a kinase, the inhibited kinase is a tyrosine kinase. In some embodiments, the tyrosine kinase is a serine/threonine kinase presented in Table 3 below.

In some embodiments of any one of the embodiments described herein relating to a method or use for inhibiting a biological activity of a kinase, the kinase is MELK, MAP4K4 and/or PI3K.

Cancer Treatment:

According to some embodiments, a small molecule compound of Formula I, II, III, IV, V, VI, VIA and/or VIB, and/or a compound presented in Table 2, as described herein in any of the respective embodiments, and any combination thereof, is capable of, or is usable, in treating cancer.

According to some embodiments, a small molecule compound of Formula I, II, III, IV, V, VI, VIA and/or VIB, and/or a compound presented in Table 2, as described herein in any of the respective embodiments, and any combination thereof, is capable of, or is usable, in inducing death of cancer cells (killing cancer cells).

According to some embodiments, a small molecule compound of Formula I, II, III, IV, V, VI, VIA and/or VIB, and/or a compound presented in Table 2, as described herein in any of the respective embodiments, and any combination thereof, is capable of, or is usable, inducing apoptosis in cancer cells.

According to some embodiments, a small molecule compound of Formula I, II, III, IV, V, VI, VIA and/or VIB, and/or a compound presented in Table 2, as described herein in any of the respective embodiments, and any combination thereof, is capable of, or is usable, in inducing growth arrest in cancer cells, and in some embodiments, the arrest is at the G2M phase of the cell cycle.

According to an aspect of some embodiments of the present invention, there is provided a method of treating a cancer in a subject in need thereof, the method comprising administering to the subject a therapeutically effective amount of a small molecule compound according to any of the embodiments described herein, thereby treating the cancer.

According to an aspect of some embodiments of the present invention, there is provided a use of a small molecule compound according to any of the embodiments described herein in the manufacture of a medicament for treating cancer.

According to an aspect of some embodiments of the present invention, there is provided a use of a small molecule compound according to any of the embodiments described herein in treating cancer.

As used herein, the terms "cancer" and "tumor" are interchangeably used. The terms refer to a malignant growth and/or tumor caused by abnormal and uncontrolled cell proliferation (cell division). The term "cancer" encompasses tumor metastases. The term "cancer cell" describes the cells forming the malignant growth or tumor.

Non-limiting examples of cancers and/or tumor metastases which can be treated according to some embodiments of any of the embodiments described herein relating to cancer (including any of the aspects described herein) include any solid or non-solid cancer and/or tumor metastasis, including, but not limiting to, tumors of the gastrointestinal tract (e.g., colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic breast cancer, susceptibility to breast cancer, type 4 breast cancer, breast cancer-1, breast cancer-3, breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B-cell lymphoma, Diffuse large B-cell lymphoma (DLBCL), Burkitt lymphoma, cutaneous T-cell lymphoma, histiocytic lymphoma, lymphoblastic lymphoma, T-cell lymphoma, thymic lymphoma), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B-cell), hypernephroma, insulinoma, islet tumor, keratoma, leiomyoblastoma, leiomyosarcoma, leukemia (e.g., acute lymphatic leukemia, acute lymphoblastic leukemia, acute lymphoblastic pre-B cell leukemia, acute lymphoblastic T cell leukemia, acute megakaryoblastic leukemia, monocytic leukemia, acute myelogenous leukemia, acute myeloid leukemia, acute myeloid leukemia with eosinophilia, B-cell leukemia, basophilic leukemia, chronic myeloid leukemia, chronic B-cell leukemia, eosinophilic leukemia, Friend leukemia, granulocytic or myelocytic leukemia, hairy cell leukemia, lymphocytic leukemia, megakaryoblastic leukemia, monocytic leukemia, monocytic-macrophage leukemia, myeloblastic leukemia, myeloid leukemia, myelomonocytic leukemia, plasma cell leukemia, pre-B cell leukemia, promyelocytic leukemia, subacute leukemia, T-cell leukemia, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme, multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

In some embodiments of any one of the embodiments described herein relating to cancer, the cancer is a leukemia, a lymphoma, ovarian cancer, neuroblastoma, a prostate cancer and/or a lung cancer.

Examples of leukemias which may be treated in the context of some embodiments of the invention include, without limitation, acute leukemias, for example, acute myeloid leukemia (AML), chronic myeloid leukemia (CML) and acute lymphoblastic leukemia.

Examples of lymphomas which may be treated in the context of some embodiments of the invention include, without limitation, diffuse large B-cell lymphoma (DLBCL), multiple myeloma and non-Hodgkin's lymphomas. Burkitt lymphoma is a non-limiting example of a non-Hodgkin's lymphoma.

Examples of lung cancers which may be treated in the context of some embodiments of the invention include, without limitation, large cell lung cancer and small cell lung cancer.

In some embodiments of any one of the embodiments described herein relating to cancer, the cancer is characterized by cells expressing CXCR4. In some such embodiments, the compound for use in treating cancer is any one of the compounds described herein as being for use in inhibiting SDF-1 and/or CXCR4 activity.

Without being bound by any particular theory, it is believed that in cancers characterized by expression of CXCR4, the activity of SDF-1 and CXCR4 is generally associated with metastasis, and thus, treatment with an inhibitor of SDF-1 and/or CXCR4 activity is particularly advantageous.

In some embodiments of any one of the embodiments described herein relating to treatment of cancer, the cancer further comprises administering at least one additional anti-cancer agent (i.e., in addition to the compound described hereinabove).

The additional anti-cancer agent may be any agent used in the medical arts to treat a cancer. Examples of anti-cancer agents include, without limitation, acivicin; aclarubicin; acodazole hydrochloride; acronine; adriamycin; Adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; combrestatin A-4 phosphate; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interferon alfa-2a; interferon alfa-2b; interferon alfa-n1; interferon alfa-n3; interferon beta-Ia; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ombrabulin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofuirin; tirapazamine; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine; vincristine sulfate; vindesine; vindesine sulfate; vinepidinee; vinglycinate; vinleurosine; vinorelbine tartrate; vinrosidine; vinzolidine; vorozole; zeniplatin; zinostatin; and zorubicin hydrochloride. Additional anti-cancer agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division), the contents of which are incorporated herein by reference.

In some embodiments of any of the embodiments described herein, the additional anti-cancer agent is characterized in that resistance of cancer cells to the agent is associated with an activity of SDF-1 and/or CXCR4 and/or any one of the kinases described in Table 1 herein. In some such embodiments, the compound for use in combination with the additional anti-cancer agent is any one of the compounds described herein.

In some embodiments of any of the embodiments described herein, the at least one additional anti-cancer agent comprises combrestatin A-4 phosphate, ombrabulin and/or any other derivative of combrestatin.

Without being bound by any particular theory, it is believed that the anti-therapeutic effect of combrestatin derivatives such as combrestatin A-4 phosphate and ombrabulin is reduced by SDF-1/CXCR4 activity.

In some embodiments of any of the embodiments described herein relating to treating a cancer, treating a cancer does not comprise illuminating the compound in situ (within or on a surface of the body of the subject) at a wavelength absorbed by the compound, e.g., as in photodynamic therapy.

Herein, the term "illuminating" refers to irradiating a target (e.g., a body of a subject) with electromagnetic radiation having a wavelength in a range of from 300 to 1000 nm.

The compounds presented in Table 2 are non-limiting examples of compounds which may be used for treating cancer according to any of the respective embodiments described herein. In some such embodiments, the compound is Compound BKT206, BKT211, BKT215, or BKT300, as presented in Table 2. In some embodiments, the compound is Compound BKT206, BKT211, or BKT300. In some embodiments, the compound is Compound BKT204, BKT214, or BKT300. In some embodiments, the compound is Compound BKT204 or BKT214.

In some embodiments of any one of the embodiments described herein relating to use of a compound having general Formula I for treating a cancer, $L_2$ in Formula I is absent or is —C(=O)— or —C($R_2$)(OH)—, in accordance with any of the respective embodiments described herein.

In some embodiments of any one of the embodiments described herein relating to use of a compound having general Formula I for treating a cancer, X in Formula I is —$CR_3$=$CR_4$—$CR_5$=$CR_6$—, a substituted or unsubstituted bicyclic hydrocarbon moiety or substituted or unsubstituted phenylene, in accordance with any of the respective embodiments described herein.

In some embodiments of any one of the embodiments described herein relating to use of a compound having general Formula I for treating a cancer, $L_2$ in Formula I is absent or is —C(=O)— or —C($R_2$)(OH)—, and X in Formula I is —$CR_3$=$CR_4$—$CR_5$=$CR_6$—, a substituted or unsubstituted bicyclic hydrocarbon moiety, or substituted or unsubstituted phenylene, in accordance with any of the respective embodiments described herein.

In some embodiments of any one of the embodiments described herein relating to use of a compound having general Formula I for treating a cancer, Z is —C(=O)OH, Y is absent and $L_2$ is absent or is —C($R_2$)(OH)—. In some such embodiments, X is cyclic, being, for example, a substituted or unsubstituted bicyclic hydrocarbon moiety, and/or a substituted or unsubstituted phenylene, according to any of the respective embodiments described herein. In some such embodiments, $L_2$ is absent.

Compound BKT206 is an example of a compound wherein Z is —C(=O)OH, $L_2$ and Y are each absent, and X is a phenylene. Compound BKT211 is an example of a compound wherein Z is —C(=O)OH, $L_2$ and Y are each absent, and X is a bicyclic hydrocarbon. As exemplified herein, Compounds BKT206 and BKT211 each exhibited anticancer activity in a leukemia cell model.

In some embodiments of any one of the embodiments described herein relating to use of a compound having general Formula II for treating cancer, Q is —C(=O)—. In some such embodiments, J is —O— or —CH=, optionally —O—. In some such embodiments, K is —$CR_{16}R_{17}$— wherein $R_{16}$ is alkyl or phenyl, each being substituted or unsubstituted.

Compounds BKT201, BKT204 and BKT300 (e.g., 78% and 98% purity) are examples of compounds in which Q is —C(=O)—. As exemplified herein, Compound BKT300 exhibited anticancer activity in a leukemia cell model.

Non-Cancerous Hyperproliferative Diseases:

Non-cancerous hyperproliferative diseases also referred to "non-neoplastic diseases" refer to diseases or disorders which onset or progression is associated with non-malignant cell proliferation. Examples of such medical conditions include, but are not limited to atherosclerosis, rheumatoid arthritis, psoriasis, fibrosis, idiopathic pulmonary fibrosis, scleroderma and cirrhosis of the live.

Inflammatory Diseases and Disorders:

Inflammatory diseases and disorders generally encompass diseases and disorders associated with inflammation.

The term "inflammation" as used herein refers to the general term for local accumulation of fluids, plasma proteins, and white blood cells initiated by physical injury, infection, or a local immune response. Inflammation may be associated with several signs e.g. redness, pain, heat, swelling and/or loss of function. Inflammation is an aspect of many diseases and disorders, including but not limited to diseases related to immune disorders, viral and bacterial infection, arthritis, autoimmune diseases, collagen diseases, allergy, asthma, pollinosis, and atopy (as described in further detail below).

Thus, inflammation can be triggered by injury, for example injury to skin, muscle, tendons, or nerves. Inflammation can be triggered as part of an immune response, e.g., pathologic autoimmune response. Inflammation can also be triggered by infection, where pathogen recognition and tissue damage can initiate an inflammatory response at the site of infection.

Inflammation according to the present teachings may be associated with chronic (long term) inflammatory diseases or disorders or acute (short term) inflammatory diseases or disorders.

According to a specific embodiment, the inflammation is associated with a disease selected from the group consisting of an infectious disease, an autoimmune disease, a hypersensitivity associated inflammation, a graft rejection and an injury.

According to a specific embodiment, the inflammation comprises a skin inflammation.

According to a specific embodiment the skin inflammation is psoriasis.

Diseases characterized by inflammation of the skin, include but are not limited to dermatitis, atopic dermatitis (eczema, atopy), contact dermatitis, dermatitis herpetiformis, generalized exfoliative dermatitis, seborrheic dermatitis, drug rashes, erythema multiforme, erythema nodosum, granuloma annulare, poison ivy, poison oak, toxic epidermal necrolysis, roseacae, psoriasis and acne. Inflammation can also result from physical injury to the skin.

Inflammation may be triggered by various kinds of injuries to muscles, tendons or nerves. Thus, for example, inflammation may be caused by repetitive movement of a part of the body i.e. repetitive strain injury (RSI). Diseases characterized by inflammation triggered by RSI include, but are not limited to, bursitis, carpal tunnel syndrome, Dupuytren's contracture, epicondylitis (e.g. tennis elbow), ganglion (i.e. inflammation in a cyst that has formed in a tendon sheath, usually occurring on the wrist), rotator cuff syndrome, tendinitis (e.g., inflammation of the Achilles tendon), tenosynovitis, and trigger finger (inflammation of the tendon sheaths of fingers or thumb accompanied by tendon swelling).

Many diseases related to infectious diseases include inflammatory responses, where the inflammatory responses are typically part of the innate immune system triggered by the invading pathogen. Inflammation can also be triggered by physical (mechanical) injury to cells and tissues resulting from the infection. Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases. According to one embodiment, examples of infections characterized by inflammation include, but are not limited to, encephalitis; meningitis; encephalomyelitis; viral gastroenteritis; viral hepatitis.

Furthermore, many immune disorders include acute or chronic inflammation. For example, arthritis is considered an immune disorder characterized by inflammation of joints, but arthritis is likewise considered an inflammatory disorder characterized by immune attack on joint tissues.

Inflammation according to the present teachings may be associated with a deficient immune response (e.g., HIV, AIDS) or with an overactive immune response (e.g., allergy, autoimmune disorders). Thus, inflammation according to the present teachings may be associated with any of the following:

Inflammatory Diseases Associated with Hypersensitivity:

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000

August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

According to a specific embodiment, the ocular disease is age-related macular degeneration (AMD).

According to a specific embodiment, the age-related macular degeneration (AMD) is atrophic, non-neovascular (aAMD).

According to a specific embodiment, the age-related macular degeneration (AMD) is neovascular.

Autoimmune Diseases:

Autoimmune diseases include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

According to one embodiment, the autoimmune disease is Crohn's disease, psoriasis, scleroderma or rheumatoid arthritis.

Graft Rejection Diseases:

Examples of diseases associated with transplantation of a graft include, but are not limited to, graft rejection, chronic graft rejection, subacute graft rejection, hyperacute graft rejection, acute graft rejection and graft versus host disease.

Allergic Diseases:

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Pharmaceutical Compositions:

The compounds described herein according to any of the aspects of embodiments of the invention described herein can be utilized (e.g., administered to a subject) per se or in a pharmaceutical composition where the compound is mixed with suitable carriers or excipients.

As used herein a "pharmaceutical composition" refers to a preparation of one or more compound according to any of the embodiments described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

When utilized per se or in a pharmaceutically acceptable composition, the compound per se (that is, not including, weight of carriers or excipients co-formulated with the compound, as described herein) is optionally at least 80% pure (by dry weight), optionally at least 90% pure (by dry weight), at least 95% pure (by dry weight), at least 98% pure (by dry weight), and optionally at least 99% pure (by dry weight). Purity may be enhanced, e.g., by removing impurities associated with synthesis of the compound or isolation of the compound from a natural source, by any suitable technique known in the art. As exemplified herein, impurities of a compound described herein (for example, BKT300) may weaken a biological effect of the compound.

Techniques for formulation and administration of drugs may be found in "Remington's Pharmaceutical Sciences", Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, breast tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the active compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of the active ingredient(s) effective to prevent, alleviate or ameliorate symptoms of a disorder (e.g., cancer or metastatic cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (see, e.g., Fingl et al. (1975), in "The Pharmacological Basis of Therapeutics", Ch. 1 p. 1).

Dosage amount and interval may be adjusted individually to provide protein (e.g., MIP3a, MCP-1, SDF-1 and/or CXCR4, and/or a kinase) inhibitory levels of the active ingredient which are sufficient to induce or suppress the biological effect (minimal effective concentration, MEC). The MEC will vary for each preparation, but can be estimated from in vitro data, e.g., based on results of a chemokine-induced (e.g., MIP3a-, MCP-1- and/or SDF-1-induced) migration inhibition assay described herein and/or results of a kinase inhibition assay and/or results of cell viability assay as described herein. Dosages necessary to achieve the MEC will depend on individual characteristics and route of administration. Detection assays can be used to determine plasma concentrations.

In some embodiments of any of the embodiments described herein, an effective amount of the compound is less than 100 μM. In some embodiments, an effective amount is less than 10 μM. In some embodiments, an effective amount is less than 5 μM. In some embodiments, an effective amount is less than 2.5 μM.

In some embodiments of any of the embodiments described herein, an effective amount is at least 100% of the IC50 of the compound towards a chemokine which is intended to be inhibited (e.g., MIP3a, MCP-1 and/or SDF-1). In some embodiments, an effective amount is at least 200% of the IC50 of the compound towards the chemokine. In some embodiments, an effective amount is at least 300% of the IC50 of the compound towards the chemokine. In some embodiments, an effective amount is at least 500% of the IC50 of the compound towards the chemokine. In some embodiments, an effective amount is at least 1000% of the IC50 of the compound towards the chemokine.

In some embodiments of any of the embodiments described herein, an effective amount is at least 100% of the IC50 of the compound towards inducing cell death of cancer cells to be inhibited. In some embodiments, an effective amount is at least 200% of the IC50 of the compound towards the cancer cells. In some embodiments, an effective amount is at least 300% of the IC50 of the compound towards the cancer cells.

In some embodiments of any of the embodiments described herein, an effective amount is at least 100% of the IC50 of the compound towards a kinase. In some embodiments, an effective amount is at least 200% of the IC50 of the compound towards a kinase. In some embodiments, an effective amount is at least 300% of the IC50 of the compound towards the kinase.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed herein.

According to another aspect described herein, there is provided a kit for the treatment of a condition (e.g., treatment of cancer or prevention of tumor metastasis or treatment of non-cancerous proliferative disease or disorder or treatment of inflammation) described herein, the kit comprising a packaging material packaging the compound described herein.

In some embodiments, the compound is identified as an inhibitor of an SDF-1 and/or CXCR4 activity associated with an onset or progression of the condition, as described herein.

In some embodiments, the compound is identified as an inhibitor of a kinase activity associated with an onset or progression of the condition, as described herein.

In some embodiments, the compound is identified as inducing apoptosis and/or cell growth arrest of cells associated with the condition, as described herein.

It will be appreciated that the compounds described herein can be provided or utilized, in any of the methods, uses, compositions and kits described herein, and any embodiments thereof, alone or in combination with other active ingredients, which are well known in the art for alleviating the medical condition.

Thus, for example, the compound may be administered with an immunomodulator, either together in a co-formulation or in separate formulations.

According to a specific embodiment, the treatment of cancer (and other hyperproliferative disorders) is effected in combination with an anti-cancer immune modulator agent.

As used herein, the term "anti-cancer immune modulator agent" refers to an agent capable of eliciting an immune response (e.g. T cell, NK cell) against a cancerous cell.

According to specific embodiment, the agent is selected from the group consisting of a cancer antigen, a cancer vaccine, an anti-cancer antibody, a cytokine capable of inducing activation and/or proliferation of a T cell and an immune-check point regulator.

Alternatively or additionally, such modulators may be immune stimulators such as immune-check point regulators which are of specific value in the treatment of cancer.

As used herein the term "immune-check point regulator" refers to a molecule that modulates the activity of one or more immune-check point proteins in an agonistic or antagonistic manner resulting in activation of an immune cell.

As used herein the term "immune-check point protein" refers to a protein that regulates an immune cell activation or function. Immune check-point proteins can be either co-stimulatory proteins (i.e. transmitting a stimulatory signal resulting in activation of an immune cell) or inhibitory proteins (i.e. transmitting an inhibitory signal resulting in suppressing activity of an immune cell). According to specific embodiment, the immune check point protein regulates activation or function of a T cell. Numerous checkpoint proteins are known in the art and include, but not limited to, PD1, PDL-1, B7H2, B7H4, CTLA-4, CD80, CD86, LAG-3, TIM-3, KIR, IDO, CD19, OX40, 4-1BB (CD137), CD27, CD70, CD40, GITR, CD28 and ICOS (CD278).

According to specific embodiments, the immune-checkpoint regulator is selected form the group consisting of anti-CTLA4, anti-PD-1, and CD40 agonist.

According to specific embodiments, the immune-check point regulator is selected form the group consisting of anti-CTLA4, anti-PD-1, anti-PDL-1, CD40 agonist, 4-1BB agonist, GITR agonist and OX40 agonist.

CTLA4 is a member of the immunoglobulin superfamily, which is expressed on the surface of Helper T cells and transmits an inhibitory signal to T cells upon ligand binding. As used herein, the term "anti-CTLA4" refers to an antagonistic molecule that binds CTLA4 (CD152) and suppresses its suppressive activity. Thus, an anti-CTLA4 prevents the transmission of the inhibitory signal and thereby acts as a co-stimulatory molecule. According to a specific embodiment, the anti-CDLA4 molecule is an antibody.

PD-1 (Programmed Death 1) is a member of the extended CD28/CTLA-4 family of T cell regulators which is expressed on the surface of activated T cells, B cells, and macrophages and transmits an inhibitory signal upon ligand binding. As used herein, the term "anti-PD1" refers to an antagonistic molecule that binds PD-1 and suppresses its suppressive activity. Thus, an anti-PD-1 prevents the transmission of the inhibitory signal and thereby acts as a co-stimulatory molecule. According to a specific embodiment, the anti-PD1 molecule is an antibody. Numerous anti-PD-1 antibodies are known in the art see e.g. Topalian, et al. NEJM 2012.

PDL-1 is a ligand of PD-1. Binding of PDL-1 to its receptor PD-1 transmits an inhibitory signal to the cell expressing the PD-1. As used herein, the term "anti-PDL-1" refers to an antagonistic molecule that inhibits PD-1 signaling by binding to or inhibiting PD-L1 from binding and/or activating PD-1. Thus, an anti-PD-1 prevents the transmission of the inhibitory signal and thereby acts as a co-stimulatory molecule. According to specific embodiments, the anti-PD-L1 is an anti-PD-L1 antibody. Numerous anti-PDL-1 antibodies are known in the art see e.g. Brahmer, et al. NEJM 2012.

CD40 (CD154) is a co-stimulatory receptor found on antigen presenting cells and transmits an activation signal upon ligand binding. As used herein, the term "CD40 agonist" refers to an agonistic molecule that binds CD40 (CD154) and thereby induces activation of the antigen presenting cell.

OX40 belongs to the TNF receptor super family and leads to expansion of CD4+ and CD8+ T cells. As used herein, the term "OX40 agonist" refers to an agonistic molecule that binds and activates OX40.

GITR (glucocorticoid-induced tumor necrosis factor receptor) is a surface receptor molecule that has been shown to be involved in inhibiting the suppressive activity of T-regulatory cells and extending the survival of T-effector cells. As used herein, the term "GITR agonist" refers to an agonistic molecule that binds and activates GITR. According to a specific embodiment, the GITR agonist is an antibody.

Definitions

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. For example, in the context of preventing metastasis and/or angiogenesis, the term "preventing" refers to arresting, halting, inhibiting the metastatic and/or angiogenetic process or progression and subsequent metastasis and/or angiogenesis.

As used herein the term "subject" refers to a mammal (e.g., human), for example, one who has been diagnosed with a condition described herein (e.g., cancer).

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein throughout, the phrase "linking group" describes a group (a substituent) that is attached to another moiety in the compound via two or more atoms thereof. In order to differentiate a linking group from a substituent that is attached to another moiety in the compound via one atom thereof, the latter will be referred to herein and throughout as an "end group".

As used herein, the term "amine" describes both a —NR'R" end group and a —NR'— linking group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NR'— group in cases where the amine is or forms a part of a linking group.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a medium size alkyl having 1 to 10 carbon atoms. Unless otherwise indicated, the alkyl is a lower alkyl having 1 to 4 carbon atoms. In some embodiments, the alkyl has at least 4 carbon atoms, for example, the alkyl is having 4 to 12 or 4 to 10 or 4 to 8 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfinate, sulfate, sulfonate, sulfoxide, phosphonate, oxo, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain. When an alkyl is a linking group, it is also referred to herein as "alkylene", e.g., methylene, ethylene, propylene, etc.

The term "alkenyl" describes an alkyl, as defined herein, in which at least one pair of carbon atoms are linked to one another via a double bond.

The term "alkynyl" or "alkyne" describes an alkyl, as defined herein, in which at least one pair of carbon atoms are linked to one another via a triple bond.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, oxo, sulfinate, sulfate, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, oxo, sulfinate, sulfate, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofurane, tetrahydropyrane, morpholino and the like.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, oxo, sulfinate, sulfate, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof. Preferably, the aryl is phenyl. Optionally, the aryl is naphthalenyl.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, triazine, tetrazine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N— carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof.

The term "alkaryl" describes an alkyl, as defined herein, which is substituted by one or more aryl or heteroaryl groups. An example of alkaryl is benzyl.

The term "halide" and "halo" describes fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" or "sulfinyl" describes a —S(=O)—OR' end group or an —S(=O)—O— group linking group, as these phrases are defined hereinabove, where R' is as defined hereinabove.

The term "sulfoxide" describes a —S(=O)R' end group or an —S(=O)— linking group, as these phrases are defined hereinabove, where R' is as defined hereinabove.

The term "sulfonate" or "sulfonyl" describes a —S(=O)$_2$—OR' end group (also referred to herein as —SO$_3$R' or —SO$_3$H) or an —O—S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "phosphonate" describes a —P(=O)(OR')(OR") end group or a —P(=O)(OR')(O)— linking group, as these phrases are defined hereinabove, with R' and R" as defined herein.

The term "thiophosphonate" describes a —P(=S)(OR')(OR") end group or a —P(=S)(OR')(O)— linking group, as these phrases are defined hereinabove, with R' and R" as defined herein.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxo" as used herein, described a =O end group.

The term "thiooxo" as used herein, described a =S end group.

The term "oxime" describes a =N—OH end group or a =N—O— linking group, as these phrases are defined hereinabove.

The term "hydroxyl" or "hydroxy" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" or "thio" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" or "nitrile" describes a —C≡N group.

The term "isocyanate" describes an —N=C=O group.

The term "nitro" describes an —NO$_2$ group.

The term "carboxylate" as used herein encompasses C-carboxylate and O— carboxylate.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

The term "thiocarboxylate" as used herein encompasses "C-thiocarboxylate and O-thiocarboxylate.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

The term "carbamate" as used herein encompasses N-carbamate and O-carbamate.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

The term "thiocarbamate" as used herein encompasses N-thiocarbamate and O-thiocarbamate.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

The term "dithiocarbamate" as used herein encompasses N-dithiocarbamate and S-dithiocarbamate.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "amide" as used herein encompasses C-amide and N-amide.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "guanyl" describes a R'R"NC(=N)— end group or a —R'NC(=N)— linking group, as these phrases are defined hereinabove, where R' and R" are as defined herein.

The term "guanidine" describes a —R'NC(=N)—NR"R'" end group or a —R'NC(=N)— NR"— linking group, as these phrases are defined hereinabove, where R', R" and R'" are as defined herein.

The term "hydrazine" describes a —NR'—NR"R'" end group or a —NR'—NR"— linking group, as these phrases are defined hereinabove, with R', R", and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

For any of the embodiments described herein, the compound described herein may be in a form of a salt, for example, a pharmaceutically acceptable salt, and/or in a form of a prodrug.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of some of the present embodiments, a pharmaceutically acceptable salt of the compounds described herein may optionally be a base addition salt comprising at least one acidic (e.g., phenol and/or carboxylic acid) group of the compound which is in a negatively charged form (e.g., wherein the acidic group is deprotonated), in combination with at least one counter-ion, derived from the selected base, that forms a pharmaceutically acceptable salt.

The base addition salts of the compounds described herein may therefore be complexes formed between one or more acidic groups of the drug and one or more equivalents of a base.

The base addition salts may include a variety of organic and inorganic counter-ions and bases, such as, but not limited to, sodium (e.g., by addition of NaOH), potassium (e.g., by addition of KOH), calcium (e.g., by addition of $Ca(OH)_2$, magnesium (e.g., by addition of $Mg(OH)_2$), aluminum (e.g., by addition of $Al(OH)_3$ and ammonium (e.g., by addition of ammonia). Each of these acid addition salts can be either a mono-addition salt or a poly-addition salt, as these terms are defined herein.

Depending on the stoichiometric proportions between the charged group(s) in the compound and the counter-ion in the salt, the acid or base additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

As used herein, the term "prodrug" refers to a compound which is converted in the body to an active compound (e.g., the compound of the formula described hereinabove). A prodrug is typically designed to facilitate administration, e.g., by enhancing absorption. A prodrug may comprise, for example, the active compound modified with ester groups, for example, wherein any one or more of the hydroxyl groups of a compound is modified by an acyl group, optionally $(C_{1-4})$acyl (e.g., acetyl) group to form an ester group, and/or any one or more of the carboxylic acid groups of the compound is modified by an alkoxy or aryloxy group, optionally $(C_{1-4})$alkoxy (e.g., methyl, ethyl) group to form an ester group.

Further, each of the compounds described herein, including the salts thereof, can be in a form of a solvate or a hydrate thereof.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The compounds described herein can be used as polymorphs and the present embodiments further encompass any isomorph of the compounds and any combination thereof.

The present embodiments further encompass any enantiomers and diastereomers of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems. In the context of the present embodiments, a compound may exhibit one or more chiral centers, each of which exhibiting an R- or an S-configuration and any combination, and compounds according to some embodiments of the present invention, can have any their chiral centers exhibit an R- or an S-configuration.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, embodiments of the present invention encompass compounds with multiple chiral centers that occur in any combination of stereoconfiguration, namely any diastereomer.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:

Anti-human IgG-XL665 antibody was obtained from Cisbio Bioassays.

Ficoll Histopaque® 1077 was obtained from Sigma (Israel).

Biotin was obtained from Sigma (Israel).

Biotinylated MIP3a was obtained from Almac Sciences (UK).

Terbium cryptate-conjugated streptavidin (Lumi4®) was obtained from Cisbio Bioassays.

BKT130 was prepared as described in International Application publication WO2010/146584, in which BKT130 is referred to as "BKT-P2-FC". The sequence of BKT130 is also presented therein.

Compound BKT300 was obtained from AnalytiCon Discovery GmbH at 78% purity and at high purity. Using NMR spectroscopy, the high purity sample was determined to have a purity of about 98%, whereas the other sample was confirmed to have about 78% purity.

Migration Assay:

600 µl of RPMI medium was added to the lower chambers of Transwell® transmigration plates, supplemented with 2 µg/ml of MIP3a, 100 ng/ml of SDF-1 or 10 ng/ml of MCP-1. The tested small molecule was added to the lower chambers at the indicated concentration, except in control samples. The MIP3a, SDF-1 or MCP-1 was incubated with the small molecule for 30 minutes at room temperature before the initiation of the migration assay. Following 30 minutes of incubation $2 \times 10^5$ immune cells were added to the upper chambers of the transmigration plates in a total volume of 100 µl. Cells which migrated within 3 hours to the bottom chamber of the Transwell® plates were counted using a FACScalibur™ flow cytometer.

To evaluate migration toward MIP3a, peripheral blood mononuclear cells (PBMCs) were isolated from heparinized venous blood by centrifugation over Ficoll Histopaque® 1077. CD4+ T cells were further isolated with RosetteSep™ human CD4+ T-cell Enrichment cocktail (StemCell Technologies Inc.), according to the manufacturer's instructions. CD4+ T cells were re-suspended in RPMI medium containing 1% fetal calf serum (FCS).

To evaluate migration towards SDF-1, Jurkat cells were re-suspended in RPMI medium containing 1% fetal calf serum (FCS).

To evaluate migration towards MCP-1, THP-1 cells were re-suspended in RPMI medium containing 1% fetal calf serum (FCS).

Example 1

Screening Assay and Activity Assays Identifying Small Molecules which Bind to and Affect Migration of MIP3a A homogeneous time-resolved fluorescence (HTRF) assay was designed as a platform for high-throughput screening (HTS). This assay detected the interaction of BKT130 with MIP3a, using BKT130, biotinylated MIP3a, anti-human IgG-XL665 antibody (which binds to the Fc domain of BKT130) and Lumi4® terbium cryptate-conjugated streptavidin (which binds to the biotin moiety attached to MIP3a).

Biotinylated MIP3a or biotin was diluted in an assay buffer of phosphate buffer saline (PBS) with 0.1% bovine serum albumin (BSA) to a final concentration of 16.7 nM. A detection mix was formed by diluting BKT130, terbium-conjugated streptavidin and anti-human IgG-XL665 antibody in the assay buffer to concentrations of 92.5 nM, 0.01 ng/ml, and 0.9 ng/ml, respectively. 23 µl reactions were incubated in black non-binding 384-well plates (Greiner 784900) at room temperature for 45 minutes, and then read in a PHERAstar FS® high-throughput microplate reader (BMG LABTECH) with a dedicated HTRF laser excitation. HTRF reads are a function of resonant energy transfer from the terbium donor (emitting at a wavelength of 625) to the XL665 acceptor, which becomes excited and emits a fluorescent signal at a wavelength of 665 nm. Only donor/acceptor pairs that are brought into close proximity by binding of MIP3a to BKT130 will result in resonant energy transfer. Binding is expressed as the ratio of the signal High-throughput screening (HTS) was performed using an automated workstation with integrated 50 nl pin tool and BioTek™ EL406 dispenser. Compounds from a natural library of about 3,500 compounds were maintained in DMSO stock solutions of approximately 10 mM and then transferred to an assay mix containing biotin-MIP3a (or biotin control), and incubated for 15 minutes at room temperature to allow for compound binding. The detection mix was then added; plates were then incubated for a further 45 minutes at room temperature, and then read as described hereinabove.

Compounds with a significant inhibition of binding were selected and picked from the library for repeat assays in serial dilution to obtain dose response curves.

Analysis of the screen and curve fitting was done using the Genedata Screener® software package.

In the presence of BKT130 and biotinylated-MIP3a without any additional compounds, the signal ratio was 3621 (±409), which corresponded to 0% inhibition of binding (neutral control). In the presence of biotin alone and BKT130, the obtained signal ratio was 763 (±23), corresponding to 100% inhibition of binding (inhibitor control).

FIG. 1 shows the distribution of signals obtained from the HTS of the 3,500 compounds.

As shown in FIG. 1 and in Table 1, 32 of the 3,500 screened compounds inhibited the binding of BKT130 to MIP3a (as expressed by the ratio of the signal at 665 nm to the signal at 625 nm) by more than 40%.

TABLE 1

Effect of 32 most inhibitory compounds on binding of BKT130 to MIP3a

| Compound No. | FRET Signal Ratio | Change in binding |
|---|---|---|
| 1 | 915 | −92.2% |
| 2 | 946 | −91.5% |
| 3 | 1040 | −86.3% |
| 4 | 1265 | −78.8% |
| 5 | 1320 | −77.1% |
| 6 | 1528 | −68.6% |
| 7 | 1692 | −60.2% |
| 8 | 1615 | −60.0% |
| 9 | 1751 | −59.7% |
| 10 | 1722 | −59.7% |
| 11 | 1777 | −58.1% |
| 12 | 1748 | −57.7% |

TABLE 1-continued

Effect of 32 most inhibitory compounds on binding of BKT130 to MIP3a

| Compound No. | FRET Signal Ratio | Change in binding |
|---|---|---|
| 13 | 1797 | −57.5% |
| 14 | 1829 | −56.2% |
| 15 | 1814 | −54.9% |
| 16 | 1721 | −54.2% |
| 17 | 1842 | −54.1% |
| 18 | 1834 | −53.9% |
| 19 | 1927 | −52.2% |
| 20 | 1779 | −51.5% |
| 21 | 1911 | −51.2% |
| 22 | 1911 | −50.7% |
| 23 | 1945 | −49.8% |
| 24 | 2004 | −49.3% |
| 25 | 1793 | −49.3% |
| 26 | 2040 | −47.5% |
| 27 | 2021 | −46.6% |
| 28 | 2033 | −46.1% |
| 29 | 2098 | −45.4% |
| 30 | 1918 | −43.2% |
| 31 | 2143 | −41.5% |
| 32 | 2148 | −41.5% |

Of these 32 small molecules, 18 small molecules were found to both significantly inhibit the interaction between BKT130 and MIP3a in the high-throughput screening and showed a dose response curve in the serial dilution assay, and were selected for further analysis. The structures of the 18 small molecules are presented in Table 2 below.

TABLE 2

Compounds which exhibited dose response curve for MIP3a binding

| Comp. No. | Name | Structure |
|---|---|---|
| BKT200 | | 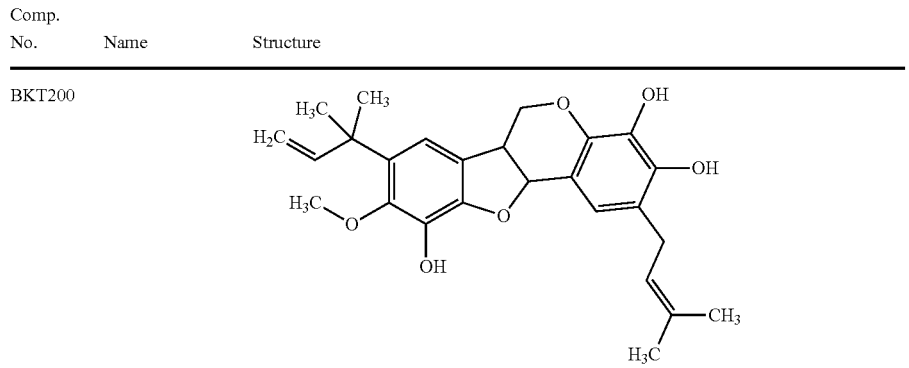 |
| BKT201 | | 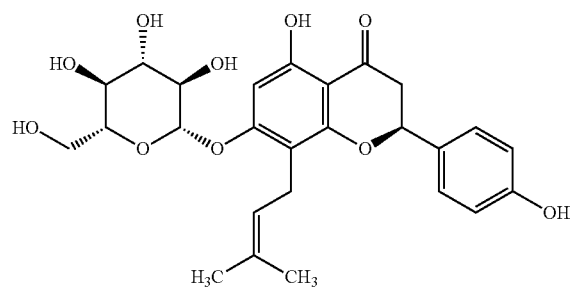 [SMILES: CC(C)=CCc1c(O[C@@H]2O[C@H](CO)[C@@H](O)[C@H](O)[C@H]2O)cc(O)c2c1O[C@H](c1ccc(O)cc1)CC2=O] |

TABLE 2-continued
Compounds which exhibited dose response curve for MIP3a binding
| Comp. No. | Name | Structure |
|---|---|---|
| BKT202 | | 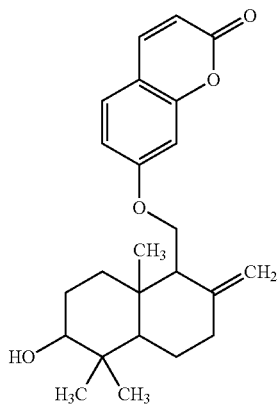 [SMILES: C=C1CCC2C(C)(C)C(O)CCC2(C)C1COc1ccc2ccc(=O)oc2c1] |
| BKT203 | Hypericin | 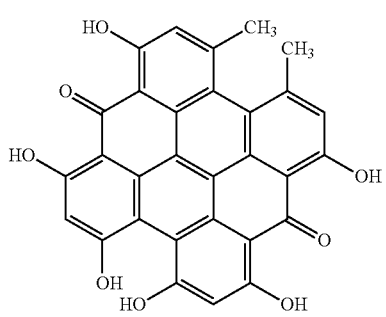 [SMILES: Cc1cc(O)c2c(=O)c3c(O)cc(O)c4c5c(O)cc(O)c6c(=O)c7c(O)cc(C)c8c1c2c(c34)c(c78)c65] |
| BKT204 | Cyrtominetin | 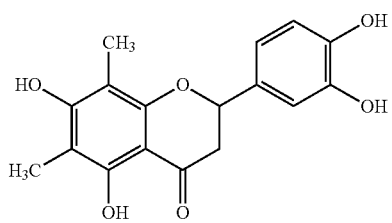 [SMILES: Cc1c(O)c(C)c2c(c1O)C(=O)CC(c1ccc(O)c(O)c1)O2] |
| BKT205 | | 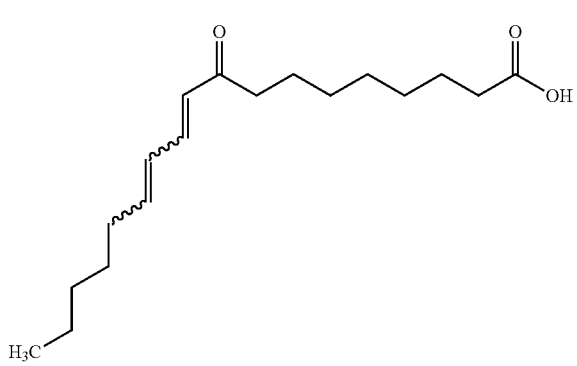 [SMILES: CCCCCC=CC=CC(=O)CCCCCCCC(=O)O] |
| BKT206 | | 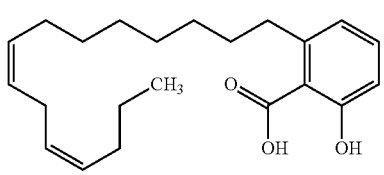 [SMILES: CCC/C=C\C/C=C\CCCCCCCc1cccc(O)c1C(=O)O] |

TABLE 2-continued
Compounds which exhibited dose response curve for MIP3a binding
| Comp. No. | Name | Structure |
|---|---|---|
| BKT207 | Aloesaponarin I | 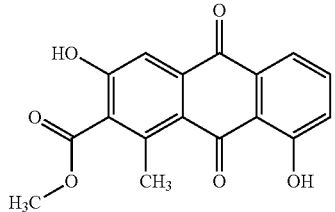 [SMILES: COC(=O)c1c(O)cc2c(c1C)C(=O)c1c(O)cccc1C2=O] |
| BKT208 | Trichoclin | 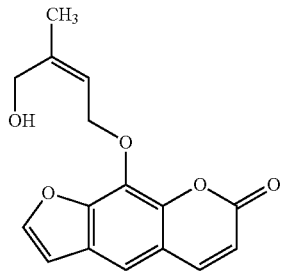 [SMILES: C/C(=C/COc1c2occc2cc2ccc(=O)oc12)CO] |
| BKT209 | | 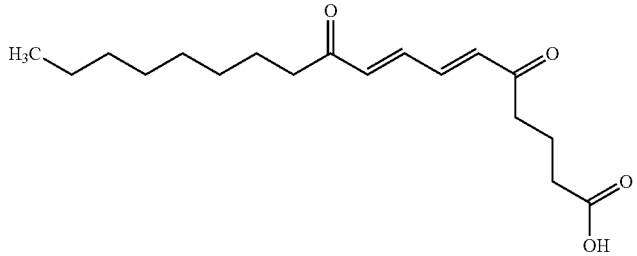 [SMILES: CCCCCCCCC(=O)/C=C/C=C/C(=O)CCCC(=O)O] |
| BKT210 | Sennoside A | 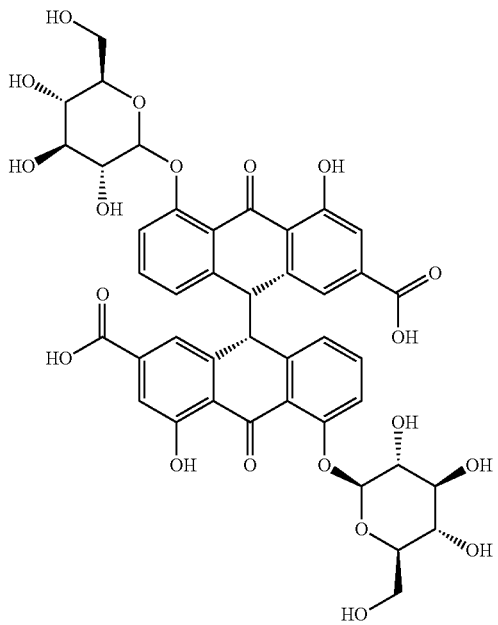 |

TABLE 2-continued
Compounds which exhibited dose response curve for MIP3a binding
| Comp. No. | Name | Structure |
|---|---|---|
| BKT211 | | 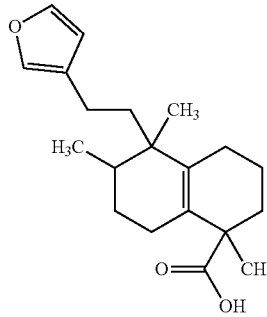 |
| BKT212 | Falcarindiol | 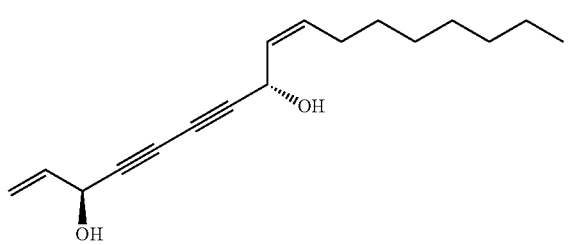 [SMILES: C=C[C@H](O)C#CC#C[C@@H](O)/C=C\CCCCCCC] |
| BKT213 | | 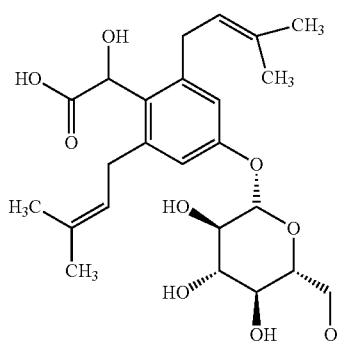 |
| BKT214 | | 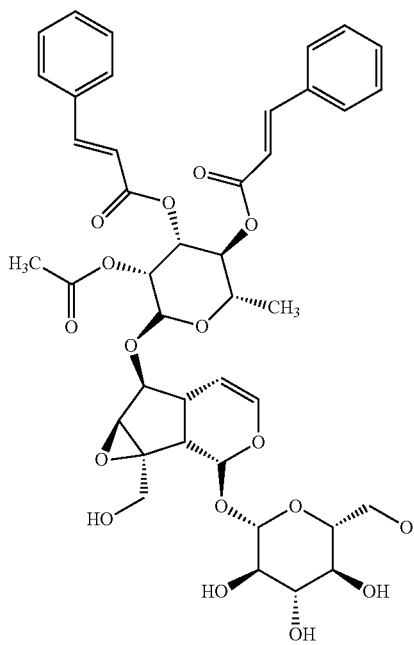 |

TABLE 2-continued

Compounds which exhibited dose response curve for MIP3a binding

| Comp. No. | Name | Structure |
|---|---|---|
| BKT215 | Auraptene | 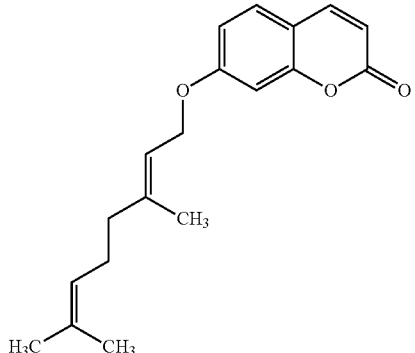 [SMILES: CC(C)=CCC/C(C)=C/COc1ccc2ccc(=O)oc2c1] |
| BKT216 | Arjunolic acid | 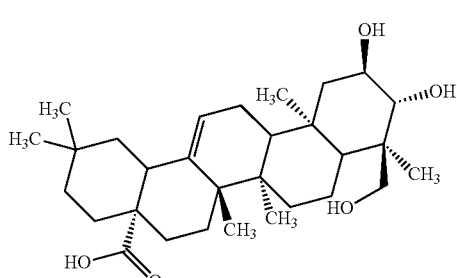 |
| BKT300 | | 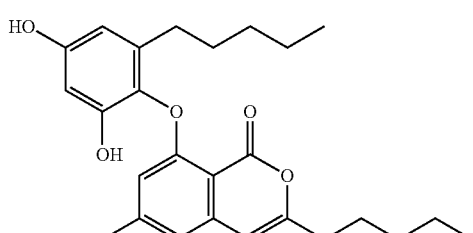 |

The 18 compounds uncovered by the screening assay were further tested for their ability, at final concentrations of 10 and 50 μg/ml, to inhibit the migration of human CD4+ T-cells toward MIP3a; using the procedures described in the Materials and Methods section hereinabove.

The results for 3 exemplary compounds presented in Table 2, Compounds BKT210, BKT203 and BKT207, which exhibited inhibition of CD4+ T-cells migration toward MIP3a, are presented herein.

Figure 2A:
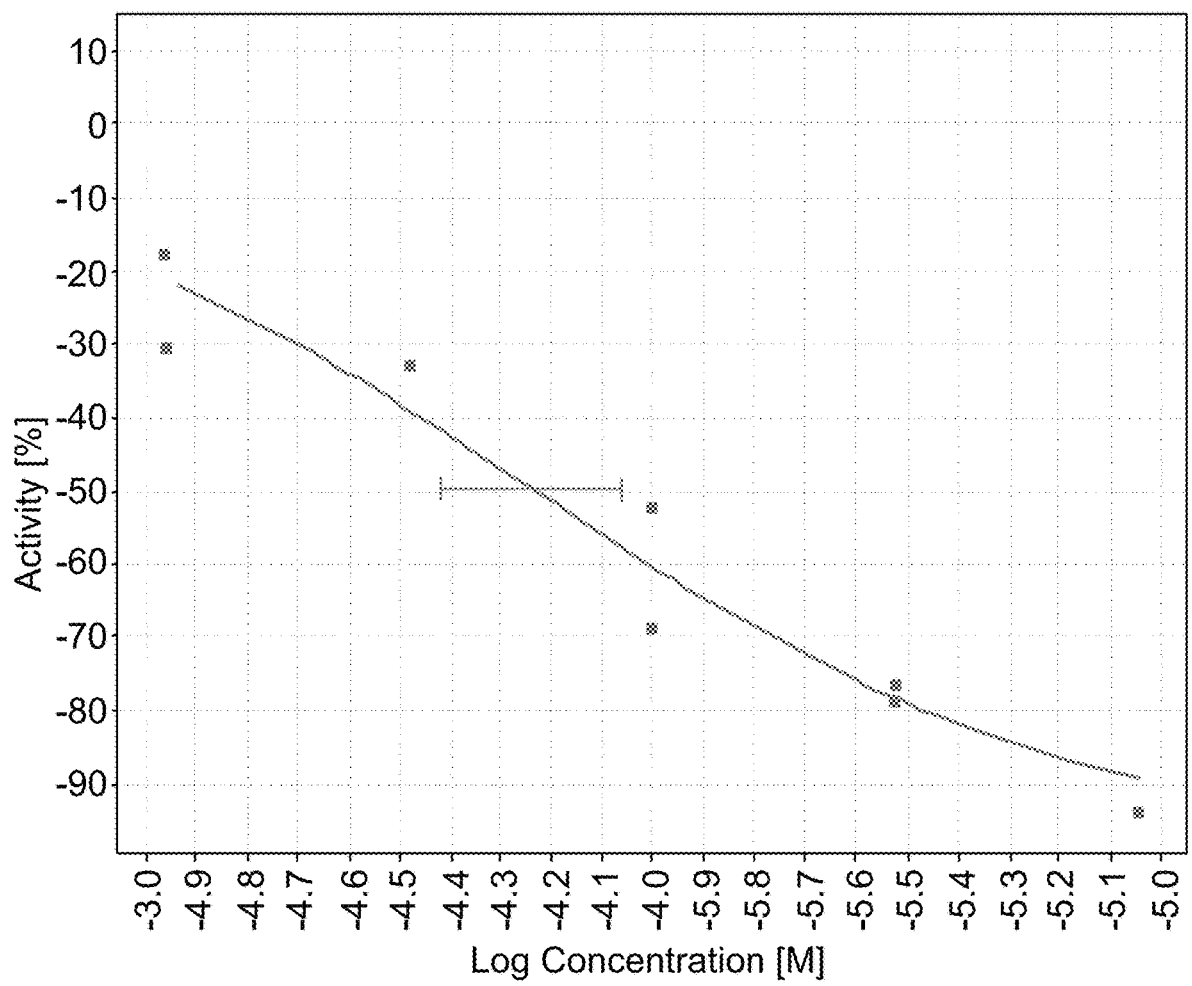
FIGS. 2A-2C are graphs showing the activity (inhibition of binding of BKT130 to MIP3a) of 3 exemplary compounds (one in each of FIGS. 2A-2C) as a function of concentration.
Figure 2B:
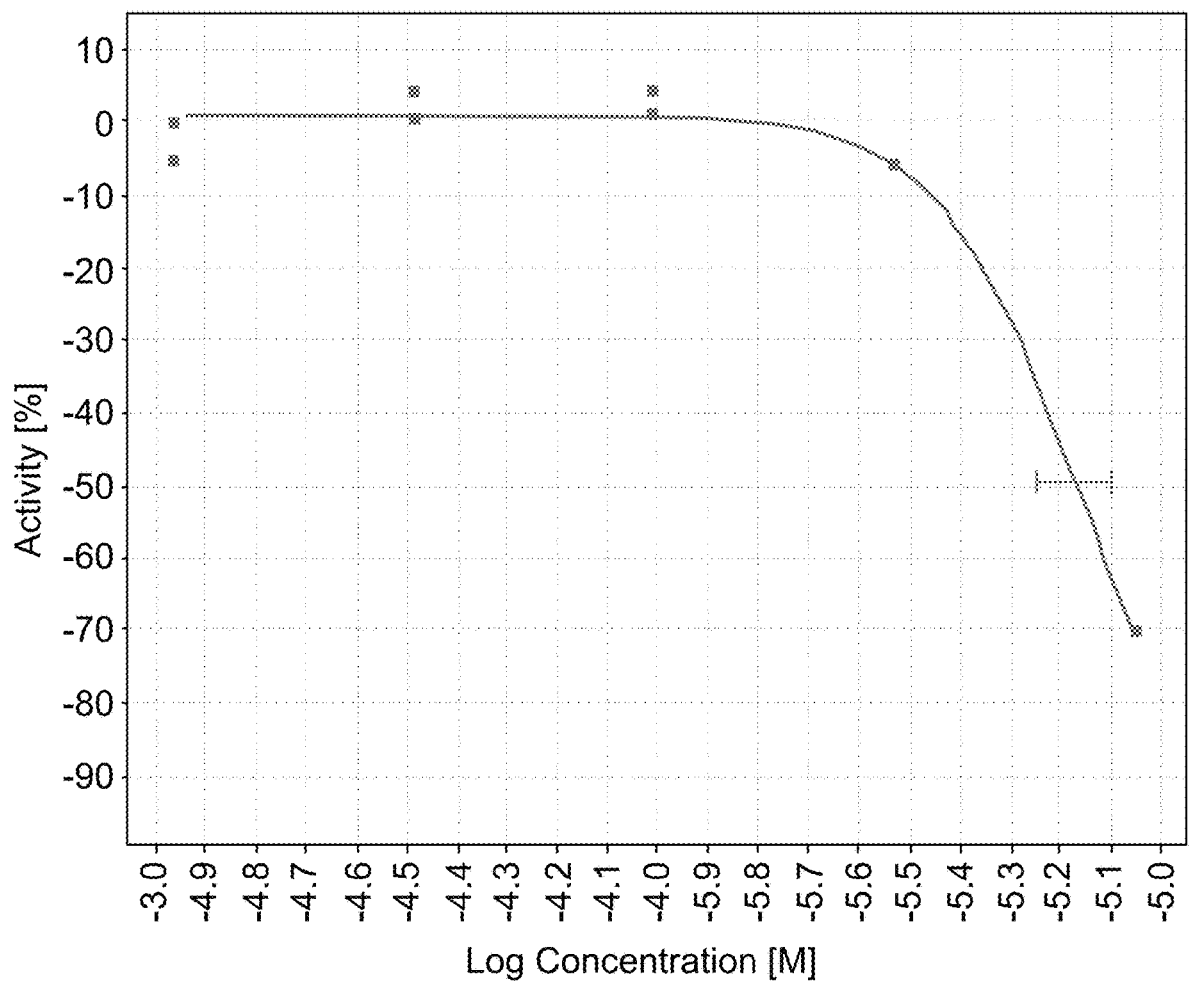
Figure 2C:
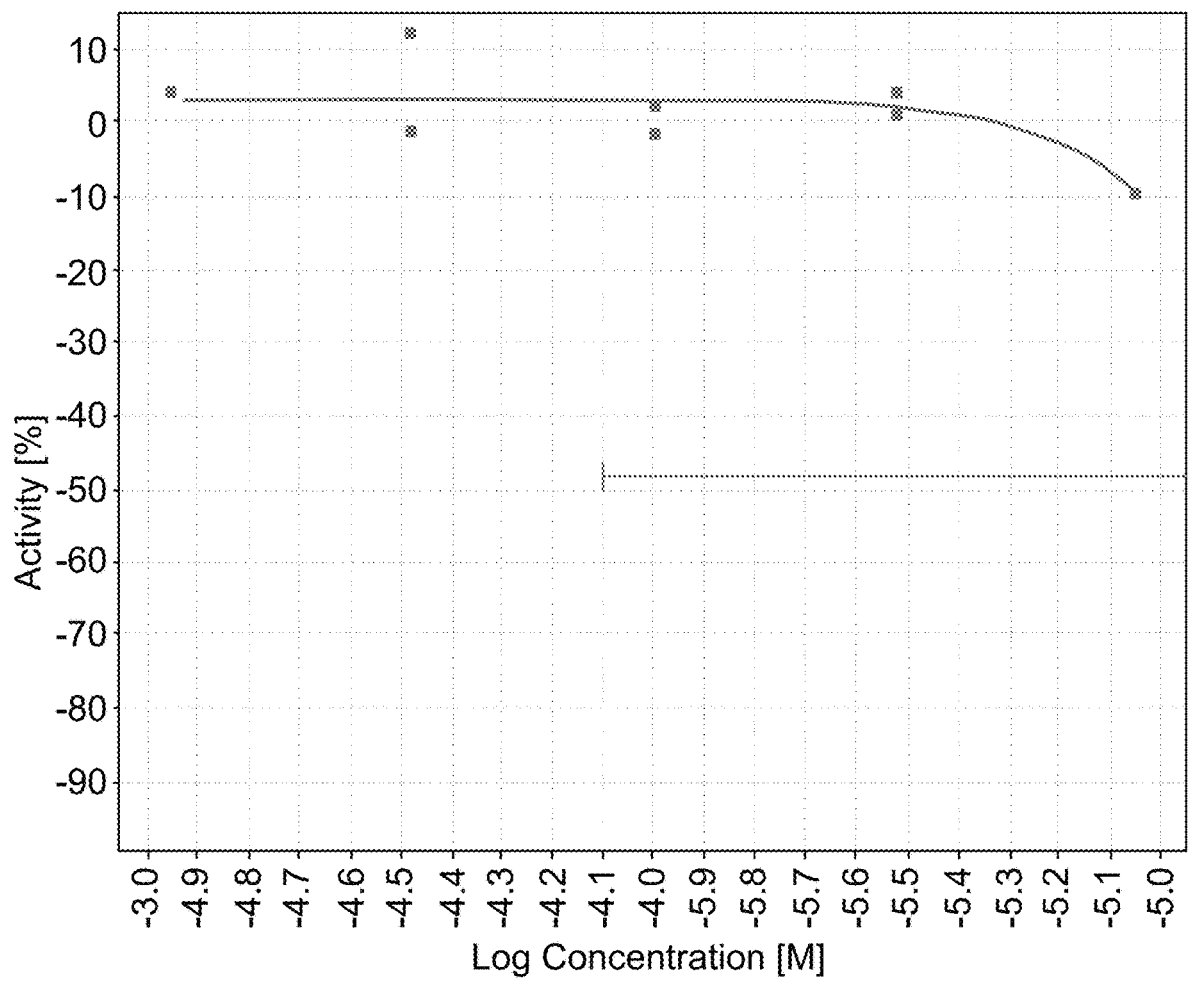
Figure 3:
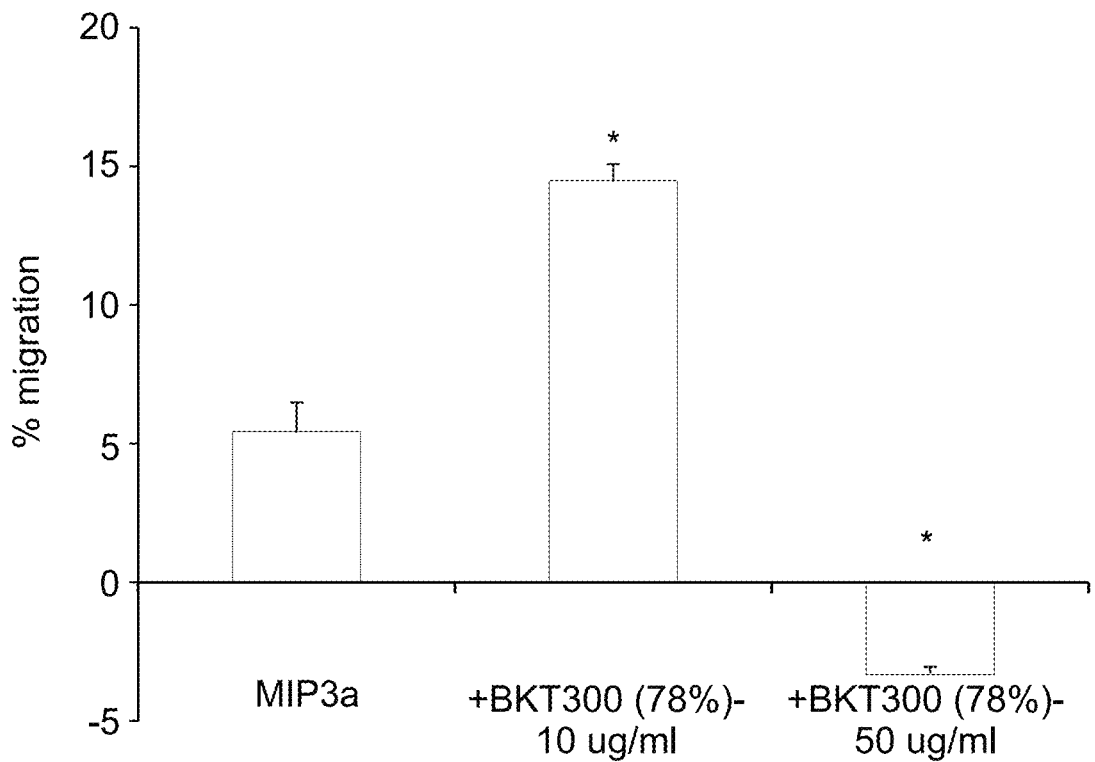
FIG. 3 is a bar graph showing the effect of Compound BKT300 (at 78% purity) (at concentrations of 10 and 50 μg/ml) on migration of CD4+ cells towards MIP3a (* indicates $p<0.05$ vs. zero concentration).
Figure 4:
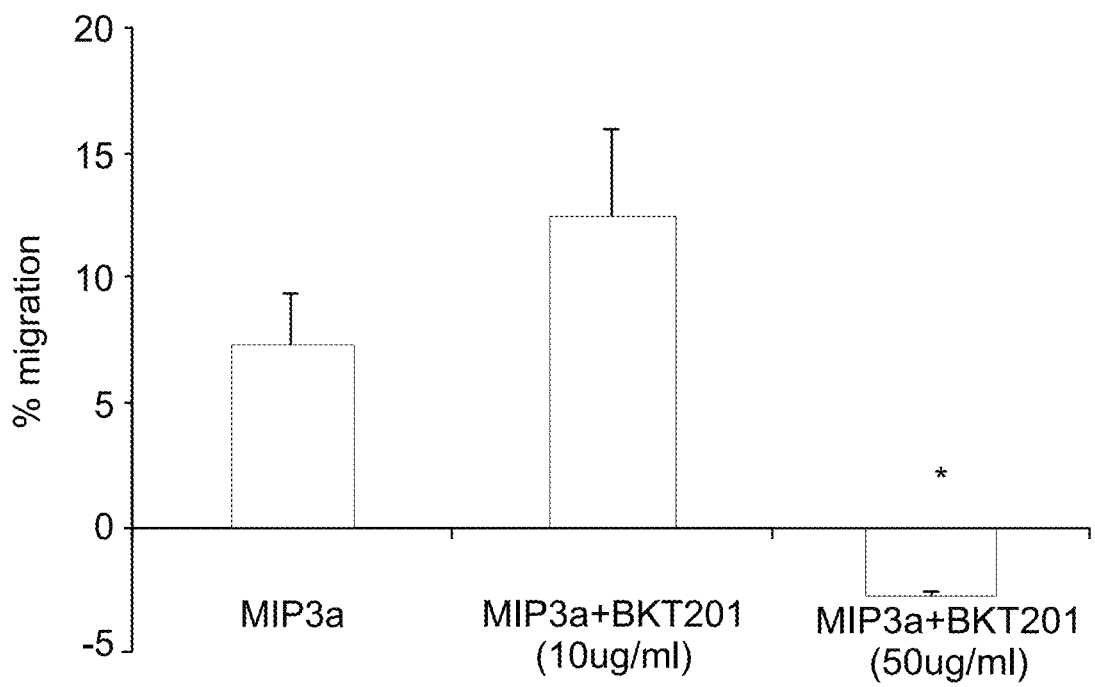
FIG. 4 is a bar graph showing the effect of Compound BKT201 (at concentrations of 10 and 50 μg/ml) on migration of CD4+ cells towards MIP3a (* indicates $p<0.05$ vs. zero concentration).
Figure 5:
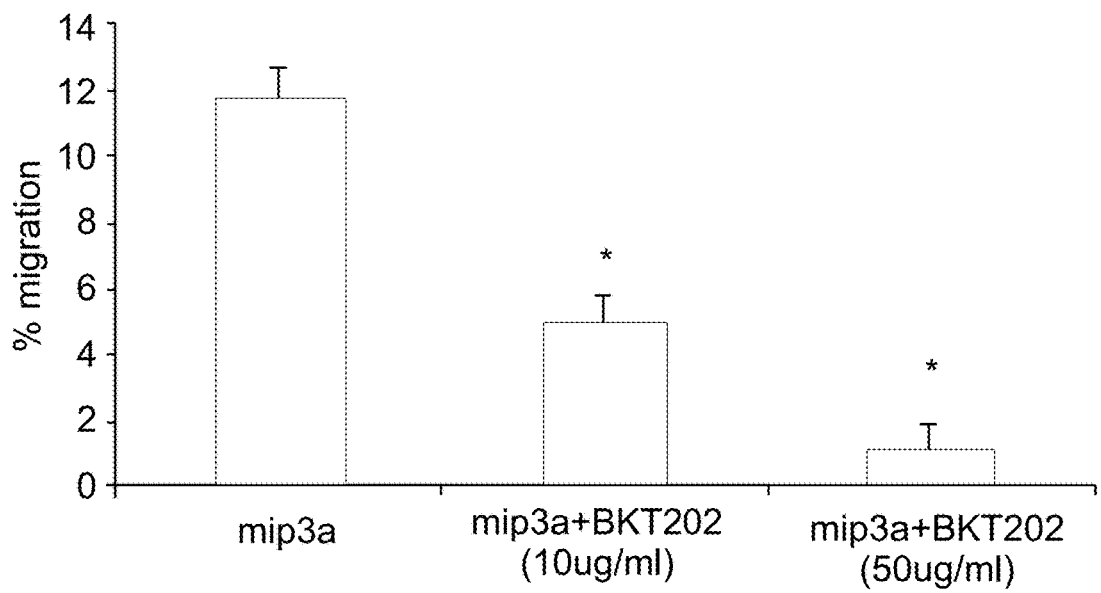
FIG. 5 is a bar graph showing the effect of Compound BKT202 (at concentrations of 10 and 50 μg/ml) on migration of CD4+ cells towards MIP3a (* indicates $p<0.05$ vs. zero concentration).
Figure 6:
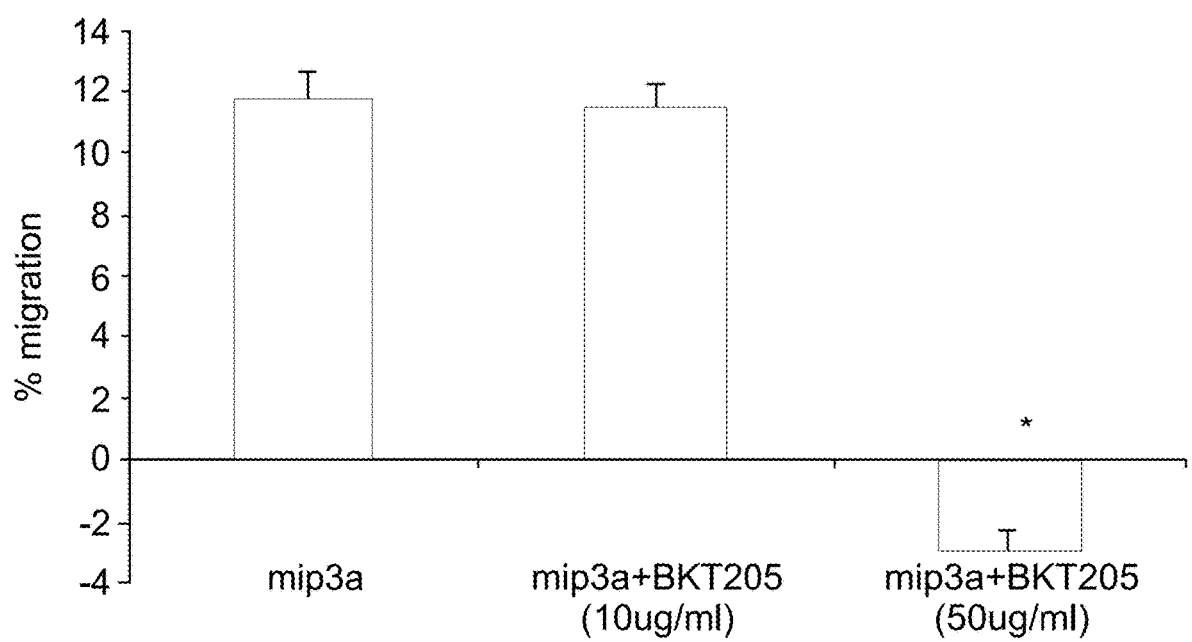
FIG. 6 is a bar graph showing the effect of Compound BKT205 (at concentrations of 10 and 50 μg/ml) on migration of CD4+ cells towards MIP3a (* indicates $p<0.05$ vs. zero concentration).
Figure 7:
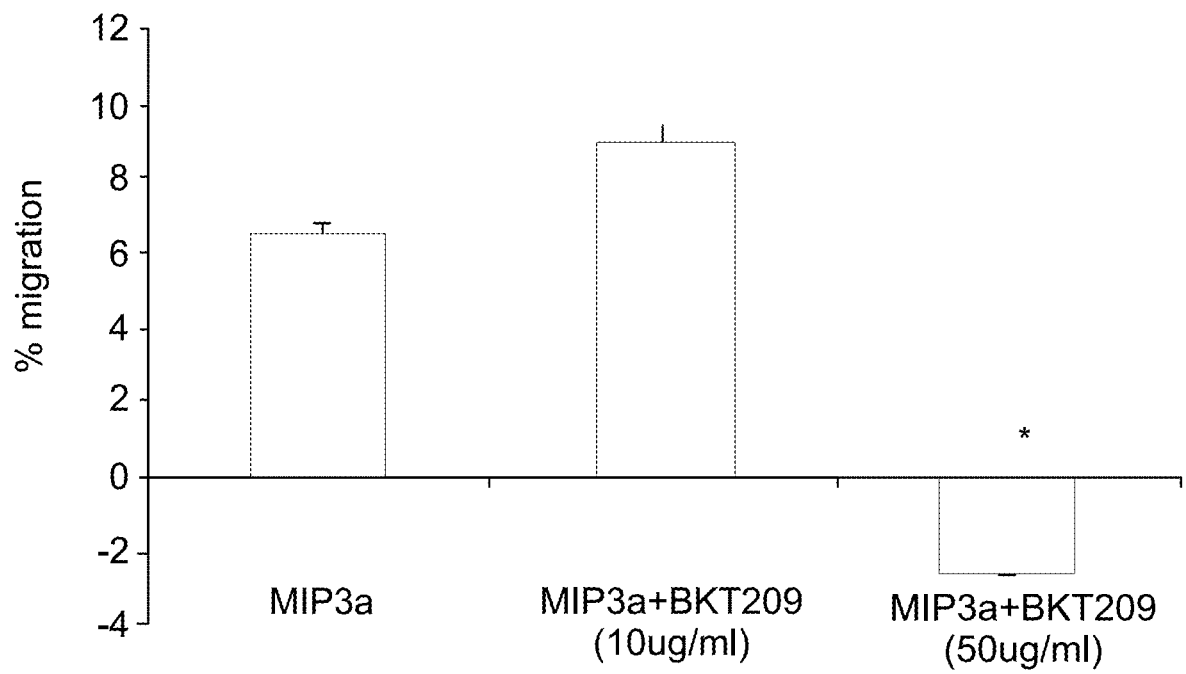
FIG. 7 is a bar graph showing the effect of Compound BKT209 (at concentrations of 10 and 50 μg/ml) on migration of CD4+ cells towards MIP3a (* indicates $p<0.05$ vs. zero concentration).
Figure 8:
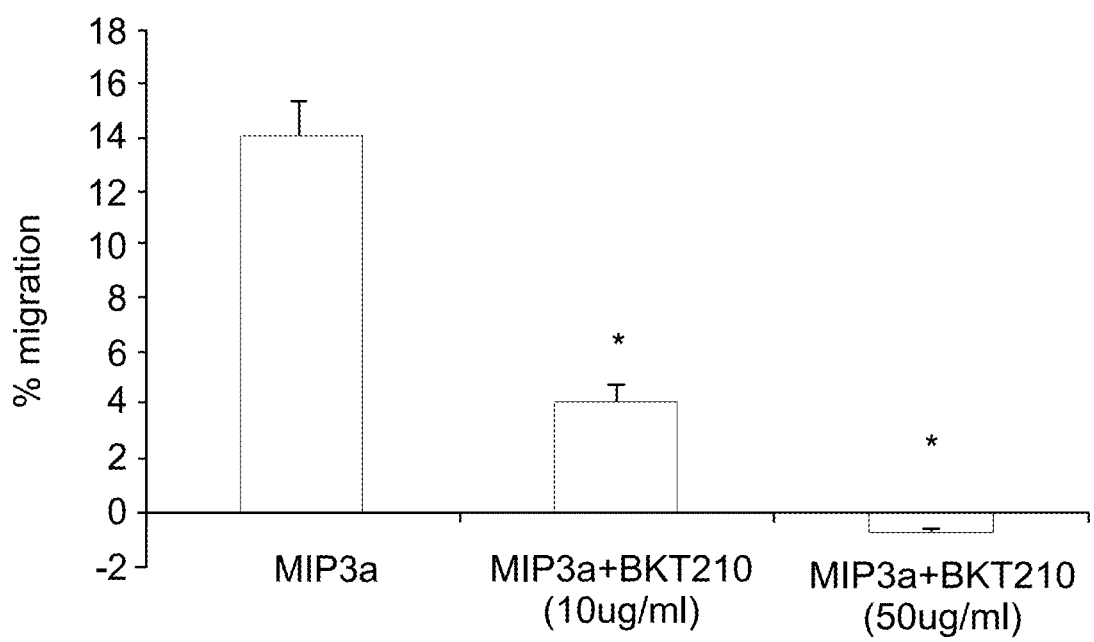
FIG. 8 is a bar graph showing the effect of Compound BKT210 (at concentrations of 10 and 50 μg/ml) on migration of CD4+ cells towards MIP3a (* indicates $p<0.05$ vs. zero concentration).
Figure 9:
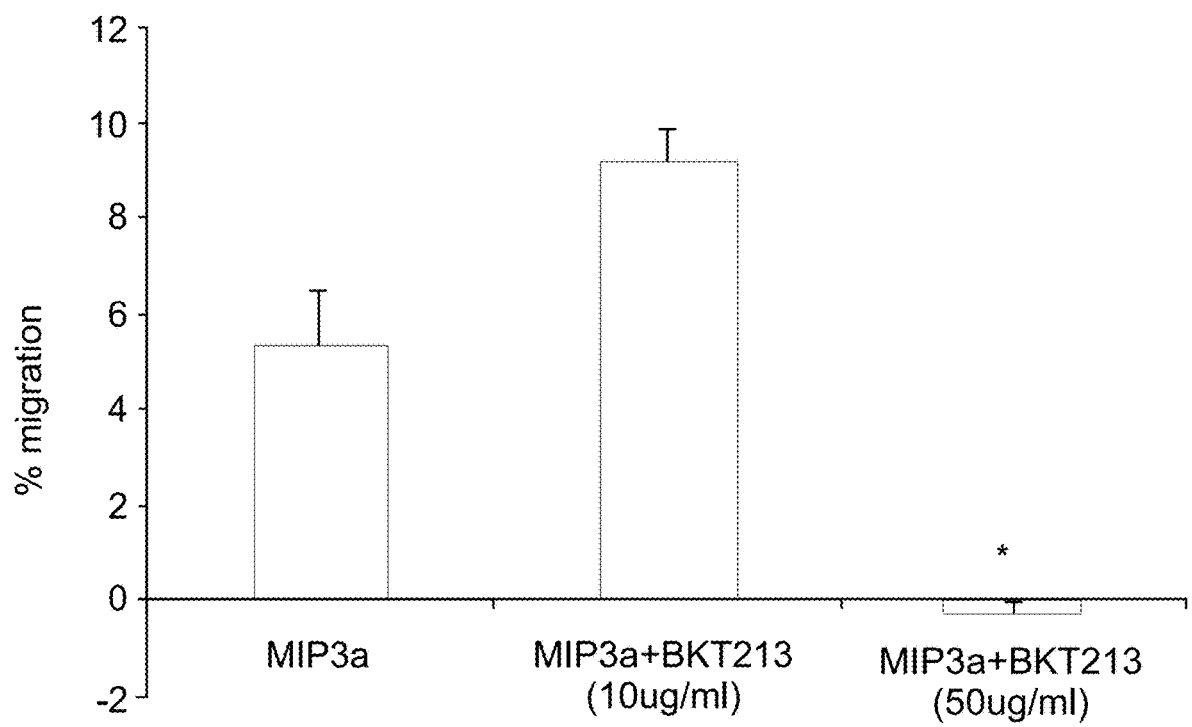
FIG. 9 is a bar graph showing the effect of Compound BKT213 (at concentrations of 10 and 50 μg/ml) on migration of CD4+ cells towards MIP3a (* indicates $p<0.05$ vs. zero concentration).
Figure 10:
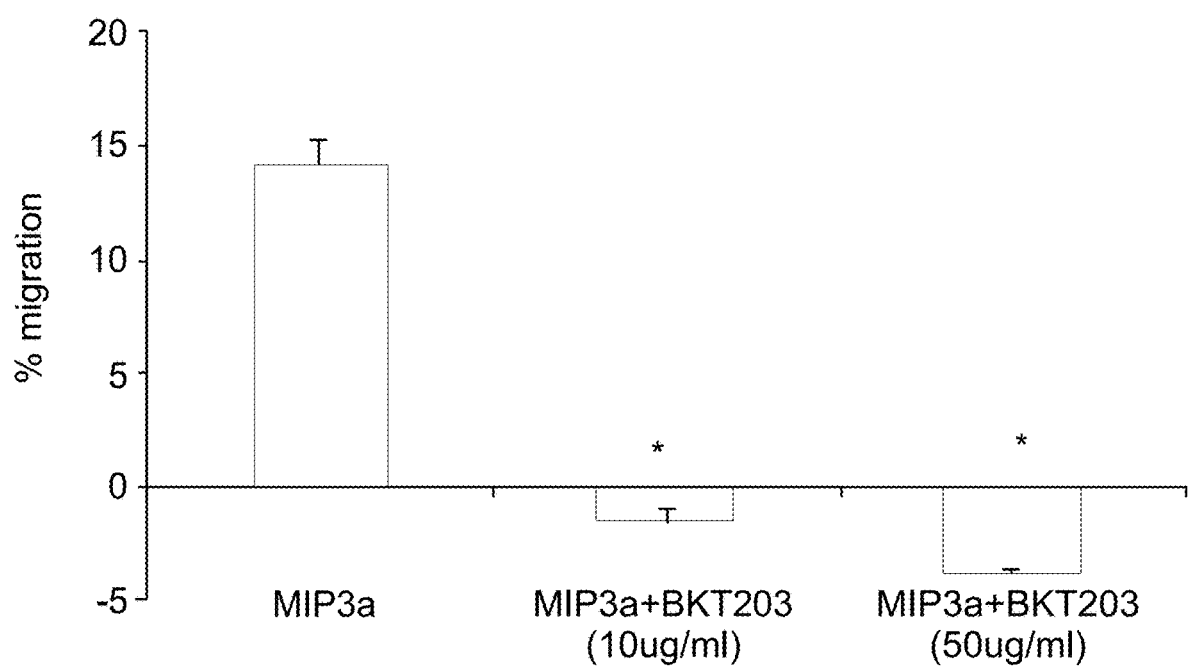
FIG. 10 is a bar graph showing the effect of Compound BKT203 (at concentrations of 10 and 50 μg/ml) on migration of CD4+ cells towards MIP3a (* indicates $p<0.01$ vs. zero concentration).
Figure 11:
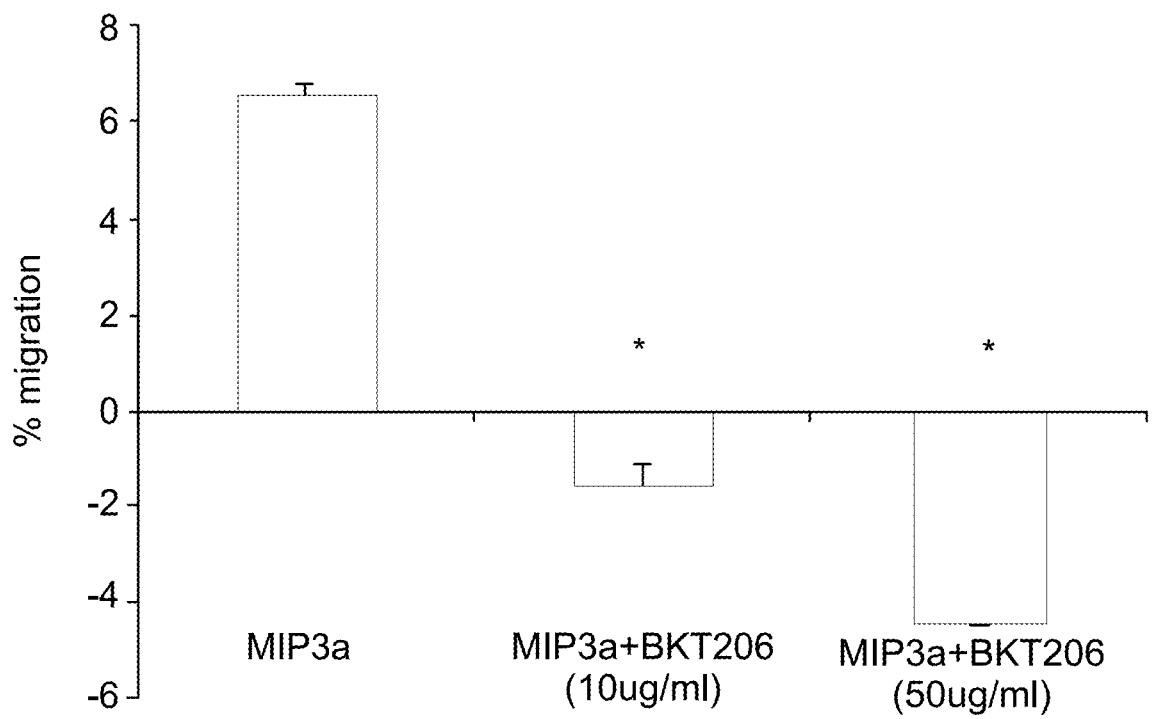
FIG. 11 is a bar graph showing the effect of Compound BKT206 (at concentrations of 10 and 50 μg/ml) on migration of CD4+ cells towards MIP3a (* indicates $p<0.01$ vs. zero concentration).
Figure 12:
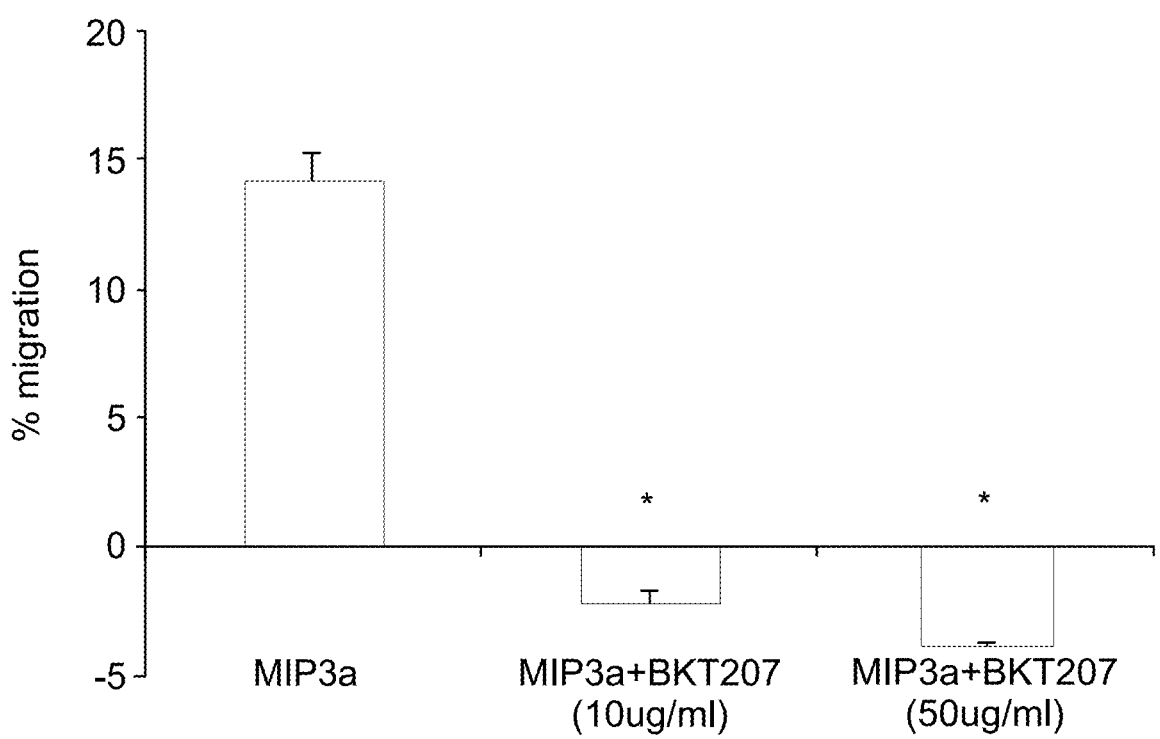
FIG. 12 is a bar graph showing the effect of Compound BKT207 (at concentrations of 10 and 50 μg/ml) on migration of CD4+ cells towards MIP3a (* indicates $p<0.01$ vs. zero concentration).
Figure 13:
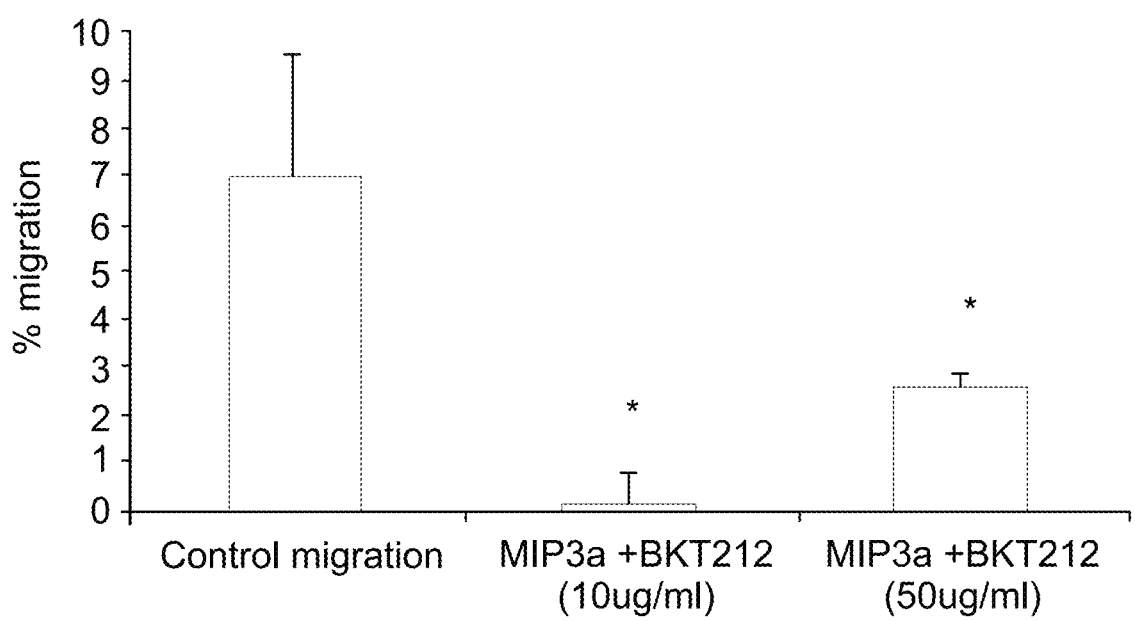
FIG. 13 is a bar graph showing the effect of Compound BKT212 (at concentrations of 10 and 50 μg/ml) on migration of CD4+ cells towards MIP3a (* indicates $p<0.01$ vs. zero concentration).

FIGS. 2A-2C present the dose response curves of Compounds BKT210, BKT203 and BKT207, respectively.

As shown in FIGS. 3-9, Compounds BKT300 (at 78% purity) (FIG. 3), BKT201 (FIG. 4), BKT202 (FIG. 5), BKT205 (FIG. 6), BKT209 (FIG. 7), BKT210 (FIG. 8) and BKT213 (FIG. 9), at a concentration of 50 μg/ml, completely inhibited CD4+ T-cell migration towards MIP3a, thus indicating that the binding of the compound to MIP3a (as detected in the HTS assay) is associated with inhibition of MIP3a activity. As further shown in FIGS. 5 and 8, Compounds BKT202 and BKT210, at a concentration of 10 μg/ml, significantly inhibited CD4+ T-cell migration towards MIP3a.

As shown in FIGS. 10-13, Compounds BKT203 (FIG. 10), BKT206 (FIG. 11), BKT207 (FIG. 12) and BKT212 (FIG. 13), at a concentration of 10 μg/ml, each completely inhibited CD4+ T-cell migration towards MIP3a.

These results confirm that the binding of the compounds to MIP3a (as detected in the HTS assay) is associated with inhibition of MIP3a activity.

Example 2

Effect of Exemplary Compounds on Cytokine-Induced Migration

The set of 18 small molecules presented in Table 2 was screened for an ability to inhibit the migration of immune cells in response to MCP-1 and SDF-1, using the procedures described in the Materials and Methods section hereinabove, in accordance with the screening process described in Example 1.

Figure 14A:
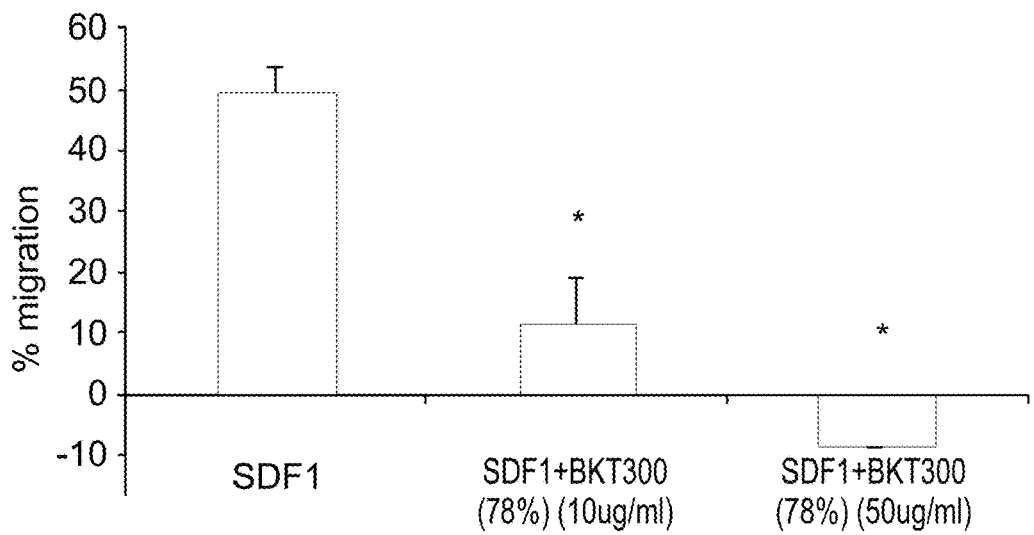
FIGS. 14A and 14B present bar graphs showing the effect of 10 and 50 μg/ml BKT300 (at 78% purity) on migration of Jurkat cells towards SDF-1 (FIG. 14A), and the effect of 1 and 10 μg/ml of Compound BKT300 (at 98% purity) on migration of Jurkat cells towards SDF-1 (* indicates $p<0.05$ vs. zero concentration).
Figure 14B:
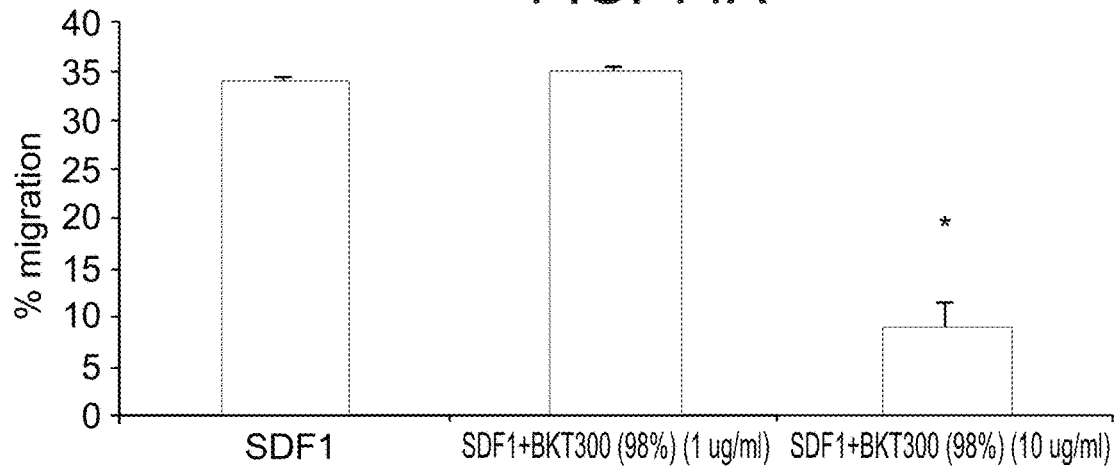

FIGS. 14A and 14B show that BKT300, at a purity of 78% (FIG. 14A) and of 98% (FIG. 14B) at a concentration of 10 μg/ml, significantly inhibited the migration of lymphocytic Jurkat cells towards SDF-1.

Figure 15:
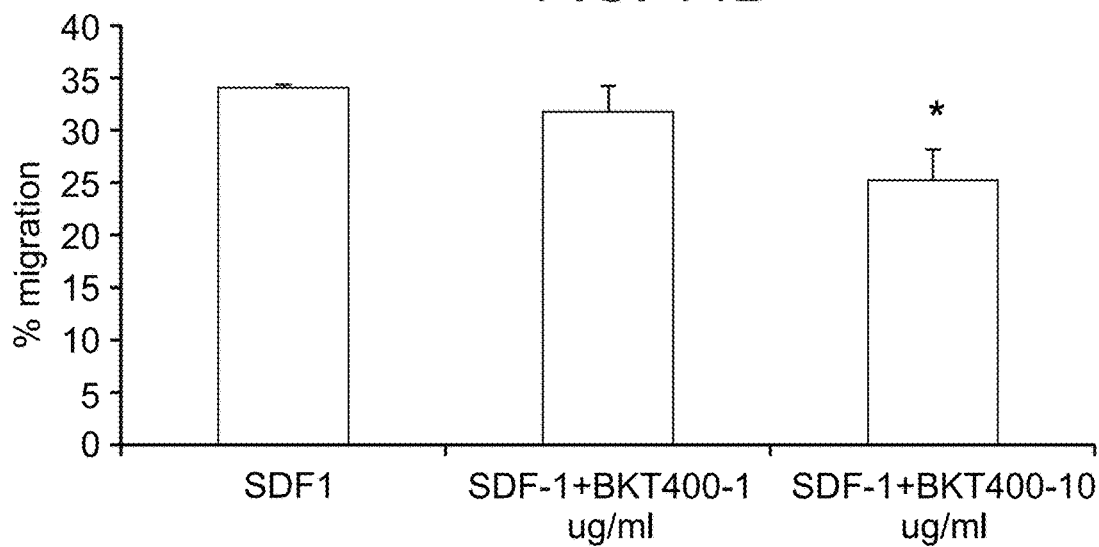
FIG. 15 is a bar graph showing the effect of 1 and 10 μg/ml of Compound BKT400 on migration of Jurkat cells towards SDF-1 (* indicates $p<0.05$ vs. zero concentration).
Figure 16:
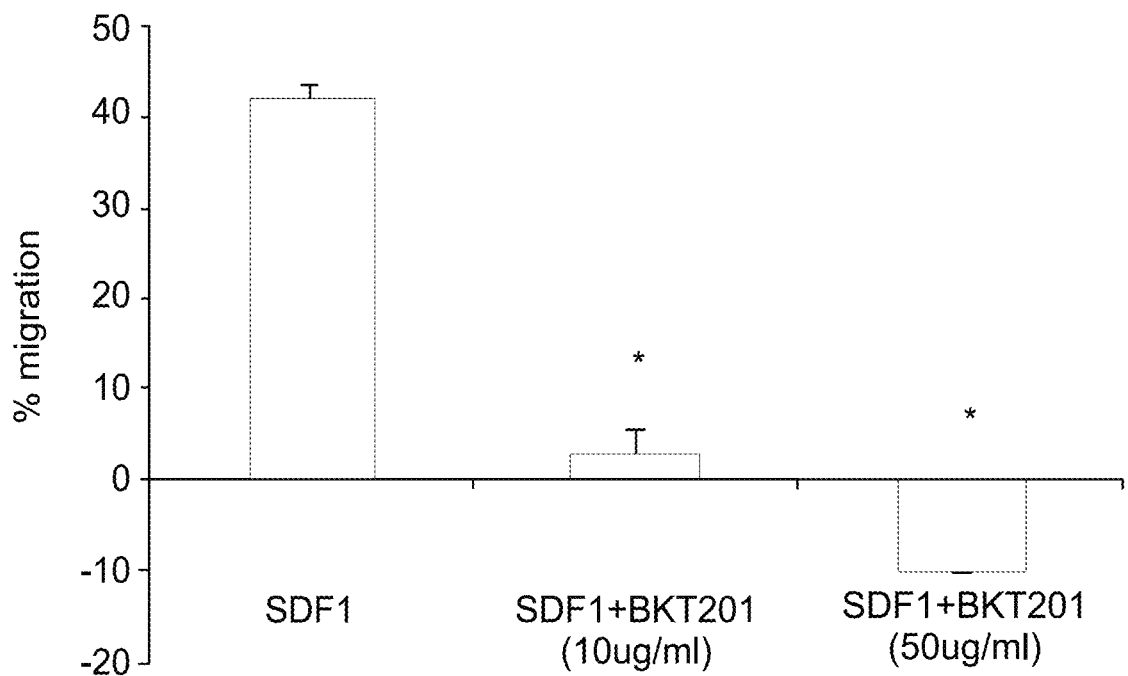
FIG. 16 is a bar graph showing the effect of Compound BKT201 (at concentrations of 10 and 50 μg/ml) on migration of Jurkat cells towards SDF-1 (* indicates $p<0.01$ vs. zero concentration).
Figure 17:
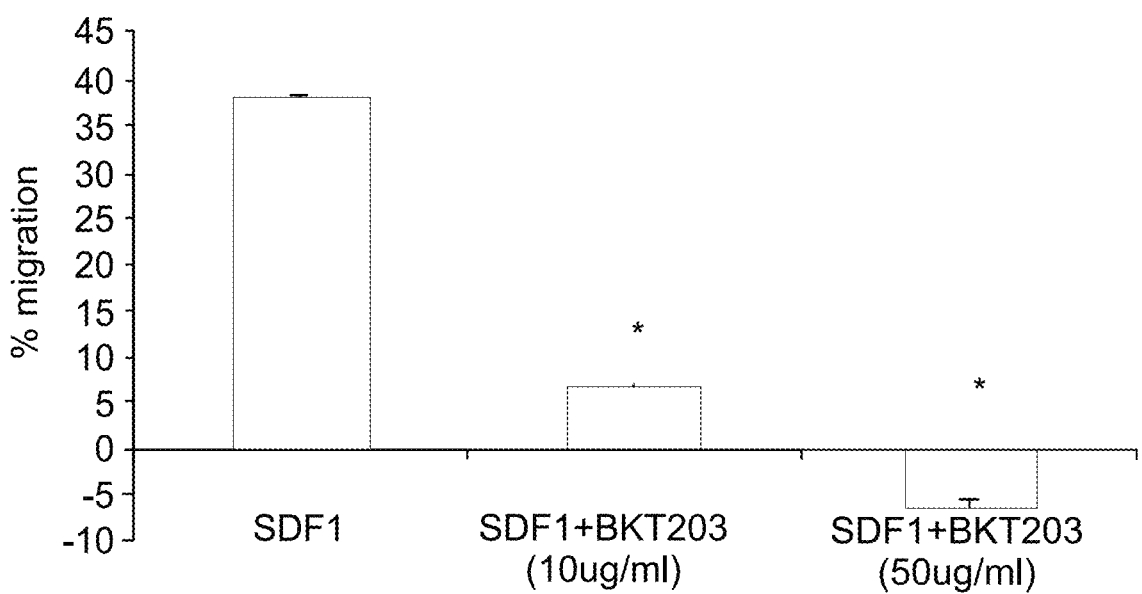
FIG. 17 is a bar graph showing the effect of Compound BKT203 (at concentrations of 10 and 50 μg/ml) on migration of Jurkat cells towards SDF-1 (* indicates $p<0.05$ vs. zero concentration).
Figure 18:
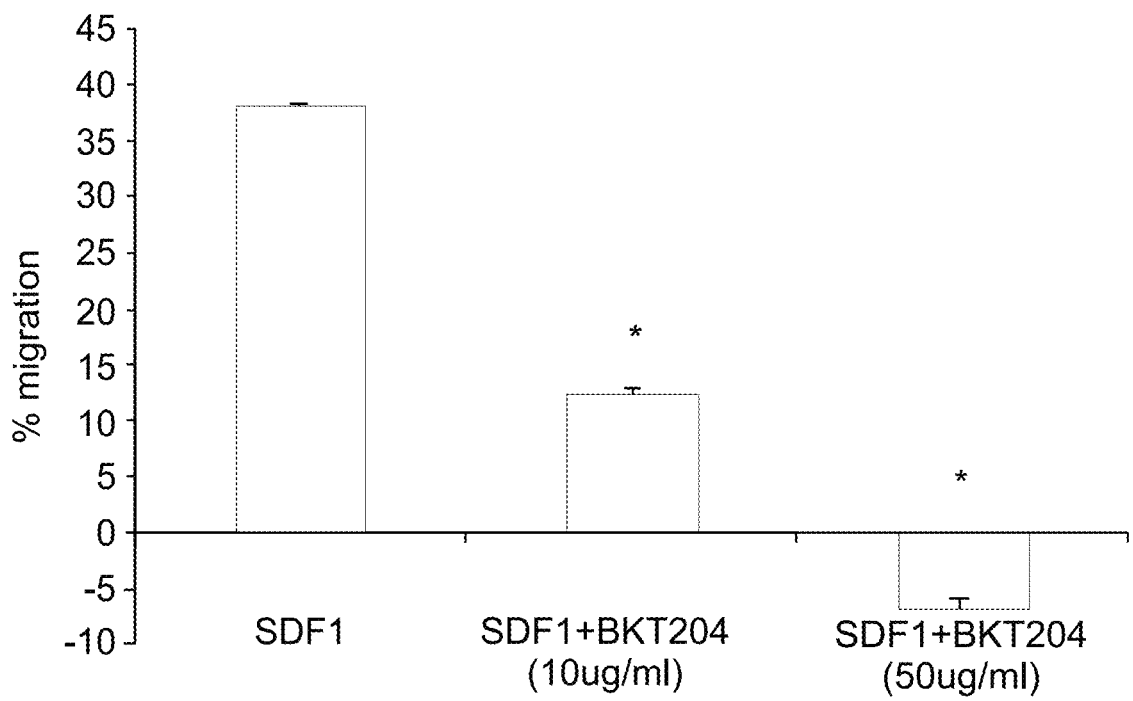
FIG. 18 is a bar graph showing the effect of Compound BKT204 (at concentrations of 10 and 50 μg/ml) on migration of Jurkat cells towards SDF-1 (* indicates $p<0.05$ vs. zero concentration).
Figure 19:
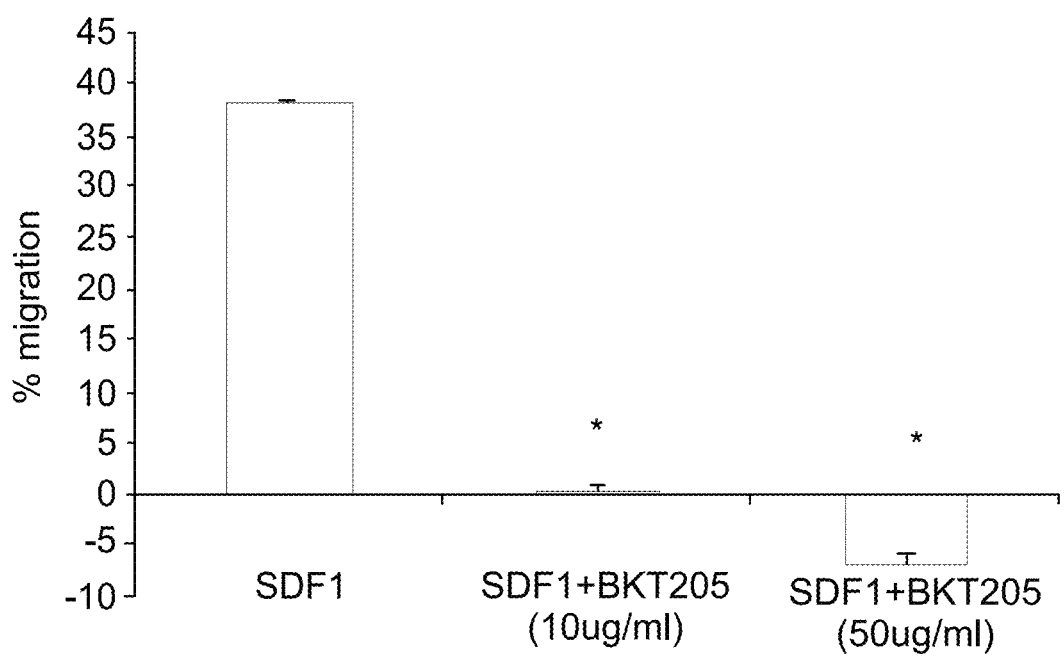
FIG. 19 is a bar graph showing the effect of Compound BKT205 (at concentrations of 10 and 50 μg/ml) on migration of Jurkat cells towards SDF-1 (* indicates $p<0.01$ vs. zero concentration).
Figure 20:
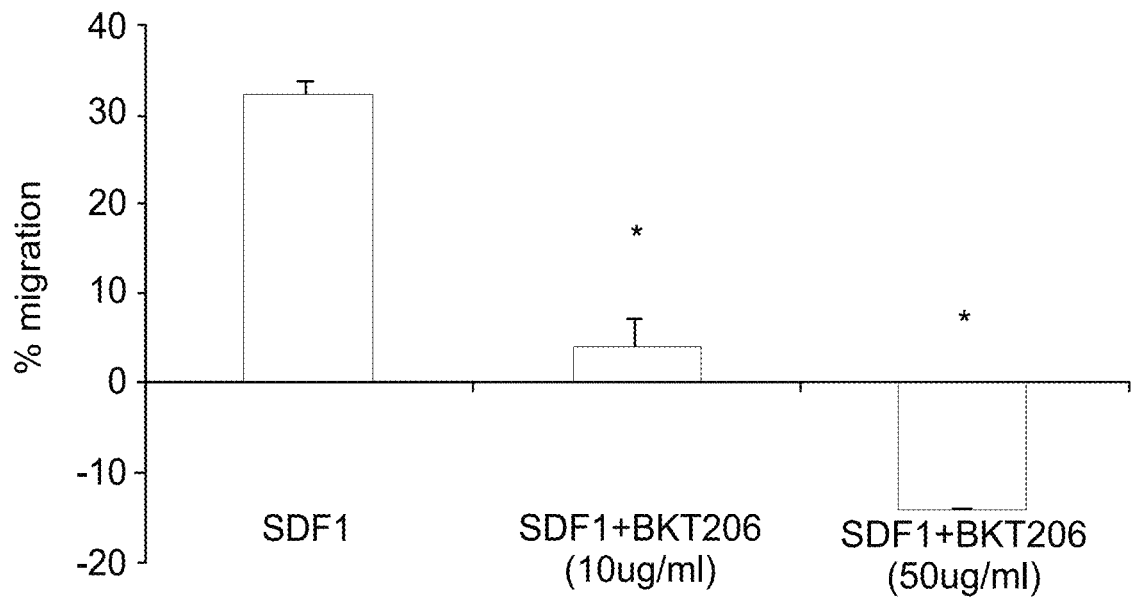
FIG. 20 is a bar graph showing the effect of Compound BKT206 (at concentrations of 10 and 50 μg/ml) on migration of Jurkat cells towards SDF-1 (* indicates $p<0.05$ vs. zero concentration).
Figure 21:
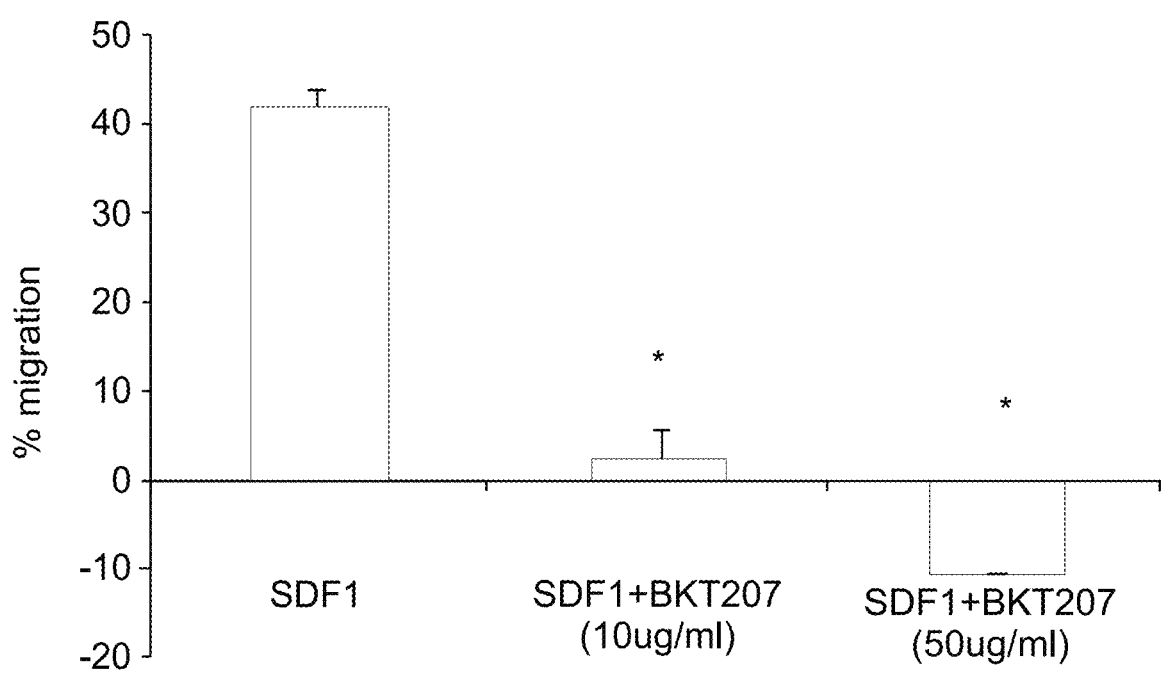
FIG. 21 is a bar graph showing the effect of Compound BKT207 (at concentrations of 10 and 50 μg/ml) on migration of Jurkat cells towards SDF-1 (* indicates $p<0.05$ vs. zero concentration).
Figure 22:
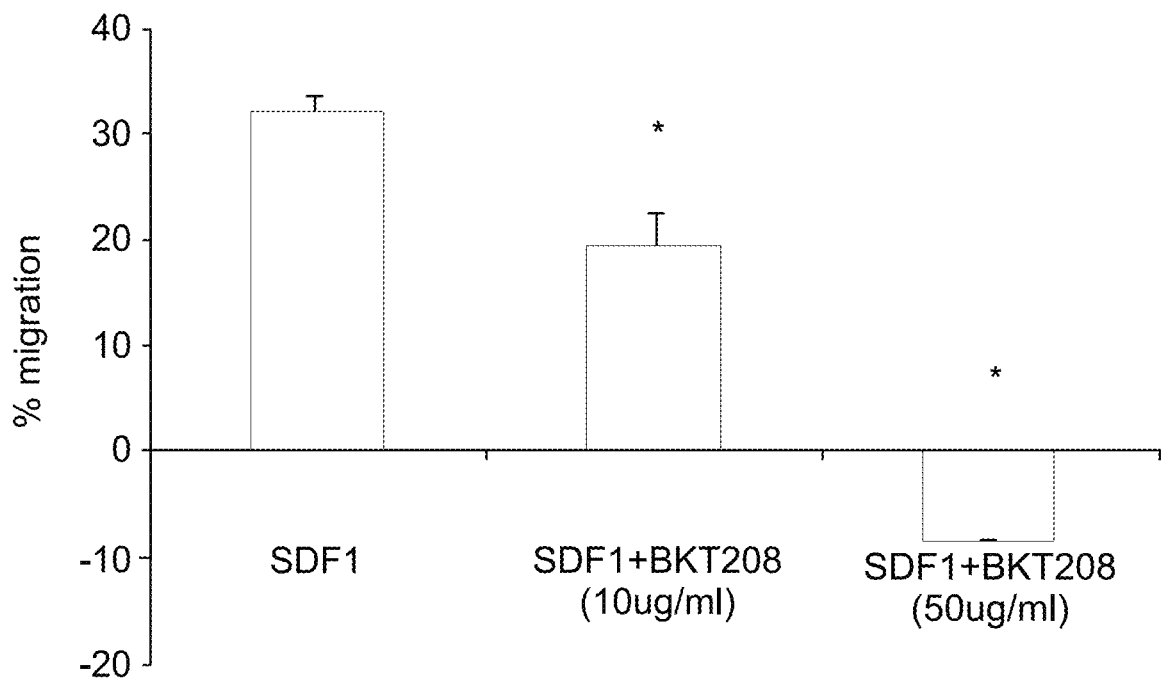
FIG. 22 is a bar graph showing the effect of Compound BKT208 (at concentrations of 10 and 50 μg/ml) on migration of Jurkat cells towards SDF-1 (* indicates $p<0.05$ vs. zero concentration).
Figure 23:
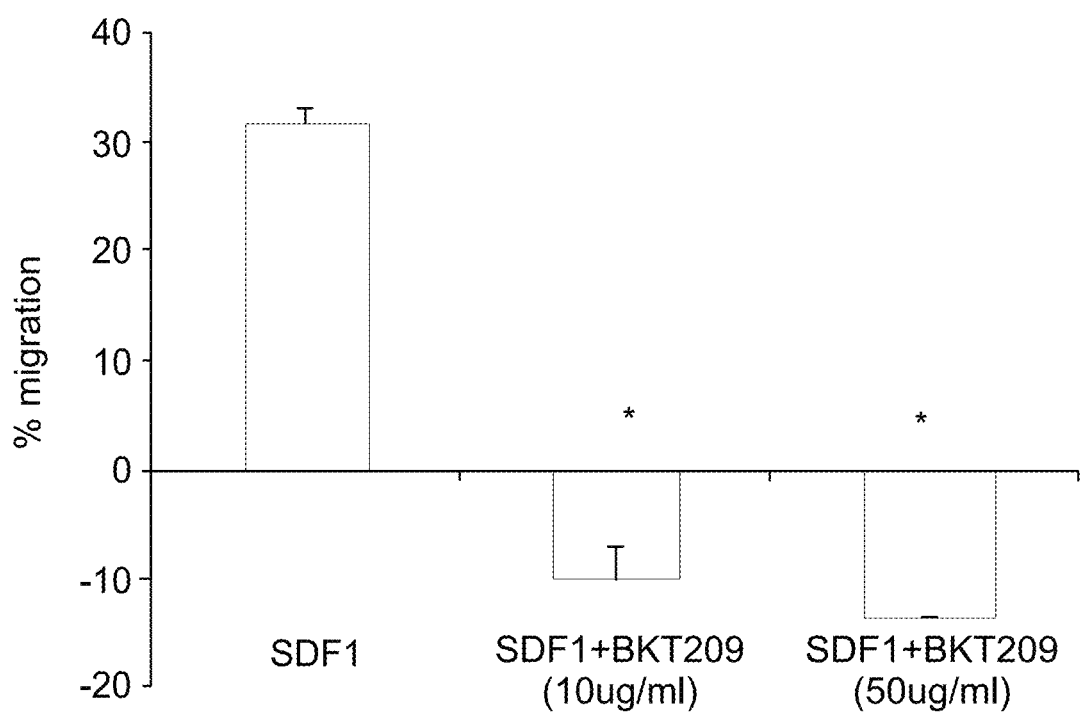
FIG. 23 is a bar graph showing the effect of Compound BKT209 (at concentrations of 10 and 50 μg/ml) on migration of Jurkat cells towards SDF-1 (* indicates $p<0.01$ vs. zero concentration).
Figure 24:
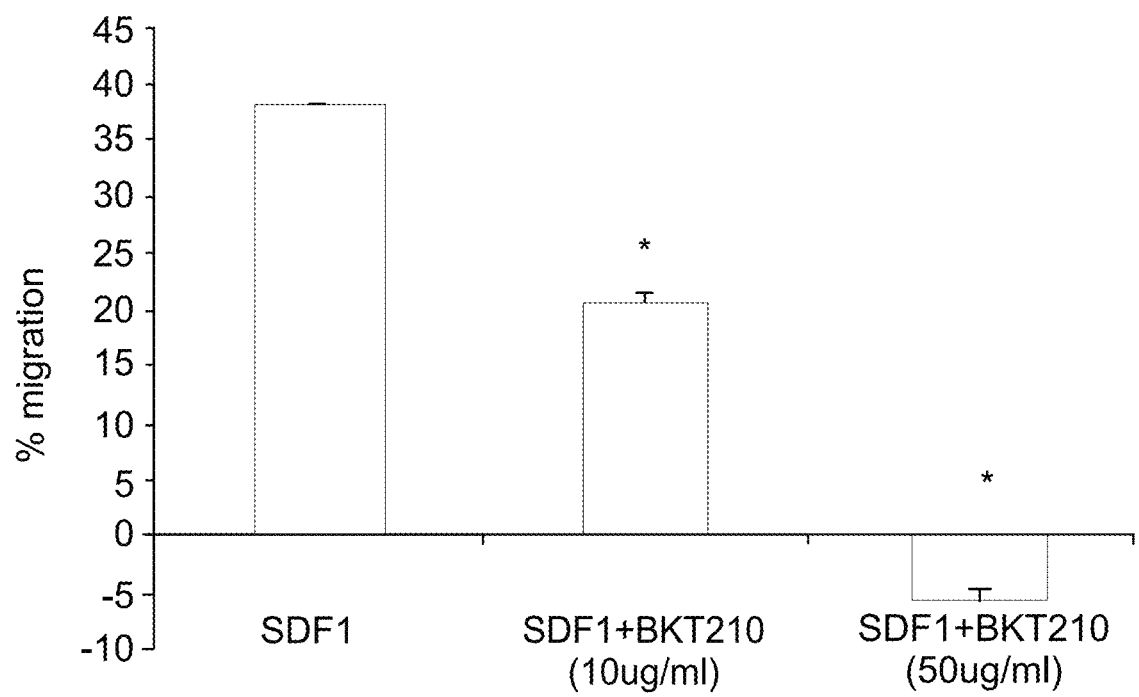
FIG. 24 is a bar graph showing the effect of Compound BKT210 (at concentrations of 10 and 50 μg/ml) on migration of Jurkat cells towards SDF-1 (* indicates $p<0.05$ vs. zero concentration).
Figure 25:
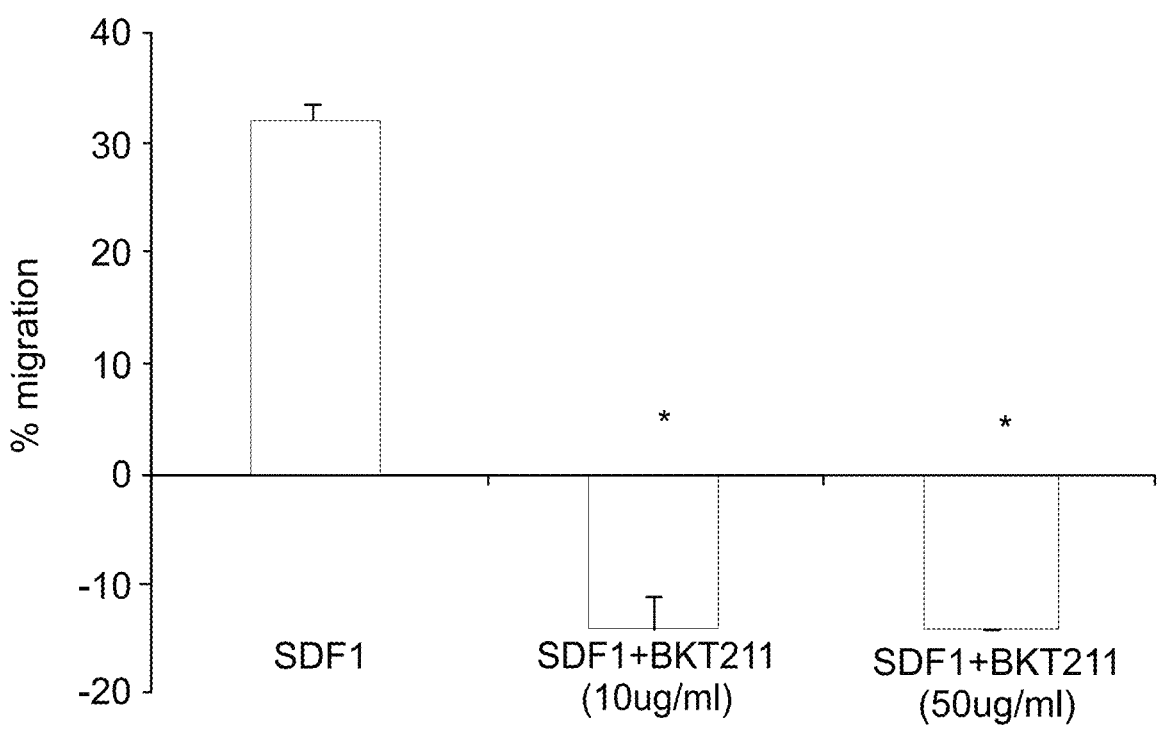
FIG. 25 is a bar graph showing the effect of Compound BKT211 (at concentrations of 10 and 50 µg/ml) on migration of Jurkat cells towards SDF-1 (* indicates $p<0.05$ vs. zero concentration).
Figure 26:
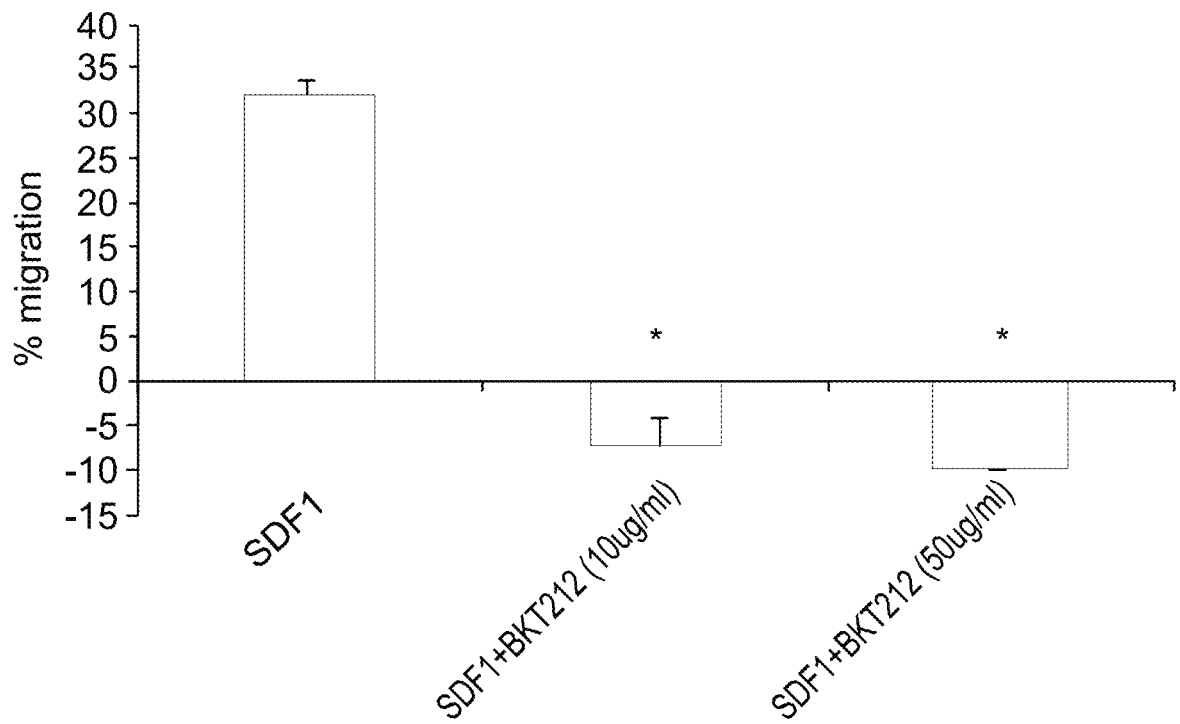
FIG. 26 is a bar graph showing the effect of Compound BKT212 (at concentrations of 10 and 50 µg/ml) on migration of Jurkat cells towards SDF-1 (* indicates $p<0.05$ vs. zero concentration).
Figure 27:
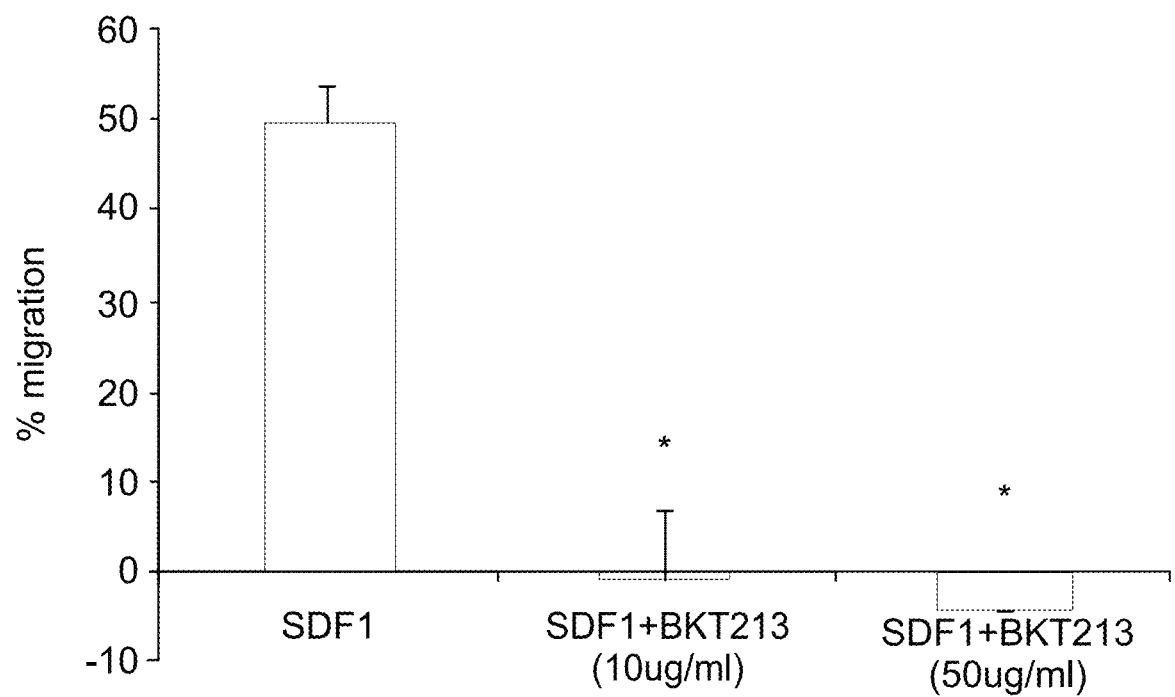
FIG. 27 is a bar graph showing the effect of Compound BKT213 (at concentrations of 10 and 50 µg/ml) on migration of Jurkat cells towards SDF-1 (* indicates $p<0.01$ vs. zero concentration).
Figure 28:
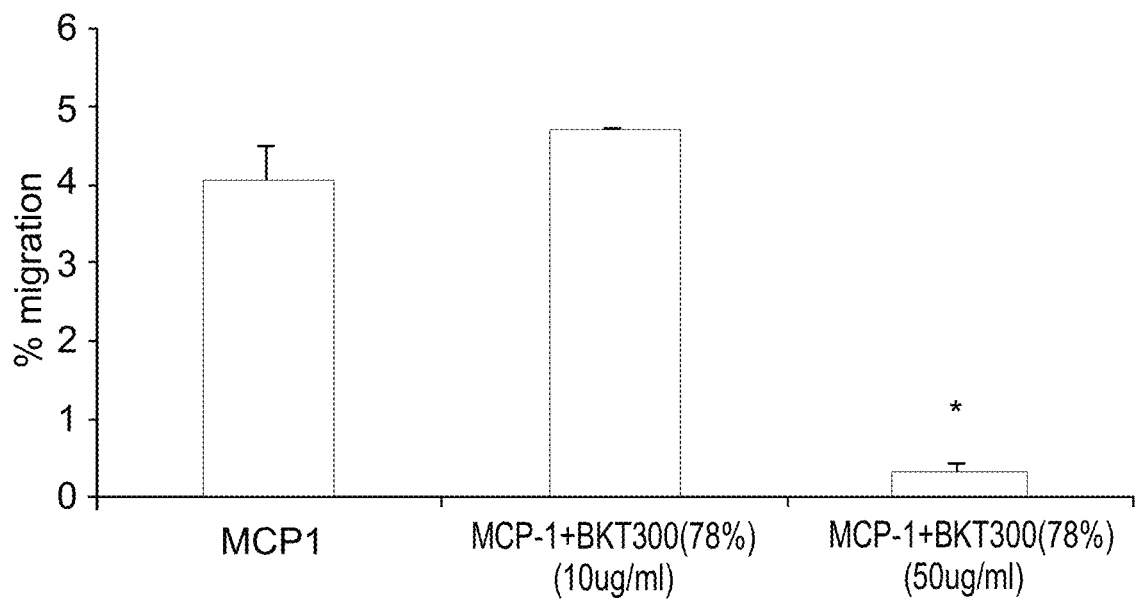
FIG. 28 is a bar graph showing the effect of 10 and 50 µg/ml of Compound BKT300 (at 78% purity) on migration of THP-1 cells towards MCP-1 (* indicates $p<0.05$ vs. zero concentration).
Figure 29:
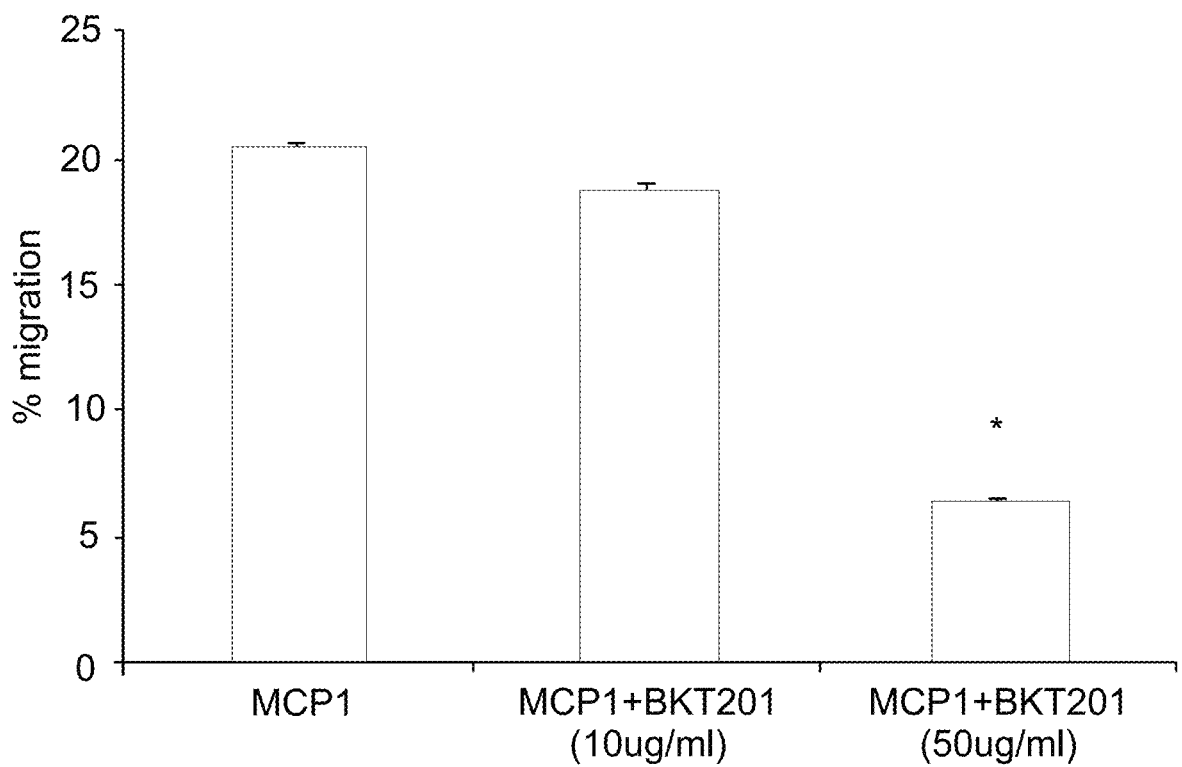
FIG. 29 is a bar graph showing the effect of Compound BKT201 (at concentrations of 10 and 50 µg/ml) on migration of THP-1 cells towards MCP-1 (* indicates $p<0.05$ vs. zero concentration).

A compound structurally similar to BKT300, termed BKT400, was also found to inhibit the migration of lymphocytic Jurkat cells towards SDF-1, as shown in FIG. 15.

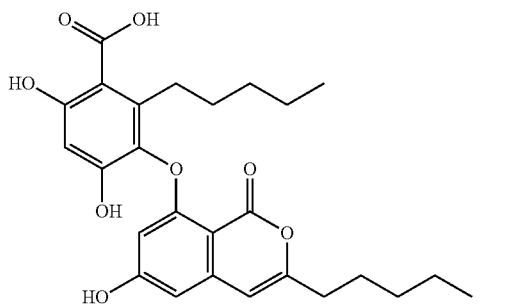

BKT400

Furthermore, as shown in FIGS. 16-27, BKT201 (FIG. 16), BKT203 (FIG. 17), BKT204 (FIG. 18), BKT205 (FIG. 19), BKT206 (FIG. 20), BKT207 (FIG. 21), BKT208 (FIG. 22), BKT209 (FIG. 23), BKT210 (FIG. 24), BKT211 (FIG. 25), BKT212 (FIG. 26) and BKT213 (FIG. 27), at a concentration of 10 μg/ml, significantly inhibited the migration of lymphocytic Jurkat cells towards SDF-1, with BKT201, BKT203, BKT205, BKT206, BKT207, BKT209, BKT211, BKT212 and BKT213 exhibiting strong inhibition at this concentration.

These results indicate that the abovementioned compounds are effective inhibitors of SDF-1 function, and suggest that these compounds are effective for treating conditions associated with activity of SDF-1 and CXCR4 (the receptor of SDF-1).

Furthermore, as shown in FIGS. 28-35, Compounds BKT300 (78% purity) (FIG. 28), BKT201 (FIG. 29), BKT204 (FIG. 30), BKT205 (FIG. 31), BKT206 (FIG. 32), BKT209 (FIG. 33), BKT211 (FIG. 34) and BKT216 (FIG. 35), at a concentration of 50 μg/ml, exhibited strong inhibition of migration of monocytic THP-1 cells towards MCP-1.

As shown in FIGS. 28, 29, 31 and 33, at a concentration of 10 μg/ml, Compounds BKT300 (78% purity) (FIG. 28), BKT201 (FIG. 29), BKT205 (FIG. 31) and BKT209 (FIG. 33) had no apparent effect on the migration of monocytic THP-1 cells towards MCP-1.

Figure 30:
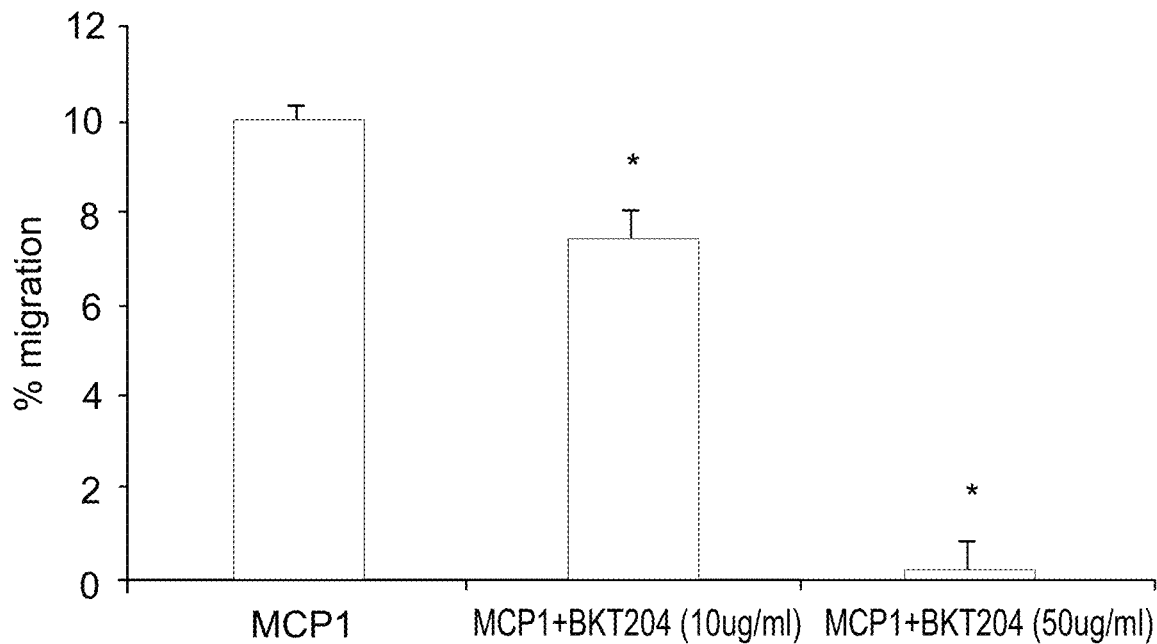
FIG. 30 is a bar graph showing the effect of Compound BKT204 (at concentrations of 10 and 50 µg/ml) on migration of THP-1 cells towards MCP-1 (* indicates $p<0.05$ vs. zero concentration).
Figure 31:
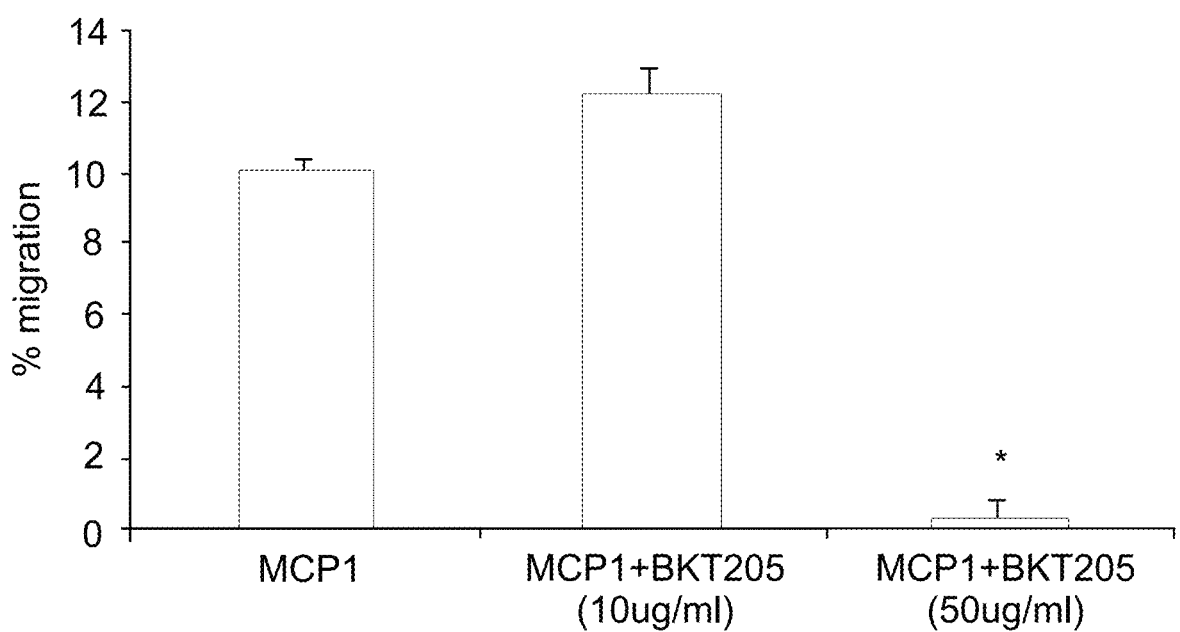
FIG. 31 is a bar graph showing the effect of Compound BKT205 (at concentrations of 10 and 50 µg/ml) on migration of THP-1 cells towards MCP-1 (* indicates $p<0.05$ vs. zero concentration).
Figure 32:
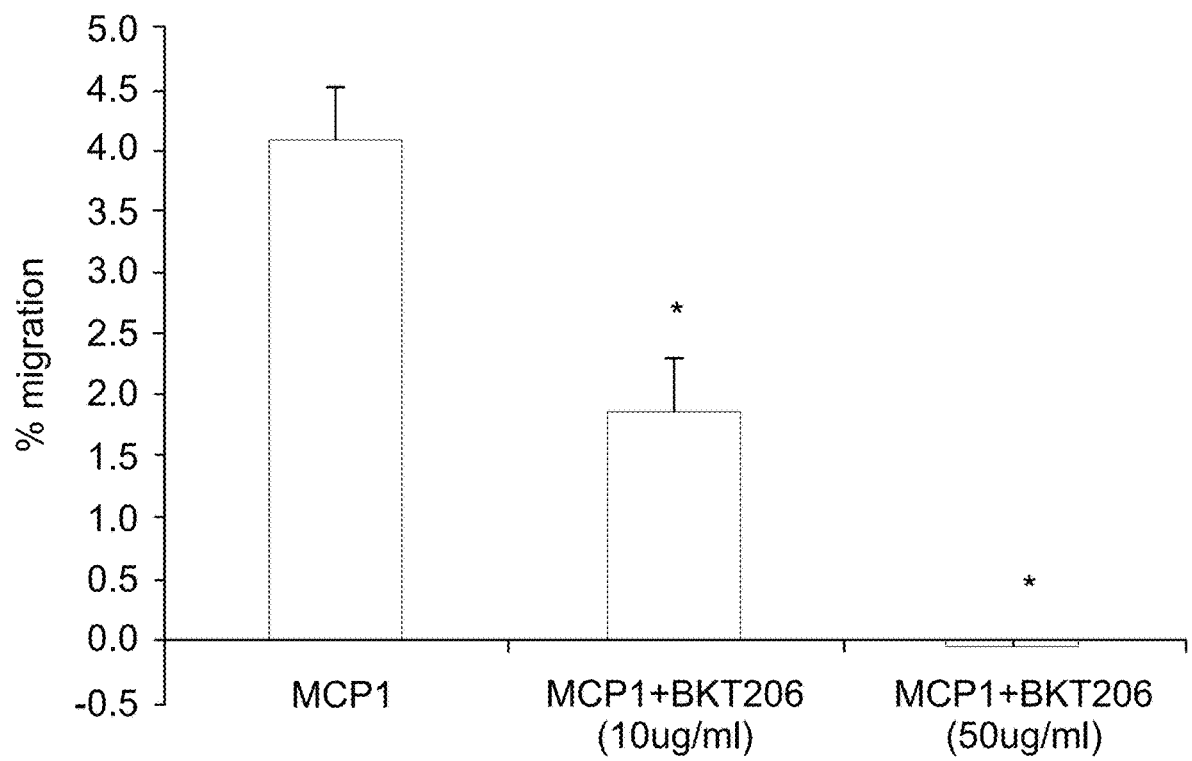
FIG. 32 is a bar graph showing the effect of Compound BKT206 (at concentrations of 10 and 50 µg/ml) on migration of THP-1 cells towards MCP-1 (* indicates $p<0.05$ vs. zero concentration).
Figure 33:
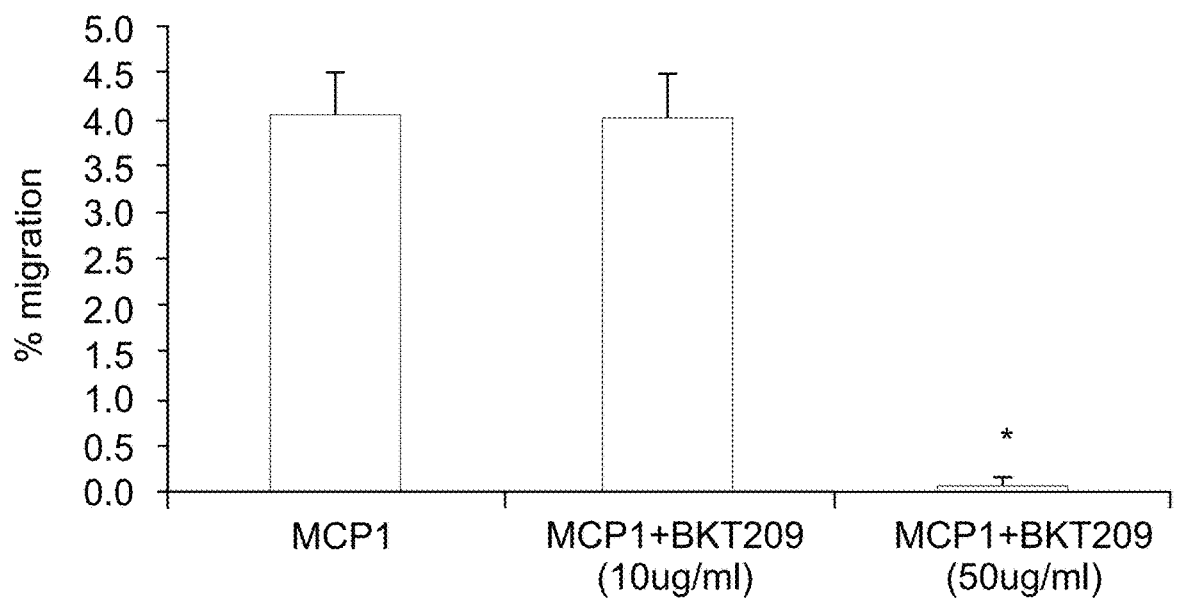
FIG. 33 is a bar graph showing the effect of Compound BKT209 (at concentrations of 10 and 50 µg/ml) on migration of THP-1 cells towards MCP-1 (* indicates $p<0.05$ vs. zero concentration).
Figure 35:
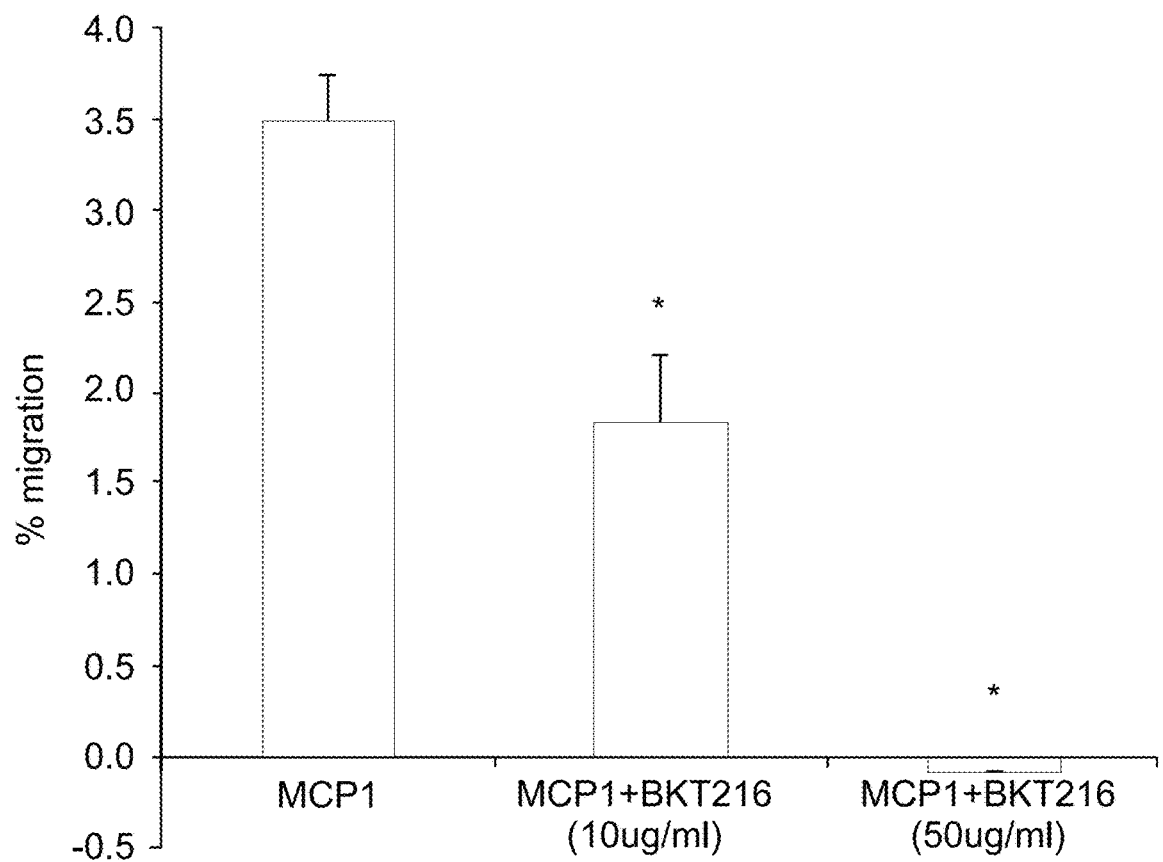
FIG. 35 is a bar graph showing the effect of Compound BKT216 (at concentrations of 10 and 50 µg/ml) on migration of THP-1 cells towards MCP-1 (* indicates $p<0.05$ vs. zero concentration).

As shown in FIGS. 30, 32 and 35, at a concentration of 10 μg/ml, Compounds BKT204 (FIG. 30), BKT206 (FIG. 32) and BKT216 (FIG. 35) exhibited partial inhibition of migration towards MCP-1.

Figure 34:
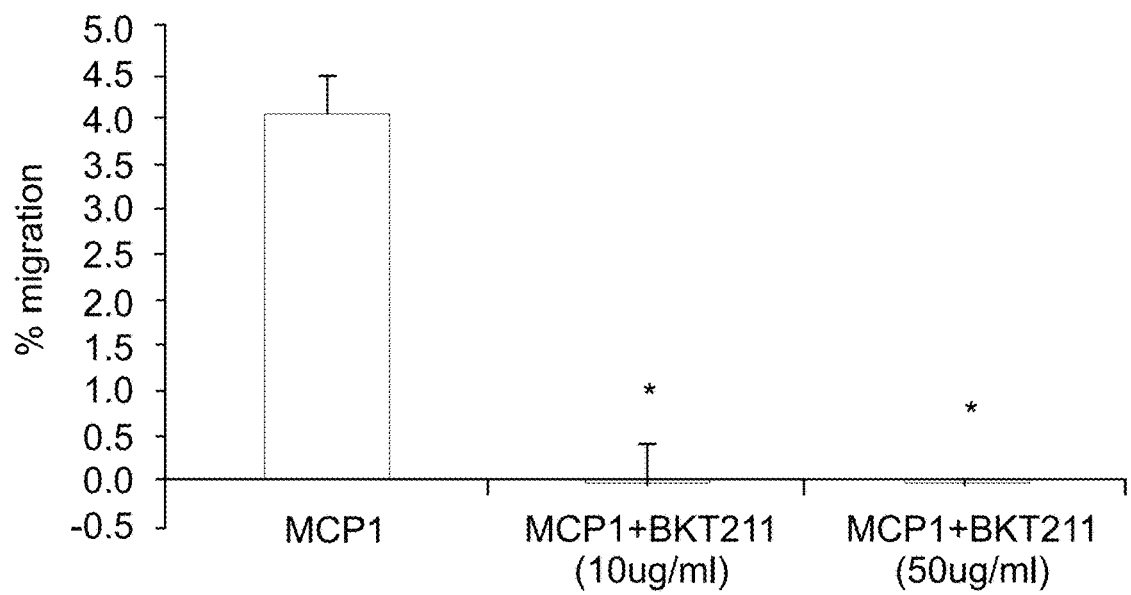
FIG. 34 is a bar graph showing the effect of Compound BKT211 (at concentrations of 10 and 50 µg/ml) on migration of THP-1 cells towards MCP-1 (* indicates $p<0.01$ vs. zero concentration).

As shown in FIG. 34, 10 μg/ml of Compound BKT211 exhibited complete inhibition of THP-1 cell migration towards MCP-1. This result suggests that Compound BKT211 is effective for treating conditions associated with activity of MCP-1.

Taken together with the results described in Example 1 (e.g., as shown in FIGS. 3, 4, 6, 7 and 9), the above results indicate that Compounds BKT300, BKT201, BKT205, BKT209 and BKT213 potently inhibit SDF-1 function in a relatively selective manner, with considerably weaker inhibition of MCP-1 and/or MIP3a function (e.g., at a concentration of about 10 μg/ml), and suggest that Compounds BKT300, BKT201, BKT205, BKT209 and BKT213 are particularly effective for treating conditions associated with activity of SDF-1 and CXCR4 (the receptor of SDF-1).

Example 3

Effect of Exemplary Compounds on Cancer Cell Viability

In order to assess the effect of compounds of Table 2 on cancer cell viability, the in vitro effect of the compounds on MV4-11 human acute myeloid leukemia cells was evaluated. The cancer cells were incubated in RPMI cell medium with 1% fetal calf serum (FCS) at a concentration of $2 \times 10^5$ cells/well at a final volume of 250 μl in 96-well plate. The compounds were added to the cells at the indicated concentrations. The cells were incubated for 24 hours and the number of dead and viable cells was then evaluated by fluorescence-activated cell sorting (FACS), using propidium iodide (PI) staining. The IC50 of chemokine-induced cell death was determined using GraphPad Prism software.

Figure 36A:
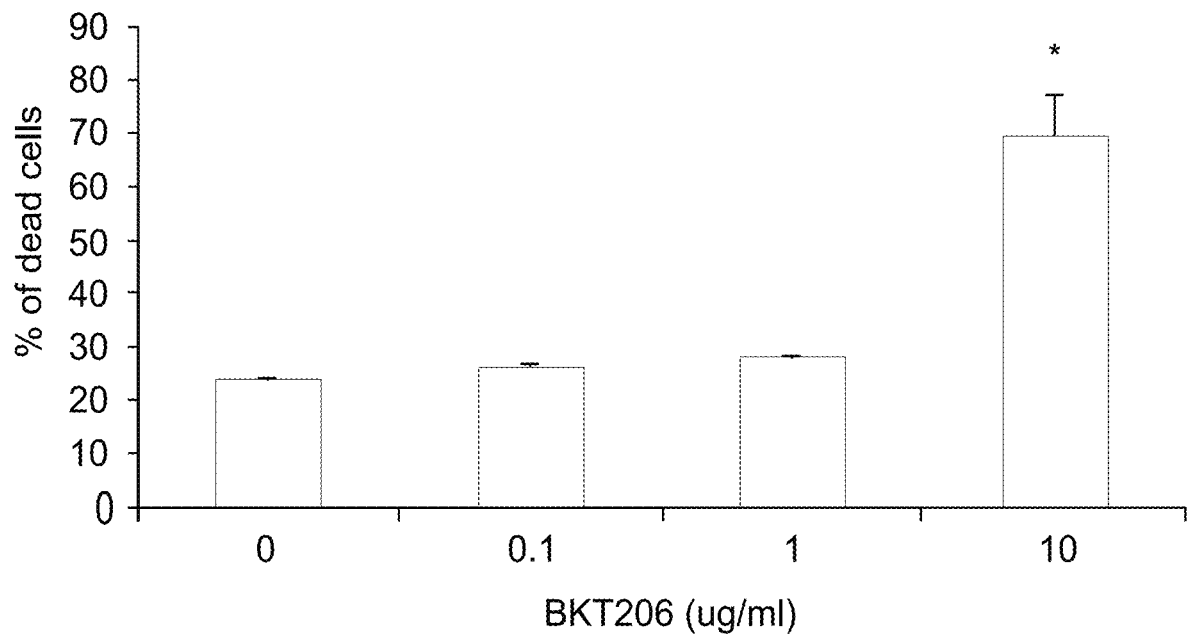
FIGS. 36A and 36B are bar graphs showing the effect of 0, 0.1, 1 and 10 µg/ml of Compound BKT206 on the viability of MV4-11 cells, as expressed by percentage of dead cells (FIG. 36A) and the number of viable cells (FIG. 36B), as determined by propidium iodide staining (* indicates $p<0.05$ vs. zero concentration).
Figure 36B:
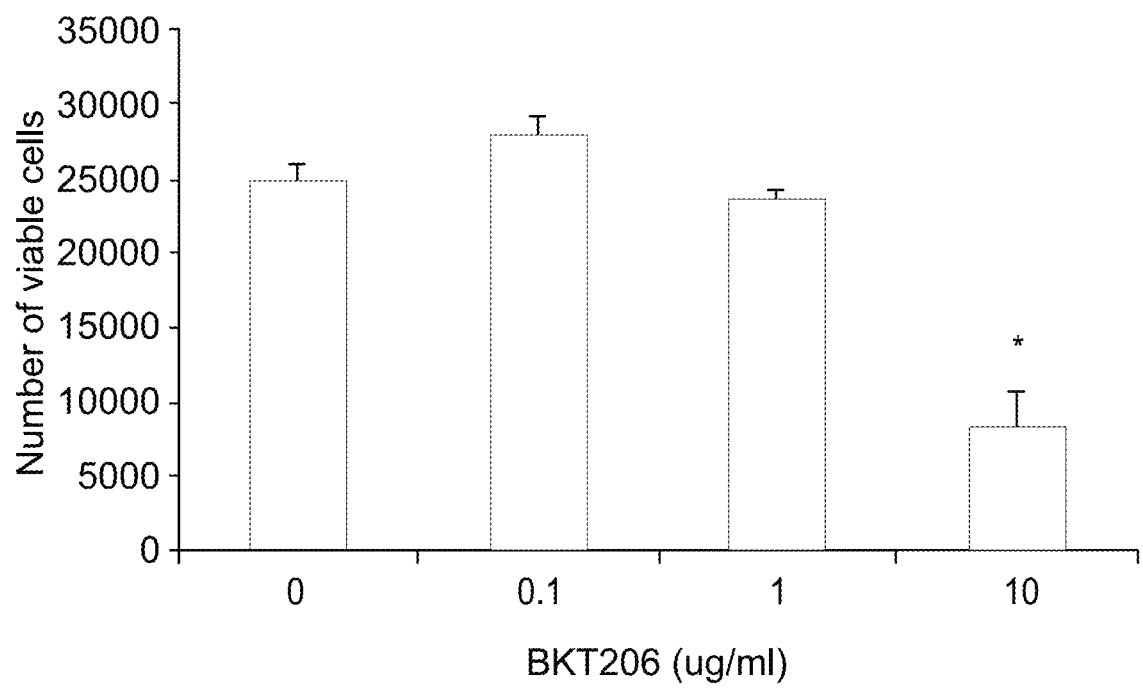

As shown in FIGS. 36A and 36B, Compound BKT206 induced cell death of MV4-11 human acute myeloid leukemia cells at concentrations of 10 μg/ml.

Figure 37A:
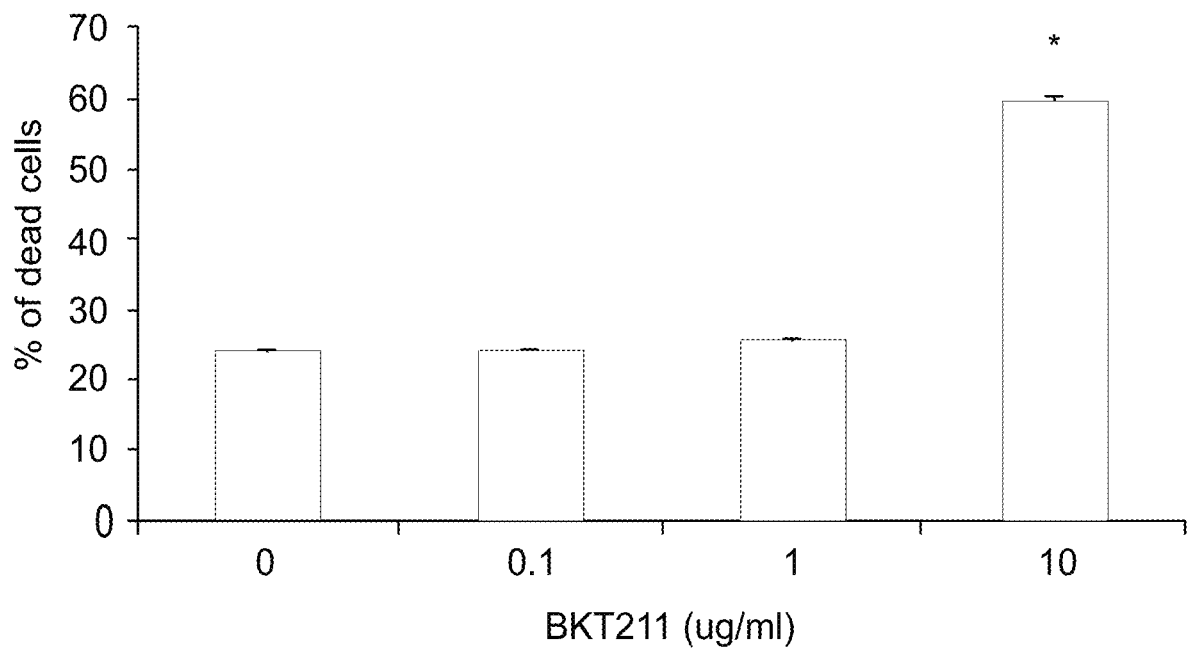
FIGS. 37A and 37B are bar graphs showing the effect of 0, 0.1, 1 and 10 µg/ml of Compound BKT211 on the viability of MV4-11 cells, as expressed by percentage of dead cells (FIG. 37A) and the number of viable cells (FIG. 37B), as determined by propidium iodide staining (* indicates $p<0.05$ vs. zero concentration).
Figure 37B:
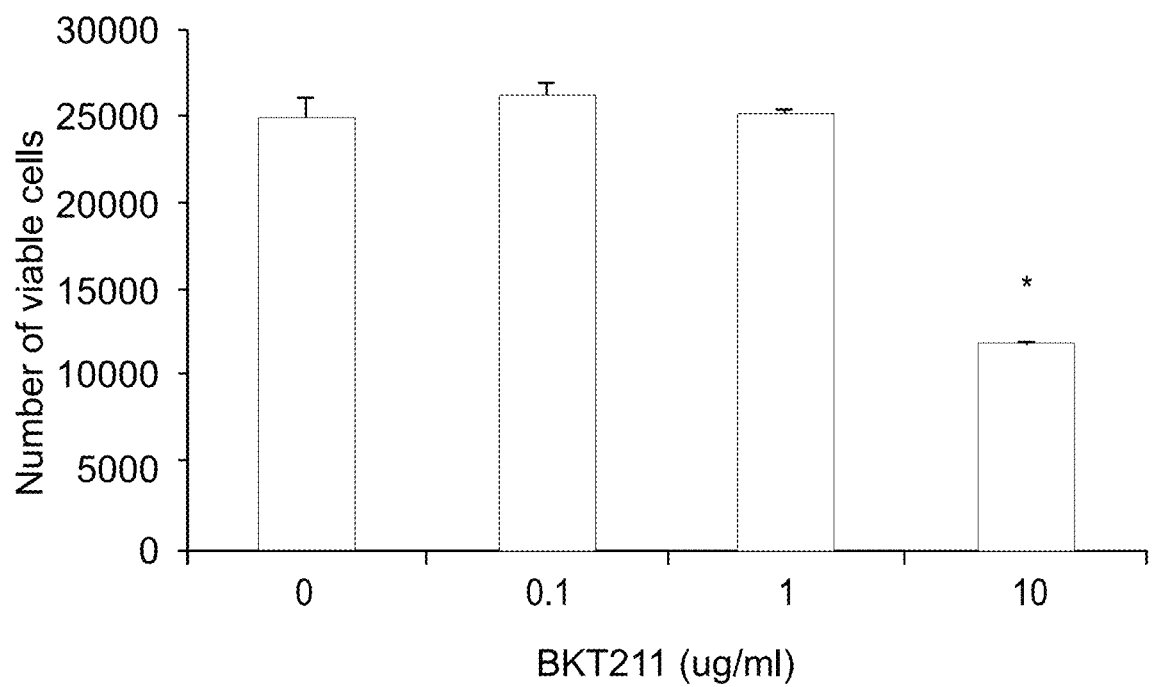

As shown in FIGS. 37A and 37B, Compound BKT211 induced cell death of MV4-11 human acute myeloid leukemia cells at concentrations of 10 μg/ml.

Figure 38A:
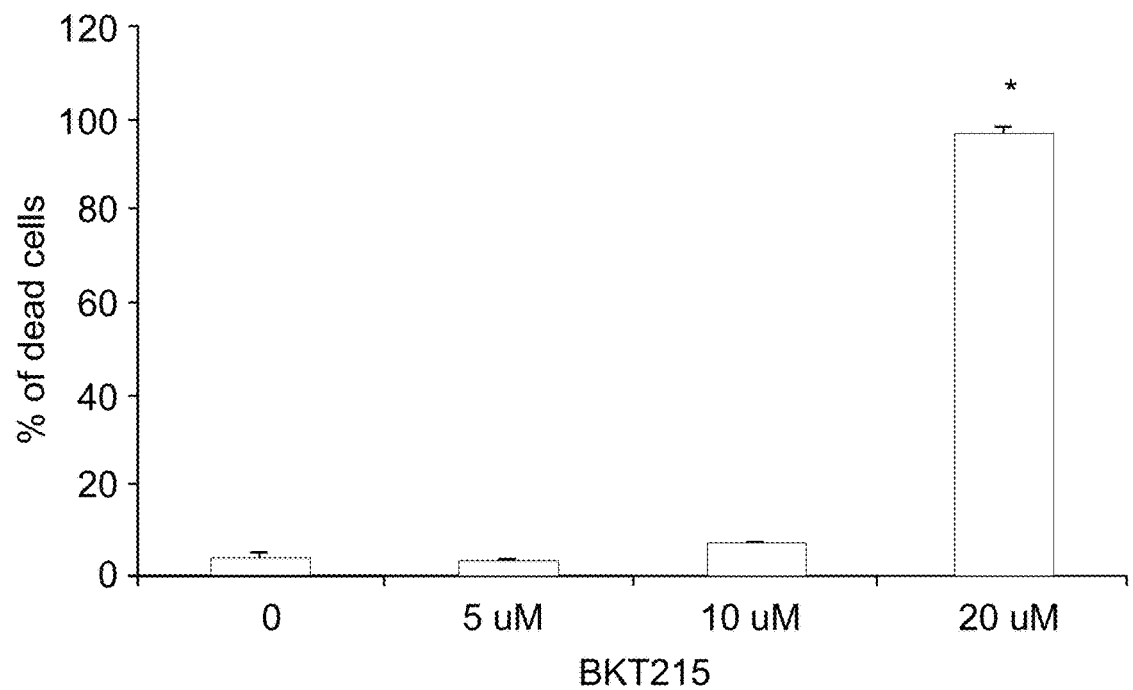
FIGS. 38A and 38B are bar graphs showing the effect of 0, 5, 10 and 20 µM (equivalent to 0, 1.5, 3 and 6 µg/ml) of BKT215 on the viability of MV4-11 cells, as expressed by percentage of dead cells (FIG. 38A) and the number of viable cells (FIG. 38B), as determined by propidium iodide staining (* indicates $p<0.05$ vs. zero concentration).
Figure 38B:
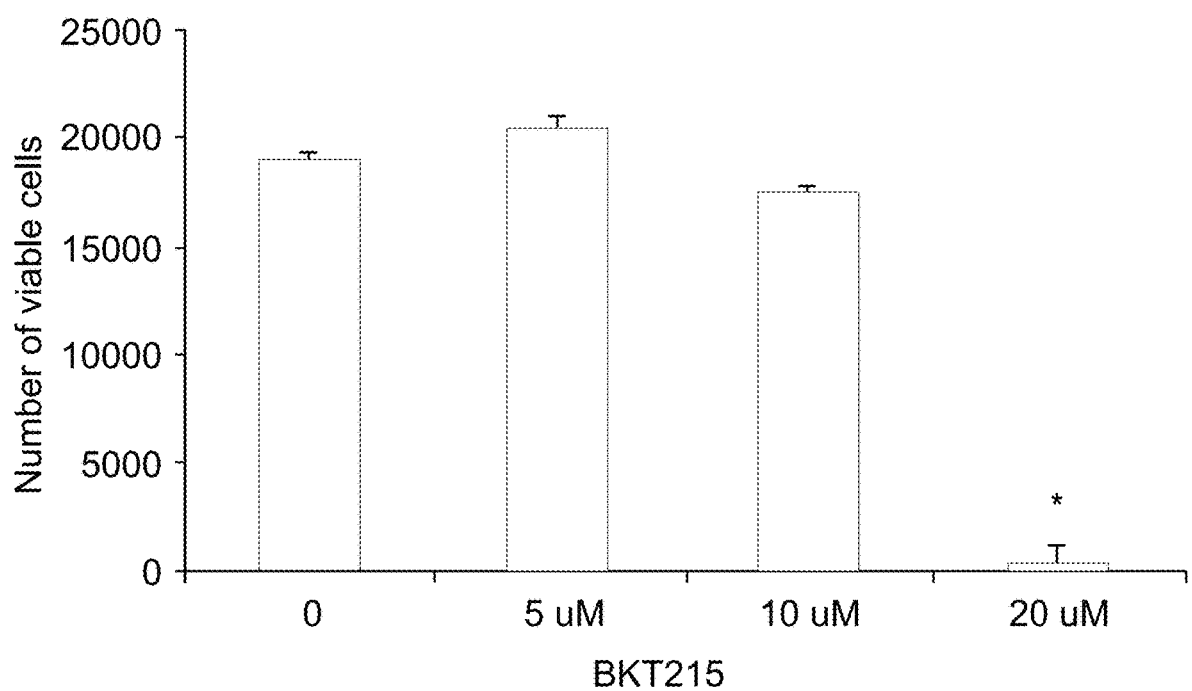

As shown in FIGS. 38A and 38B, Compound BKT215 induced cell death of MV4-11 human acute myeloid leukemia cells at concentrations of 20 am (equivalent to 6 μg/ml).

Figure 39A:
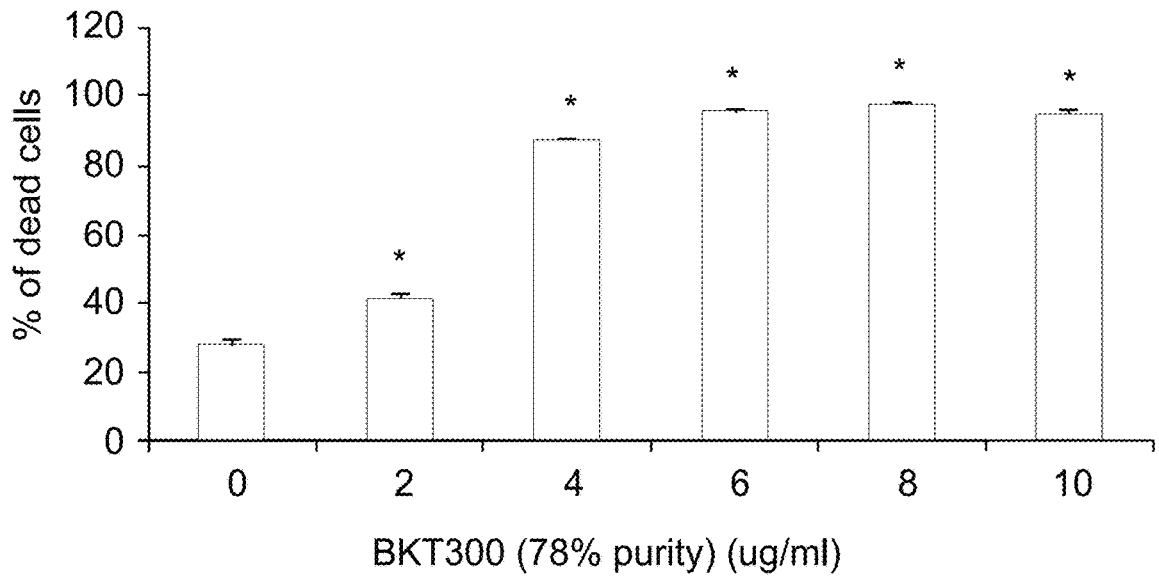
FIGS. 39A and 39B are bar graphs showing the effect of 0, 2, 4, 6, 8 and 10 µg/ml of BKT300 (at 78% purity) on the viability of MV4-11 cells, as expressed by percentage of dead cells (FIG. 39A) and the number of viable cells (FIG. 39B), as determined by propidium iodide staining (* indicates $p<0.05$ vs. zero concentration).
Figure 39B:
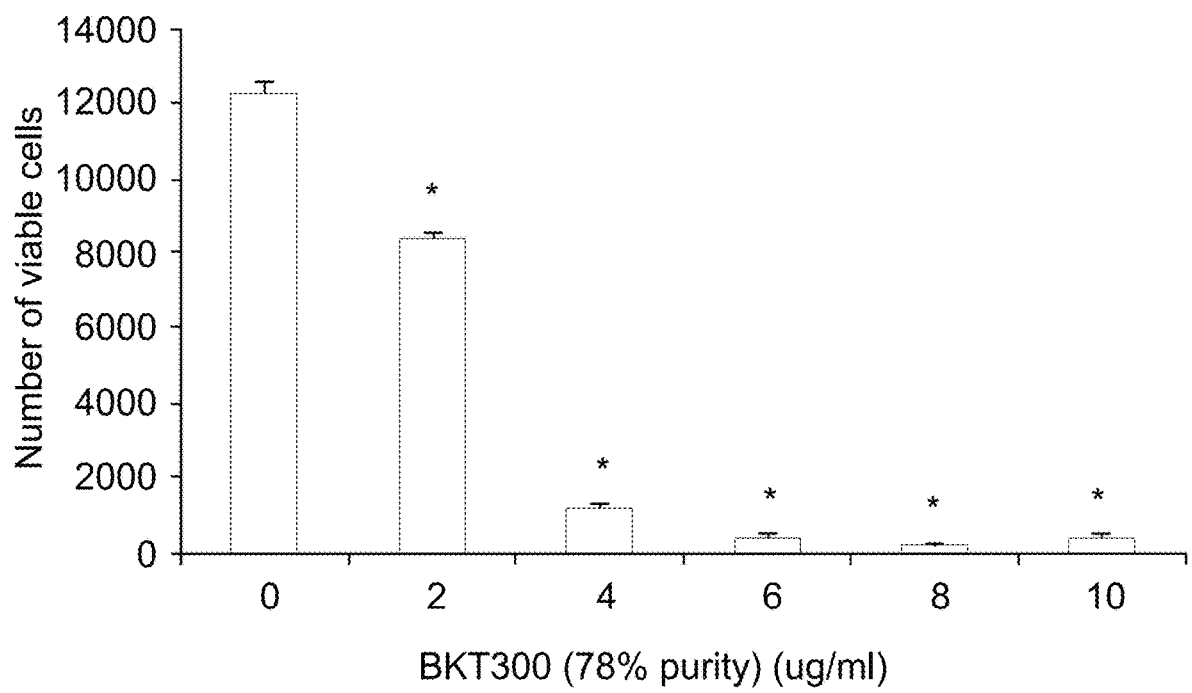
Figure 40A:
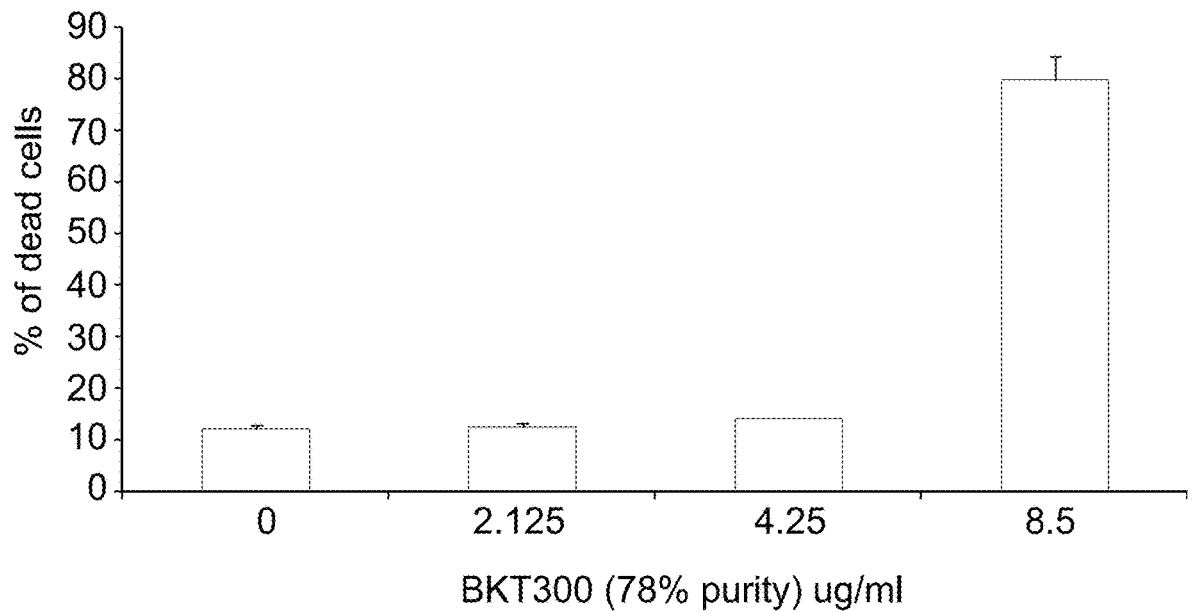
FIGS. 40A-40D are bar graphs showing the effect of 0, 2.125, 4.25 and 8.5 µg/ml (equivalent to 0, 5, 10 and 20 µM) of BKT300 at 78% purity (FIGS. 40A and 40B) and at 98% purity (FIGS. 40C and 40D) on the viability of MV4-11 cells, as expressed by percentage of dead cells (FIGS. 40A and 40C) and the number of viable cells (FIGS. 40B and 40D), as determined by propidium iodide staining (* indicates $p<0.05$ vs. zero concentration).
Figure 40B:
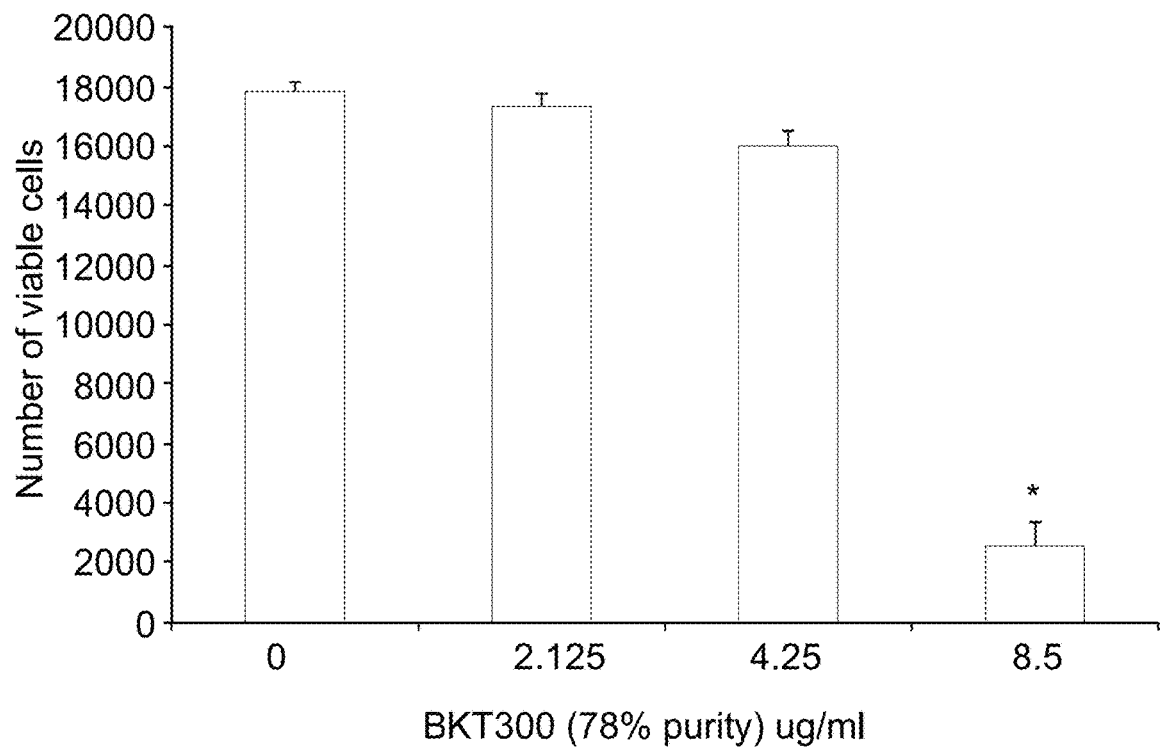
Figure 40C:
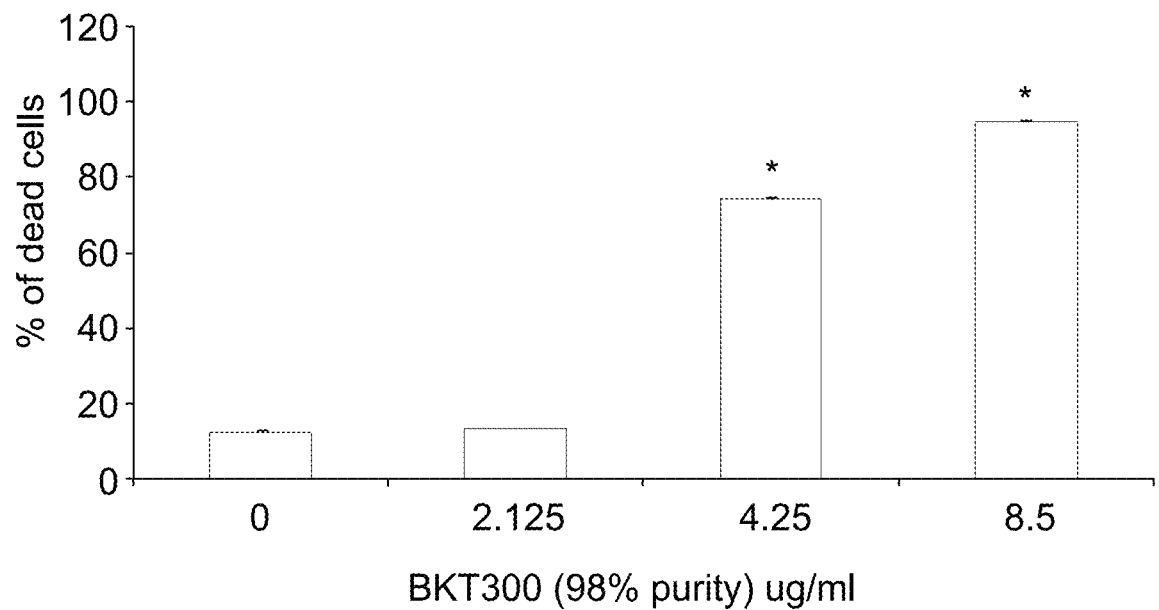
Figure 40D:
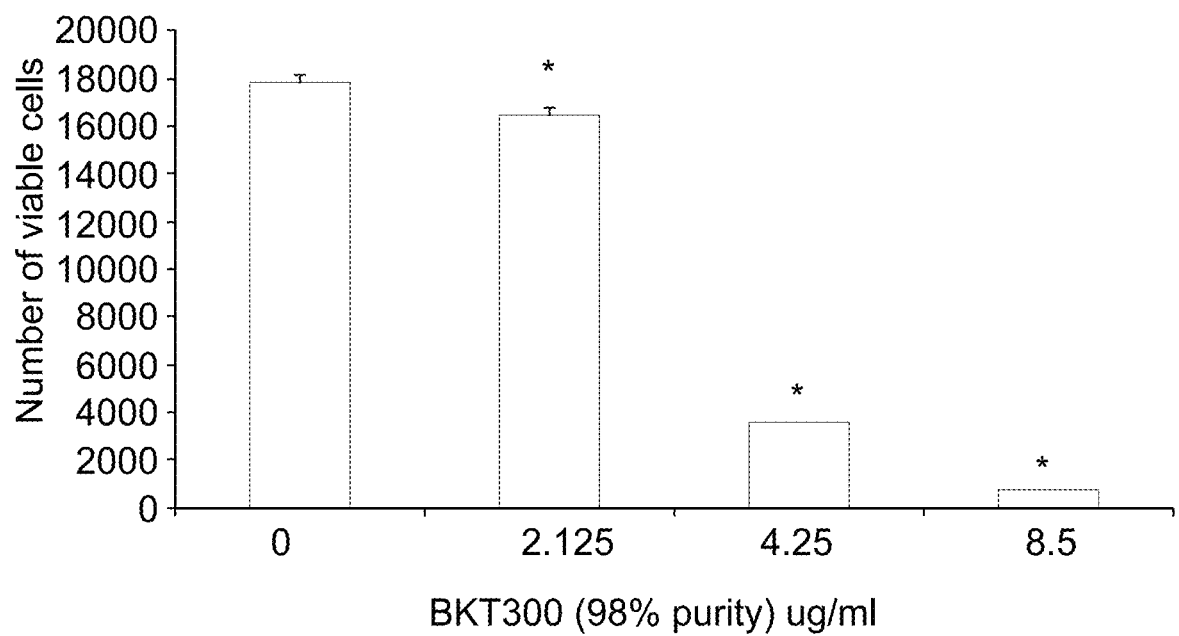

As shown in FIGS. 39A and 39B, BKT300 (at 78% purity) induced cell death of MV4-11 human acute myeloid leukemia cells at concentrations as low as 2 μg/ml (the lowest tested concentration). The $IC_{50}$ for BKT300 (78% purity)-induced death of MV4-11 cells was 2.72 μg/ml.

Induction of cell death by BKT300 was repeated while comparing the effects of a sample of BKT300 at 78% purity with a sample of BKT300 at 98% purity.

As shown in FIGS. 40A-40D, BKT300 at 98% purity was significantly more effective than BKT300 at 78% purity at inducing cell death. For example, BKT300 at 98% purity induced a considerably greater degree of cell death at 4.25 μg/ml than did BKT300 at 78% purity.

These results suggest that impurities present in BKT300 (e.g., BKT300 at 78% purity) may reduce the cell death induced by BKT300 per se, and that BKT300 at a high degree of purity (e.g., 98%) is particularly potent in comparison to other compounds described herein.

These results indicate that chemokine-binding activity of compounds described herein is associated with anticancer activity.

The in vitro effect of BKT300 (at 78% purity) on cancer cell viability was further evaluated using a variety of additional cancer cell lines, using procedures as described hereinabove with respect to MV4-11 cells.

Figure 41A:
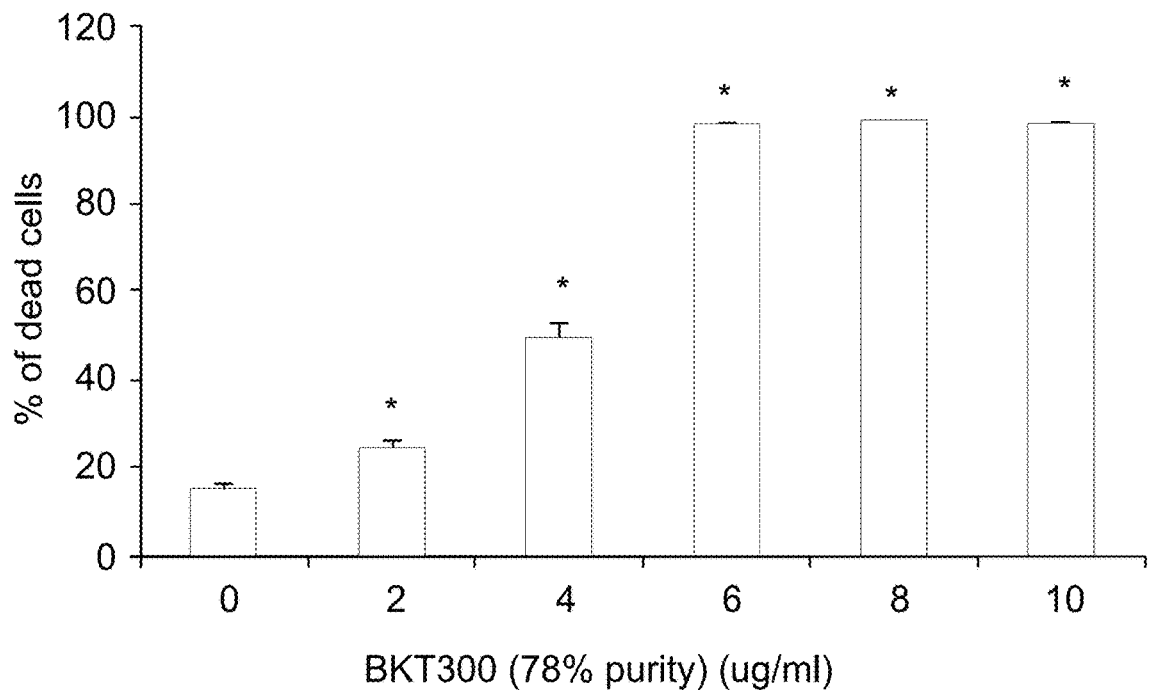
FIGS. 41A and 41B are bar graphs showing the effect of 0, 2, 4, 6, 8 and 10 g/ml of BKT300 (at 78% purity) on the viability of RPMI cells, as expressed by percentage of dead cells (FIG. 41A) and the number of viable cells (FIG. 41B), as determined by propidium iodide staining (* indicates $p<0.05$ vs. zero concentration).
Figure 41B:
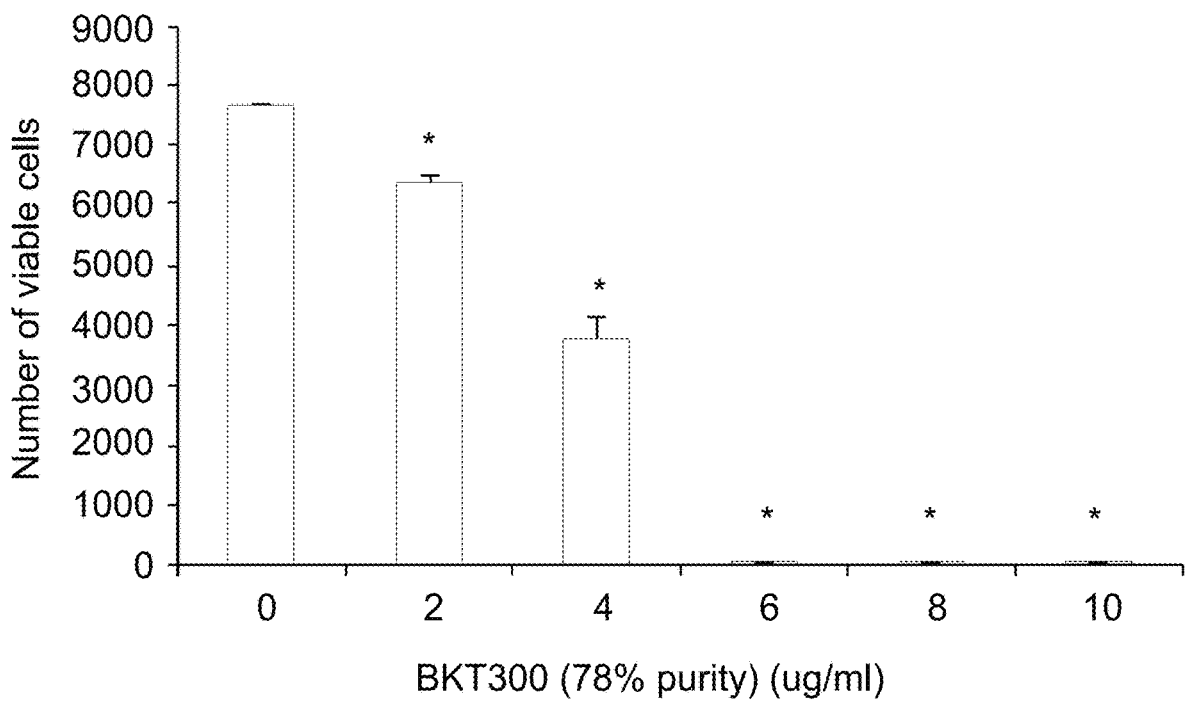

As shown in FIGS. 41A and 41B, BKT300 (at 78% purity) induced cell death of RPMI human multiple myeloma cells at concentrations as low as 2 μg/ml (the lowest tested concentration).

Figure 42A:
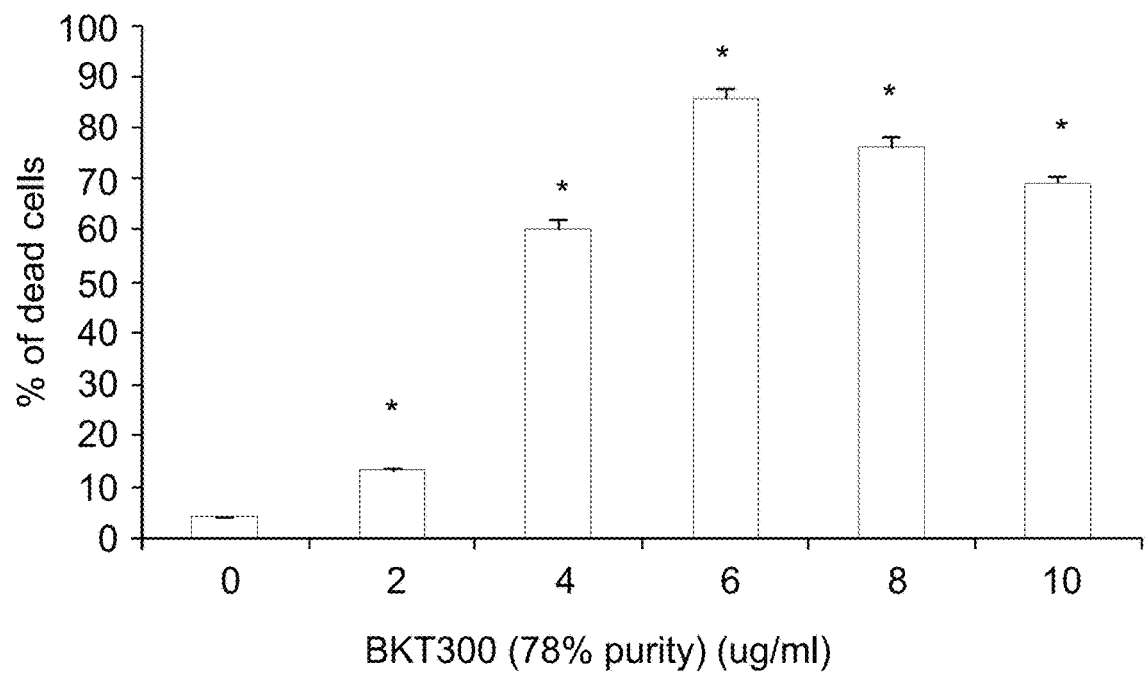
FIGS. 42A and 42B are bar graphs showing the effect of 0, 5, 10 and 20 µM (equivalent to 0, 2.125, 4.25 and 8.5 µg/ml) of BKT300 (at 78% purity) on the viability of Jurkat cells, as expressed by percentage of dead cells (FIG. 42A) and the number of viable cells (FIG. 42B), as determined by propidium iodide staining (* indicates $p<0.05$ vs. zero concentration).
Figure 42B:
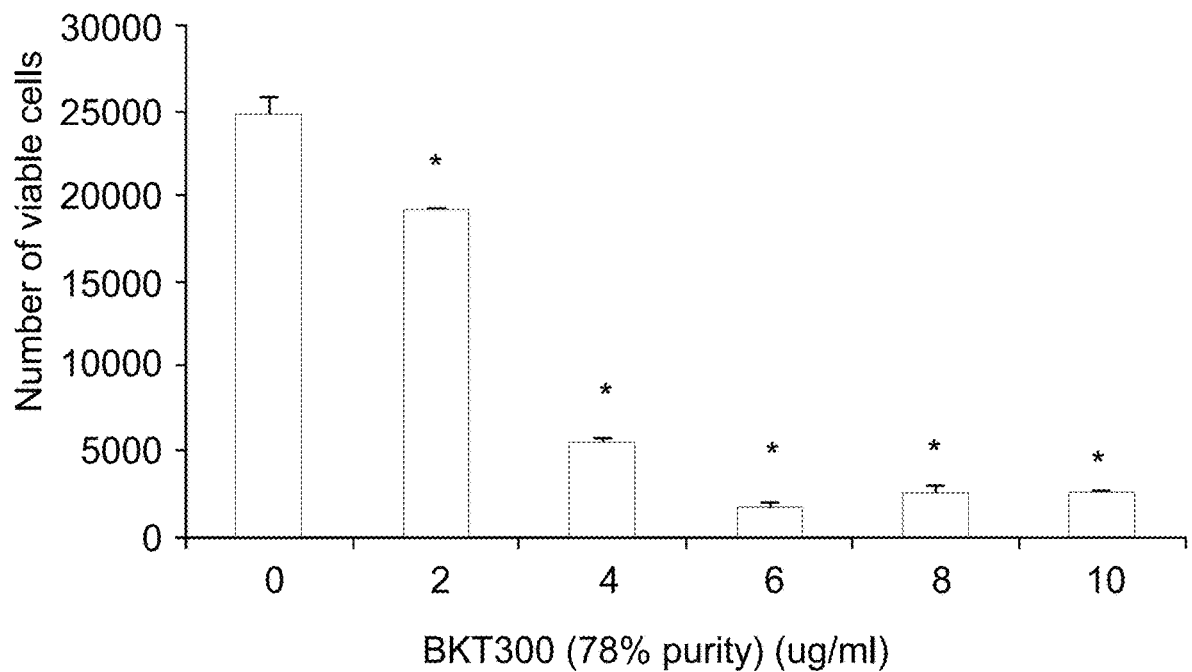

As shown in FIGS. 42A and 42B, BKT300 (at 78% purity) induced cell death of Jurkat human acute lymphoblastic leukemia cells at concentrations as low as 2 μg/ml (the lowest tested concentration). The IC50 for BKT300-induced death of Jurkat cells was 3.5 μg/ml.

Figure 43A:
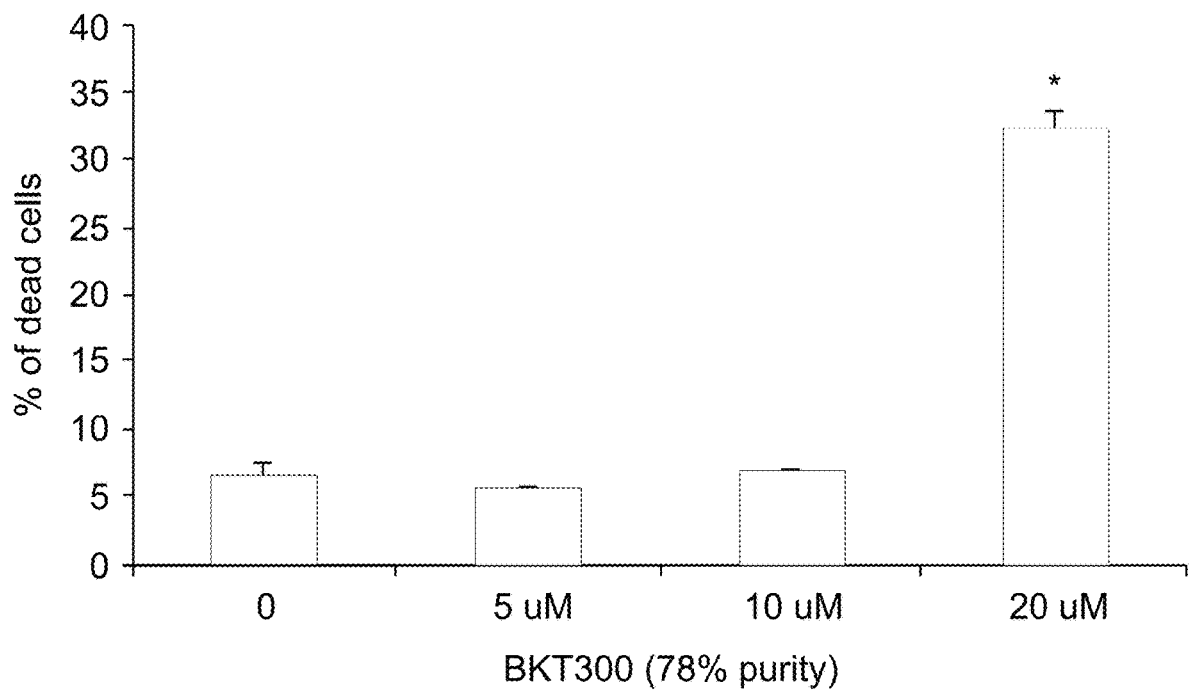
FIGS. 43A and 43B are bar graphs showing the effect of 0, 5, 10 and 20 µM (equivalent to 0, 2.125, 4.25 and 8.5 µg/ml) of BKT300 (at 78% purity) on the viability of Raji cells, as expressed by percentage of dead cells (FIG. 43A) and the number of viable cells (FIG. 43B), as determined by propidium iodide staining (* indicates $p<0.05$ vs. zero concentration).
Figure 43B:
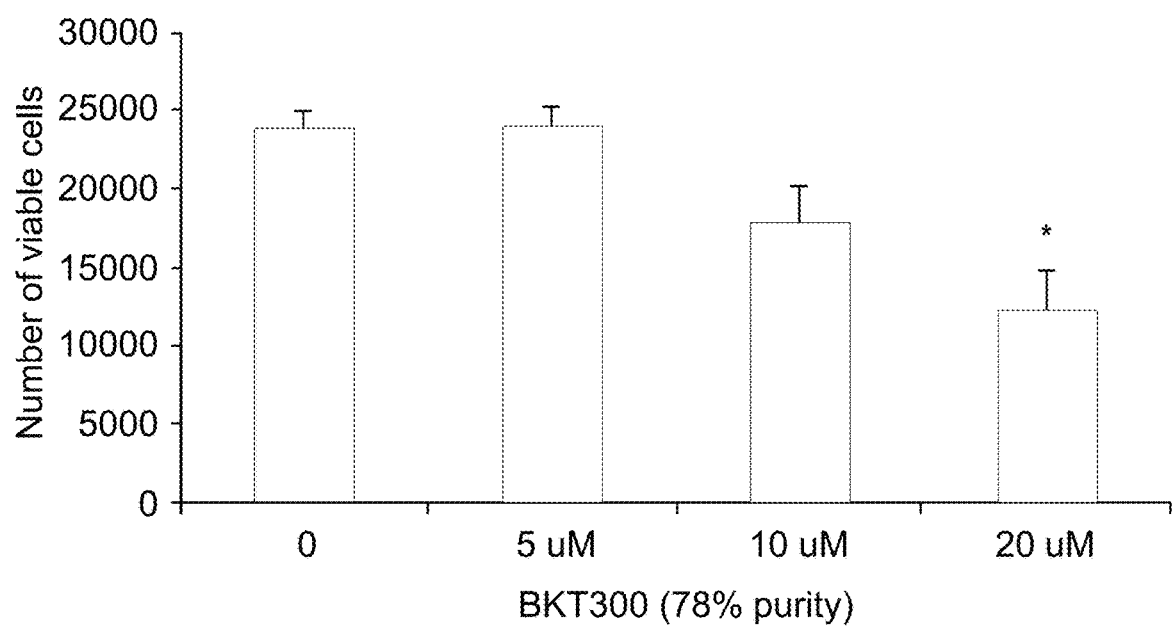
Figure 44A:
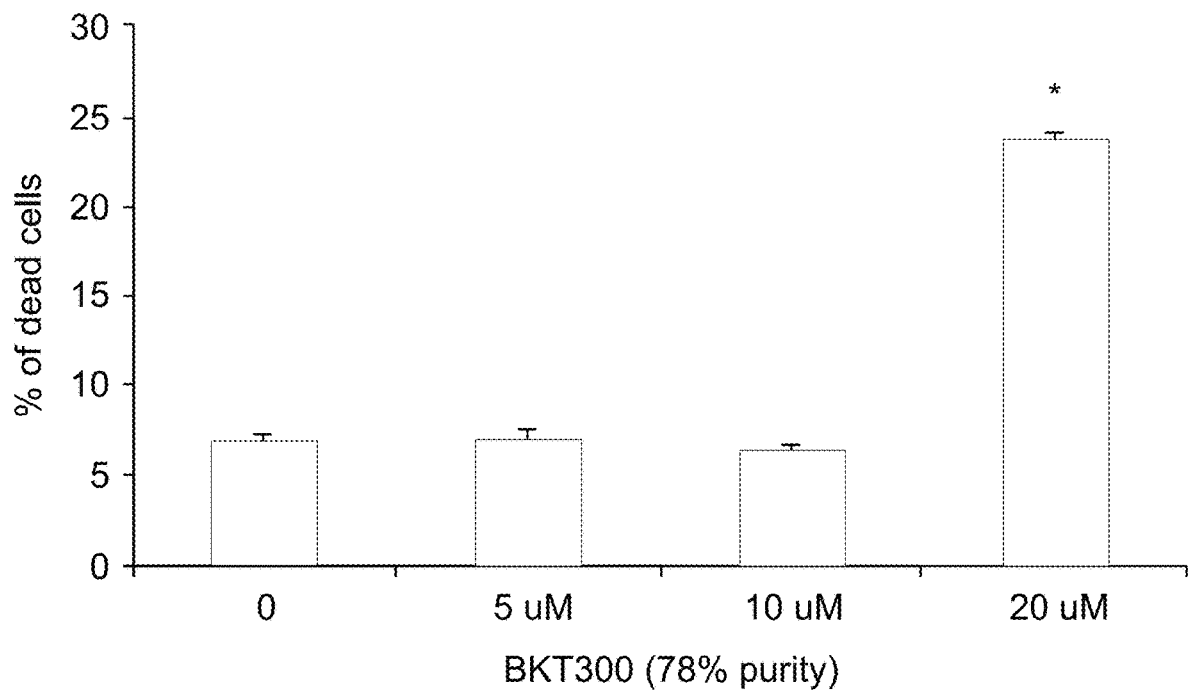
FIGS. 44A and 44B are bar graphs showing the effect of 0, 5, 10 and 20 µM (equivalent to 0, 2.125, 4.25 and 8.5 µg/ml) of BKT300 (at 78% purity) on the viability of Bjab cells, as expressed by percentage of dead cells (FIG. 44A) and the number of viable cells (FIG. 44B), as determined by propidium iodide staining (* indicates $p<0.05$ vs. zero concentration).
Figure 44B:
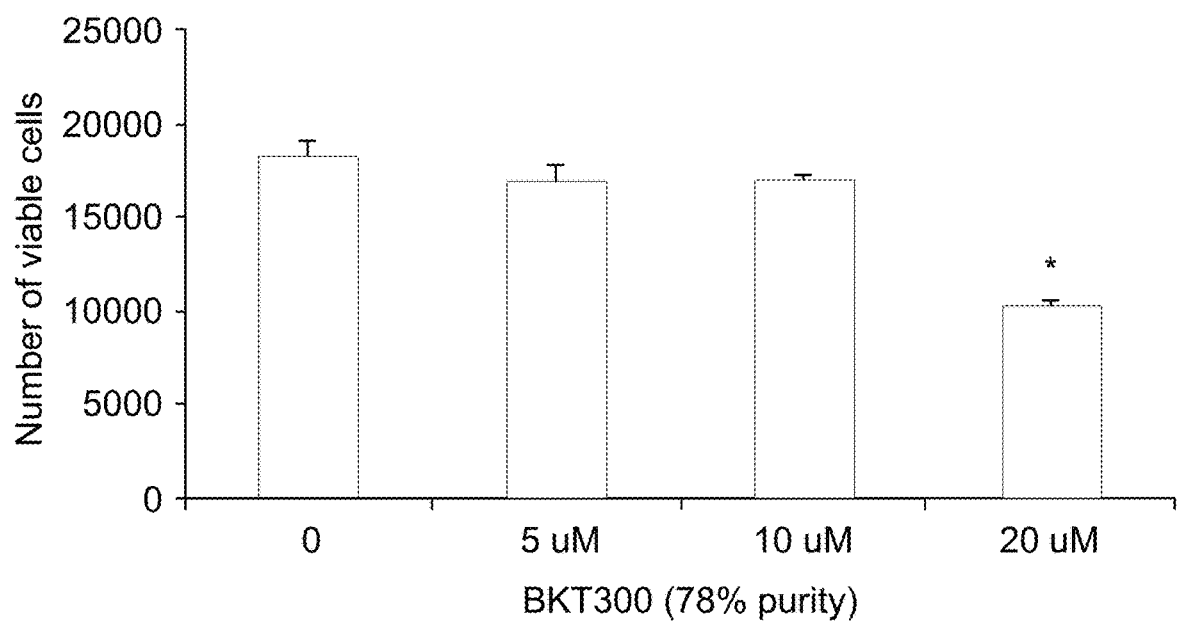

As shown in FIGS. 43A-44B, BKT300 (at 78% purity) induced cell death of about 30% of Raji (FIGS. 43A and 43B) and Bjab (FIGS. 44A and 44B) human lymphoma cells at a concentration of 8.5 μg/ml, and further induced slight cell death of Raji cells at a concentration of 4.25 μg/ml (FIGS. 43A and 43B).

Figure 45A:
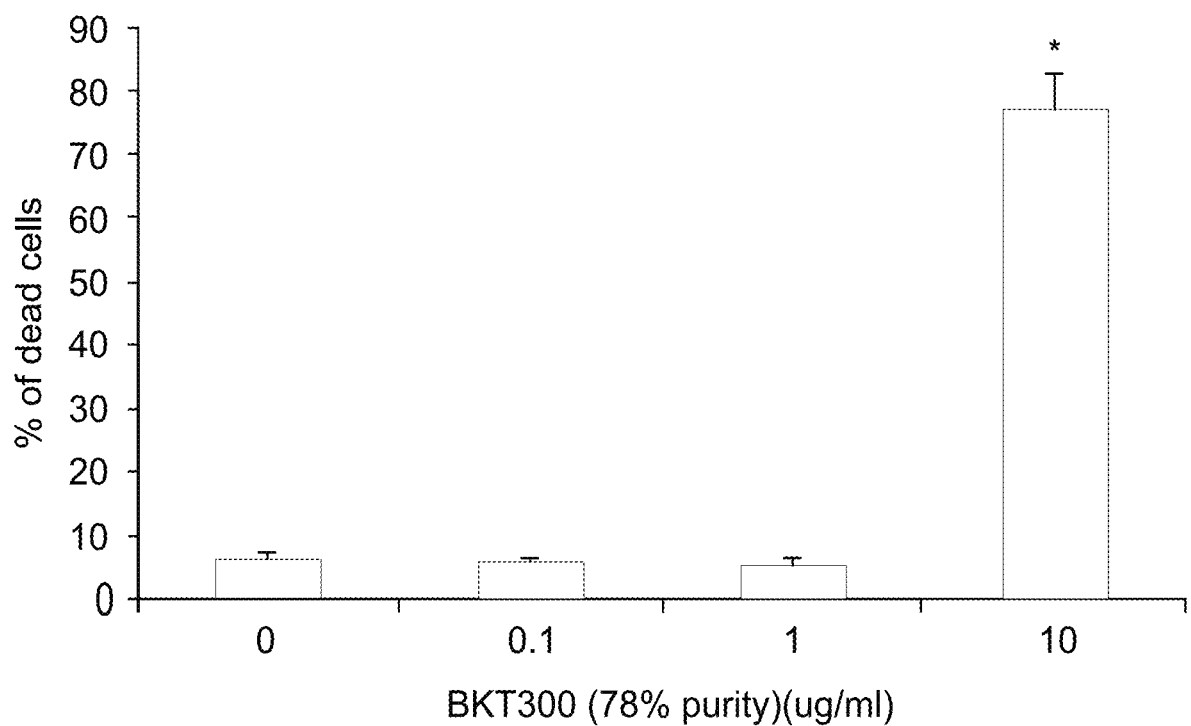
FIGS. 45A and 45B are bar graphs showing the effect of 0, 0.1, 1 and 10 µg/ml of BKT300 (at 78% purity) on the viability of H-460 cells, as expressed by percentage of dead cells (FIG. 45A) and the number of viable cells (FIG. 45B), as determined by propidium iodide staining (* indicates $p<0.05$ vs. zero concentration).
Figure 45B:
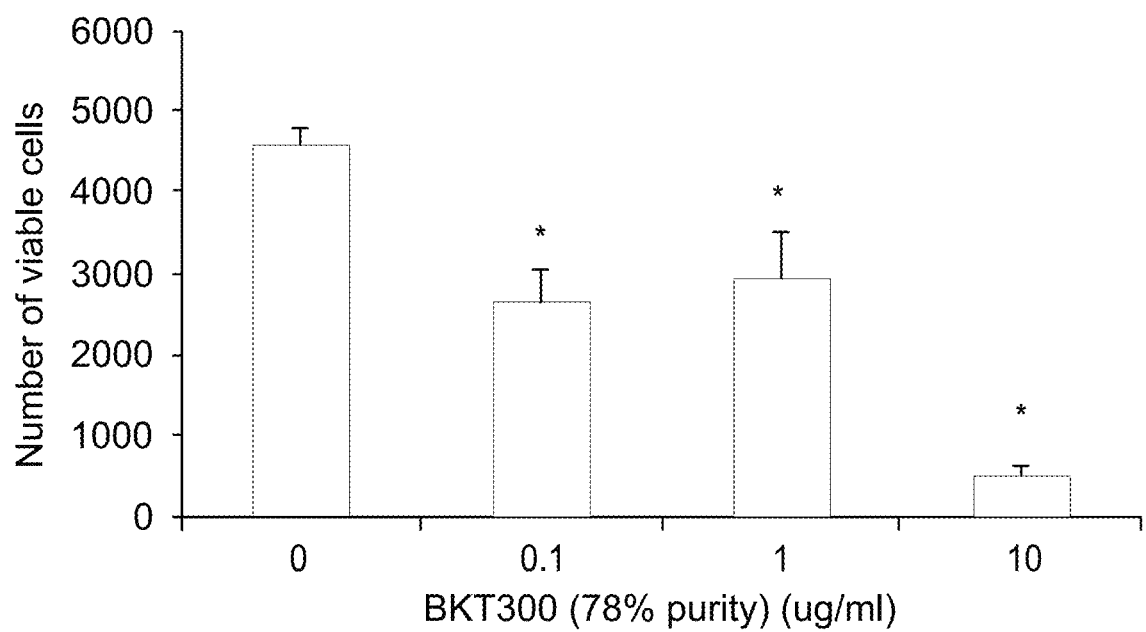

As shown in FIGS. 45A and 45B, BKT300 (at 78% purity) induced cell death of about 80% of H460 human large cell lung cancer cells at a concentration of 10 μg/ml.

Figure 46A:
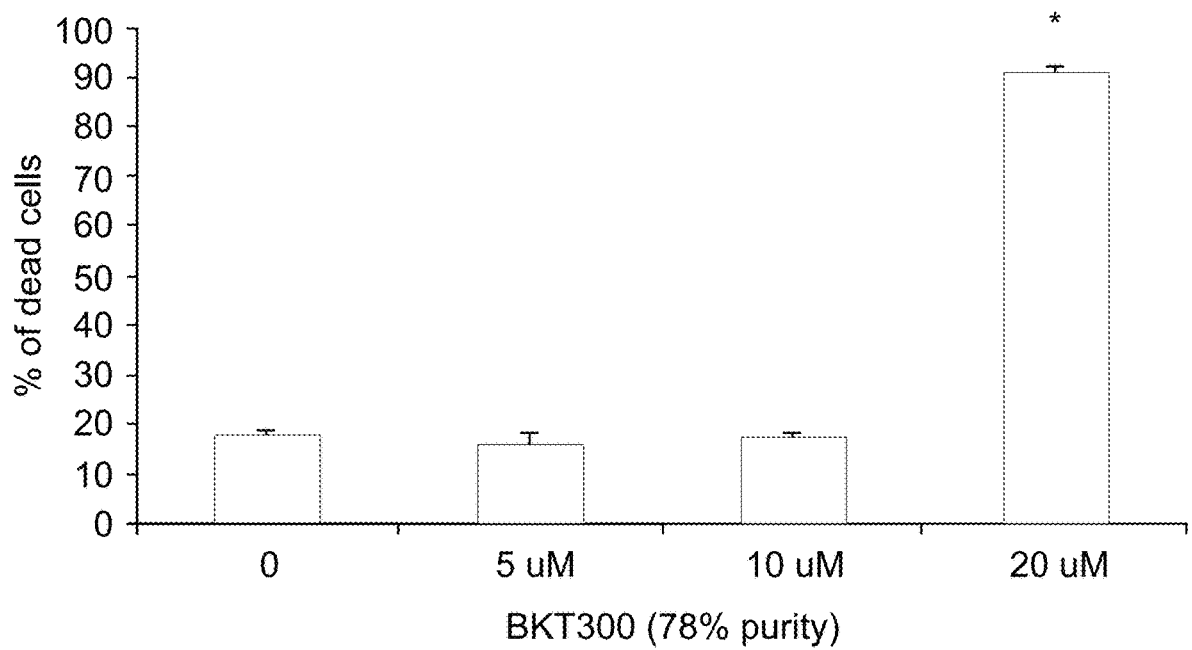
FIGS. 46A and 46B are bar graphs showing the effect of 0, 5, 10 and 20 µM (equivalent to 0, 2.125, 4.25 and 8.5 µg/ml) of BKT300 (at 78% purity) on the viability of H345 cells, as expressed by percentage of dead cells (FIG. 46A) and the number of viable cells (FIG. 46B), as determined by propidium iodide staining (* indicates $p<0.05$ vs. zero concentration).
Figure 46B:
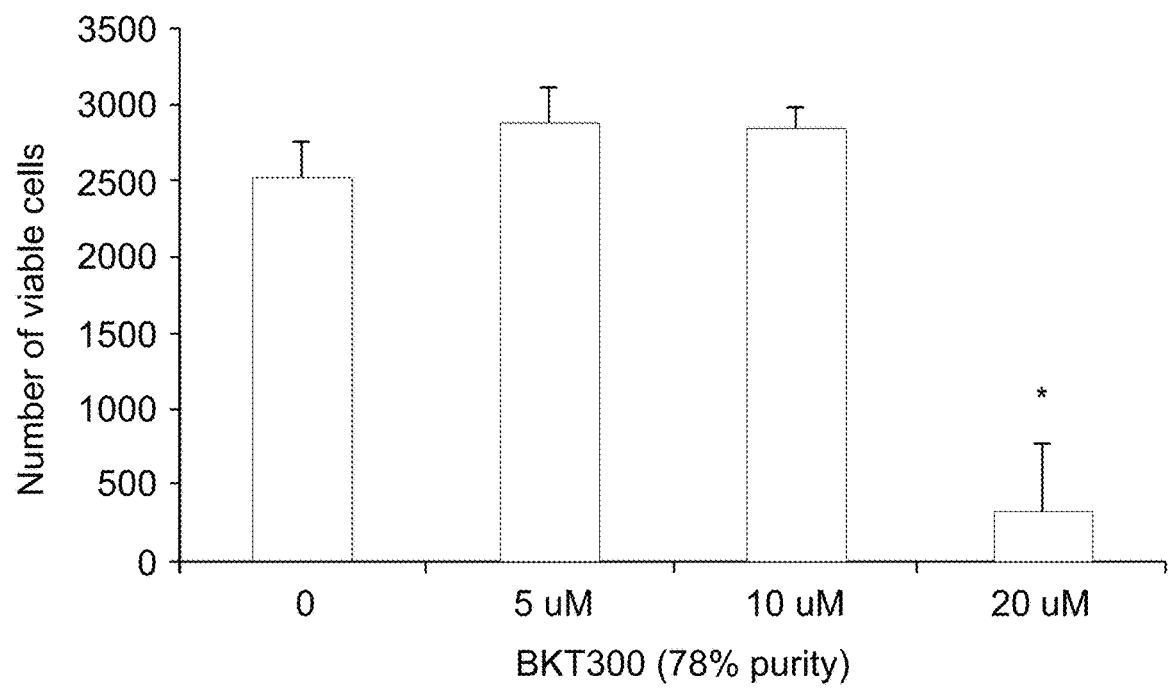

As shown in FIGS. 46A and 46B, BKT300 (at 78% purity) induced cell death of over 90% of H345 human small cell lung cancer cells at a concentration of 8.5 μg/ml.

These results indicate that BKT300 is effective at inducing cell death of a wide variety of cancer cell types.

Example 4

Effect of Exemplary Compound on Cancer Cells In Vivo

The effect of BKT300 (at 98% purity) on the proliferation of AML cells in vivo was examined by treatment of NOD scid gamma (NSG) mice transplanted with MV4-11 (FLT3-ITD) cells.

The mice were subjected to irradiation with 300 rad and on the following day were transplanted by IV injection with MV4-11 (FLT3-ITD) cells, 10×10$^6$ cells/mouse. 21 days following transplantation, the treated group was injected intraperitoneally with 1 mg/Kg of BKT300 (98% purity) per injection for three consecutive days. On day 25 following transplantation, mice were sacrificed and the survival of the human AML blasts in the blood, spleen and the bone marrow was evaluated using anti human CD45.

The study protocol is presented in the following table and some of the results are presented in FIGS. 47A-47C.

| | | Treatments | | | |
|---|---|---|---|---|---|
| Day (−1) | Day 0 | Day 21 | Day 22 | Day 23 | Day 24 | End of Exp. Day 25 |
| Irradiation 300 rad | Cells transplantation 10 × 10$^6$ MV4-11 (IV) 1 mg/Kg/mouse | + | + | + | + | Mice sacrifice Blood BM spleen |

As shown in FIG. 47B, BKT300 administration dramatically reduced the number and percentage of AML cells in the bone marrow of mice.

FIGS. 47B and 47C present data obtained in a representative FACS analysis showing the presence of human MV4-11 cells with in the bone marrow of untreated mice (FIG. 47C) and of mice treated with BKT300, which further demonstrate the ability of BKT300 to eradicate the leukemic cells.

Example 5

Inhibition of Kinase Activity by BKT300

In order to further characterize the effect of BKT300 on cell signaling, kinase profiling of BKT300 (at 78% purity) was performed (by the Life Technologies SelectScreen® Biochemical Profiling Lab) using a LanthaScreen® europium kinase binding assay to screen 440 kinases.

Figure 48:
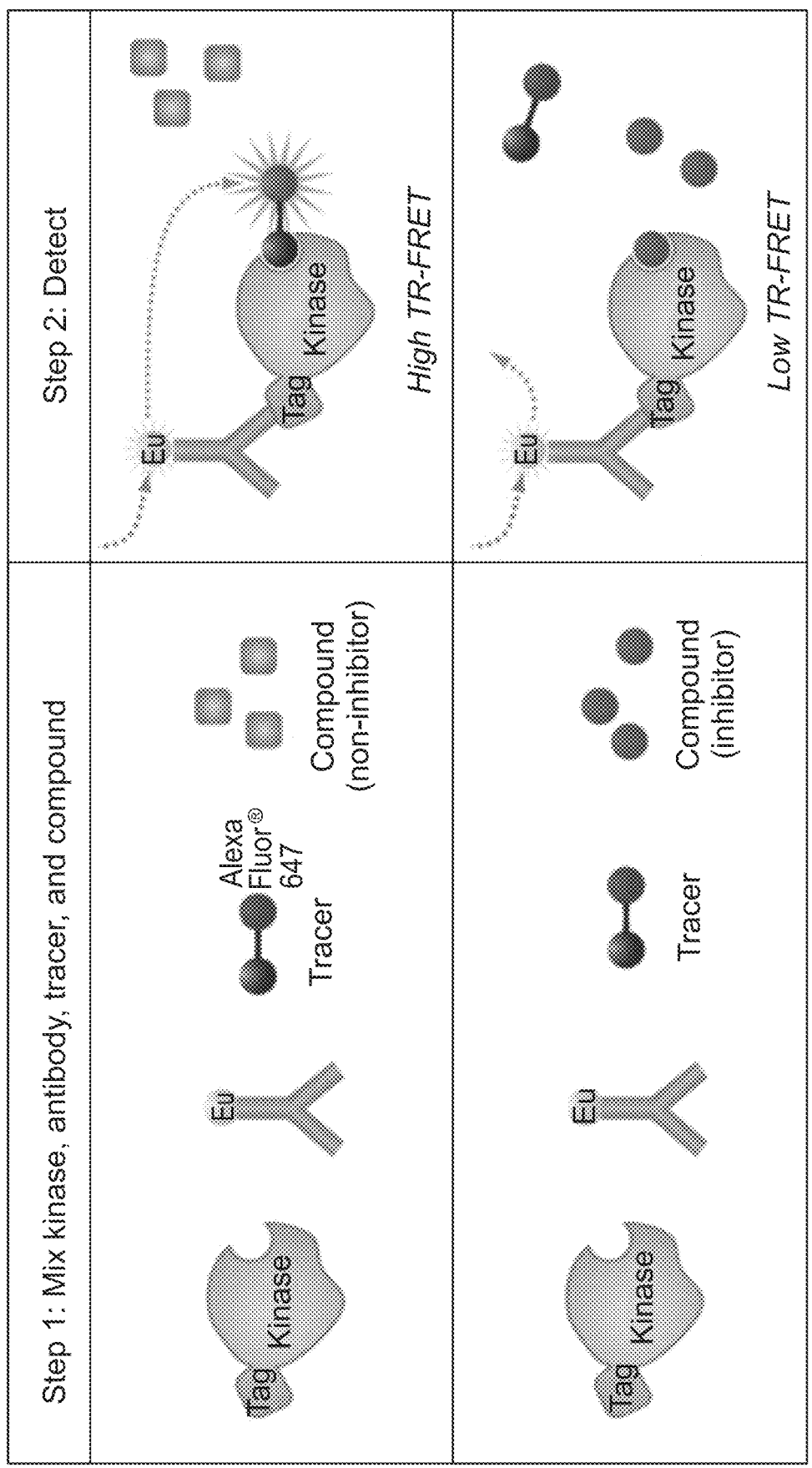
FIG. 48 presents a scheme showing the principles of a FRET assay for determining binding of a compound (inhibitor) to an active site of kinases, wherein resonant energy transfer of energy from a europium (Eu)-labeled antibody which binds to the kinase to an Alexa Fluor®-labeled tracer which binds to the active site is prevented by a compound (inhibitor) which binds to the active site.

The principle of the LanthaScreen® assay is depicted in FIG. 48. Binding of an Alexa Fluor® conjugate or "tracer" to a kinase is detected by addition of a europium (Eu)-labeled anti-tag antibody. Binding of the tracer and antibody to a kinase results in a high degree of FRET, whereas displacement of the tracer with a kinase inhibitor results in a loss of FRET. The kinase tracers are based on ATP-competitive kinase inhibitors, making them suitable for detection of any compounds that bind to the ATP site. Inhibitors that bind the ATP site include both Type I kinase inhibitors, which bind solely to the ATP site, and Type II inhibitors (e.g., imatinib, sorafenib, BIRB-796), which bind to both the ATP site and a second site often referred to as the allosteric site.

Of the 440 screened kinases, BKT300 inhibited 36 kinases by more than 40%. These kinases are presented in Table 3 below.

As shown in Table 3, most of the kinases inhibited by BKT300 were serine/threonine kinases.

Many such kinases are involved in cancer, and some in immune regulation. These results suggest that kinase inhibition by BKT300 can be utilized for treating cancer, particularly by cancer immunotherapy.

TABLE 3

Inhibition of kinases by BKT300

| Kinase | % Inhibition | Kinase Type |
|---|---|---|
| DYRK3 | 47 | ST |
| EPHA8 | 50 | ND |
| GRK4 | 63 | ST |
| GRK5 | 65 | ST |
| MAP4K2 (GCK) | 48 | ND |
| MAP4K4 (HGK) | 40 | ST |
| MELK | 41 | ST |
| PAK7 (KIAA1264) | 40 | ST |
| SGK2 | 43 | ST |
| SRC N1 | 41 | TK |
| ACVRL1 (ALK1) | 47 | ST |
| BMPR1A (ALK3) | 58 | ST |
| CDC7/DBF4 | 53 | ST |
| CDK1/cyclin A2 | 45 | ST |
| CDK11 (Inactive) | 57 | ST |
| CDK8/cyclin C | 64 | ND |
| CLK4 | 73 | ST |
| DAPK2 | 65 | ST |
| DYRK2 | 62 | ST |
| ICK | 41 | ST |
| KIT D820E | 42 | TK* |
| KIT T670E | 51 | TK* |
| MAP4K1 (HPK1) | 45 | ST |
| MAPK10 (JNK3) | 49 | ST |
| MLCK (MLCK2) | 58 | ST |
| MYLK (MLCK) | 63 | ST |
| NUAK2 | 89 | ST |
| STK17A (DRAK1) | 48 | ST |
| STK17B (DRAK2) | 107 | ST |
| STK38 (NDR) | 41 | ST |
| STK38L (NDR2) | 45 | ST |
| TGFBR2 | 43 | ST |
| TTK | 52 | STTK |
| DAPK1 | 43 | ST |
| PIK3CA | 64 | |
| PIK3CD | 77 | |

ST = serine/threonine kinase

TK = tyrosine kinase

STTK = serine/threonine tyrosine kinase

ND = kinase type not determined

Example 6

Computational Binding Model of BKT300 to Kinases

All modeling work was performed using the Accelrys software package "Discovery Studio".

Pharmacophore models were constructed manually (not using the automated pharmacophore tools of the package).

All small molecule conformations were generated using the "BEST" conformational search algorithm.

Pharmacophore mapping was performed using the "Pharmacophore mapping" tool of Discovery Studio, with the "flexible" option turned on.

All results of pharmacophore mapping were visually inspected in order to choose best candidate poses.

Design of a Binding Model to Kinases:

As demonstrated in Examples 1-4 hereinabove, BKT300 was identified through a cell-based assay as a promising active agent against leukemia cell lines. As shown in Example 5 hereinabove, in a screen of inhibition against the human kinome it was shown to inhibit a selection of kinases. Based on this inhibition data, coupled with gene expression data and biological considerations, four kinases were chosen as potential targets that could, possibly in some combination, mediate the anti-leukemia effect of BKT300: MELK, MAP4K4 and two Pi3-kinases (Pik3Cα and Pik3Cδ; also referred to as PIK3CA and PIK3CD), highlighted in Table 3 hereinabove.

Structural analysis of these four kinases was performed using all available structures in the public domain (PDB). For a preliminary construction of pharmacophoric models, the two protein-kinases, MELK and MAP4K4, were selected.

A literature search was performed to identify experimentally-verified "hot spots" (amino acid residues that if mutated result in loss of an order of magnitude or more in activity) for each of the kinases. Two such amino acid residues were identified: Lys40 and Asp 150, both positioned within the ATP binding site of the kinases.

Figure 49:
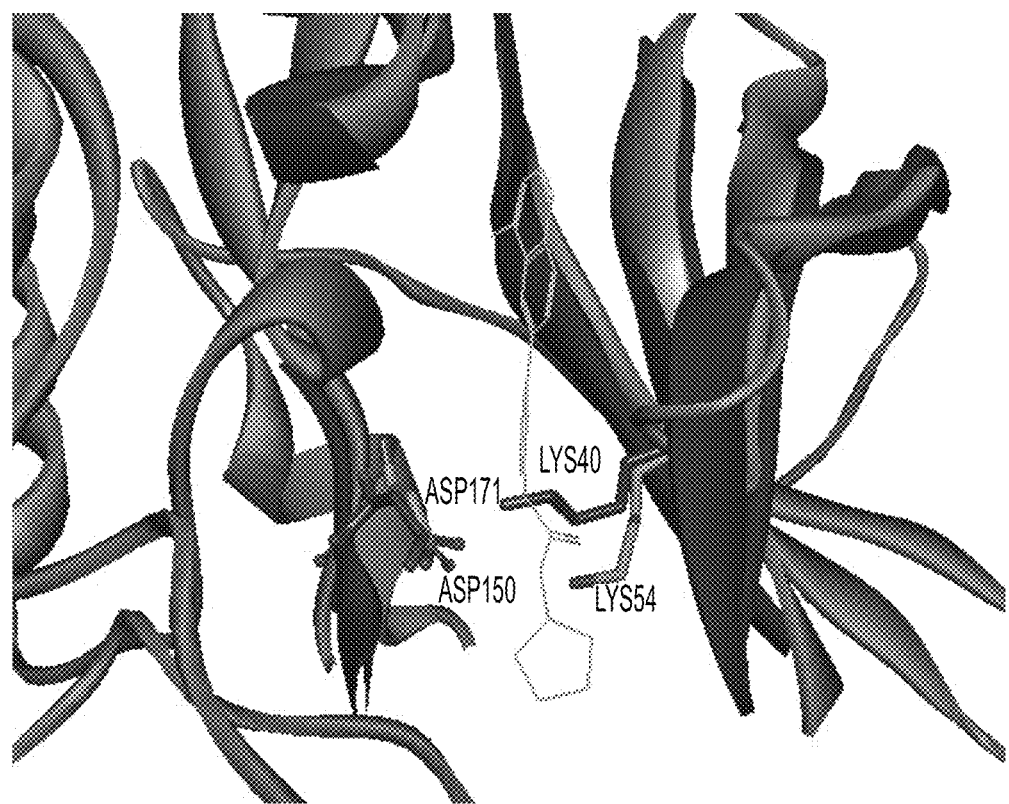
FIG. 49 presents an illustration of the alignment of MELK and MAPK4K active sites; MELK is shown in blue (PDB 4BKY); MAPK4K is shown in green (PDB 4OBQ); the small molecule is an inhibitor of MAPK4K (PDB 4OBQ).

The two protein kinases were then aligned so as to achieve the best possible alignment of the ATP binding pocket, and in particular of Lys40 and Asp150. The alignment is shown in FIG. 49.

Inhibitors of these two kinases known in the art were used both to develop a binding model, and to develop a scoring function for ranking potential compounds with respect to their predicted ability to inhibit MELK and MAP4K4.

Two datasets were compiled: (i) a dataset of MELK inhibitors which includes 76 compounds with affinities to the enzyme in the range of from 4.9 to more than 10000 nM; and (ii) a dataset of MAPK4K inhibitors which includes 8 compounds with affinities to the enzyme in the range of from 140 to more than 10000 nM.

Using the crystal structures of available MELK and MAPK4K inhibitors, a binding model that contains a pharmacophore, and overall shape of the ligands were constructed. The pharmacophore was designed such that the bound ligands are required to interact with Lys40 and Asp150.

Validation of the model was performed by mapping the known MELK and MAPK4K inhibitors from the above datasets onto the model. 90% of all of the evaluated MELK inhibitors were successfully mapped to the pharmacophore, whereby for the high affinity inhibitors, featuring KD lower than 1000 nM, 100% were successfully mapped onto the model. For the MAPK4K inhibitors, all of the 8 inhibitors were successfully mapped to the model.

These results indicated that the designed binding model is valid and can be used in predicting the binding mode of BKT300.

Figure 50:
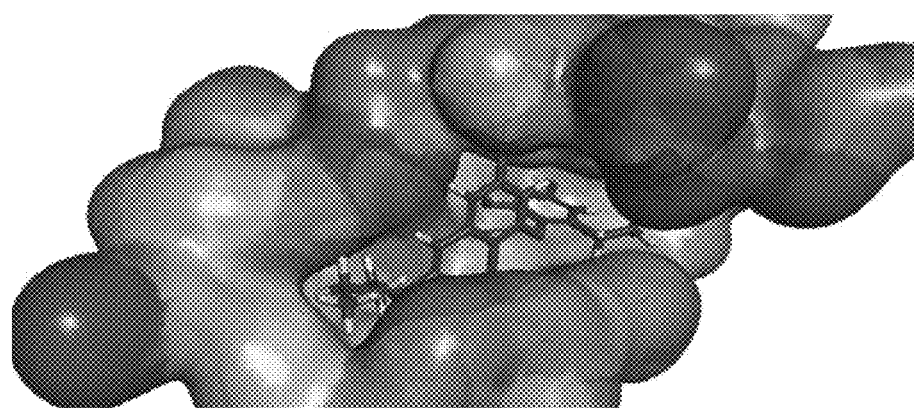
FIG. 50 is an illustration of BKT300 docked into the ATP binding pocket of MELK.

Predicting the Binding Conformation of BKT300 to Kinases:

BKT300 was mapped to the designed binding model: all low energy conformations of BKT300 were generated, and mapped to the model. All successfully mapped conformers were then docked to the binding site of MELK using the model as a guide, and the docked complex was energetically minimized, allowing the side chains of the protein to adjust to each pose. 165 successful conformations/poses were obtained, and each was visually inspected to evaluate the interaction of the ligand with MELK, to thereby select the most suitable conformation and pose, which is depicted in FIG. 50.

In order to provide additional support for this pose, known crystal structures of MELK inhibitors were screened in order to identify compounds that feature groups that occupy the same positions of the kinase as do the aliphatic groups ("tails") of BKT300, flanking the 3-ring skeleton.

Figure 51:
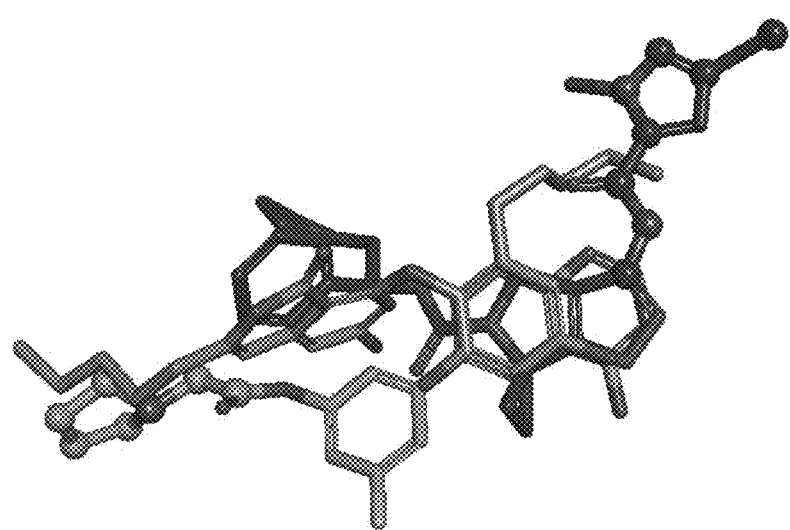
FIG. 51 is an illustration showing BKT300 (in pink) overlaid on a representative small molecule inhibitor of MAPK4K (PDB 4OBQ; in green), and a representative small molecule inhibitor of MELK (PDB 4BKY; in blue); the atoms of the known inhibitors that are close to the aliphatic tails of BKT300 are marked as balls.
Figure 52A:
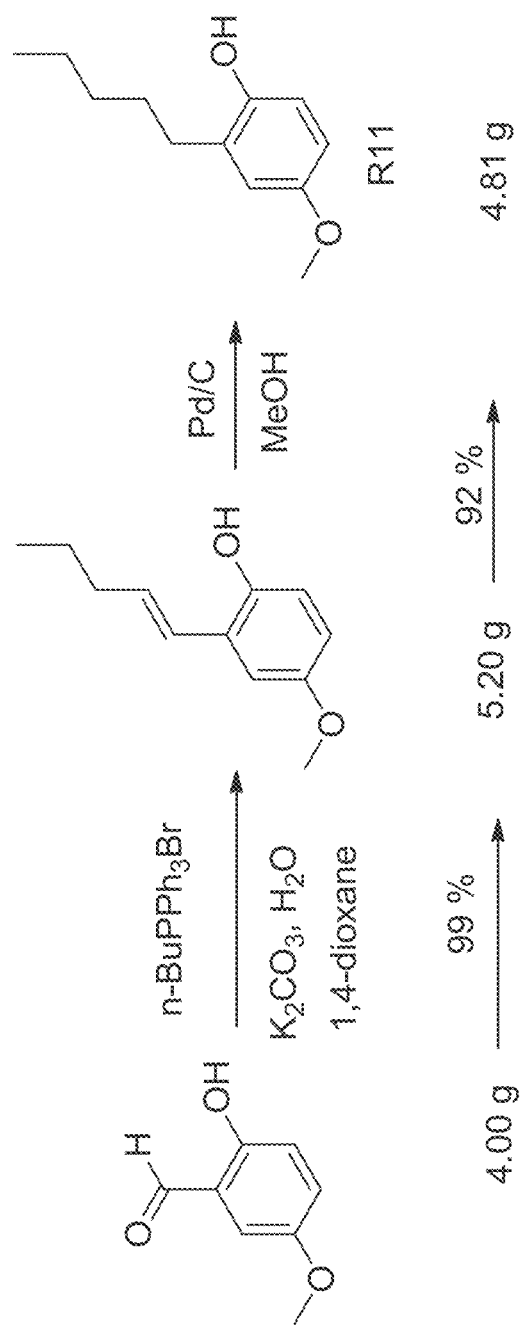
FIGS. 52A-52B present schemes depicting an exemplary synthesis of BKT300-7 (FIG. 52B) and of a reactant R11 usable in the synthesis (FIG. 52A), according to some embodiments of the present invention.
Figure 52B:
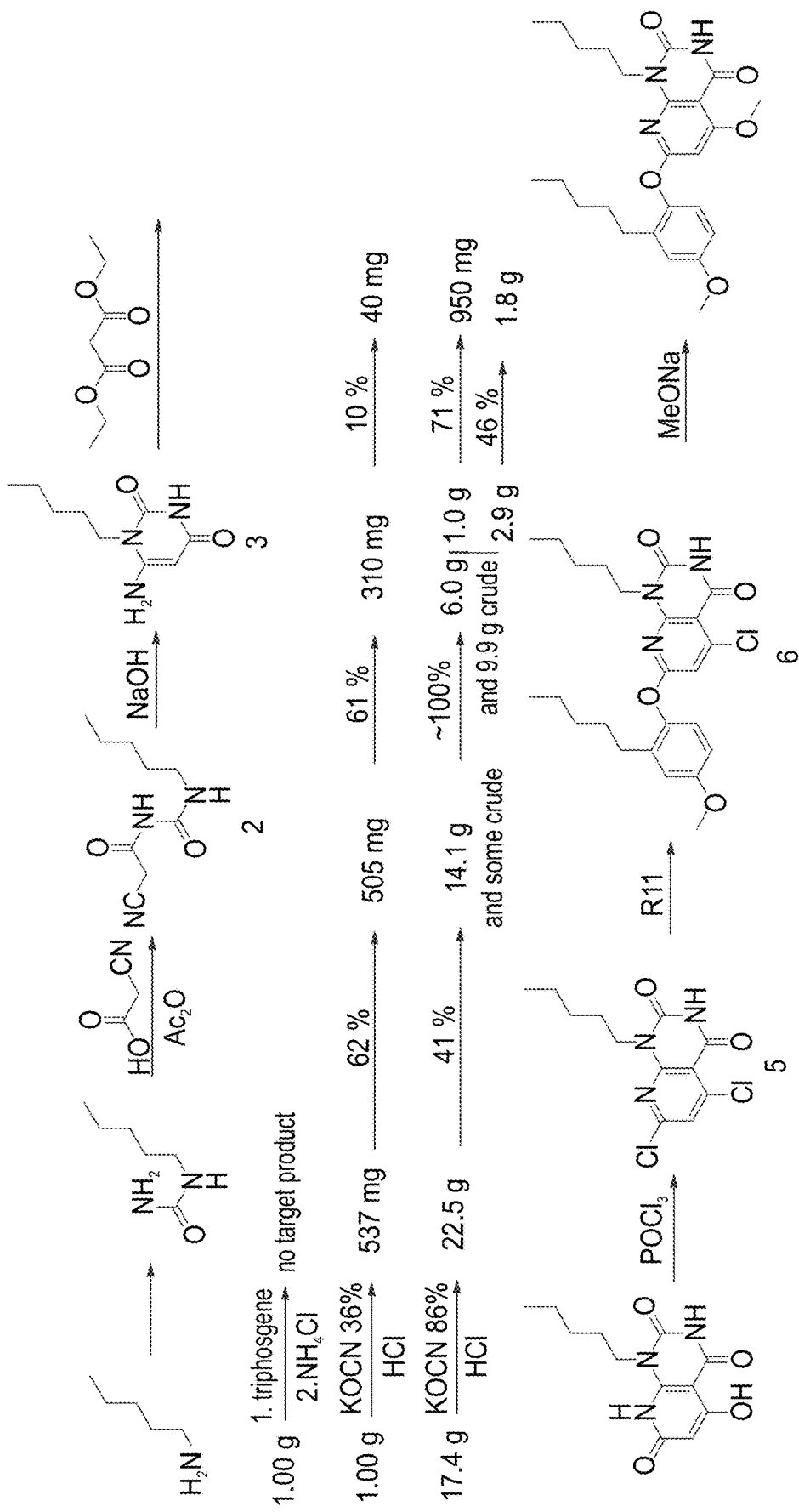
Figure 52B:
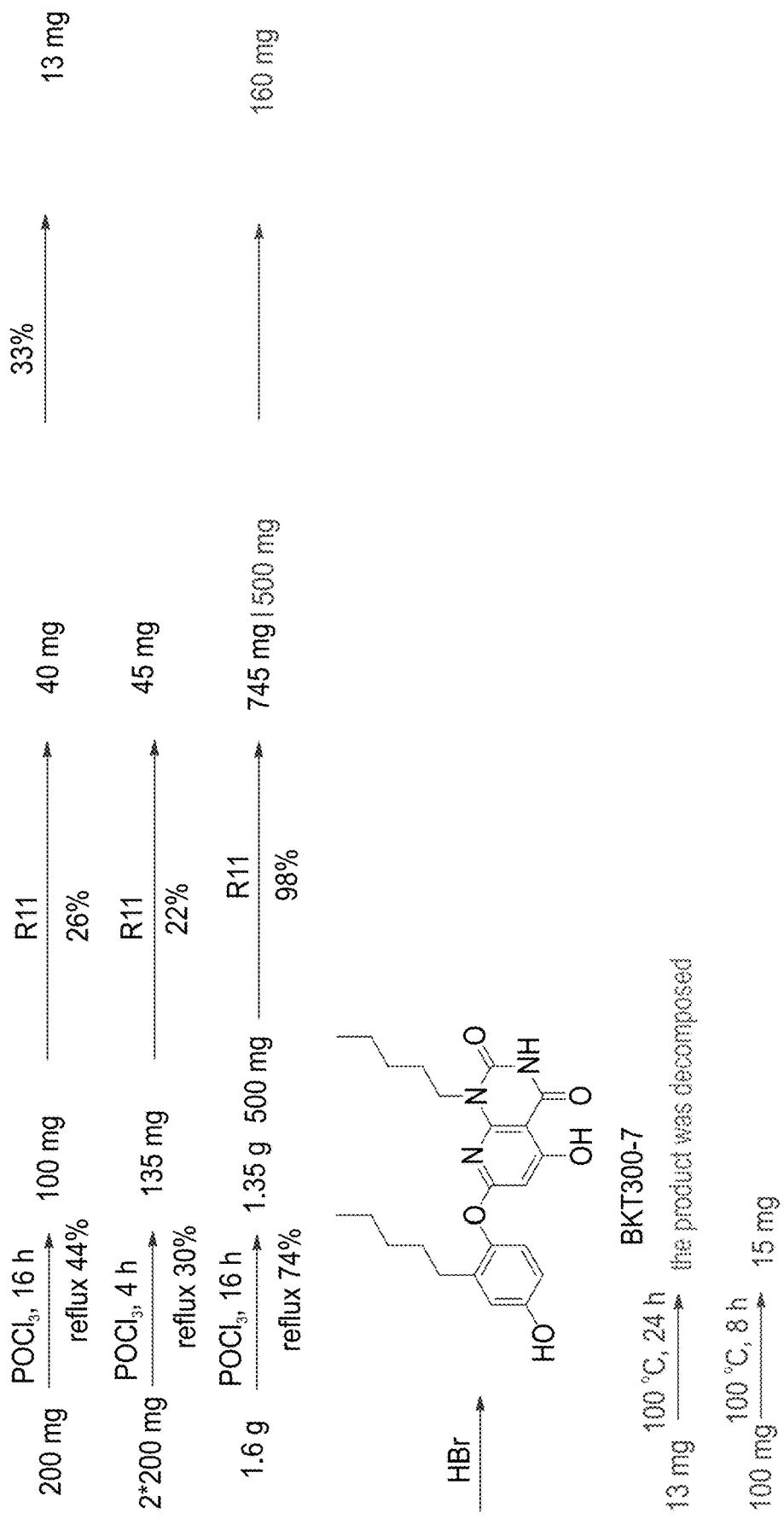
Figure 53A:
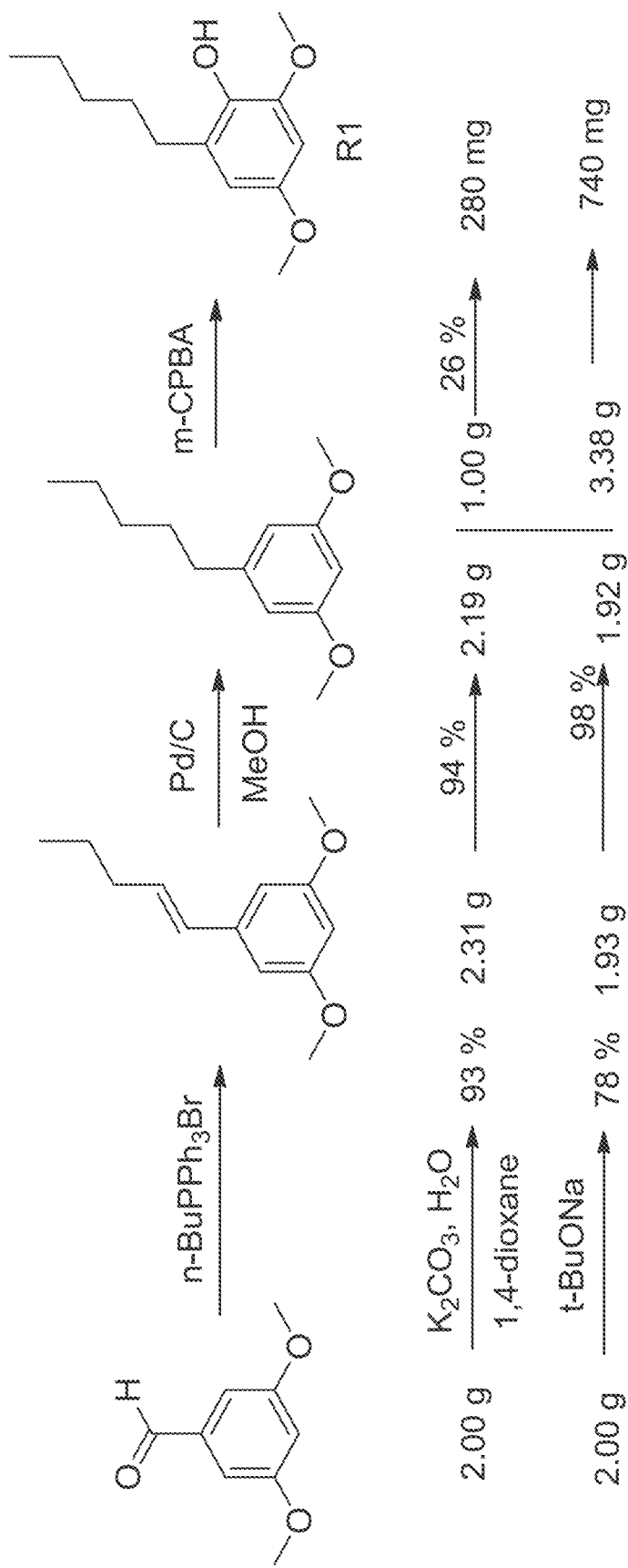
FIGS. 53A-53B present schemes depicting an exemplary synthesis of BKT300-23 (FIG. 53B) and of a reactant R11 usable in the synthesis (FIG. 53A), according to some embodiments of the present invention.
Figure 53B:
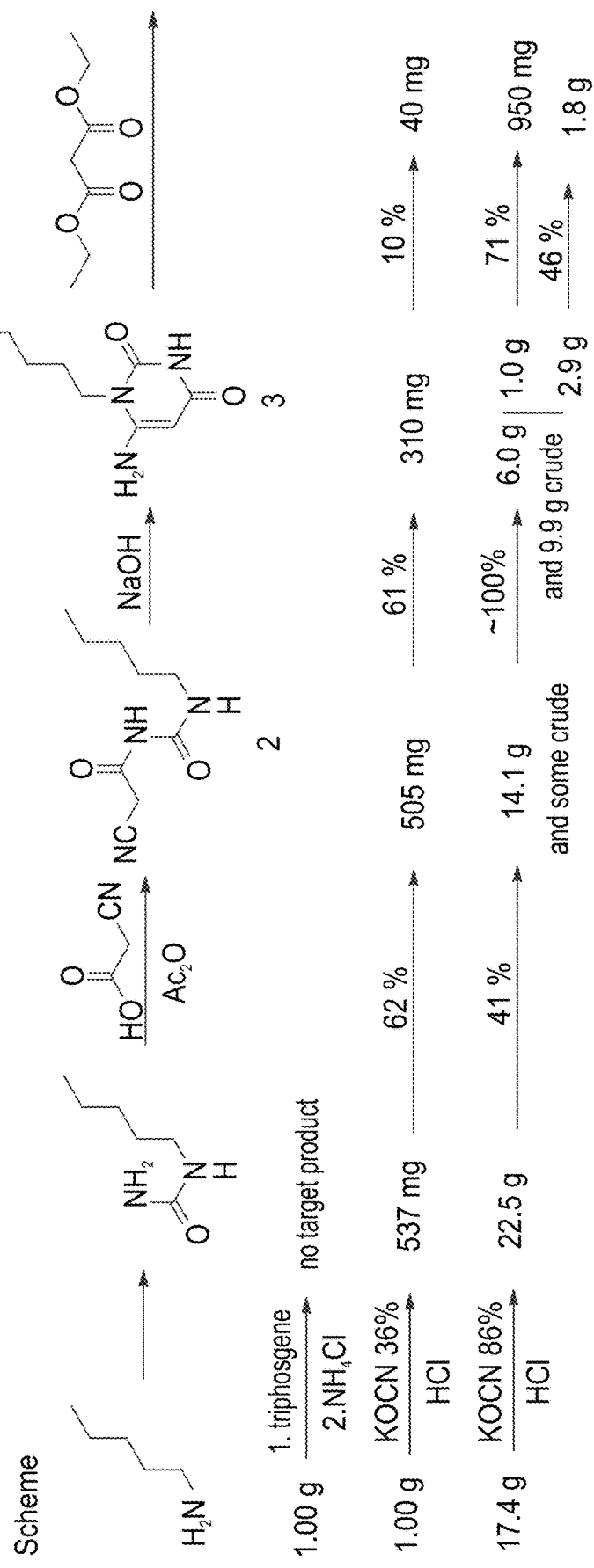
Figure 53B:
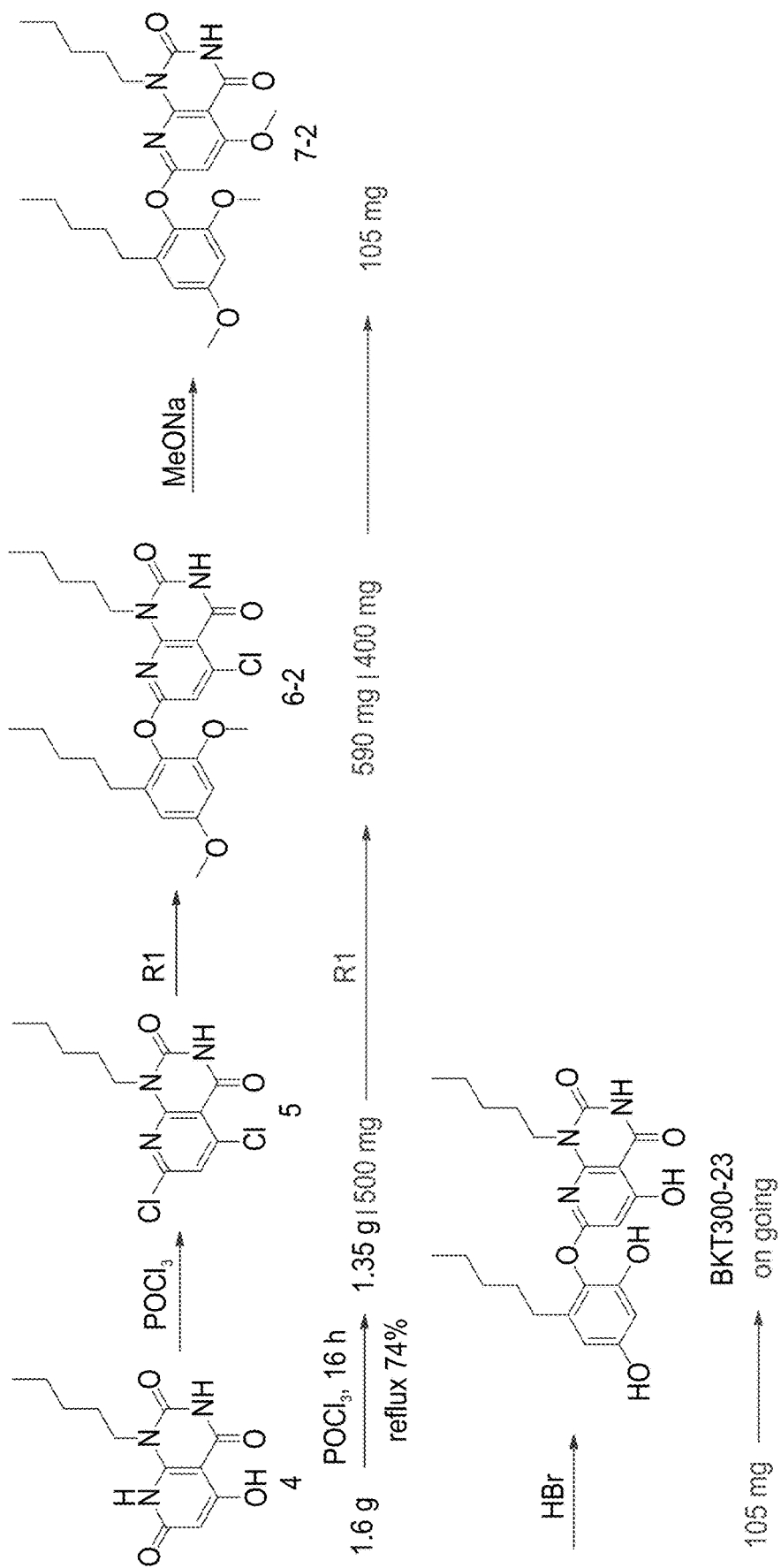

Two such structures were found: N-[3-(4-aminoquinazolin-6-yl)-5-fluorophenyl]-2-(pyrrolidin-1-yl)acetamide (PDB 4OBQ) and 3'-{[(4-bromo-1-methyl-1H-pyrrol-2-yl)carbonyl]amino}-N-[(1S)-1-phenyl-2-(pyrrolidin-1-yl)ethyl]-1',4'-dihydro-5'H-spiro[cyclopropane-1,6'-pyrrolo[3,4-c]pyrazole]-5'-carboxamide (PDB 4BKY). These structures were overlaid on the selected pose of BKT300, as shown in FIG. 51.

It is noted that the chemical nature of the flanking groups ("tails") of these inhibitors differ from the flanking alkyl groups of BKT300, yet occupy the same sub-pockets in the protein kinase. It is further noted that the affinity of BKT300 is relatively low (few tens of µM based on the kinase screening assay summarized in Table 3 hereinabove), whereby the affinities of the overlaid inhibitors is significantly higher (at the nM range).

Example 7

Preparation of BKT300 Analogs

Using the above-described binding model, catalogs of more than 40 million compounds were screened in order to identify compounds that feature the same topology (same spatial arrangement/conformation) as the selected pose of BKT300 shown in FIG. 51. Each compound that matched the BKT300 topology was mapped onto the binding model, and its ability to fit the MELK and MAPK4K binding site was evaluated by visual inspection. The top scoring compounds constituted a set of about 20 compounds, the structures of which are presented in Table 4 below.

Notably, all of the retrieved compounds were of the same supplier, Angene Chemical, yet were found to be commercially unavailable.

TABLE 4

| Pub Chem Compound ID | PUBCHEM_IUPAC_CAS_NAME | Structure |
|---|---|---|
| 23564003 | 4-[(4-fluoro-6-methyl-1,3,5-triazin-2-yl)amino]-5-hydroxy-7-(trihydroxy-$1^{4}$-sulfanyl)-2-naphthalenesulfonic acid | 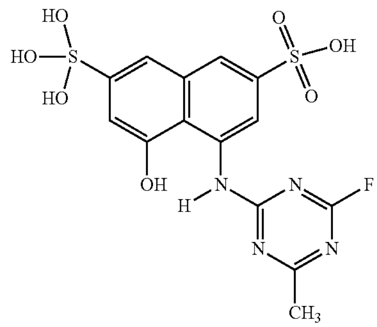 [SMILES: Cc1nc(F)nc(Nc2cc(S(=O)(=O)O)cc3cc(S(O)(O)O)cc(O)c23)n1] |
| 25226044 | 2,4-diamino-5,7-dianilino-8-chloro-6-quinazolinecarbonitrile | 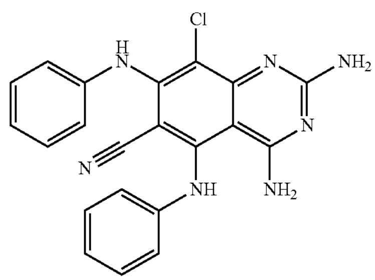 [SMILES: N#Cc1c(Nc2ccccc2)c(Cl)c2nc(N)nc(N)c2c1Nc1ccccc1] |
| 59055724 | 4-[[4-chloro-6-(1-naphthalenylamino)-1,3,5-triazin-2-yl]amino]-5-hydroxy-7-(trihydroxy-$1^{4}$-sulfanyl)-1-naphthalenesulfonic acid | 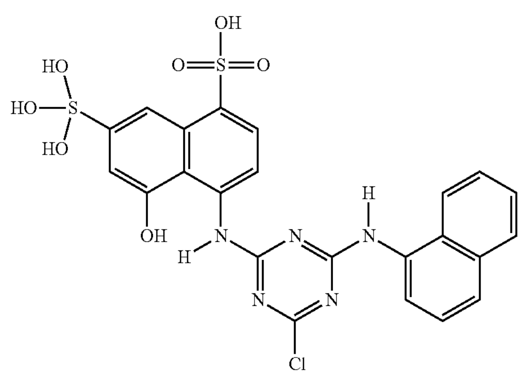 [SMILES: O=S(=O)(O)c1ccc(Nc2nc(Cl)nc(Nc3cccc4ccccc34)n2)c2c(O)cc(S(O)(O)O)cc12] |
| 59055720 | 4-[[4-chloro-6-(1 naphthalenylamino)-1,3,5-triazin-2-yl]amino]-5-hydroxy-7-(trihydroxy-$1^{4}$-sulfanyl)-2-naphthalenesulfonic acid | 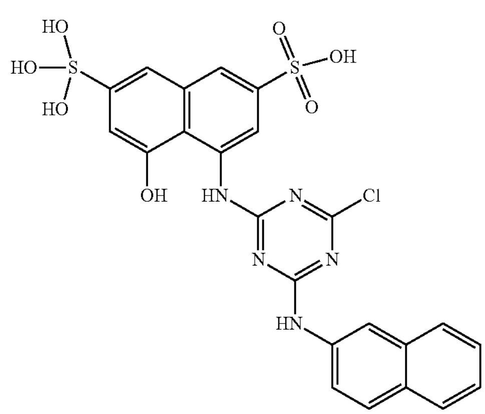 [SMILES: O=S(=O)(O)c1cc(Nc2nc(Cl)nc(Nc3ccc4ccccc4c3)n2)c2c(O)cc(S(O)(O)O)cc2c1] |

TABLE 4-continued

| Pub Chem Compound ID | PUBCHEM_IUPAC_CAS_NAME | Structure |
|---|---|---|
| 59372660 | 5-[(4,6-dimethyl-1,3,5-triazin-2-yl)amino]-4-hydroxy-2-naphthalenesulfenic acid hydroperoxy ester | 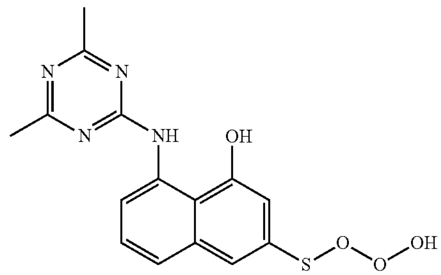 [SMILES: Cc1nc(C)nc(Nc2cccc3cc(SOOO)cc(O)c23)n1] |
| 15480413 | (5-benzoyl-4,8-dihydroxy-1-naphthalenyl)-phenylmethanone | 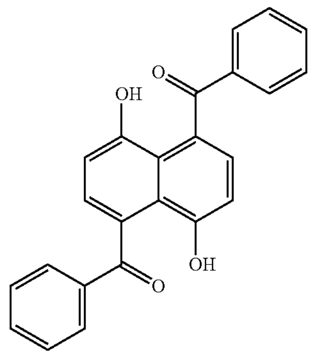 [SMILES: O=C(c1ccccc1)c1ccc(O)c2c(C(=O)c3ccccc3)ccc(O)c12] |
| 19771237 | 4-[[4-(2-aminoethylamino)-6-chloro-1,3,5-triazin-2-yl]amino]-5-hydroxynaphthalene-2,7-disulfonic acid | 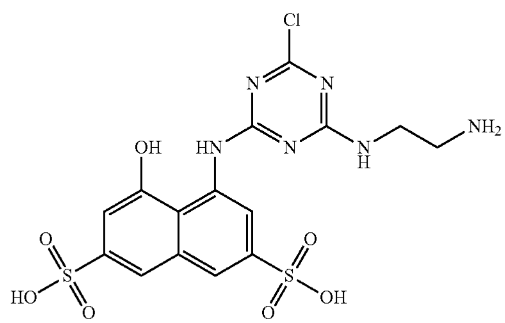 [SMILES: NCCNc1nc(Cl)nc(Nc2cc(S(=O)(=O)O)cc3cc(S(=O)(=O)O)cc(O)c23)n1] |
| 25226217 | 2,4-diamino-8-chloro-5,7-bis(phenylthio)-6-quinazolinecarbonitrile | 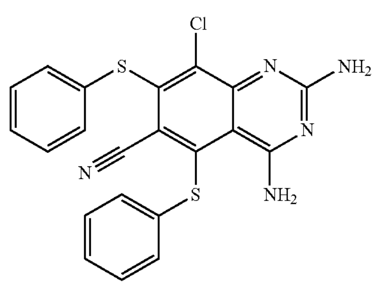 |
| 23038808 | acetic acid [8-(2,6-dichlorophenyl)sulfinyl-4-hydroxy-2,3-dimethoxy-1-naphthalenyl] ester | 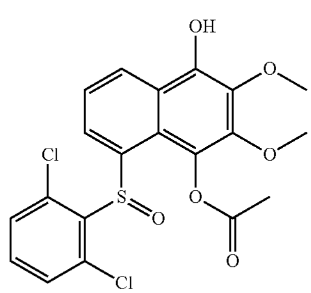 [SMILES: COc1c(OC)c(OC(C)=O)c2c(S(=O)c3c(Cl)cccc3Cl)cccc2c1O] |

TABLE 4-continued

| Pub Chem Compound ID | PUBCHEM_IUPAC_CAS_NAME | Structure |
|---|---|---|
| 49862178 | 2,4-diamino-8-chloro-5,7-diphenoxy-6-quinazolinecarbonitrile | 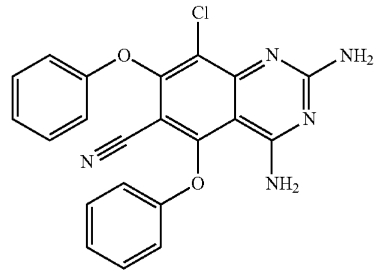 |
| 25226218 | 2,4-diamino-8-fluoro-5,7-bis(phenylthio)-6-quinazolinecarbonitrile | 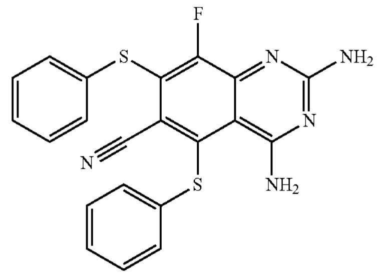 [SMILES: N#Cc1c(Sc2ccccc2)c(F)c2nc(N)nc(N)c2c1Sc1ccccc1] |
| 23038659 | acetic acid [8-(2-bromophenyl)sulfinyl-4-hydroxy-2,3-dimethoxy-1-naphthalenyl] ester | 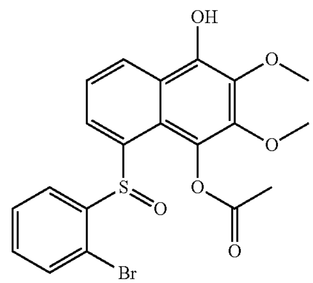 [SMILES: COc1c(OC)c(OC(C)=O)c2c(S(=O)c3ccccc3Br)cccc2c1O] |
| 19090340 | 5-[[4-fluoro-6-(2-sulfoethylamino)-1,3,5-triazin-2-yl]amino]-4-hydroxy-2-naphthalenesulfonic acid | 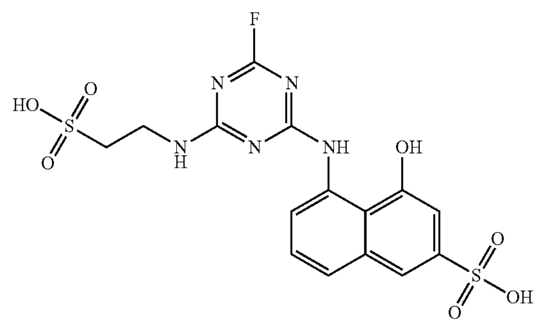 [SMILES: O=S(=O)(O)CCNc1nc(F)nc(Nc2cccc3cc(S(=O)(=O)O)cc(O)c23)n1] |
| 11245388 | 8-[(4-hydroxy-1-naphthalenyl)oxy]-4-(methoxymethoxy)-1-naphthalenol | 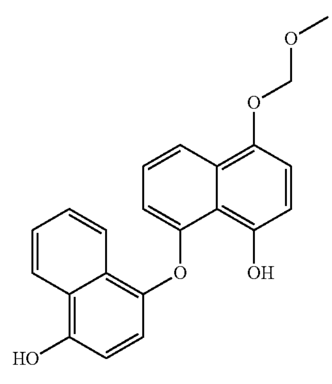 [SMILES: COCOc1ccc(O)c2c(Oc3ccc(O)c4ccccc34)cccc12] |

TABLE 4-continued
| Pub Chem Compound ID | PUBCHEM_IUPAC_CAS_NAME | Structure |
|---|---|---|
| 17891057 | 5-[(2,4-diamino-5-pyrimidinyl)methyl]-2,3-dimethoxy-4-(2-phenylethynyl)naphthalene-1,7-diol | 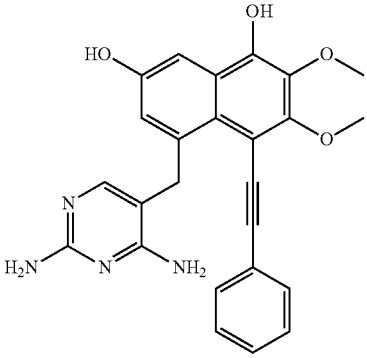 [SMILES: COc1c(OC)c(C#Cc2ccccc2)c2c(Cc3cnc(N)nc3N)cc(O)cc2c1O] |
| 17903633 | 4-(1H-indazol-5-ylamino)-5,7-dimethoxy-3-quinolinecarbonitrile | 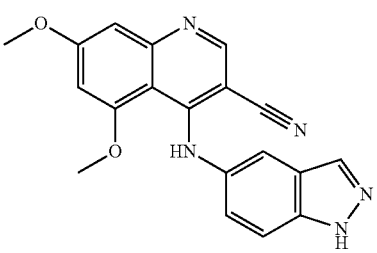 [SMILES: COc1cc(OC)c2c(Nc3ccc4[nH]ncc4c3)c(C#N)cnc2c1] |
| 53738023 | 2-[4-hydroxy-3-methoxy-5-(phenylmethyl)-1-naphthalenyl]-3-phenyl-2-propenoic acid | 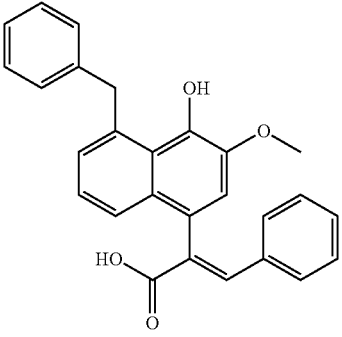 [SMILES: COc1cc(/C(=C\c2ccccc2)C(=O)O)c2cccc(Cc3ccccc3)c2c1O] |
| 21149542 | 4-[(2-aminophenyl)-oxomethyl]-5-hydroxynaphthalene-1,7-disulfonic acid | 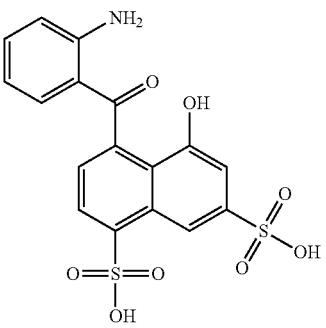 [SMILES: Nc1ccccc1C(=O)c1ccc(S(=O)(=O)O)c2cc(S(=O)(=O)O)cc(O)c12] |

TABLE 4-continued
| Pub Chem Compound ID | PUBCHEM_IUPAC_CAS_NAME | Structure |
|---|---|---|
| 1895649 | (5-benzoyl-4-hydroxy-8-methoxynaphthalen-1-yl)-phenylmethanone | 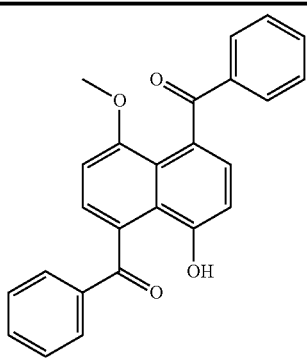 |
20
In parallel, compounds which are structural analogs of BKT300 were designed, the structures of which are presented in Table 5 below.
TABLE 5
| Molecule | Name |
|---|---|
| 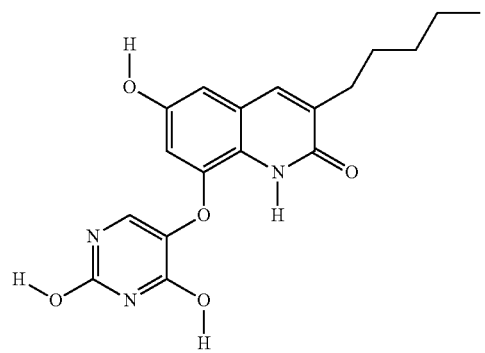 [SMILES: CCCCCc1cc2cc(O)cc(Oc3cnc(O)nc3O)c2[nH]c1=O] | BKT300-1 |
|  | BKT300-2 |

TABLE 5-continued
| Molecule | Name |
|---|---|
| 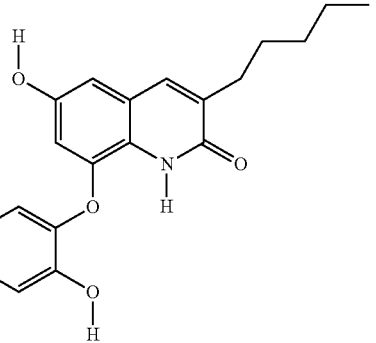 | BKT300-3 |
| 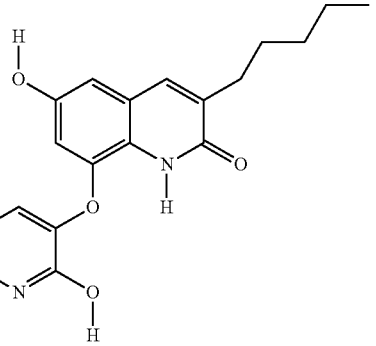 | BKT300-4 |
| 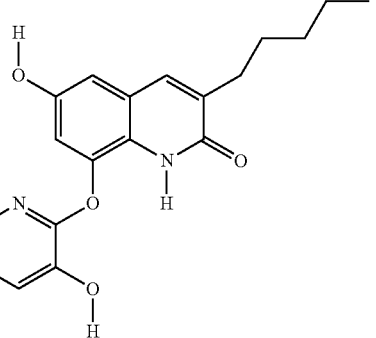 | BKT300-5 |
| 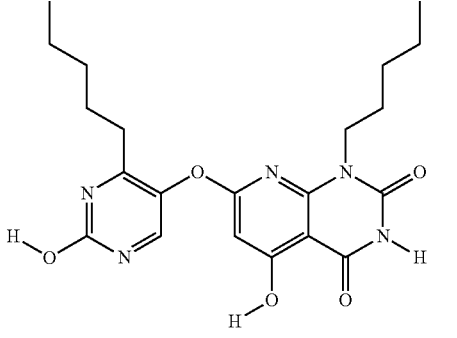 [SMILES: CCCCCc1nc(O)ncc1Oc1cc(O)c2c(=O)[nH]c(=O)n(CCCCC)c2n1] | BKT300-6 |

TABLE 5-continued
| Molecule | Name |
| --- | --- |
| 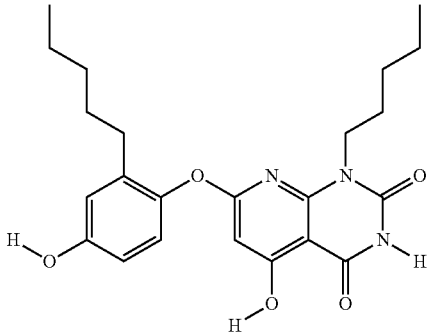 [SMILES: CCCCCc1cc(O)ccc1Oc1cc(O)c2c(=O)[nH]c(=O)n(CCCCC)c2n1] | BKT300-7 |
| 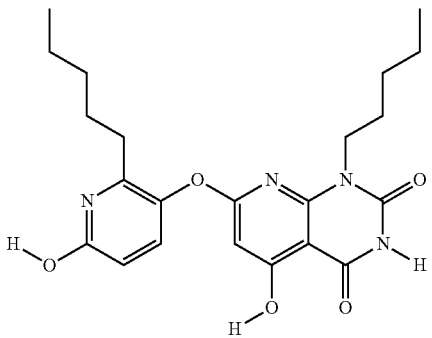 [SMILES: CCCCCc1nc(O)ccc1Oc1cc(O)c2c(=O)[nH]c(=O)n(CCCCC)c2n1] | BKT300-8 |
| 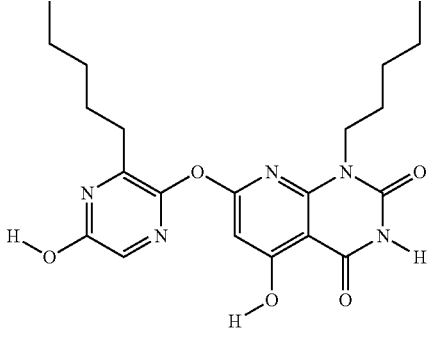 [SMILES: CCCCCc1nc(O)cnc1Oc1cc(O)c2c(=O)[nH]c(=O)n(CCCCC)c2n1] | BKT300-9 |
| 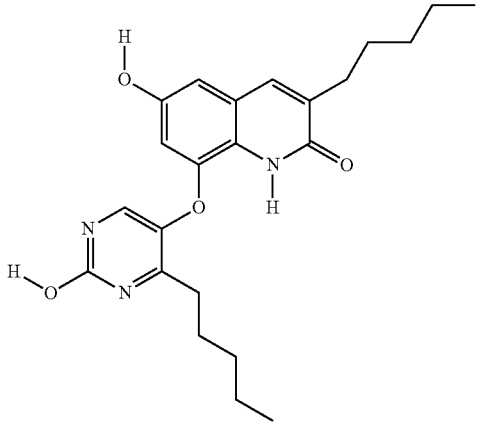 [SMILES: CCCCCc1nc(O)ncc1Oc1cc(O)cc2cc(CCCCC)c(=O)[nH]c12] | BKT300-10 |

TABLE 5-continued

| Molecule | Name |
| --- | --- |
| | BKT300-11 |
| | BKT300-12 |
| | BKT300-13 |
| | BKT300-14 |

TABLE 5-continued

| Molecule | Name |
| --- | --- |
| | BKT300-15 |
| | BKT300-16 |
| | BKT300-17 |
| | BKT300-18 |

TABLE 5-continued

| Molecule | Name |
|---|---|
| [structure] | BKT300-19 |
| [structure] | BKT300-20 |
| [structure] | BKT300-21 |
| [structure] | BKT300-22 |

TABLE 5-continued

| Molecule | Name |
|---|---|
| | BKT300-23 |

Compounds BKT300-7, BKT300-23, BKT300-1, BKT300-3 and BKT300-11 (Table 5) were synthesized as depicted in FIGS. 52A-B, 53A-B and 54-56, respectively. In addition, the preparation of the exemplary Compounds BKT300-1, BKT300-3 and BKT300-11 is described in detail herein below.

The compounds' structures were verified by LC-MS and NMR.

Other compounds can be similarly prepared by using corresponding reactants.

Figure 54:
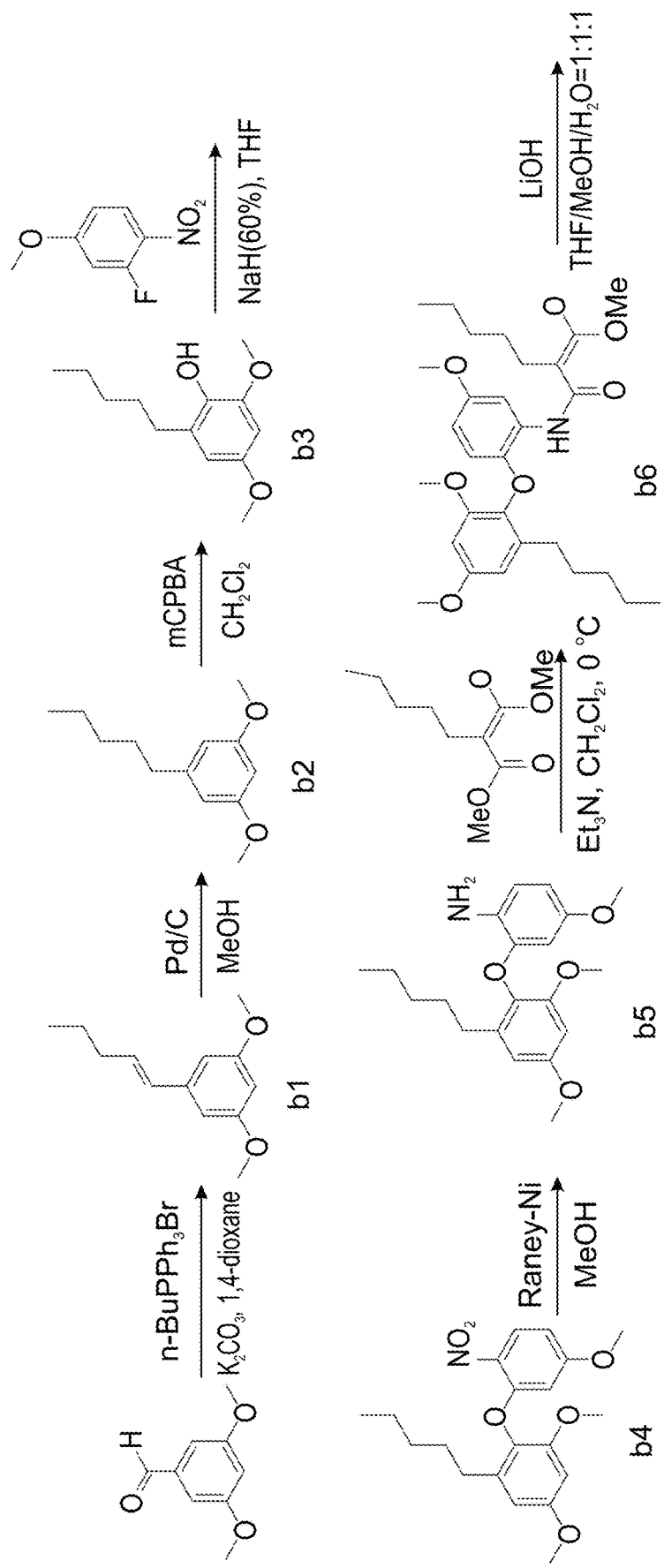
FIG. 54 presents schemes depicting an exemplary synthesis of BKT300-1, according to some embodiments of the present invention.
Figure 54:
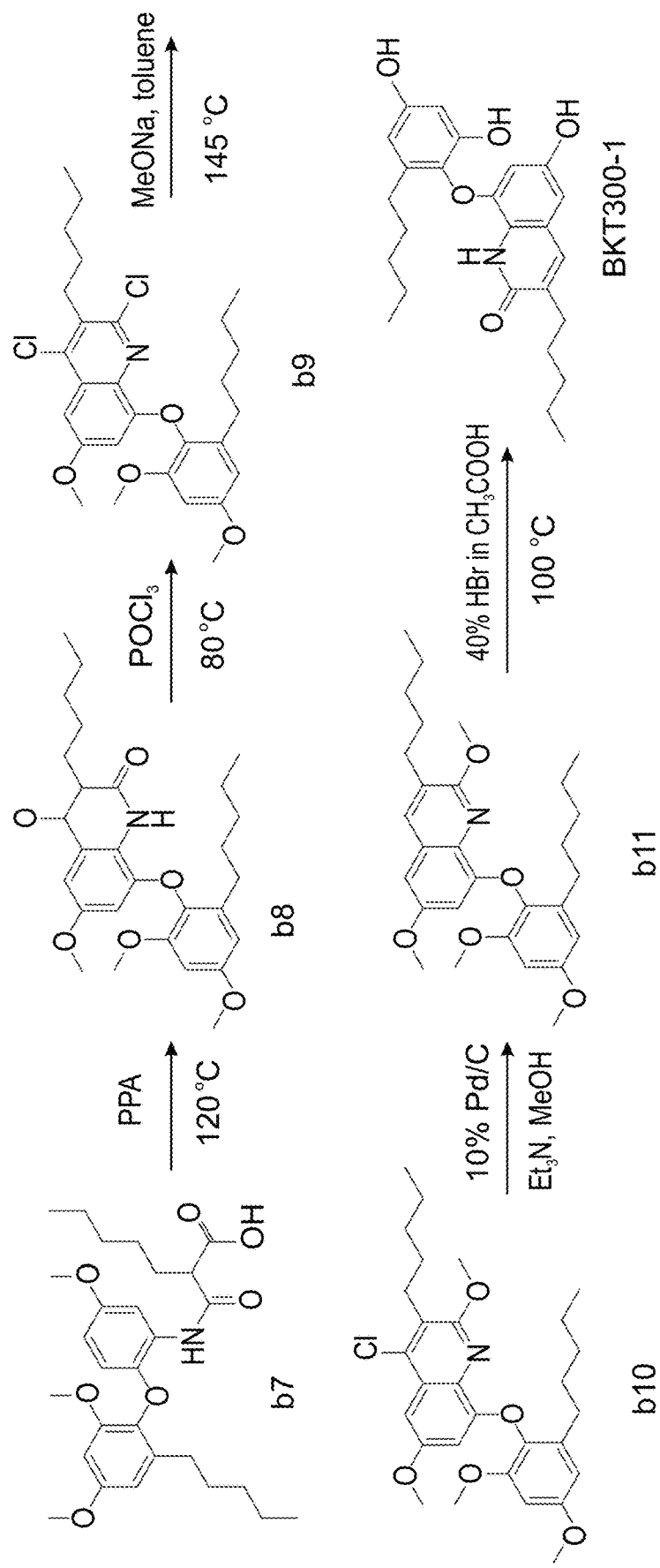

Preparation of BKT300-1:

A scheme presenting the synthesis of BKT300-1 is presented in FIG. 54.

1. Preparation of 1,5-dimethoxy-2-(5-methoxy-2-nitrophenoxy)-3-pentylbenzene (BKT300-1-b4)

To a solution of 2,4-dimethoxy-6-pentylphenol (b3) (2.2 grams, 0.981 mmol) in tetrahydrofuran (THF) (20 ml) was added NaH (60%) (78.48 mg, 1.962 mmol). The reaction mixture was stirred at 0° C. for 30 minutes. Then, 2-fluoro-4-methoxy-1-nitrobenzene (1.68 gram, 0.981 mmol) was added at 0° C. The reaction mixture was stirred at room temperature overnight. TLC (thin layer chromatography) showed the reaction was completed (EtOAc:Petroleum Ether=1:10). The reaction mixture was poured into ice-water and extracted with EtOAc (2×20 ml). The organic layer was washed with brine (2×50 ml), dried over anhydrous $Na_2SO_4$, and filtered. The filtrate was concentrated in vacuum to give the product 1,5-dimethoxy-2-(5-methoxy-2-nitrophenoxy)-3-pentylbenzene (BKT300-1-b4) as a yellow oil (1.86 gram, 50.5% yield).

2. Preparation of 2-(2,4-dimethoxy-6-pentylphenoxy)-4-methoxyaniline (BKT300-1-b5)

A mixture of 1,5-dimethoxy-2-(5-methoxy-2-nitrophenoxy)-3-pentyl benzene (BKT300-1-b4) (1.86 gram, 4.95 mmol) and Raney nickel (200 mg) in MeOH (20 ml) was stirred at room temperature for 4 hours. LC-MS (liquid chromatography-mass spectroscopy) showed the reaction was completed. The reaction mixture was filtered. The filtrate was concentrated in vacuum to give the product 2-(2,4-dimethoxy-6-pentylphenoxy)-4-methoxyaniline (BKT300-1-b5) as a black oil (1.21 gram, 70.7% yield). LC-MS: m/z 346.0 (M++H).

3. Preparation of methyl 2-((2-(2,4-dimethoxy-6-pentylphenoxy)-5-methoxyphenyl)carbamoyl)heptanoate (BKT300-1-b6)

A mixture of 2-(2,4-dimethoxy-6-pentylphenoxy)-4-methoxyaniline (BKT300-1-b5) (1.21 gram, 3.50 mmol), dimethyl-2-pentylmalonate (1.416 gram, 7.00 mmol) and pyridine (0.553 gram, 7.00 mmol) in toluene (20 ml) was stirred at reflux for 40 hours. LC-MS (liquid chromatography-mass spectroscopy) showed the reaction was completed. The reaction mixture was concentrated in vacuum. The residue was purified by silica gel chromatography eluted with (EtOAc:Petroleum Ether=1:20-1:10) to give the product methyl 2-((2-(2,4-dimethoxy-6-pentyl phenoxy)-5-methoxyphenyl)carbamoyl)heptanoate (BKT300-1-b6) as a yellow oil (1.882 gram, 100% yield). LC-MS: m/z 516.0 (M++H).

4. Preparation of 2-((2-(2,4-dimethoxy-6-pentylphenoxy)-5-methoxyphenyl)carbamoyl)heptanoic acid (BKT300-1-b7)

To a solution of methyl 2-((2-(2,4-dimethoxy-6-pentyl phenoxy)-5-methoxyphenyl)carbamoyl)heptanoate (BKT300-1-b6) (1.882 gram, 3.65 mmol) in a mixture solution of THF (10 ml), MeOH (10 ml) and water (10 ml) was added LiOH—$H_2O$ (307 mg, 7.30 mmol). The reaction was stirred at room temperature for 16 hours. LC-MS (liquid chromatography-mass spectroscopy) showed the reaction was completed. The reaction mixture was concentrated in vacuum. The residue was dissolved in water (50 ml) and acidified to pH 2-3 using concentrated HCl. The reaction mixture was extracted with EtOAc (2×20 ml). The organic layer was washed with brine (2×50 ml), dried over anhydrous $Na_2SO_4$, and filtered. The filtrate was concentrated in vacuum to give the product 2-((2-(2,4-dimethoxy-6-pentyl phenoxy)-5-methoxyphenyl) carbamoyl)heptanoic acid (BKT300-1-b7) as a yellow solid (1.68 gram, 91.8% yield). LC-MS: m/z 502.0 (M++H).

5. Preparation of 8-(2,4-dimethoxy-6-pentylphenoxy)-6-methoxy-3-pentylquinoline-2,4(1H,3H)-dione (BKT300-1-b8)

To a PPA solution (10 ml) at 120° C. was added 2-((2-(2,4-dimethoxy-6-pentyl phenoxy)-5-methoxyphenyl) carbamoyl)heptanoic acid (BKT300-1-b7) (3.63 grams, 7.24 mmol) portion-wise. The reaction mixture was stirred at 120° C. for 2 hours. LC-MS (liquid chromatography-mass spectroscopy) showed the reaction was completed. The reaction mixture was poured into water (100 ml) and extracted with EtOAc (2×20 ml). The organic layer was washed with brine (2×50 ml), dried over anhydrous $Na_2SO_4$, and filtered. The filtrate was concentrated in vacuum. The residue was purified by silica gel chromatography eluted with (EtOAc:Petroleum Ether=1:10-1:5) to give the product 8-(2,4-dimethoxy-6-pentylphenoxy)-6-methoxy-3-pentylquinoline-2,4(1H,3H)-dione (BKT300-1-b8) as a yellow solid (320 mg, 8.67% yield). LC-MS: m/z 484.7 (M++H).

6. Preparation of 2,4-dichloro-6-methoxy-8-(4-methoxy-2-pentylphenoxy)-3-pentylquinoline (BKT300-1-b9)

A mixture of 8-(2,4-dimethoxy-6-pentylphenoxy)-6-methoxy-3-pentyl quino line-2,4(1H,3H)-dione (BKT300-1-b8) (280 mg, 0.58 mmol) in $POCl_3$ (10 ml) was stirred at 80° C. for 6 hours. LC-MS (liquid chromatography-mass spectroscopy) showed the reaction was completed. The reaction mixture was concentrated in vacuum. The residue was dissolved in EtOAc (20 ml) and washed successively with saturated $NaHCO_3$(2×20 ml) and brine (20 ml), dried over anhydrous $Na_2SO_4$, and filtered. The filtrate was concentrated in vacuum to give the product 2,4-dichloro-6-methoxy-8-(4-methoxy-2-pentylphenoxy)-3-pentylquinoline (BKT300-1-b9) as a light yellow solid (301 mg, 100% yield). LC-MS: m/z 521.0 (M++H).

7. Preparation of 4-chloro-8-(2,4-dimethoxy-6-pentylphenoxy)-2,6-dimethoxy-3-pentylquinoline (BKT300-1-b10)

A mixture of 2,4-dichloro-6-methoxy-8-(4-methoxy-2-pentylphenoxy)-3-pentylquinoline (BKT300-1-b9) (301 mg, 0.58 mmol) and MeONa (307 mg, 5.8 mmol) in toluene (10 ml) was stirred at 145° C. in a sealed tube for 21 hours. TLC showed the reaction was completed (EtOAc:Petroleum Ether=1:50). The reaction mixture was concentrated in vacuum. Water was poured into the residue and extracted with EtOAc (2×20 ml). The organic layer was washed with brine (2×20 ml), dried over anhydrous $Na_2SO_4$, and filtered. The filtrate was concentrated in vacuum. The residue was purified by TLC eluted with (EtOAc:Petroleum Ether=1:100) to give the product 4-chloro-8-(2,4-dimethoxy-6-pentylphenoxy)-2,6-dimethoxy-3-pentylquinoline (BKT300-1-b10) as a white solid (310 mg, 100% yield). LC-MS: m/z 516.0 (M++H).

8. Preparation of 8-(2,4-dimethoxy-6-pentylphenoxy)-2,6-dimethoxy-3-pentylquinoline (BKT300-1-b11)

A mixture of 4-chloro-8-(2,4-dimethoxy-6-pentylphenoxy)-2,6-dimethoxy-3-pentylquinoline (BKT300-1-b10) (310 mg, 0.6 mmol) and 10% Pd/C (30 mg) in MeOH (20 ml) and $Et_3N$ (2 ml) was stirred at room temperature for 2.0 hours. TLC showed the reaction was completed (EtOAc:Petroleum Ether=1:20). The reaction mixture was filtered. The filtrate was concentrated in vacuum. The residue was dissolved in EtOAc (20 ml) and washed with brine (2×20 ml). The organic layer was dried over anhydrous $Na_2SO_4$, and filtered. The filtrate was concentrated in vacuum to give the product 8-(2,4-dimethoxy-6-pentylphenoxy)-2,6-dimethoxy-3-pentyl quinoline (BKT300-1-b11) as a light yellow solid (300 mg, 100% yield). LC-MS: m/z 482.1 (M++H).

9. Preparation of 8-(2,4-dihydroxy-6-pentylphenoxy)-6-hydroxy-3-pentylquinolin-2(1H)-one (BKT300-1)

A mixture of 8-(2,4-dimethoxy-6-pentylphenoxy)-2,6-dimethoxy-3-pentyl quinoline (BKT300-1-b11) (300 mg, 0.623 mmol) in 30% HBr in $CH_3COOH$ (4 mL) was stirred at 120° C. for 16 hours. Then the reaction mixture was concentrated in vacuum. The residue was dissolved in 30% HBr in $CH_3COOH$ (4 ml) in a sealed tube and was stirred at 120° C. for 4 hours. The reaction mixture was concentrated in vacuum. The residue was purified by pre-HPLC to give 8-(2,4-dihydroxy-6-pentyl phenoxy)-6-hydroxy-3-pentylquinolin-2(1H)-one (BKT300-1) as a yellow solid (77 mg, yield 29%). LC-MS: m/z 426.0 (M++H).

Figure 55:
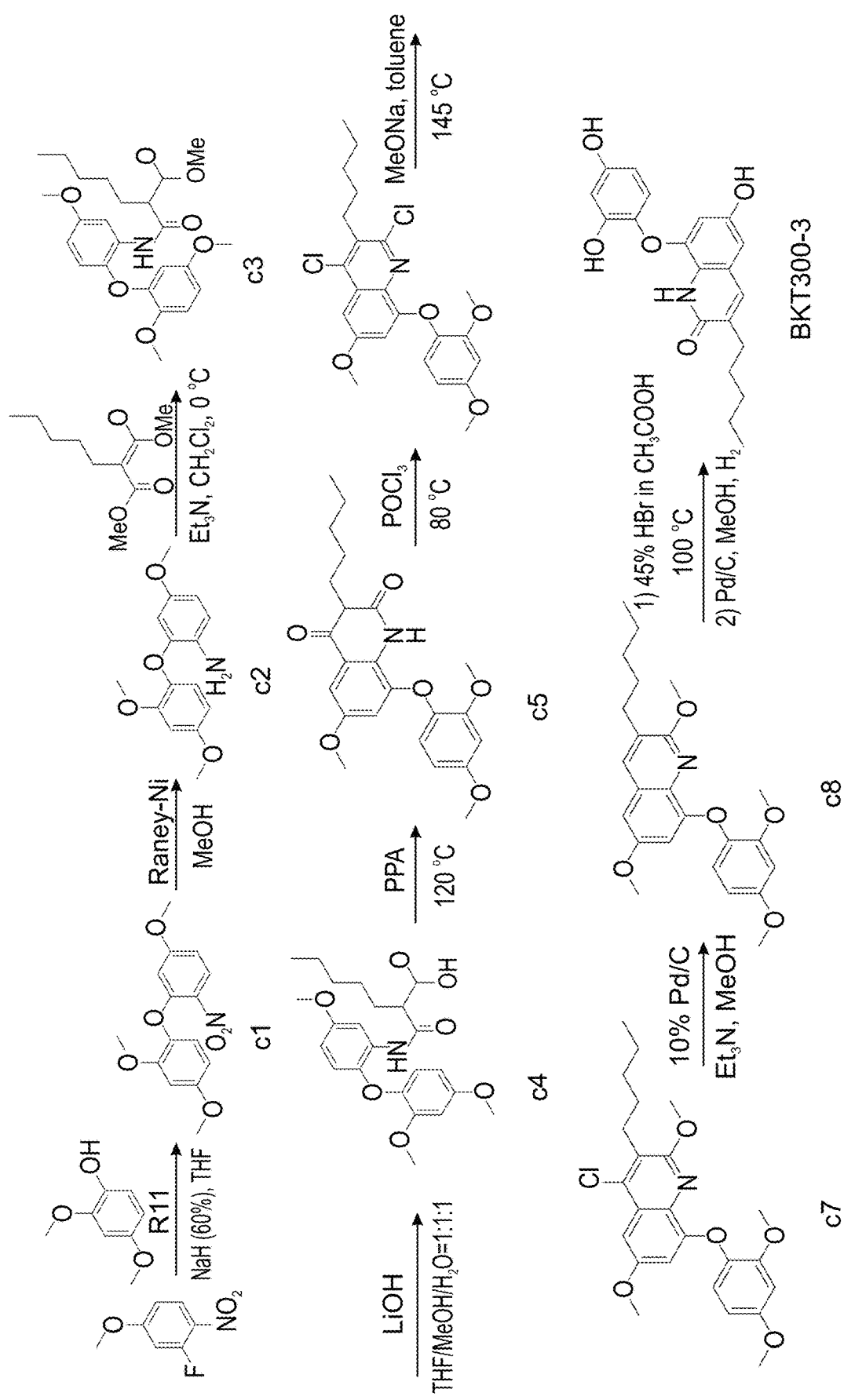
FIG. 55 presents schemes depicting an exemplary synthesis of BKT300-3, according to some embodiments of the present invention.

Preparation of BKT300-3:

A scheme presenting the synthesis of BKT300-3 is presented in FIG. 55.

1. Preparation of 2-(2,4-dimethoxyphenoxy)-4-methoxy-1-nitrobenzene (BKT300-3-c1)

To a solution of 2,4-dimethoxyphenol (R11) (2.0 grams, 13.00 mmol) in tetrahydrofuran (THF) (50 ml) was added NaH (60%) (450 mg, 26.00 mmol). The reaction mixture was stirred at 0° C. for 30 minutes. Then, 2-fluoro-4-methoxy-1-nitrobenzene (2.22 grams, 13.00 mmol) was added at 0° C. The reaction mixture was stirred at room temperature overnight. TLC showed the reaction was completed (EtOAc:Petroleum Ether=1:10). The reaction mixture was poured into ice-water and extracted with EtOAc (2×20 ml). The organic layer was washed with brine (2×50 ml), dried over anhydrous $Na_2SO_4$, and filtered. The filtrate was concentrated in vacuum to give the product 2-(2,4-dimethoxyphenoxy)-4-methoxy-1-nitrobenzene (BKT300-3-c1) as a yellow oil (3.04 grams, 76.8% yield).

2. Preparation of 2-(2,4-dimethoxyphenoxy)-4-methoxyaniline (BKT300-3-c2)

A mixture of 2-(2,4-dimethoxyphenoxy)-4-methoxy-1-nitrobenzene (BKT300-3-c1) (3.04 grams, 10.00 mmol) and Raney nickel (770 mg) in MeOH (100 ml) was stirred at room temperature for 4 hours. LC-MS (liquid chromatography-mass spectroscopy) showed the reaction was completed. The reaction mixture was filtered. The filtrate was concentrated in vacuum to give the product 2-(2,4-dimethoxyphenoxy)-4-methoxyaniline (BKT300-3-c2) as a black oil (2.58 grams, 94.2% yield). LC-MS: m/z 276.0 (M++H).

3. Preparation of methyl 2-((2-(2,5-dimethoxyphenoxy)-5-methoxyphenyl) carbamoyl)heptanoate (BKT300-3-c3)

A mixture of 2-(2,4-dimethoxyphenoxy)-4-methoxyaniline (BKT300-3-c2) (3.75 grams, 13.62 mmol), dimethyl 2-pentylmalonate (5.5 grams, 27.2 mmol) and pyridine (2.15 grams, 27.2 mmol) in toluene (40 ml) was stirred at reflux for 40 hours. LC-MS (liquid chromatography-mass spectroscopy) showed the reaction was completed. The reaction mixture was concentrated in vacuum. The residue was purified by silica gel chromatography eluted with (EtOAc:Petroleum Ether=1:20-1:10) to give the product methyl 2-((2-(2,5-dimethoxyphenoxy)-5-methoxyphenyl) carbamoyl)heptanoate (BKT300-3-c3) as a yellow oil (5.0 grams, 82.45% yield). LC-MS: m/z 446.0 (M++H).

4. Preparation of 2-((2-(2,4-dimethoxyphenoxy)-5-methoxyphenyl)carbamoyl)heptanoic acid (BKT300-3-c4)

To a solution of methyl 2-((2-(2,5-dimethoxyphenoxy)-5-methoxyphenyl) carbamoyl)heptanoate (BKT300-3-c3) (5.0 grams, 11.23 mmol) in a mixture solution of THF (10 ml), MeOH (10 ml) and water (10 ml) was added LiOH—$H_2O$ (944 mg, 22.46 mmol). The reaction was stirred at room temperature for 16 hours. LC-MS (liquid chromatography-mass spectroscopy) showed the reaction was completed. The reaction mixture was concentrated in vacuum. The residue was dissolved in water (50 ml) and acidified to pH 2-3 using concentrated HCl. The reaction mixture was extracted with EtOAc (2×20 ml). The organic layer was washed with brine (2×50 ml), dried over anhydrous $Na_2SO_4$, and filtered. The filtrate was concentrated in vacuum to give the product 2-((2-(2,4-dimethoxyphenoxy)-5-methoxyphenyl)carbamoyl)heptanoic acid (BKT300-3-c4) as a yellow solid (4.85 grams, 100% yield). LC-MS: m/z 432.0 (M++H).

5. Preparation of 8-(2,4-dimethoxyphenoxy)-6-methoxy-3-pentylquinoline-2,4(1H,3H)-dione (BKT300-3-c5)

To a PPA solution (8 mL) at 120° C. was added 2-((2-(2,4-dimethoxyphenoxy)-5-methoxyphenyl)carbamoyl)heptanoic acid (BKT300-3-c4) (2.0 grams, 4.64 mmol) portionwise. The reaction mixture was stirred at 120° C. for 6 hours. LC-MS (liquid chromatography-mass spectroscopy) showed the reaction was completed. The reaction mixture was poured into water (100 ml) and extracted with EtOAc (2×20 ml). The organic layer was washed with brine (2×50 ml), dried over anhydrous $Na_2SO_4$, and filtered. The filtrate was concentrated in vacuum. The residue was purified by silica gel chromatography eluted with (EtOAc:Petroleum Ether=1:10-1:5) to give the product 8-(2,4-dimethoxyphenoxy)-6-methoxy-3-pentylquinoline-2,4(1H,3H)-dione (BKT300-3-c5) as a yellow solid (240 mg, 12.5% yield). LC-MS: m/z 414.7 (M++H).

6. Preparation of 2,4-dichloro-8-(2,4-dimethoxyphenoxy)-6-methoxy-3-pentylquinoline (BKT300-3-c6)

A mixture of 8-(2,4-dimethoxyphenoxy)-6-methoxy-3-pentylquinoline-2,4(1H,3H)-dione (BKT300-3-c5) (230 mg, 0.557 mmol) in $POCl_3$ (2 ml) was stirred at 110° C. for 4 hours. LC-MS (liquid chromatography-mass spectroscopy) showed the reaction was completed. The reaction mixture was concentrated in vacuum. The residue was dissolved in EtOAc (20 ml) and washed successively with saturated $NaHCO_3$(2×20 ml) and brine (20 ml), dried over anhydrous $Na_2SO_4$, and filtered. The filtrate was concentrated in vacuum to give the product 2,4-dichloro-8-(2,4-dimethoxy phenoxy)-6-methoxy-3-pentylquinoline (BKT300-3-c6) as a light yellow solid (250 mg, 100% yield). LC-MS: m/z 451.0 (M++H).

7. Preparation of 4-chloro-8-(2,4-dimethoxyphenoxy)-2,6-dimethoxy-3-pentylquinoline (BKT300-3-c7)

A mixture of 2,4-dichloro-8-(2,4-dimethoxy phenoxy)-6-methoxy-3-pentyl quinoline (BKT300-3-c6) (250 mg, 0.55 mmol) and MeONa (300 mg, 5.5 mmol) in toluene (4 ml) was stirred at 145° C. in a sealed tube for 20 hours. TLC showed the reaction was completed (EtOAc:Petroleum Ether=1:50). The reaction mixture was concentrated in vacuum. Water was poured into the residue and extracted with EtOAc (2×20 ml). The organic layer was washed with brine (2×20 ml), dried over anhydrous $Na_2SO_4$, and filtered. The filtrate was concentrated in vacuum. The residue was purified by TLC eluted with (EtOAc:Petroleum Ether=1:100) to give the product 4-chloro-8-(2,4-dimethoxyphenoxy)-2,6-dimethoxy-3-pentylquinoline (BKT300-3-c7) as a white solid (180 mg, 72.8% yield). LC-MS: m/z 447.0 (M++H).

8. Preparation of 8-(2,4-dimethoxyphenoxy)-2,6-dimethoxy-3-pentylquinoline (BKT300-3-c8)

A mixture of 4-chloro-8-(2,4-dimethoxyphenoxy)-2,6-dimethoxy-3-pentyl quinoline (BKT300-3-c7) (180 mg, 0.40 mmol) and 10% Pd/C (20 mg) in MeOH (20 ml) and $Et_3N$ (2 ml) was stirred at room temperature for 2.0 hours. TLC showed the reaction was completed (EtOAc:Petroleum Ether=1:20). The reaction mixture was filtered. The filtrate was concentrated in vacuum. The residue was dissolved in EtOAc (20 ml) and washed with brine (2×20 ml). The organic layer was dried over anhydrous $Na_2SO_4$, and filtered. The filtrate was concentrated in vacuum to give the product 8-(2,4-dimethoxyphenoxy)-2,6-dimethoxy-3-pentylquinoline (BKT300-3-c8) as a light yellow solid (120 mg, 72.3% yield). LC-MS: m/z 412.1 (M++H).

9. Preparation of 8-(2,4-dihydroxyphenoxy)-6-hydroxy-3-pentylquinolin-2(1H)-one (BKT300-3)

A mixture of 8-(2,4-dimethoxyphenoxy)-2,6-dimethoxy-3-pentylquinoline (BKT300-3-c8) (30 mg, 0.073 mmol) in 30% HBr in $CH_3COOH$ (4 ml) was stirred at 120° C. for 36 hours. The reaction mixture was then concentrated in vacuum. The residue and 10% Pd/C (2 mg) in MeOH (6 ml) was stirred at room temperature for 1 hour. The reaction mixture was filtered and the filtrate was concentrated in vacuum. The residue was purified by pre-HPLC to give 8-(2,4-dihydroxyphenoxy)-6-hydroxy-3-pentylquinolin-2 (1H)-one (BKT300-3) as a yellow solid (4 mg, yield 15.3%). LC-MS: m/z 356.8 (M++H).

Figure 56:
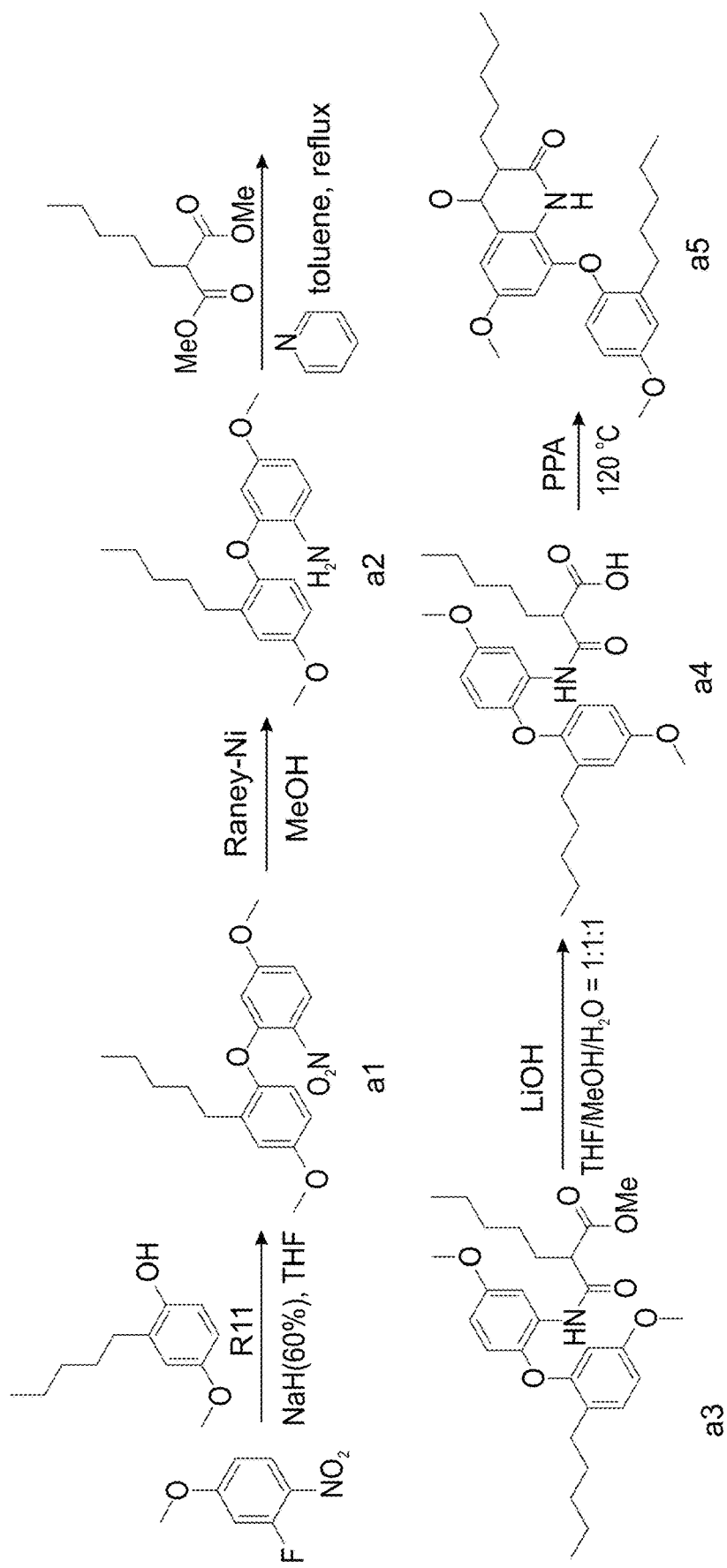
FIG. 56 presents schemes depicting an exemplary synthesis of BKT300-11, according to some embodiments of the present invention.
Figure 56:
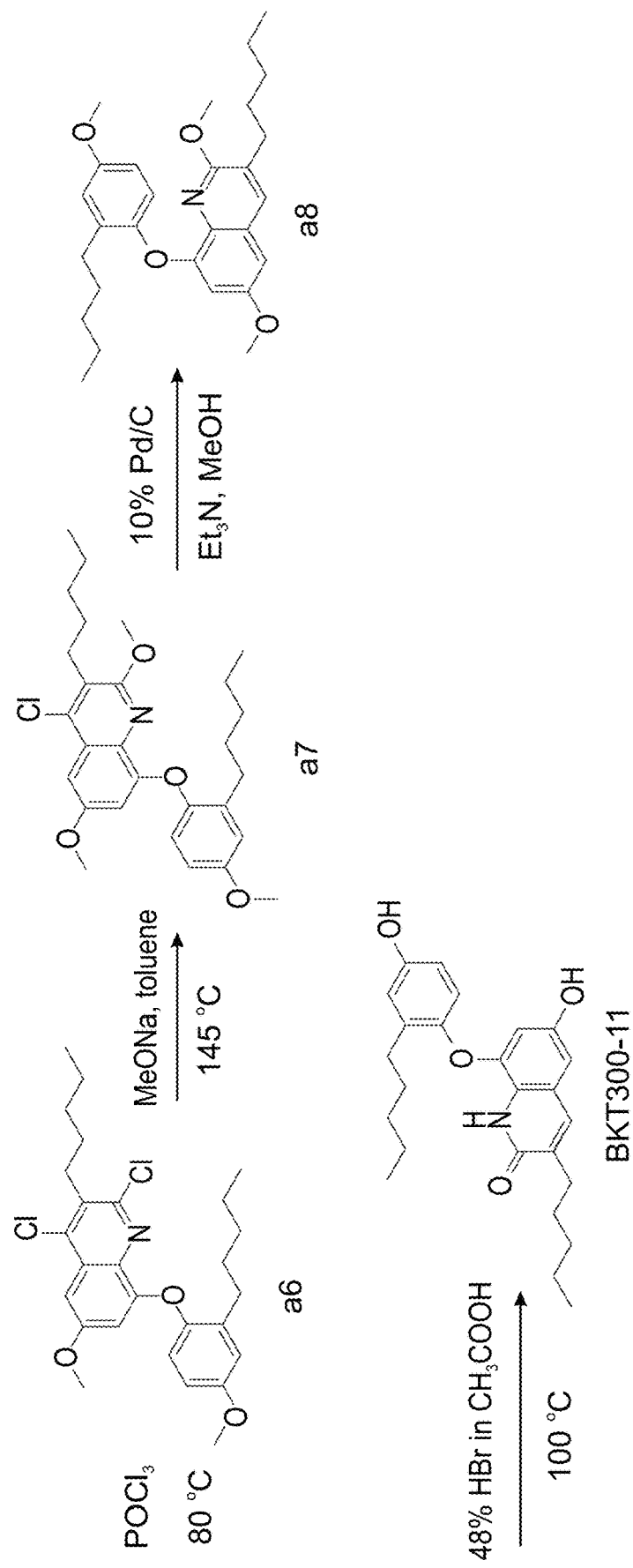

Preparation of BKT300-11:

A scheme presenting the synthesis of BKT300-11 is presented in FIG. 56.

1. Preparation of 4-methoxy-1-(5-methoxy-2-nitrophenoxy)-2-pentylbenzene (BKT300-11-a1)

To a solution of 4-methoxy-2-pentylphenol (R11) (2.5 grams, 11.15 mmol) in THF (50 ml) was added NaH (60%) (892 mg, 22.30 mmol). The reaction mixture was stirred at 0° C. for 30 minutes. Then, 2-fluoro-4-methoxy-1-nitrobenzene (1.91 gram, 11.15 mmol) was added at 0° C. The reaction mixture was stirred at room temperature overnight. TLC showed the reaction was completed (EtOAc:Petroleum Ether=1:10). The reaction mixture was poured into ice-water and extracted with EtOAc (2×20 ml). The organic layer was washed with brine (2×50 ml), dried over anhydrous $Na_2SO_4$, and filtered. The filtrate was concentrated in vacuum to give the product 4-methoxy-1-(5-methoxy-2-nitrophenoxy)-2-pentylbenzene (BKT300-11-a1) as a yellow oil (3.85 grams, 100% yield).

2. Preparation of 4-methoxy-2-(4-methoxy-2-pentylphenoxy)aniline (BKT300-11-a2)

A mixture of 4-methoxy-1-(5-methoxy-2-nitrophenoxy)-2-pentylbenzene (BKT300-11-a1) (3.85 grams, 11.15 mmol, 1.0 eq.) and Raney nickel (770 mg) in MeOH (100 ml) was stirred at room temperature for 4 hours. LC-MS (liquid chromatography-mass spectroscopy) showed the reaction was completed. The reaction mixture was filtered. The filtrate was concentrated in vacuum to give the product 4-methoxy-2-(4-methoxy-2-pentyl phenoxy)aniline (BKT300-11-a2) as a black oil (4.41 grams, 100% yield). LC-MS: m/z 316.0 (M++H).

3. Preparation of methyl 2-((5-methoxy-2-(5-methoxy-2-pentylphenoxy) phenyl)carbamoyl)heptanoate (BKT300-11-a3)

A mixture of 4-methoxy-1-(5-methoxy-2-nitrophenoxy)-2-pentylbenzene (BKT300-11-a1) (4.145 grams, 13.14 mmol), dimethyl 2-pentylmalonate (3.98 grams, 19.71 mmol) and pyridine (2.08 grams, 26.28 mmol) in toluene (80 ml) was stirred at reflux for 40 hours. LC-MS (liquid chromatography-mass spectroscopy) showed the reaction was completed. The reaction mixture was concentrated in vacuum. The residue was purified by silica gel chromatography eluted with (EtOAc:Petroleum Ether=1:20-1:10) to give the product methyl 2-((5-methoxy-2-(5-methoxy-2-pentylphenoxy)phenyl)carbamoyl)heptanoate (BKT300-11-a3) as a yellow oil (7.2 grams, 100% yield). LC-MS: m/z 486.0 (M++H).

4. Preparation of 2-((5-methoxy-2-(4-methoxy-2-pentylphenoxy)phenyl)carbamoyl)heptanoic acid (BKT300-11-a4)

To a solution of methyl 2-((5-methoxy-2-(5-methoxy-2-pentyl phenoxy)phenyl)carbamoyl)heptanoate (BKT300-11-a3) (3.0 grams, 6.19 mmol) in a mixture solution of THF (10 ml), MeOH (10 ml) and water (10 ml) was added LiOH—$H_2O$ (520 mg, 12.37 mmol). The reaction was stirred at room temperature for 16 hours. LC-MS (liquid chromatography-mass spectroscopy) showed the reaction was completed. The reaction mixture was concentrated in vacuum. The residue was dissolved in water (50 ml) and acidified to pH 2-3 using concentrated HCl. The reaction mixture was extracted with EtOAc (2×20 ml). The organic layer was washed with brine (2×50 ml), dried over anhydrous $Na_2SO_4$, and filtered. The filtrate was concentrated in vacuum to give the product 2-((5-methoxy-2-(4-methoxy-2-pentylphenoxy)phenyl)carbamoyl)heptanoic acid (BKT300-11-a4) as a yellow solid (2.5 grams, 85.6% yield). LC-MS: m/z 472.0 (M++H).

5. Preparation of 6-methoxy-8-(4-methoxy-2-pentylphenoxy)-3-pentylquinoline-2,4(1H,3H)-dione (BKT300-11-a5)

To a PPA solution (8 ml) at 120° C. was added 2-((5-methoxy-2-(4-methoxy-2-pentylphenoxy)phenyl)carbamoyl)heptanoic acid (BKT300-11-a4) (1.0 gram, 2.12 mmol) portion-wise. The reaction mixture was stirred at 120° C. for 6 hours. LC-MS (liquid chromatography-mass spectroscopy) showed the reaction was completed. The reaction mixture was poured into water (100 ml) and extracted with EtOAc (2×20 ml). The organic layer was washed with brine (2×50 ml), dried over anhydrous $Na_2SO_4$, and filtered. The filtrate was concentrated in vacuum. The residue was purified by silica gel chromatography eluted with (EtOAc:Petroleum Ether=1:10-1:5) to give the product 6-methoxy-8-(4-methoxy-2-pentylphenoxy)-3-pentylquinoline-2,4(1H,3H)-dione (BKT300-11-a5) as a yellow solid (260 mg, 27.1% yield). LC-MS: m/z 454.7 (M++H).

1H NMR (400 MHz, DMSO-d6): δ 11.76 (s, 1H), 7.56 (s, 1H), 4.05 (t, J=6.8 Hz, 2H), 1.63-1.56 (m, 2H), 1.36-1.27 (m, 4H), 0.88 (t, J=6.8 Hz, 3H).

6. Preparation of 2,4-dichloro-6-methoxy-8-(4-methoxy-2-pentylphenoxy)-3-pentylquinoline (BKT300-11-a6)

A mixture of 6-methoxy-8-(4-methoxy-2-pentylphenoxy)-3-pentyl quinolone-2,4(1H,3H)-dione (BKT300-11-a5) (260 mg, 0.573 mmol) in $POCl_3$ (2 ml) was stirred at 80° C. for 4 hours. LC-MS (liquid chromatography-mass spectroscopy) showed the reaction was completed. The reaction mixture was concentrated in vacuum. The residue was dissolved in EtOAc (20 ml) and washed successively with saturated $NaHCO_3$ (2×20 ml) and brine (20 ml), dried over anhydrous $Na_2SO_4$, and filtered. The filtrate was concentrated in vacuum to give the product 2,4-dichloro-6-methoxy-8-(4-methoxy-2-pentylphenoxy)-3-pentylquinoline (BKT300-11-a6) as a light yellow solid (266 mg, 94.7% yield). LC-MS: m/z 490.0 (M++H). 7. Preparation of 4-chloro-2,6-dimethoxy-8-(4-methoxy-2-pentylphenoxy)-3-pentylquinoline (BKT300-11-a7)

A mixture of 2,4-dichloro-6-methoxy-8-(4-methoxy-2-pentylphenoxy)-3-pentylquinoline (BKT300-11-a6) (71 mg, 0.144 mmol) and MeONa (76.8 mg, 14.4 mmol) in toluene (4 ml) was stirred at 145° C. in a sealed tube for 20 hours. TLC showed the reaction was completed (EtOAc:Petroleum Ether=1:50). The reaction mixture was concentrated in vacuum. Water was poured into the residue and extracted with EtOAc (2×20 ml). The organic layer was washed with brine (2×20 ml), dried over anhydrous $Na_2SO_4$, and filtered. The filtrate was concentrated in vacuum. The residue was purified by TLC eluted with (EtOAc:Petroleum Ether=1:100) to give the product 4-chloro-2,6-dimethoxy-8-(4-methoxy-2-pentylphenoxy)-3-pentyl quinoline (BKT300-11-a7) as a white solid (40 mg, 56.3% yield). LC-MS: m/z 486.0 (M++H).

8. Preparation of 2,6-dimethoxy-8-(4-methoxy-2-pentylphenoxy)-3-pentylquinoline (BKT300-11-a8)

A mixture of 4-chloro-2,6-dimethoxy-8-(4-methoxy-2-pentylphenoxy)-3-pentyl quinoline (BKT300-11-a7) (40 mg, 0.082 mmol) and 10% Pd/C (20 mg) in MeOH (20 ml) and $Et_3N$ (2 ml) was stirred at room temperature for 2.0 hours. TLC showed the reaction was completed (EtOAc:Petroleum Ether=1:20). The reaction mixture was filtered. The filtrate was concentrated in vacuum. The residue was dissolved in EtOAc (20 ml) and washed with brine (2×20 ml). The organic layer was dried over anhydrous $Na_2SO_4$, and filtered. The filtrate was concentrated in vacuum to give the product 2,6-dimethoxy-8-(4-methoxy-2-pentylphenoxy)-3-pentyl quinoline (BKT300-11-a8) as a light yellow solid (30 mg, 80.6% yield). LC-MS: m/z 452.1 (M++H).

9. Preparation of 6-hydroxy-8-(4-hydroxy-2-pentylphenoxy)-3-pentylquinolin-2(1H)-one (BKT300-11)

A mixture of 2,6-dimethoxy-8-(4-methoxy-2-pentylphenoxy)-3-pentyl quinolone (BKT300-11-a8) (130 mg, 0.066 mmol) in 30% HBr in CH$_3$COOH (4 ml) was stirred at 120° C. for 16 hours. Then the reaction mixture was concentrated in vacuum. The residue was dissolved in 30% HBr in CH$_3$COOH (4 ml) in a sealed tube and was stirred at 120° C. for 4 hours. The reaction mixture was concentrated in vacuum. The residue was purified by pre-HPLC to give 6-hydroxy-8-(4-hydroxy-2-pentyl phenoxy)-3-pentylquinolin-2(1H)-one (BKT300-11) as a yellow solid (36 mg, yield 31.5%). LC-MS: m/z 410.8 (M++H).

1H NMR (400 MHz, CDCl3): δ 7.99 (s, 1H), 6.42 (s, 1H), 6.40 (s, 1H), 6.23 (s, 1H), 4.23 (t, J=7.6 Hz, 2H), 3.84 (s, 3H), 3.73 (s, 3H), 2.46 (t, J=7.6 Hz, 2H), 1.74-1.71 (m, 2H), 1.65-1.63 (m, 1H), 1.51-1.47 (m, 1H), 1.39 (m, 4H), 1.25 (m, 4H), 0.93 (t, J=6.4 Hz, 3H), 0.82 (t, J=6.4 Hz, 3H).

Activity Assays:

Each of the compounds presented in Table 5 are tested in a cell migration assay as described hereinabove, under the "methods" section, so as to determine its effect on a biological activity of the tested chemokines, and hence its activity in treating diseases associated with the chemokine.

Of these tested compounds, compounds exhibiting modulation of a biological activity of chemokines are tested in vitro and in vivo in cancer models, as described hereinabove.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating age-related macular degeneration (AMD) in a subject in need thereof, the method comprising administering to the subject a compound represented by the Formula:

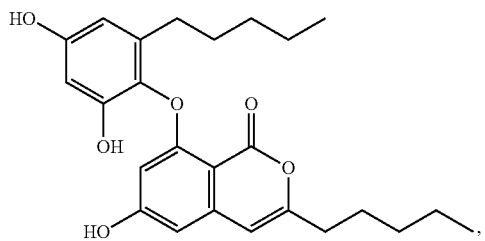 [SMILES: CCCCCc1cc2cc(O)cc(Oc3c(O)cc(O)cc3CCCCC)c2c(=O)o1]

thereby treating the age-related macular degeneration (AMD).

2. The method of claim 1, wherein the age-related macular degeneration (AMD) is atrophic, non-neovascular (aAMD).

3. The method of claim 1, wherein the age-related macular degeneration (AMD) is neovascular.

* * * * *